(12) United States Patent
Marciniak et al.

(10) Patent No.: US 8,748,441 B2
(45) Date of Patent: Jun. 10, 2014

(54) THERAPEUTIC USES OF QUINAZOLINEDIONE DERIVATIVES

(75) Inventors: Gilbert Marciniak, Paris (FR); Jean-Francois Nave, Paris (FR); Fabrice Viviani, Paris (FR)

(73) Assignee: SANOFI, Paris (FR)

( * ) Notice: Subject to any disclaimer, the term of this patent is extended or adjusted under 35 U.S.C. 154(b) by 14 days.

(21) Appl. No.: 13/259,888

(22) PCT Filed: Mar. 25, 2010

(86) PCT No.: PCT/FR2010/050549
§ 371 (c)(1),
(2), (4) Date: Oct. 31, 2011

(87) PCT Pub. No.: WO2010/109148
PCT Pub. Date: Sep. 30, 2010

(65) Prior Publication Data
US 2012/0058987 A1 Mar. 8, 2012

(30) Foreign Application Priority Data

Mar. 27, 2009 (FR) .................................. 09 01460

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ............... 514/266.2; 514/266.1; 544/283; 544/284

(58) Field of Classification Search
USPC ............... 544/283, 284; 514/266.1, 266.2
See application file for complete search history.

(56) References Cited

FOREIGN PATENT DOCUMENTS

| EP | 1 348 701 A1 | 10/2003 |
|---|---|---|
| WO | WO2006/003148 A1 | 1/2006 |
| WO | WO2008/119057 A2 | 10/2008 |
| WO | WO2009/077680 A1 | 6/2009 |

OTHER PUBLICATIONS

Perez-Torres, S. et al., "Alterations on phosphodiesterase type 7 and 8 isozyme mRNA expression in Alzheimer's disease brains examined by in situ hybridization," Experimental Neurology (2003), vol. 182, pp. 322-334.
Lowe, John A. et al., "Structure-Activity Relationship of Quinazolinedione Inhibitors of Calcium-Independent Phosphodiesterase," Journal of Medicinal Chemistry (1991), vol. 34, pp. 624-628.
International Search Report dated Jul. 2, 2010 issued in PCT/FR2010/050549.
International Preliminary Report on Patentability dated Sep. 27, 2011 issued in PCT/FR2010/050549.
Menniti et al. "Phosphodiestrases in the CNS: targets for drug development" Nature, vol. 5, Aug. 2006, pp. 660-670.
Perez-Torres et al. "Alterations on phosphodiesterase type 7 and 8 isozyme mRNA expression in Alzheimer's disease brains examined by in situ hybridization" Experimental Neurology 182 (2003) pp. 322-334.
Reyes-Irisarri et al. "Neuronal Expression of cAMP-Specific Phosphodiesterase 7B imRNA in the Rat Brain" Neuroscience 132 (2005) pp. 1173-1185.
Sasaki et al. "Transcriptional activation of phosphodiesterase 7B1 ... neurons" Journal of Neurochemistry (2004), 89, pp. 474-483.
Miro et al. "Differential Distribution of cAMP-Specific Phosphodiesterase 7A mRNA in Rat Brain and Peripheral Organs" Synapse 40:201-214 (2001).

*Primary Examiner* — Paul V. Ward
(74) *Attorney, Agent, or Firm* — Scully, Scott, Murphy & Presser, P.C.

(57) ABSTRACT

The subject matter of the present invention is the use of compounds of formula (I) in the form of a base, a hydrate or a solvate, or of mixtures thereof, as a medicament or for preparing a medicament intended for the treatment and/or prevention of disorders associated with the central nervous system (abbreviated to CNS) and/or associated with the peripheral nervous system (abbreviated to PNS).

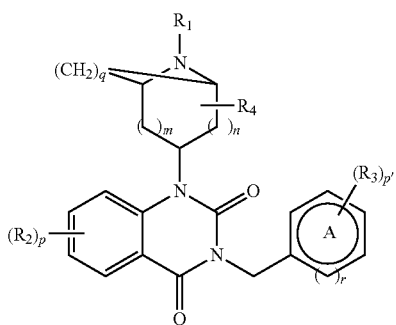

4 Claims, No Drawings

THERAPEUTIC USES OF QUINAZOLINEDIONE DERIVATIVES

A subject-matter of the invention is the use of quinazolinedione derivatives as medicaments or for manufacturing a medicament intended for the treatment and/or prevention of disorders related to the central nervous system (abbreviated CNS) and/or related to the peripheral nervous system (abbreviated PNS). The invention relates more particularly to the use of quinazolinedione derivatives as medicaments or for manufacturing a medicament intended for the treatment and/or prevention of psychiatric disorder(s) and/or intended for the treatment and/or prevention of neurological disorder(s).

The central nervous system or CNS comprises the brain, the spinal cord and the cranial nerves.

The peripheral nervous system or PNS is the part of the nervous system formed of ganglions and nerves which brings about the movement of information between the organs and the central nervous system or CNS and which carries out the motor commands of the latter. It comprises the somatic nervous system and the autonomic nervous system.

The invention relates to quinazolinedione derivatives which are inhibitors of phosphodiesterase 7 (PDE7). Some of these derivatives also inhibit phosphodiesterase 8 (PDE8).

Phosphodiesterases (PDEs) are intracellular enzymes responsible for the hydrolysis of cAMP (cyclic adenosine 3',5'-monophosphate) and cGMP (cyclic guanosine 3',5'-monophosphate) secondary messengers to give inactive 5'-monophosphate nucleotides. cAMP and cGMP play an essential role in cell signalling pathways and are involved in numerous physiological processes.

The inhibition of phosphodiesterases is reflected by an increase in intracellular concentrations of cAMP and cGMP, resulting in the specific activation of phosphorylation pathways involved in varied functional responses. The increase in the intracellular concentrations of cAMP or of cGMP using selective inhibitors of phosphodiesterases appears to be a promising approach in the treatment of various diseases (Bender and Beavo, Pharmacol. Rev., (2006) 58, 488-520). The inhibitors of phosphodiesterases are thus of interest as therapeutic agents and as pharmacological tools.

To date, eleven families of phosphodiesterases have been identified. They are distinguished by their primary structure, their substrate specificity and their sensitivity with regard to various effectors and inhibitors specific for PDEs. Each family is composed of one or more genes which are expressed in various tissues in the form of splicing variants (Bender and Beavo, Pharmacol. Rev., (2006) 58, 488-520; Lugnier, Pharmacol. Therapeut., (2006) 109, 366-398).

PDE4, PDE7 and PDE8 specifically hydrolyse cAMP and PDE5, PDE6 and PDE9 specifically hydrolyse cGMP.

The family PDE7 is represented by the isoforms PDE7A and PDE7B originating from two distinct genes.

Human PDE7A (Michaeli et al., J. Biol. Chem., (1993) 268, 12925-12932; Han et al., J. Biol. Chem., (1997) 272, 16152-16157; Wang et al., Biochem. Biophys. Res. Commun., (2000) 276, 1271-1277) and human PDE7B (Sasaki et al., Biochem. Biophys. Res. Commun., (2000), 271, 575-583; Gardner et al., Biochem. Biophys. Res. Commun., (2000) 272, 186-192) selectively hydrolyse cAMP with Michaelis constants (Km) of 0.1 to 0.2 µM and 0.13 to 0.2 µM respectively. The catalytic part of PDE7B exhibits approximately 67% homology with that of PDE7A.

Three splicing variants are known for PDE7A. PDE7A1 and PDE7A3 are expressed mainly in the cells of the immune system and of the lungs, while PDE7A2 is above all expressed in the muscles of the skeleton, the heart and the kidneys. For PDE7B, three variants have also recently been identified (Giembycz and Smith, Drugs Future, (2006) 31, 207-229).

The tissue distribution profiles for PDE7A and PDE7B are very different, suggesting that these two isoforms have distinct functions from the physiological viewpoint. While PDE7A is copiously expressed in haematopoietic cells, the lungs, the placenta, Leydig cells, the spleen, the collecting tubes of the kidneys, and the adrenal glands, strong expression of PDE7B is detected in the pancreas, the heart, the thyroid and the muscles of the skeleton (Giembycz and Smith, Drugs Future, (2006) 31, 207-229). However, coexpression of the messenger RNAs (mRNAs) of PDE7A and PDE7B is observed in some tissues. This is the case in the osteoblasts (Ahlstrom et al., Cell Mol. Biol. Lett., (2005) 10, 305-319) and in some regions of the brain: several areas of the cortex, the dentate gyrus, the majority of the components of the olfactory system, the striatum, numerous nuclei of the thalamus and the pyramidal cells of the hippocampus (Miro et al., Synapse, (2001) 40, 201-214; Reyes-Irisarri et al., Neuroscience, (2005) 132, 1173-1185). In contrast, in some areas of the brain, only one of the two isoforms is expressed. Thus, only the mRNAs of PDE7A are present in many nuclei of the brain stem. Likewise, the mRNAs of PDE7B are present at high concentrations in the nucleus accombens and the dorsal motor nucleus of the vagus nerve, while the mRNAs of PDE7A are not detected there (Miro et al., Synapse, (2001) 40, 201-214; Reyes-Irisarri et al., Neuroscience, (2005) 132, 1173-1185).

The document WO2008/119057 describes a method for the treatment of movement anomalies associated with a neurological movement disorder pathology, such as Parkinson's disease, the treatment method comprising the administration to a patient of an amount of an agent which is an inhibitor of PDE7 which is effective in inhibiting the enzymatic activity of PDE7.

A subject-matter of the present invention is in particular therapeutic applications of quinazolinedione derivatives, which may prove to be powerful inhibitors of PDE7, or of PDE7 and of PDE8, according to the derivatives.

The invention relates to the use of a compound corresponding to the following general formula (I):

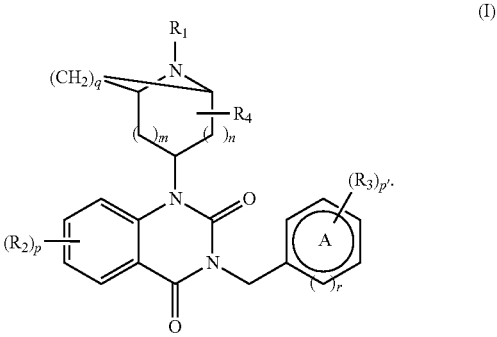

in which
A represents an aryl group or a heteroaryl group;
$R_1$ represents:
a hydrogen atom,
—C(O)R in which R is a hydrogen atom, a $(C_1$-$C_6)$alkoxy group, an aryl group, a $(C_3$-$C_6)$cycloalkyl group or a $(C_1$-$C_6)$alkyl group, the said alkyl optionally being substituted by:

one or more hydroxyl group(s),
a benzyloxy group,
a ($C_1$-$C_6$)alkoxy group, optionally substituted by an aryl, or
a ($C_3$-$C_6$)cycloalkyl group,
an optionally substituted ($C_1$-$C_6$)alkyl group;

$R_2$ represents:
a hydrogen atom,
a halogen atom,
a cyano group,
a nitro group,
a ($C_1$-$C_6$)alkyl group optionally substituted by an —$NH_2$ or else by an —NHC(O)Rb group, with Rb as defined below,
an —ORa group in which Ra represents:
  a hydrogen atom,
  a ($C_1$-$C_6$)alkyl group optionally substituted by one or more halogen atom(s), by one or more hydroxyl group(s), by an aryl group and/or by one or more cyano group(s),
  a ($C_2$-$C_6$)alkynyl group,
  an aryl group;

$R_3$ represents:
a hydrogen atom,
a halogen atom,
a hydroxyl group,
a cyano group,
an —$SCF_3$ group,
a nitro group,
an oxo group,
an —$S(O)_{0-2}$-alkyl group, an —$S(O)_{0-2}$-heterocycloalkyl group, an —O—$SO_2$-aryl group optionally substituted by one or more halogen atom(s);
an -alkylaminoalkyl or -cycloalkylaminoalkyl group, each optionally substituted on the end alkyl,
an optionally substituted sulphonamide group,
an aryl group or a heteroaryl group, the said group being monocyclic or polycyclic and in addition optionally being substituted by a ($C_1$-$C_6$)alkyl group, by one or more halogen atom(s) or by a ($C_1$-$C_6$)alkoxy group,
a heterocycloalkyl group optionally substituted by a ($C_1$-$C_6$)alkyl group,
a ($C_1$-$C_6$)alkyl group optionally substituted by:
  one or more halogen atom(s),
  an aryl group which can be substituted by one or more halogen atom(s) or by one or more hydroxyl group(s),
  a heteroaryl group,
  one or more hydroxyl group(s) which can be substituted by an aryl group itself optionally substituted by one or more halogen atom(s), or
  a heterocycloalkyl group optionally substituted by a CO(O)Ra group or by a ($C_1$-$C_6$)alkyl group, Ra being as defined above,
a —C(O)NRbRc group, with Rb and Rc being as defined below,
a —C(O)ORc group or an —O—C(O)ORc group, with Rc being as defined below,
a ($C_1$-$C_6$)alkoxy group, optionally substituted by
  an aminoalkyl group,
  an aminocycloalkyl group,
  a cycloalkyl group,
  a heterocycloalkyl group,
  a monocyclic or polycyclic heteroaryl group,
  one or more hydroxyl group(s),
  one or more halogen atom(s),
  a ($C_1$-$C_6$)alkoxy group,
  a —C(O)ORc group, with Rc being as defined below,
  a —C(O)NRbRc group, with Rb and Rc being as defined below,
  an oxo group, and/or
  an aryl group, itself optionally substituted by one or more halogen atom(s), a cyano group, a ($C_1$-$C_6$) alkoxy group, an —O-haloalkyl group and/or a haloalkyl group,
an —O-cycloalkyl group, an —O-aryl group or an —O-heterocycloalkyl group, each optionally substituted by
  an aryl group, itself optionally substituted by one or more halogen atom(s) or by a ($C_1$-$C_6$)alkyl group,
  an oxo group,
  one or more halogen atom(s), and/or
  a ($C_1$-$C_6$)alkyl group, which can itself be substituted by an aryl group and/or an oxo group,
an —NH—CO—NH-aryl group, an —NH—CO—NH-heteroaryl group or an —NH—CO—NH—($C_1$-$C_6$) alkyl group, each optionally being substituted by one or more halogen atom(s), by a cyano group, by a nitro group, by one or more hydroxyl group(s) or by a ($C_1$-$C_6$)alkoxy group,
an —N—($C_1$-$C_6$)alkyl group, it being possible for the ($C_1$-$C_6$)alkyl group to be substituted by
  one or more oxo group(s), and/or
  one or more aryl group(s) optionally substituted by one or more halogen atom(s) and/or by an $SO_2$ group,
  an —NH—CO-aryl group or an —NH—CO-heteroaryl group, each optionally being substituted by one or more halogen atom(s);
or else $R_3$ forms, with A, a polycyclic heteroaryl group optionally substituted by a ($C_1$-$C_6$)alkoxy group or a ($C_1$-$C_6$) alkyl group optionally substituted by an aryl group which can itself be substituted by one or more halogen atom(s);

$R_4$ represents a hydrogen atom, an oxo group or a ($C_1$-$C_6$) alkyl group;

Rb represents:
a hydrogen atom,
a ($C_1$-$C_6$)alkyl group optionally substituted by one or more halogen atom(s), by one or more hydroxyl, cyano, amino, heterocycloalkyl or ($C_1$-$C_6$)alkoxy group(s) or by an aryl group optionally substituted by one or more halogen atom(s),
a ($C_3$-$C_6$)cycloalkyl group,
a ($C_2$-$C_6$)alkynyl group,
a ($C_1$-$C_6$)alkoxy group,
an aryl group optionally substituted by one or more halogen atom(s);

Rc represents a hydrogen atom or a ($C_1$-$C_6$)alkyl group optionally substituted by one or more halogen atom(s);
or then Rb and Rc form, together with the nitrogen atom to which they are attached, a polycyclic heteroaryl group or a heterocycloalkyl group;

m and n represent, independently of one another, the value 0, 1 or 2, it being understood that m+n≤3;

p and p' represent, independently of one another, the value 1, 2 or 3, it being understood that, when p is greater than or equal to 2, then the $R_2$ groups are on separate carbon atoms and can be different from one another and, when p' is greater than or equal to 2, then the $R_3$ groups are on separate carbon atoms and can be different from one another;

q represents the value 0 or 2, it being understood that, when q=0, then the nitrogenous heterocyclic group attached to the nitrogen situated in the 1 position of the 2,4-dioxo-1,2,3,4-tetrahydroquinazoline ring system is no longer bridged and is of the type:

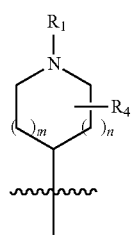

with $R_1$, $R_4$, m and n as defined above, r represents the value 0 or 1, as medicament or in the preparation of a medicament intended for the treatment and/or prevention of disorders related to the central nervous system and/or related to the peripheral nervous system.

According to one embodiment, the said disorders are chosen from psychiatric disorders and neurological disorders.

The compounds of general formula (I) can comprise one or more asymmetric carbons. They can thus exist in the form of enantiomers or of diastereoisomers. These enantiomers or diastereoisomers, and their mixtures, including racemic mixtures, come within the invention.

Due to their structure, the compounds of general formula (I) can also exist in the form of isomers of rotamer or atropisomer type.

The compounds of formula (I) can also exist in the form of bases or addition salts with acids. Such addition salts come within the invention.

These salts are advantageously prepared with pharmaceutically acceptable acids but the salts of other acids, for example of use in the purification or separation of the compounds of general formula (I) also come within the invention.

The compounds of general formula (I) can also occur in the crystalline, amorphous or oily form, these forms coming within the invention.

The compounds of general formula (I) can in addition occur in the form of hydrates or of solvates, namely in the form of combinations or of associations with one or more molecules of water or with a solvent. Such hydrates and solvates also come within the invention.

According to the present invention, the N-oxides of the compounds comprising an amine also come within the invention.

The compounds of formula (I) in accordance with the invention also comprise those in which one or more hydrogen, carbon or halogen, in particular chlorine or fluorine, atoms have been replaced by their radioactive isotopes, for example tritium, in order to replace hydrogen, or carbon-14, in order to replace carbon-12. Such labelled compounds are of use in research, metabolism or pharmacokinetic studies or in biological and pharmacological assays as tools.

In the context of the invention, the following definitions apply:

in ($C_1$-$C_6$), the numerical indices determine the possible number of carbon atoms present in a chain or a ring. Thus, by way of example, $C_1$-$C_6$ represents a carbon chain which can have from 1 to 6 carbon atoms. Likewise, by way of example, ($C_1$-$C_5$) represents a carbon chain which can have from 1 to 5 carbon atoms or also ($C_3$-$C_6$) can represent a saturated carbon ring which can have from 3 to 6 carbon atoms;

alkoxy: an —O-alkyl group comprising a saturated, linear or branched, aliphatic chain;

alkynyl: a mono- or polyunsaturated, linear or branched, aliphatic group comprising, for example, one or two acetylenic unsaturations. For example, a ($C_2$-$C_6$)alkynyl group can represent an ethynyl, propynyl, and the like;

alkyl: a saturated, linear or branched, aliphatic group; for example, a ($C_1$-$C_6$)alkyl group represents a linear or branched carbon chain of 1 to 6 carbon atoms, in particular a methyl, ethyl, propyl, isopropyl, butyl, isobutyl, sec-butyl, tert-butyl or pentyl;

aminoalkyl: an —NH($C_1$-$C_6$)alkyl or also —N(($C_1$-$C_6$)alkyl)$_2$ group;

aryl: an optionally substituted monocyclic aromatic system comprising from 5 to 14 members per ring, preferably from 5 to 10 members per ring. Mention may be made, as examples of monocyclic aryl groups, of phenyl or naphthyl; the aryl group can be substituted by a group which can be one or more halogen atom(s), a hydroxyl group, a cyano group, a trifluoromethylthio group, a nitro group, an alkyl group, an alkoxy group, an alkylthio group, a methylsulphonyl group, an alkylaminoalkyl group or alkylaminocycloalkyl group which is optionally substituted, an alkylaminoalkoxy or cycloalkylaminoalkoxy group or a sulphonamide group, for example:

polycyclic aryl: an optionally substituted polycyclic aromatic system comprising from 5 to 14 members per ring, preferably from 5 to 10 members per ring, and comprising from 2 to 10 rings, at least one of the rings of which is aromatic. Mention may be made, as examples of polycyclic aryl groups, of aceanthrylene, anthracene, azulene, coronene, rubicene or naphthalene; the polycyclic aryl group can be substituted by a group which can be one or more halogen atom(s), a hydroxyl group, a cyano group, a trifluoromethylthio group, a nitro group, an alkyl group, an alkoxy group, an alkylthio group, a methylsulphonyl group, an alkylaminoalkyl or alkylaminocycloalkyl group which is optionally substituted, an alkylaminoalkoxy or cycloalkylaminoalkoxy group or a sulphonamide group, for example;

a bridged ring: a bicyclic structure comprising, according to the invention, a nitrogen atom, in which at least two carbon atoms are connected via a single bond or a carbon chain which can comprise 2 carbon atoms. By way of example, the above-mentioned ring is of the type:

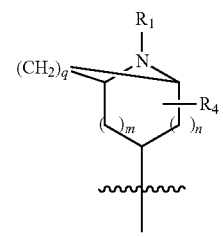

with q=1 or 2 and with the other groups and indices as defined above;

cycloalkyl: a saturated cyclic aliphatic group comprising from 3 to 8 carbon atoms. Mention may be made, by way of example, of a cyclopropyl, methylcyclopropyl, cyclobutyl, cyclopentyl or cyclohexyl group;

halogen: a fluorine, a chlorine, a bromine or an iodine;

haloalkyl: ($C_1$-$C_6$)alkyl substituted by one to three halogen atom(s);

heteroaryl: a monocyclic aromatic system comprising from 5 to 14 ring members, preferably from 5 to 10 ring members, and comprising one to several heteroatoms, such as nitrogen, oxygen or sulphur atoms. The nitrogen atoms can be in the form of N-oxides. For example, a monocyclic heterocycle can be a pyran, a pyrazine, a pyrazole, a pyridazine, a pyridine, a pyrimidine, a pyrrole, an isothiazole, an isoxazole, a furan, an imidazole, a morpholine, a thiophene, a piperazine, a diazetidine, a dihydropyrrolidine, a piperidine, an azepine, and the like; a bicyclic heterocycle can be an isoquinoline, a pteridine, a chroman, and the like; a tricyclic heterocycle can be a phenanthroline, a xanthene, and the like;

polycyclic heteroaryl: an optionally substituted polycyclic aromatic system comprising from 5 to 14 members per ring, preferably from 5 to 10 members per ring, and comprising from 2 to 10 rings, additionally comprising one to several heteroatoms, such as nitrogen, oxygen or sulphur atoms, in at least one of the rings, and at least one of the rings of which is aromatic. Mention may be made, as examples of polycyclic heteroaryl groups, of indole, benzofuran, benzimidazole, benzothiophene, benzotriazole, benzothiazole, benzoxazole, quinoline, isoquinoline, indazole, quinazoline, phthalazine, quinoxaline, naphthyridine, 2,3-dihydro-1H-indole, 2,3-dihydrobenzofuran, 2,3-dihydroindene, tetrahydroquinoline, tetrahydroisoquinoline or tetrahydroisoquinazoline;

a heterocycloalkyl: an optionally substituted saturated ring comprising from 3 to 8 atoms and comprising one to several heteroatoms, such as nitrogen, oxygen or sulphur atoms, in at least one of the rings, or several heteroatoms which are identical to or different from one another. For example, a heterocycloalkyl can be a pyrrolidine, a morpholine, a piperazine, a diazetidine, a dihydropyrrolidine, a piperidine, a piperadine, an azepane, an imidazolidine, a thiomorpholine, a tetrahydropyran, a tetrahydrothiopyran, a piperazine, a diazepane, and the like;

hydroxyl: an —OH group;
nitro: an —$NO_2$ group;
oxo: a —C(O)— group;
sulphonamide: group corresponding to the formula $SO_2$—N-alkyl or $SO_2$—N-cycloalkyl, alkyl and cycloalkyl being as defined above;
trifluoromethylthio is defined by the formula —S—$CF_3$.

Furthermore, it is understood that, in the present description, when an atom or a group is substituted or optionally substituted by one or more defined group(s) or atom(s), the substituents can be identical to or different from one another and may be carried, if appropriate, by the same atom or different atoms.

Mention may be made, among the compounds which are a subject-matter of the invention, of a group of compounds of formula (I) in which A represents an aryl group, in particular a phenyl or heteroaryl group, in particular a pyridyl group, and all the other substituents and indices are as defined in the general formula (I) defined above.

Mention may be made, among the compounds in accordance with the invention, of a group of compounds of formula (I) in which q=0, m and n each represents 1, and all the other substituents and indices are as defined in the general formula (I) defined above.

Mention may be made, among the compounds in accordance with the invention, of a group of compounds of formula (I) in which $R_2$ represents a ($C_1$-$C_6$)alkyl group, in particular a methyl, substituted by an —NHC(O)Rb group in which Rb and the other substituents and indices are as defined for the compound of general formula (I) defined above.

Mention may be made, among the compounds in accordance with the invention, of a group of compounds of general formula (I) in which $R_2$ represents an —ORa group, the Ra group and all the other substituents and indices being as defined in the general formula (I) defined above.

Mention may be made, among the compounds in accordance with the invention, of a group of compounds of general formula (I) in which $R_2$ is a halogen atom or a cyano or a hydrogen or a hydroxyl or a ($C_1$-$C_6$)alkyl optionally substituted by an —$NH_2$, or else by an —NHC(O)Rb group, Rb and the other substituents and indices being as defined in the general formula (I) defined above.

Mention may be made, among the compounds in accordance with the invention, of a group of compounds of general formula (I) in which A is a phenyl, $R_1$ is a —C(O)R group in which R represents a hydrogen atom, q is equal to 0, n and m each have the value 1, and $R_2$ represents —ORa, Ra and the other substituents and indices being as defined in the general formula (I) defined above.

Mention may be made, among the compounds in accordance with the invention, of a group of compounds of general formula (I) in which A is a phenyl, $R_1$ is a —C(O)R group in which R represents a hydrogen atom, q is equal to 0, n and m each have the value 1, p is equal to 2, one of the $R_2$ groups is —ORa and the other of the $R_2$ groups is a halogen atom, Ra and the other substituents and indices being as defined in the general formula (I) defined above.

Mention may be made, among the compounds in accordance with the invention, of a group of compounds of general formula (I) in which A is a phenyl, $R_1$ is a —C(O)R group in which R represents a hydrogen atom, q is equal to 0, n and m each have the value 1, p=1 and $R_2$ is a methyl substituted by an —NH—CO—Rb group, Rb and the other substituents and indices being as defined in the general formula (I) defined above.

Advantageously, in the compounds of formula (I), the $R_2$ group is in the 6 position of the 2,4-dioxo-1,2,3,4-tetrahydroquinazoline ring system. The compounds of formula (I) can also have an $R_2$ group in the 7 position of the 2,4-dioxo-1,2,3,4-tetrahydroquinazoline ring system. The $R_2$ groups in the 6 and 7 positions can be identical or different.

Advantageously, in the compounds of formula (I), p is equal to 1 or 2.

The compounds of general formula (I) can be in the base, hydrate or solvate form, in the form of isomers or in the form of their mixtures.

In a specific form, when p'=2, then the two $R_3$ groups are in the 3 and 4 positions of the ring system A and can be different from one another.

The combinations of the groups of compounds in accordance with the invention mentioned above also come within the invention.

Mention may be made, as examples of preferred compounds in accordance with the invention, of the following compounds:

No. 1: 2-{[3-(3,4-dimethoxybenzyl)-1-(1-formylpiperidin-4-yl)-2,4-dioxo-1,2,3,4-tetrahydroquinazolin-6-yl]oxy}propanenitrile No. 2: 1-(1-acetylpiperidin-4-yl)-3-(3,4-dimethoxybenzyl)-6-hydroxyquinazoline-2,4(1H,3H)-dione No. 3: {[1-(1-acetylpiperidin-4-yl)-3-(3,4-dimethoxybenzyl)-2,4-dioxo-1,2,3,4-tetrahydroquinazolin-6-yl]oxy}acetonitrile No. 4: 2-{[1-(1-acetylpiperidin-4-yl)-3-(3,4-dimethoxybenzyl)-2,4-dioxo-1,2,3,4-tetrahydroquinazolin-6-yl]oxy}propanenitrile No. 5: {[3-(3,4-dimethoxybenzyl)-1-(1-formylpiperidin-4-yl)-2,4-dioxo-1,2,3,4-tetrahydroquinazolin-6-yl]oxy}acetonitrile No. 11: 4-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde No. 12: 1-(1-acetylpiperidin-4-yl)-3-(3,4-dimethoxybenzyl)-6-[2-fluoro-1-(fluoromethyl)ethoxy]quinazoline-2,4(1H,3H)-dione No. 13: 4-[3-(3,4-dimethoxybenzyl)-2,4-dioxo-6-(2,2,2-trifluoroethoxy)-3,4-dihydroquinazolin-1(2H)-yl]piperidine-1-carbaldehyde No. 14: 1-(1-acetylpiperidin-4-yl)-6-(2,2-difluoroethoxy)-3-(3,4-dimethoxybenzyl)quinazoline-2,4(1H,3H)-dione No. 16: 4-[6-(2,2-difluoroethoxy)-3-(3,4-dimethoxybenzyl)-2,4-dioxo-3,4-dihydroquinazolin-1(2H)-yl]piperidine-1-carbaldehyde No. 20: N-{[3-(3,4-dimethoxybenzyl)-1-(1-formylpiperidin-4-yl)-2,4-dioxo-1,2,3,4-tetrahydroquinazolin-6-yl]methyl}acetamide No. 22: 1-(1-acetylpiperidin-4-yl)-6-(aminomethyl)-3-(3,4-dimethoxybenzyl)quinazoline-2,4(1H,3H)-dione hydrochloride No. 23: N-{[3-(3,4-dimethoxybenzyl)-1-(1-formylpiperidin-4-yl)-2,4-dioxo-1,2,3,4-tetrahydroquinazolin-6-yl]methyl}formamide No. 24: N-{[1-(1-acetylpiperidin-4-yl)-3-(3,4-dimethoxybenzyl)-2,4-dioxo-1,2,3,4-tetrahydroquinazolin-6-yl]methyl}formamide No. 25: N-{[1-(1-acetylpiperidin-4-yl)-3-(3,4-dimethoxybenzyl)-2,4-dioxo-1,2,3,4-tetrahydroquinazolin-6-yl]methyl}acetamide No. 32: 4-[6-(2,2-difluoroethoxy)-2,4-dioxo-3,4-dihydroquinazolin-1(2H)-yl]piperidine-1-carbaldehyde No. 33: 4-[3-(3,4-dichlorobenzyl)-6-(2,2-difluoroethoxy)-2,4-dioxo-3,4-dihydroquinazolin-1(2H)-yl]piperidine-1-carbaldehyde No. 34: 4-[3-(4-chlorobenzyl)-6-(2,2-difluoroethoxy)-2,4-dioxo-3,4-dihydroquinazolin-1(2H)-yl]piperidine-1-carbaldehyde No. 35: methyl 4-{[6-(2,2-difluoroethoxy)-1-(1-formylpiperidin-4-yl)-2,4-dioxo-1,4-dihydroquinazolin-3(2H)-yl]methyl}benzoate No. 36: 4-{[6-(2,2-difluoroethoxy)-1-(1-formylpiperidin-4-yl)-2,4-dioxo-1,4-dihydroquinazolin-3(2H)-yl]methyl}benzoic acid No. 37: 4-{[6-(2,2-difluoroethoxy)-1-(1-formylpiperidin-4-yl)-2,4-dioxo-1,4-dihydroquinazolin-3(2H)-yl]methyl}-N-(2-methoxyethyl)benzamide No. 38: 4-[3-(3,4-dimethoxybenzyl)-6-methyl-2,4-dioxo-3,4-dihydroquinazolin-1(2H)-yl]piperidine-1-carbaldehyde No. 39: 4-[6-(2,2-difluoroethoxy)-3-(3-hydroxy-4-methoxybenzyl)-2,4-dioxo-3,4-dihydroquinazolin-1(2H)-yl]piperidine-1-carbaldehyde No. 40: 4-[6-(2,2-difluoroethoxy)-3-[3-(2-hydroxyethoxy)-4-methoxybenzyl]-2,4-dioxo-3,4-dihydroquinazolin-1(2H)-yl]piperidine-1-carbaldehyde No. 41: 4-[6-(2,2-difluoroethoxy)-3-(3-ethoxy-4-methoxybenzyl)-2,4-dioxo-3,4-dihydroquinazolin-1(2H)-yl]piperidine-1-carbaldehyde No. 42: 4-[6-(2,2-difluoroethoxy)-3-[4-methoxy-3-(2-methoxyethoxy)benzyl]-2,4-dioxo-3,4-dihydroquinazolin-1(2H)-yl]piperidine-1-carbaldehyde No. 43: 4-[6-(2,2-difluoroethoxy)-3-(3,4-dimethoxybenzyl)-2,4-dioxo-3,4-dihydroquinazolin-1(2H)-yl]azepane-1-carbaldehyde No. 47: 4-[6-(2,2-difluoroethoxy)-3-[3-(3-hydroxypropoxy)-4-methoxybenzyl]-2,4-dioxo-3,4-dihydroquinazolin-1(2H)-yl]piperidine-1-carbaldehyde No. 48: 4-[5-chloro-3-(3,4-dimethoxybenzyl)-2,4-dioxo-3,4-dihydroquinazolin-1(2H)-yl]piperidine-1-carbaldehyde No. 49: 4-{3-[3-(cyclopentyloxy)-4-methoxybenzyl]-6-(2,2-difluoroethoxy)-2,4-dioxo-3,4-dihydroquinazolin-1(2H)-yl}piperidine-1-carbaldehyde No. 50: 2-(5-{[6-(2,2-difluoroethoxy)-1-(1-formylpiperidin-4-yl)-2,4-dioxo-1,4-dihydroquinazolin-3(2H)-yl]methyl}-2-methoxyphenoxy)acetamide No. 51: 4-[6-(2,2-difluoroethoxy)-3-(3,4-dimethoxybenzyl)-2,4-dioxo-3,4-dihydroquinazolin-1(2H)-yl]-3-methylpiperidine-1-carbaldehyde No. 52: 3-[6-(2,2-difluoroethoxy)-3-(3,4-dimethoxybenzyl)-2,4-dioxo-3,4-dihydroquinazolin-1(2H)-yl]-8-azabicyclo[3.2.1]octane-8-carbaldehyde No. 56: 4-{3-[4-(cyclopentyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 57: 4-[3-(3-chlorobenzyl)-6-[2-fluoro-1-(fluoromethyl)ethoxy]-2,4-dioxo-3,4-dihydroquinazolin-1(2H)-yl]piperidine-1-carbaldehyde No. 58: 4-[3-(4-chlorobenzyl)-6-[2-fluoro-1-(fluoromethyl)ethoxy]-2,4-dioxo-3,4-dihydroquinazolin-1(2H)-yl]piperidine-1-carbaldehyde No. 59: 4-{3-[3-(cyclopentyloxy)-4-methoxybenzyl]6-[2-fluoro-1-(fluoromethyl)ethoxy]-2,4-dioxo-3,4-dihydroquinazolin-1(2H)-yl}piperidine-1-carbaldehyde No. 72: 4-[3-(3,4-dimethoxybenzyl)-6-(2-hydroxyethoxy)-2,4-dioxo-3,4-dihydroquinazolin-1(2H)-yl]piperidine-1-carbaldehyde No. 74: 4-[3-(3,4-dichlorobenzyl)-6-[2-fluoro-1-(fluoromethyl)ethoxy]-2,4-dioxo-3,4-dihydroquinazolin-1(2H)-yl]piperidine-1-carbaldehyde No. 76: 4-{3-[(6-chloropyridin-3-yl)methyl]-6-[2-fluoro-1-(fluoromethyl)ethoxy]-2,4-dioxo-3,4-dihydroquinazolin-1(2H)-yl}piperidine-1-carbaldehyde No. 78: 4-[3-(3-chloro-4-methoxybenzyl)-6-[2-fluoro-1-(fluoromethyl)ethoxy]-2,4-dioxo-3,4-dihydroquinazolin-1(2H)-yl]piperidine-1-carbaldehyde No. 79: 4-[3-(3,4-dimethoxybenzyl)-6-(2-fluoroethoxy)-2,4-dioxo-3,4-dihydroquinazolin-1(2H)-yl]piperidine-1-carbaldehyde No. 89: 2-[5-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]acetamide No. 90: 4-{6-[2-fluoro-1-(fluoromethyl)ethoxy]-3-(3-hydroxy-4-methoxybenzyl)-2,4-dioxo-3,4-dihydroquinazolin-1(2H)-yl}piperidine-1-carbaldehyde No. 91: 4-[3-(3,4-dimethoxybenzyl)-6-ethoxy-2,4-dioxo-3,4-dihydroquinazolin-1(2H)-yl]piperidine-1-carbaldehyde No. 97: 4-[5,7-dichloro-3-(3,4-dimethoxybenzyl)-2,4-dioxo-3,4-dihydroquinazolin-1(2H)-yl]piperidine-1-carbaldehyde No. 102: 4-[7-chloro-3-(3,4-dimethoxybenzyl)-2,4-dioxo-3,4-dihydroquinazolin-1(2H)-yl]piperidine-1-carbaldehyde No. 108: 4-{6-[2-fluoro-1-(fluoromethyl)ethoxy]-3-(3-fluoro-4-methoxybenzyl)-2,4-dioxo-3,4-dihydroquinazolin-1(2H)-yl}piperidine-1-carbaldehyde No. 111: 4-[6-(difluoromethoxy)-3-(3,4-dimethoxybenzyl)-2,4-dioxo-3,4-dihydroquinazolin-1(2H)-yl]piperidine-1-carbaldehyde No. 112: 4-[3-(3,4-dimethoxybenzyl)-6-(1-methylethoxy)-2,4-dioxo-3,4-dihydroquinazolin-1(2H)-yl]piperidine-1-carbaldehyde No. 114: 4-{6-[2-fluoro-1-(fluoromethyl)ethoxy]-3-[4-methoxy-3-(1-methylethoxy)benzyl]-2,4-dioxo-3,4-dihydroquinazolin-1(2H)-yl}piperidine-1-carbaldehyde No. 116: 4-{6-[2-fluoro-1-(fluoromethyl)ethoxy]-3-(3-methoxybenzyl)-2,4-dioxo-3,4-dihydroquinazolin-1(2H)-yl}piperidine-1-carbaldehyde No. 117: 4-{3-[3,5-bis(trifluoromethyl)benzyl]-6-[2-fluoro-1-(fluoromethyl)ethoxy]-2,4-dioxo-3,4-dihydroquinazolin-1(2H)-yl}piperidine-1-carbaldehyde No. 118: 4-[3-(3-ethoxybenzyl)-6-[2-fluoro-1-(fluoromethyl)ethoxy]-2,4-dioxo-3,4-dihydroquinazolin-1(2H)-yl]piperidine-1-carbaldehyde No. 124: 4-{3-[3-chloro-4-(2-methoxyethoxy)benzyl]-6-[2-fluoro-1-(fluoromethyl)ethoxy]-2,4-dioxo-3,4-dihydroquinazolin-1(2H)-yl}piperidine-1-carbaldehyde No. 130: 4-[3-(3,4-diethoxybenzyl)-6-[2-fluoro-1-(fluoromethyl)ethoxy]-2,4-dioxo-3,4-dihydroquinazolin-1(2H)-yl]piperidine-1-carbaldehyde No. 131: 4-[3-(4-ethoxy-3-methoxybenzyl)-6-[2-fluoro-1-(fluoromethyl)ethoxy]-2,4-dioxo-3,4-dihydroquinazolin-1(2H)-yl]piperidine-1-carbaldehyde No. 133: 4-{6-[2-fluoro-1-(fluoromethyl)ethoxy]-3-(4-methoxy-3-methylbenzyl)-2,4-dioxo-3,4-dihydroquinazolin-1(2H)-yl}piperidine-1-carbaldehyde No. 134: 4-{6-[2-fluoro-1-(fluoromethyl)ethoxy]-2,4-dioxo-3-[4-(trifluoromethyl)benzyl]-3,4-dihydroquinazolin-1(2H)-yl}piperidine-1-carbaldehyde No. 135: 4-{6-[2-fluoro-1-(fluoromethyl)ethoxy]-2,4-dioxo-3-[4-(trifluoromethyl)benzyl]-3,4-dihydroquinazolin-1(2H)-yl}piperidine-1-carbaldehyde No. 143: 4-{3-[4-(benzyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 145: 4-{6-[2-fluoro-1-(fluoromethyl)ethoxy]-3-(3-methoxy-4-nitrobenzyl)-2,4-dioxo-3,4-dihydroquinazolin-1(2H)-yl}piperidine-1-carbaldehyde No. 155: 4-[3-(4-ethoxybenzyl)-6-[2-fluoro-1-(fluoromethyl)ethoxy]-2,4-dioxo-3,4-dihydroquinazolin-1(2H)-yl]piperidine-1-carbaldehyde No. 158: 4-{6-[2-fluoro-1-(fluoromethyl)ethoxy]-3-[4-(morpholin-4-ylmethyl)benzyl]2,4-dioxo-3,4-dihydroquinazolin-1(2H)-yl}piperidine-1-carbaldehyde No. 160: 4-{6-[2-fluoro-1-(fluoromethyl)ethoxy]-3-(4-morpholin-4-ylbenzyl)-2,4-dioxo-3,4-dihydroquinazolin-1(2H)-yl}piperidine-1-carbaldehyde No. 165: 4-[3-(biphenyl-4-ylmethyl)-6-[2-fluoro-1-(fluoromethyl)ethoxy]-2,4-dioxo-3,4-dihydroquinazolin-1(2H)-yl]piperidine-1-carbaldehyde No. 166: 4-{6-[2-fluoro-1-(fluoromethyl)ethoxy]-3-[4-(methylsulphanyl)benzyl]-2,4-dioxo-3,4-dihydroquinazolin-1(2H)-yl}piperidine-1-carbaldehyde No. 167: 4-{6-[2-fluoro-1-(fluoromethyl)ethoxy]-2,4-dioxo-3-(4-(pyridin-3-yl)benzyl)-3,4-dihydroquinazolin-1(2H)-yl}piperidine-1-carbaldehyde No. 170: 4-{6-[2-fluoro-1-(fluoromethyl)ethoxy]-3-(3-methoxy-4-methyl benzyl)-2,4-dioxo-3,4-dihydroquinazolin-1(2H)-yl}piperidine-1-carbaldehyde No. 175: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methy)phenoxy]acetamide No. 178: 4-{6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde No. 183: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylacetamide No. 184: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N,N-dimethylacetamide No. 185: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methoxy-N-methylacetamide No. 186: 4-{3-[4-(cyclopentyloxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde No. 188: 4-{3-[4-(cyclopentyloxy)-3-(1-methylethoxy)benzyl]-6-[2-fluoro-1-(fluoromethyl)ethoxy]-2,4-dioxo-3,4-dihydroquinazolin-1(2H)-yl}piperidine-1-carbaldehyde No. 189: 4-{3-[4-(cyclopentyloxy)-3-propoxybenzyl]-6-[2-fluoro-1-(fluoromethyl)ethoxy]-2,4-dioxo-3,4-dihydroquinazolin-1(2H)-yl}piperidine-1-carbaldehyde No. 190: 4-{3-[4-(cyclopentyloxy)-3-hydroxybenzyl]-6-[2-fluoro-1-(fluoromethyl)ethoxy]-2,4-dioxo-3,4-dihydroquinazolin-1(2H)-yl}piperidine-1-carbaldehyde No. 193: 4-{3-[4-(difluoromethoxy)-3-methoxybenzyl]6-[2-fluoro-1-(fluoromethyl)ethoxy]-2,4-dioxo-3,4-dihydroquinazolin-1(2H)-yl}piperidine-1-carbaldehyde No. 194: 4-{3-[4-(difluoromethoxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde No. 200: 4-{6-[2-fluoro-1-(fluoromethyl)ethoxy]-2,4-dioxo-3-(4-(thiophen-3-yl)-benzyl)-3,4-dihydroquinazolin-1(2H)-yl}piperidine-1-carbaldehyde No. 201: 4-{6-[2-fluoro-1-(fluoromethyl)ethoxy]-2,4-dioxo-3-(4-(pyridin-4-yl)benzyl)-3,4-dihydroquinazolin-1(2H)-yl}piperidine-1-carbaldehyde No. 203: 4-{6-[2-fluoro-1-(fluoromethyl)ethoxy]-3-[(1-methyl-1H-indol-6-yl)methyl]-2,4-dioxo-3,4-dihydroquinazolin-1(2H)-yl}piperidine-1-carbaldehyde No. 206: 4-{3-[4-(cyclopropylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 207: 2-[4-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]-N-methylacetamide No. 212: 4-{6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde No. 213: 4-{6-[2-fluoro-1-(fluoromethyl)ethoxy]-2,4-dioxo-3-(4-(pyridin-2-yl)benzyl)-3,4-dihydroquinazolin-1(2H)-yl}piperidine-1-carbaldehyde No. 215: 4-{6-[2-fluoro-1-(fluoromethyl)ethoxy]-2,4-dioxo-3-(4-(thiophen-2-yl)-benzyl)-3,4-dihydroquinazolin-1(2H)-yl}piperidine-1-carbaldehyde No. 216: 4-{6-[2-fluoro-1-(fluoromethyl)ethoxy]-2,4-dioxo-3-(quinolin-7-ylmethyl)-3,4-dihydroquinazolin-1(2H)-yl}piperidine-1-carbaldehyde No. 218: 4-{6-[2-fluoro-1-(fluoromethyl)ethoxy]-3-[(6-methoxynaphthalen-2-yl)methyl]-2,4-dioxo-3,4-dihydroquinazolin-1(2H)-yl}piperidine-1-carbaldehyde No. 223: 4-{3-[4-(1H-benzimidazol-1-yl)benzyl]-6-[2-fluoro-1-(fluoromethyl)ethoxy]-2,4-dioxo-3,4-dihydroquinazolin-1(2H)-yl}piperidine-1-carbaldehyde No. 224: 4-{6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde No. 226: 4-{6-[2-fluoro-1-(fluoromethyl)ethoxy]-3-[3-methoxy-4-(tetrahydrofuran-3-yloxy)benzyl]-2,4-dioxo-3,4-dihydroquinazolin-1(2H)-yl}piperidine-1-carbaldehyde No. 228: 4-[3-{4-[(1-benzylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 230: 4-[3-(1-benzothiophen-5-ylmethyl)-6-[2-fluoro-1-(fluoromethyl)ethoxy]-2,4-dioxo-3,4-dihydroquinazolin-1(2H)-yl]piperidine-1-carbaldehyde No. 232: 4-{6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde No. 233: 4-[3-(3,4-dimethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 234: 4-[3-{4-[(1-acetylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 239: 4-[3-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 240: 4-[3-{4-[(4-chlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 242: 4-[3-{4-[(3-chlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 243: 4-{6-[2-fluoro-1-(fluoromethyl)ethoxy]-2,4-dioxo-3-(3-thiophen-3-yl)benzyl)-3,4-dihydroquinazolin-1(2H)-yl}piperidine-1-carbaldehyde No. 245: 4-[3-(4-ethoxy-3-methoxybenzyl)-6-(2-hydroxyethoxy)-2,4-dioxo-3,4-dihydroquinazolin-1(2H)-yl]piperidine-1-carbaldehyde No. 246: 4-[3-{4-[2-(2,3-dihydro-1H-indol-1-yl)-2-oxoethoxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 250: 4-[3-{4-[(3,4-dichlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 251: 4-{6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde No. 254: 4-{3-[3-ethoxy-4-(thiophen-2-ylmethoxy)benzyl]-6-[2-fluoro-1-(fluoromethyl)ethoxy]-2,4-dioxo-3,4-dihydroquinazolin-1(2H)-yl}piperidine-1-carbaldehyde No. 258: 4-[3-(3,4-dimethoxybenzyl)-6-[2-fluoro-1-(hydroxymethyl)ethoxy]-2,4-dioxo-3,4-dihydroquinazolin-1(2H)-yl]piperidine-1-carbaldehyde No. 263: (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid No. 264: 4-{6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde No. 270: 4-{6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde No. 275: 4-{6-[2-fluoro-1-(fluoromethyl)ethoxy]-2,4-dioxo-3-(4-(pyrimidin-5-yl)benzyl)-3,4-dihydroquinazolin-1(2H)-yl}piperidine-1-carbaldehyde No. 276: 4-{6-[2-fluoro-1-(fluoromethyl)ethoxy]-3-[(1-methyl-3-phenyl-1H-pyrazol-5-yl)methyl]-2,4-dioxo-3,4-dihydroquinazolin-1(2H)-yl}piperidine-1-carbaldehyde No. 278: 4-{6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde No. 279: 4-{6-[2-fluoro-1-(fluoromethyl)ethoxy]-2,4-dioxo-3-[(2-(thiophen-2-yl)pyrimidin-5-yl)methyl]-3,4-dihydroquinazolin-1(2H)-yl}piperidine-1-carbaldehyde No. 280: 4-{6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde No. 282: 4-{6-[2-fluoro-1-(fluoromethyl)ethoxy]-3-[4-(3-methyl-1,2,4-oxadiazol-5-yl)benzyl]-2,4-dioxo-3,4-dihydroquinazolin-1(2H)-yl}piperidine-1-carbaldehyde No. 283: [2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]acetic acid No. 285: 4-{6-[2-fluoro-1-(fluoromethyl)ethoxy]-2,4-dioxo-3-(thieno[2,3-b]pyridin-2-ylmethyl)-3,4-dihydroquinazolin-1(2H)-yl}piperidine-1-carbaldehyde No. 286: 4-{6-[2-fluoro-1-(fluoromethyl)ethoxy]-2,4-dioxo-3-[(6-phenypyridin-3-yl)methyl]-3,4-dihydroquinazolin-1(2H)-yl}piperidine-1-carbaldehyde No. 287: 4-{6-[2-fluoro-1-(fluoromethyl)ethoxy]-3-[(6-(morpholin-4-yl)pyridin-3-yl)methyl]-2,4-dioxo-3,4-dihydroquinazolin-1(2H)-yl}piperidine-1-carbaldehyde No. 289: 4-{6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde No. 292: 4-{6-[2-fluoro-1-(fluoromethyl)ethoxy]-3-[(1-methyl-5-phenyl-1H-pyrazol-3-yl)methyl]-2,4-dioxo-3,4-dihydroquinazolin-1(2H)-yl}piperidine-1-carbaldehyde No. 294: 4-({6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile No. 295: (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylpropanamide No. 297: 4-{7-fluoro-6-[2-fluoro-1-(fluoromethyl)ethoxy]-2,4-dioxo-3-(4-(thiophen-2-yl)benzyl)-3,4-dihydroquinazolin-1(2H)-yl}piperidine-1-carbaldehyde No. 298: 4-{6-[2-fluoro-1-(fluoromethyl)ethoxy]-3-[3-methoxy-4-(morpholin-4-ylmethyl)benzyl]-2,4-dioxo-3,4-dihydroquinazolin-1(2H)-yl}piperidine-1-carbaldehyde No. 299: 4-{6-[2-fluoro-1-(fluoromethyl)ethoxy]-3-[3-methoxy-4-(piperidin-1-ylmethyl)benzyl]-2,4-dioxo-3,4-dihydroquinazolin-1(2H)-yl}piperidine-1-carbaldehyde No. 300: 4-[3-{4-[(3,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 301: 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-ethylacetamide No. 302: (2S)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid No. 305: 4-{6-[2-fluoro-1-(fluoromethyl)ethoxy]-3-(3-methoxy-4-{[(3R)-2-oxo-1-phenylpyrrolidin-3-yl]oxy}benzyl)-2,4-dioxo-3,4-dihydroquinazolin-1(2H)-yl}piperidine-1-carbaldehyde No. 306: 4-{3-[4-(cyclobutylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde No. 307: 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde No. 308: 4-{7-fluoro-6-[2-fluoro-1-(fluoromethyl)ethoxy]-3-(4-hydroxy-3-methoxybenzyl)-2,4-dioxo-3,4-dihydroquinazolin-1(2H)-yl}piperidine-1-carbaldehyde No. 309: 4-{3-[4-(cyclopropylmethoxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde No. 310: 4-{7-fluoro-6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde No. 311: 4-{7-fluoro-6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde No. 312: 4-[3-(4-ethoxy-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 315: 4-{7-fluoro-6-[2-fluoro-1-(fluoromethyl)ethoxy]-3-{[6-(3-methoxyphenyl)pyridin-3-yl]methyl}-2,4-dioxo-3,4-dihydroquinazolin-1(2H)-yl}piperidine-1-carbaldehyde No. 316: 4-{7-fluoro-6-[2-fluoro-1-(fluoromethyl)ethoxy]-3-{[6-(2-fluorophenyl)pyridin-3-yl]methyl}-2,4-dioxo-3,4-dihydroquinazolin-1(2H)-yl}piperidine-1-carbaldehyde No. 317: 4-{7-fluoro-6-[2-fluoro-1-(fluoromethyl)ethoxy]-3-{[6-(4-fluorophenyl)pyridin-3-yl]methyl}-2,4-dioxo-3,4-dihydroquinazolin-1(2H)-yl}piperidine-1-carbaldehyde No. 318: 4-{7-fluoro-6-[2-fluoro-1-(fluoromethyl)ethoxy]-3-{[6-(4-methoxyphenyl)pyridinin-3-yl]methyl}-2,4-dioxo-3,4-dihydroquinazolin-1(2H)-yl}piperidine-1-carbaldehyde No. 319: 4-{7-fluoro-6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde No. 320: 4-{3-[3-ethoxy-4-(thiophen-2-ylmethoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde No. 321: 4-{7-fluoro-6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde No. 322: 4-{7-fluoro-6-[2-fluoro-1-(fluoromethyl)ethoxy]-2,4-dioxo-3-(4-(pyrimidin-5-yl)benzyl)-3,4-dihydroquinazolin-1(2H)-yl}piperidine-1-carbaldehyde No. 323: 4-{7-fluoro-6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde No. 324: 4-{7-fluoro-6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde No. 325: 4-[3-{4-[2-(2,3-dihydro-1H-indol-1-yl)-2-oxoethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 326: 4-{7-fluoro-6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde No. 327: 4-[3-{4-[(3-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 328: 4-[3-{[6-(3,5-dichlorophenyl)pyridin-3-yl]methyl}-6-[2-fluoro-1-(fluoromethyl)ethoxy]-2,4-dioxo-3,4-dihydroquinazolin-1(2H)-yl]piperidine-1-carbaldehyde No. 329: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile No. 330: 4-{7-fluoro-6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde No. 331: 4-{7-fluoro-6-[2-fluoro-1-(fluoromethyl)ethoxy]-3-{[6-(3-fluorophenyl)pyridin-3-yl]methyl}-2,4-dioxo-3,4-dihydroquinazolin-1(2H)-yl}piperidine-1-carbaldehyde No. 332: 3-[5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)pyridin-2-yl]benzonitrile No. 333: 4-[3-(3,4-diethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 334: 4-[3-{4-[(4-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 335: 4-{7-fluoro-6-[2-fluoro-1-(fluoromethyl)ethoxy]-3-[4-(morpholin-4-ylmethyl)benzyl]-2,4-dioxo-3,4-dihydroquinazolin-1(2H)-yl}piperidine-1-carbaldehyde No. 336: 4-{7-fluoro-6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde No. 337: 4-{7-fluoro-6-[2-fluoro-1-(fluoromethyl)ethoxy]-3-(4-(morpholin-4-yl)-benzyl)-2,4-dioxo-3,4-dihydroquinazolin-1(2H)-yl}piperidine-1-carbaldehyde No. 338: 4-{7-fluoro-6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde No. 339: 4-{3-[4-(1H-benzimidazol-1-yl)benzyl]-7-fluoro-6-[2-fluoro-1-(fluoromethyl)ethoxy]-2,4-dioxo-3,4-dihydroquinazolin-1(2H)-yl}piperidine-1-carbaldehyde No. 340: 5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxybenzonitrile No. 341: 3-(3,4-dimethoxybenzyl)-6-[2-fluoro-1-(fluoromethyl)ethoxy]-1-(1-formylpiperidin-4-yl)-2,4-dioxo-1,2,3,4-tetrahydroquinazoline-7-carbonitrile No. 342: 4-[3-(4-bromobenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 343: 4-[3-{4-[(3,4-dichlorobenzyl)oxy]-3-(2-methoxyethoxy)benzyl}-7-fluoro-6-[2-fluoro-1-(fluoromethyl)ethoxy]-2,4-dioxo-3,4-dihydroquinazolin-1(2H)-yl]piperidine-1-carbaldehyde No. 344: 4-{3-[4-(benzyloxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde No. 345: 4-[3-{4-[(3,4-dichlorobenzyl)oxy]-3-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 349: 4-[3-{4-[(3,4-dichlorobenzyl)oxy]-3-(2-fluoroethoxy)benzyl}-7-fluoro-6-[2-fluoro-1-(fluoromethyl)ethoxy]-2,4-dioxo-3,4-dihydroquinazolin-1(2H)-yl]piperidine-1-carbaldehyde No. 350: 4-[3-{4-[(2-chloro-4-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 351: 4-[3-{4-[(2,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 352: 4-[3-{4-[(2-chloro-6-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 353: 4-[3-{4-[(2,6-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 354: 4-[3-{4-[(2-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 355: 4-[7-fluoro-3-{4-[(2-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 357: 2-[(3,4-dichlorobenzyl)oxy]-5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)benzonitrile No. 358: 4-[3-{4-[(3,4-dichlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 360: 4-{7-fluoro-6-[2-fluoro-1-(fluoromethyl)ethoxy]-2,4-dioxo-3-[4-(2-phenylethyl)benzyl]-3,4-dihydroquinazolin-1(2H)-yl}piperidine-1-carbaldehyde No. 362: 4-[3-{4-[(4,5-dichloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 369: 4-[3-{4-[(4-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 371: 4-[3-{3-chloro-4-[(4-chlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 373: 4-[3-{3-chloro-4-[(2,4-dichlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 375: 4-[7-fluoro-3-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 376: 4-[3-{4-[(3,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 377: 4-[3-(4-{[4-chloro-3-(trifluoromethyl)benzyl]oxy}-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde No. 379: 4-[3-{4-[(3-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 380: 4-[3-{4-[(3,5-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 381: 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde No. 382: 4-[3-{4-[(3-chloro-5-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 383: 4-{7-fluoro-6-[2-fluoro-1-(fluoromethyl)ethoxy]-3-(3-methoxy-4-{[4-(trifluoromethyl)benzyl]oxy}benzyl)-2,4-dioxo-3,4-dihydroquinazolin-1(2H)-yl}piperidine-1-carbaldehyde No. 384: 4-[3-{4-[(2,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 385: 4-{[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl}benzonitrile No. 386: 3-{[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl}benzonitrile No. 387: 4-[3-{4-[(4-chloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 388: 4-[3-{4-[1-(3,4-dichlorophenyl)ethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 389: 4-{7-fluoro-6-[2-fluoro-1-(fluoromethyl)ethoxy]-3-{4-[(3-hydroxybenzyl)oxy]-3-methoxybenzyl}-2,4-dioxo-3,4-dihydroquinazolin-1(2H)-yl}piperidine-1-carbaldehyde No. 390: 4-[7-fluoro-3-{4-[(3-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde No. 391: 4-[3-{4-[(3,4-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde No. 392: 4-{3-[4-(5,6-dichloro-1H-benzimidazol-1-yl)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde No. 393: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)phenyl 3,4-dichlorobenzene-sulphonate No. 394: 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 3,4-dichlorobenzene-sulphonate No. 403: 3,4-dichloro-N-[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl]benzamide The compounds in accordance with the invention can be prepared by the methods illustrated in the following Schemes 1 to 4.

In that which follows, the term "leaving group" is understood to mean a group which can be easily substituted, with departure of an electron pair, by cleavage of a heterolytic bond. This group can thus be easily replaced by another group, for example during a substitution reaction. Such leaving groups are, for example, halogens or an activated hydroxyl group, such as a mesylate, tosylate, triflate, and the like. Examples of leaving groups and references for their preparation are given in "Advanced Organic Chemistry", J. March, 3rd Edition, Wiley Interscience, pp. 310-316.

The term "protective group PG" is understood to mean a group which makes it possible to prevent the reactivity of a function group or position during a chemical reaction which may affect it and which restores the molecule after cleavage according to methods known to a person skilled in the art.

The term "temporary protective group for amines or alcohols" is understood to mean the protective groups such as those described in Protective Groups in Organic Synthesis, Greene T. W. and Wuts P. G. M., published by Wiley Intersciences, 1999, and in Protecting Groups, Kocienski P. J., 1994, Georg Thieme Verlag.

Mention may be made, for example, of temporary protective groups for amines: benzyls or carbamates (such as tert-butoxycarbonyl, cleavable in an acid medium, or benzyloxycarbonyl, cleavable by hydrogenolysis), temporary protective groups for carboxylic acids: hydrogenolysable alkyl esters (such as methyl or ethyl or tert-butyl esters which can be hydrolysed in a basic or acid medium) and benzyl esters, temporary protective groups for alcohols or phenols, such as tetrahydropyranyl, methyloxymethyl or methylethoxymethyl, tert-butyl and benzyl ethers, or temporary protective groups for carbonyl derivatives, such as linear or cyclic acetals, such as, for example, 1,3-dioxan-2-yl or 1,3-dioxolan-2-yl; and reference may be made to the well known general methods described in Protective Groups, cited above.

A person skilled in the art will be in the position to choose the appropriate protective groups according to the circumstances. The compounds of formula (I) can comprise precursor groups for other functional groups which are generated subsequently in one or more other stages.

In the general synthetic schemes which follow, the starting compounds and the reactants, when their method of preparation is not described, are commercially available or are described in the literature or else can be prepared according to methods which are described therein or which are known to a person skilled in the art.

The pure enantiomers of the compounds in accordance with the invention can be obtained from enantiomerically pure precursors or else by chiral phase chromatography or else, when the compounds comprise acid or amine functional groups, by selective crystallizations of diastereoisomeric salts obtained by reaction of the compounds (I) with chiral amines or chiral acids respectively.

The compounds of general formula (I) can be obtained according to the following Schemes 1 to 4. Out of concern for clarity, the group $R_4$ has been chosen as being a hydrogen, p and p' represent 1 and 2 respectively and the $R_2$ and $R_3$ groups have been set as indicated in the schemes. However, it is to be understood that $R_4$ can be as defined in the general formula (I), and $R_2$ and $R_3$ can have the positions indicated in the general formula (I) and that p and p' can be as defined in the general formula (I).

The synthetic routes described below serve solely as illustration and are under no circumstances limiting. A person skilled in the art can apply without difficulty the teaching below to the compounds of formula (I) for which R, $R_1$, $R_2$, $R_3$, $R_4$, Ra, Rb, Rc, m, n, p, p' and q are as defined in the general formula (I).

According to Scheme 1, the compound of formula (IV) is obtained by a reductive amination reaction by reacting a compound of formula (II), in which R' represents a $(C_1-C_6)$ alkyl group and $R_2$ is as defined for the compound of formula (I) with a compound of formula (III) in an acid medium and in the presence of a reducing agent, such as sodium triacetoxyborohydride. The PG group of the compound of formula (III) is a protective group for the amine functional group which may advantageously be tert-butoxycarbonyl (boc). The compound of formula (IV) thus formed is subsequently acylated, according to methods well known to a person skilled in the art, with an alkyl or aryl chloroformate to give the compound of formula (V) in which R" represents a $(C_1-C_6)$alkyl group or an aryl group which is substituted. A hydrolysis reaction in a basic medium makes it possible to obtain the compounds of formula (VI) which, by a coupling reaction with a compound of formula (VII), in which $R_3$ is as defined for the compound of formula (I), results in the compounds of formula (VIII). An intramolecular cyclization reaction in the basic medium makes it possible to obtain the quinazolinedione derivatives of formula (IX). The protective group PG for the amine functional group is subsequently cleaved, for example in acid medium when PG is a boc, to give the compounds of formula (Ia) which give, by an acylation reaction, the compounds of formula (Ib).

The compounds of formula (Ia) are compounds of formula (I) and can act as intermediate for other compounds of formula (I), such as the compounds of formula (Ib).

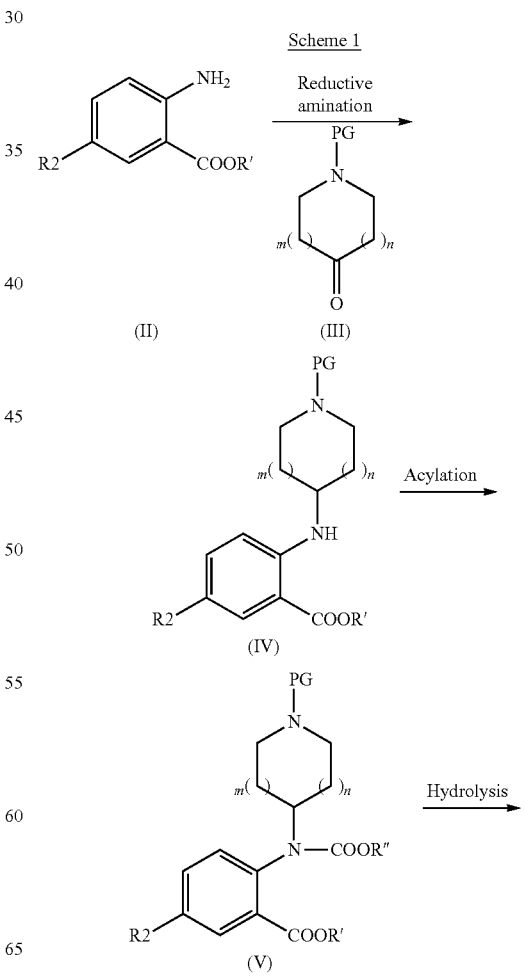

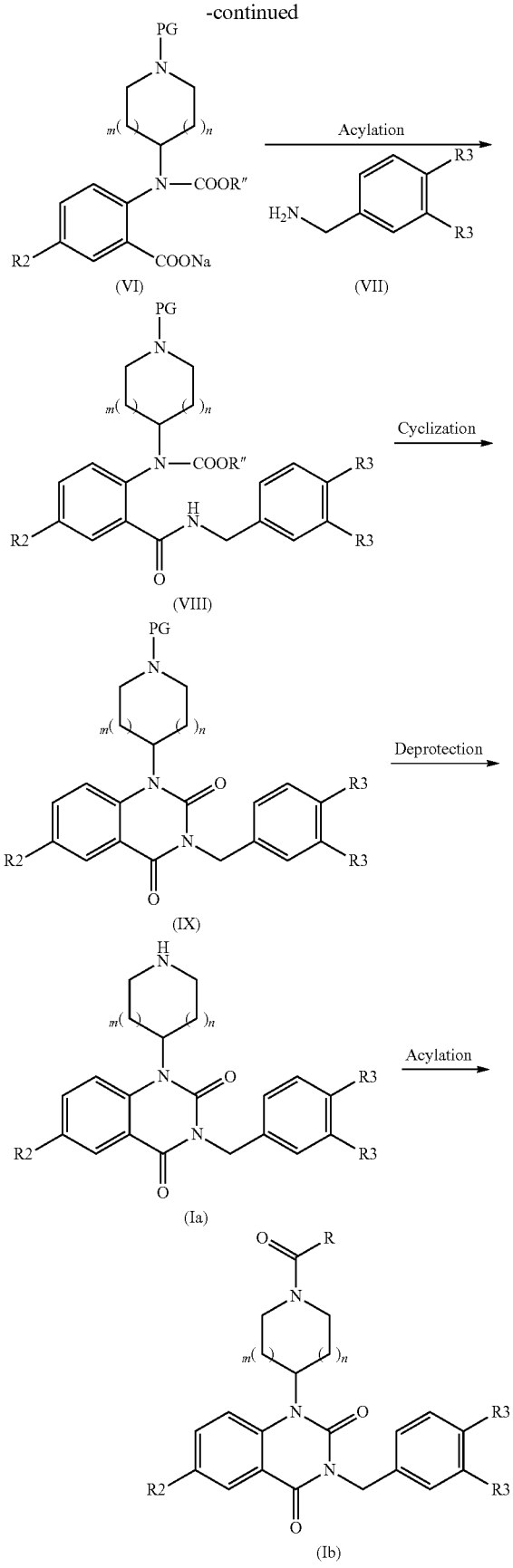

The compounds of formula (I) for which $R_2$ represents —ORa, Ra being as defined for the compound of formula (I), correspond to the formula (Id). They can be obtained from the compounds of formula (X) according to the following Scheme 2. The compounds of formula (X), obtained by a hydrogenolysis reaction on the compounds of formula (X), are subjected, for example, to an alkylation reaction with an alkylating agent of type Ra—X, in which Ra is as defined for the compound of formula (I) and X represents a leaving group (such as a halogen atom, for example), in the presence of a base, such as caesium carbonate ($Cs_2CO_3$), or also to a Mitsunobu reaction (Synthesis, 1981, 1) with an alcohol of type Ra—OH, Ra being as defined for the compound of formula (I), to give compounds of formula (Id).

The compounds of formula (X) and the compounds of formula (Ic) are compounds of formula (I) and can act as intermediate for other compounds of formula (I), such as the compounds of formula (Id).

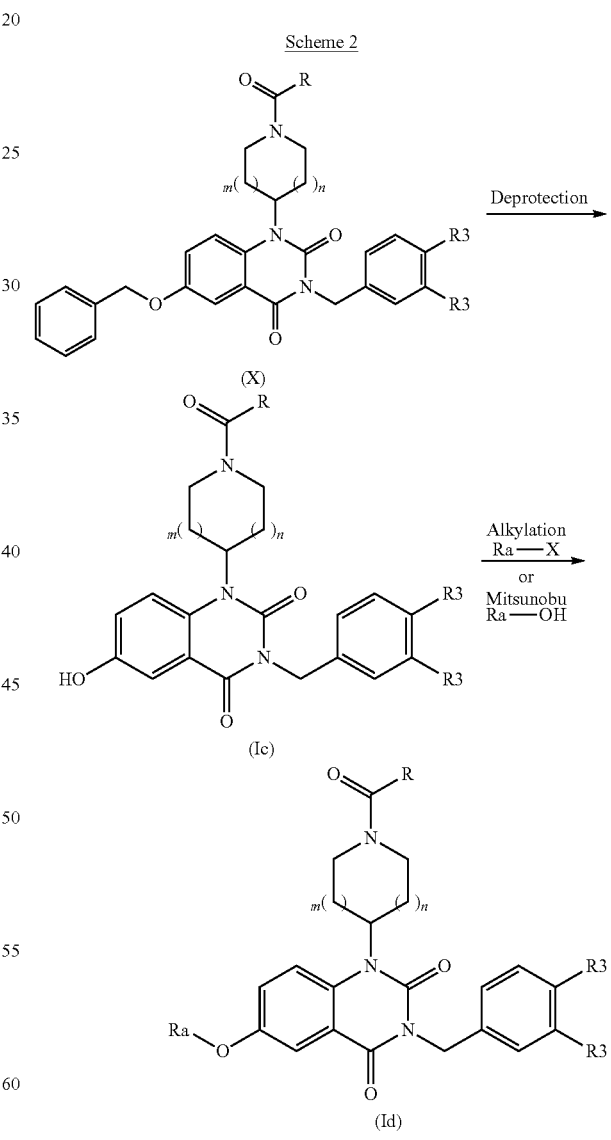

Alternatively, the compounds of formula (Id) can be obtained by following the procedure described in Scheme 3.

The compounds of formula (XII) are obtained by a nucleophilic aromatic substitution reaction involving a compound of formula (XI), in which R' is as defined above, and an alcohol of type Ra—OH, in which Ra is as defined for the compound of formula (I), in the presence of a base. The reduction of the nitro group of the compounds of formula (XII) results in the corresponding anilino derivatives (XIII). A reductive amination reaction with a compound of formula (III), in which PG is a protective group for amine functional groups, such as, for example, boc, results in the compounds of formula (XIV). The compounds of formula (XV) are obtained by reaction of a compound of formula (XIV) with potassium isocyanate (KNCO) in an acid medium. An intramolecular cyclization reaction in a basic medium makes it possible to obtain the compounds of formula (XVI). The protective group PG is cleaved by methods well known to a person skilled in the art to give the compounds of formula (XVII). An acylation reaction results in the compounds of formula (XVIII). Finally, the compounds of formula (Id) are obtained either by an alkylation reaction with a derivative of type (XIX), in which X represents a leaving group, such as a halogen atom, in the presence of a base, such as, for example, caesium carbonate, or also by a Mitsunobu reaction with a benzyl alcohol of type (XX). In the compounds (XIX) and (XX), $R_3$ is as defined above.

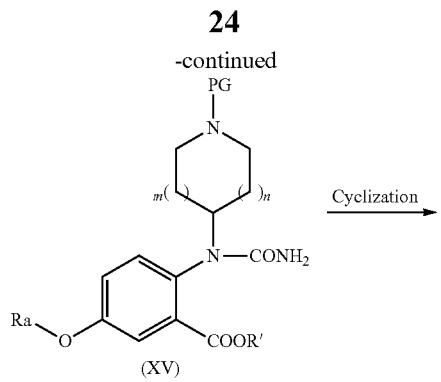

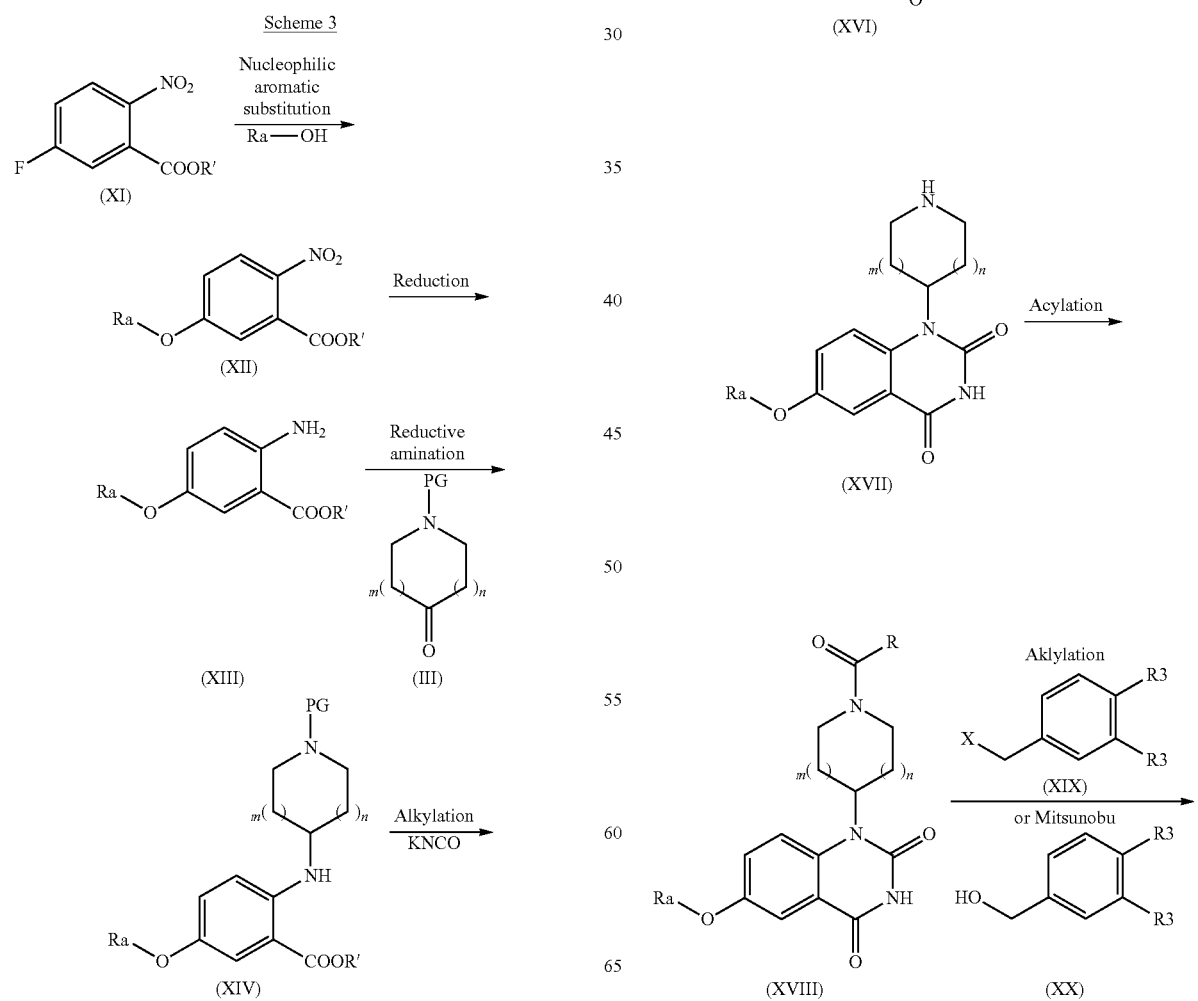

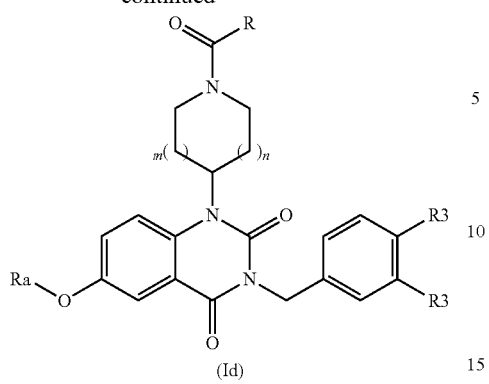

(Id)

The compounds of formula (Ie) and (If), in which $R_2$ more particularly represents a group of type —$CH_2$—NHC(O)Rb, Rb being defined as in the compound of formula (I), can be prepared according to the following Scheme 4.

It is understood that, in Scheme 3, the $R_2$ group illustrated is of —O—Ra type and is in the 6 position of the quinazolinedione structure (see, for example, compound (XVIII)) but that it is also possible to have a second $R_2$ group, as defined in the general formula (I), in the 7 position of the same quinazolinedione group.

The reduction of the nitro group of the compounds of type (XXI), in which R' and PG' are as defined above, the PG' group advantageously being boc, results in the corresponding anilino derivatives (XXII) which, by a reductive amination reaction in which they react in an acid medium and advantageously in the presence of a reducing agent, such as sodium triacetoxyborohydride, with a compound of formula (III), in which PG represents a benzyloxycarbonyl protective group for amines, give compounds of formula (XXIII). An acylation reaction with an alkyl or aryl chloroformate, in which R" represents a ($C_1$-$C_6$)alkyl group or an aryl group which is substituted, results in the compounds of formula (XXIV). The quinazolinedione analogues of formula (XXV) can be obtained by a hydrolysis reaction in a basic medium and then by a coupling reaction with a compound of formula (VII), in which $R_3$ is as defined for the compound of formula (I), followed by an intramolecular cyclization reaction in a basic medium. The PG' group (preferably a boc) is subsequently cleaved in an acid medium to result in the compounds of formula (XXVI) which, by acylation, give compounds of formula (XXVII), in which Rb is as defined for the compound of formula (I). The PG protective group of (XXVII) is cleaved by a hydrogenolysis reaction to give the compounds of formula (Ie). Finally, the compounds of formula (If) are obtained by an acylation reaction on the compounds of formula (Ie).

Scheme 4

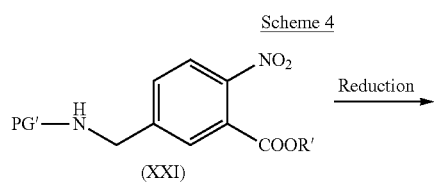

(XXI)

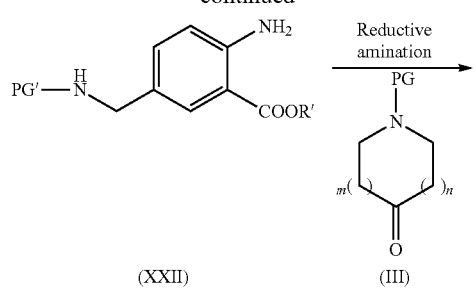

(XXII) (III)

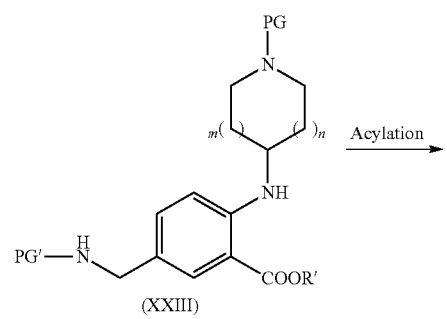

(XXIII)

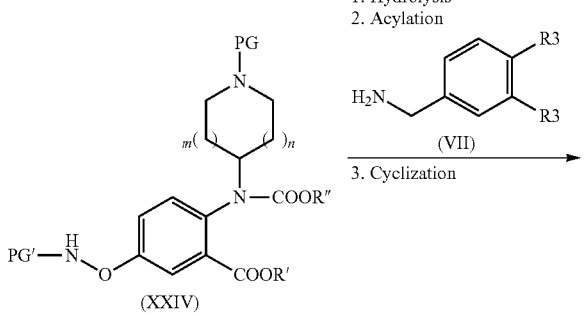

(XXIV)

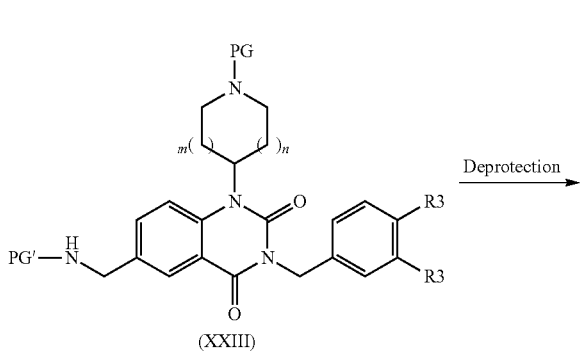

(XXIII)

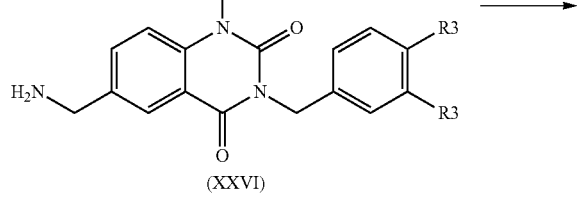

(XXVI)

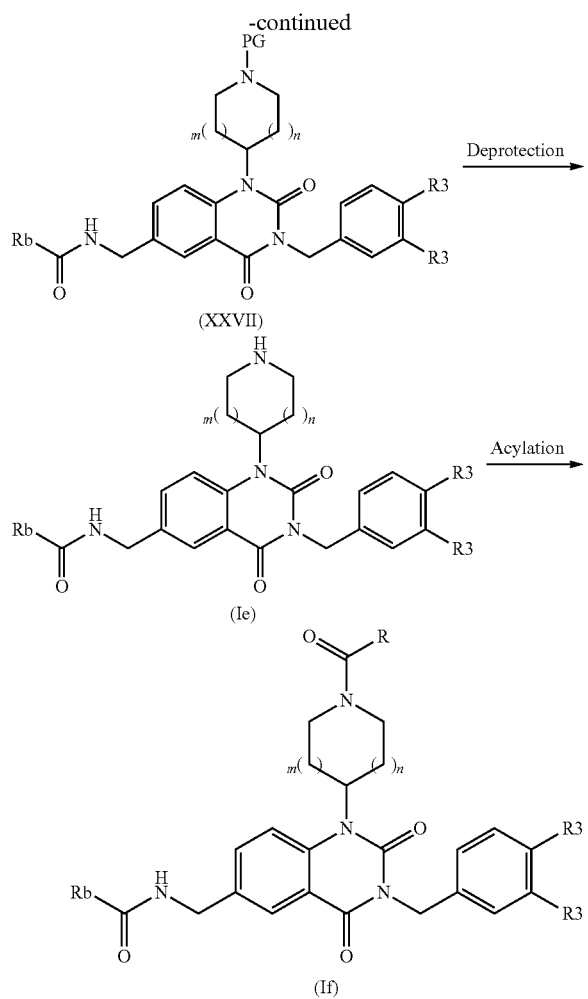

It is obvious that a person skilled in the art will be in a position to choose, in the light of his knowledge and the literature, other appropriate protective groups which make possible the introduction of all the groups described in the general formula (I).

When the compound of formula (I) comprises a bridged ring, it can be obtained without distinction by one of the synthetic routes described above.

The following procedures and examples describe the preparation of some compounds in accordance with the invention. These procedures and examples are not limiting and serve only to illustrate the present invention.

In the procedures and examples below:
the mass spectra are produced on a quadrupole spectrometer of Platform LCZ type (Waters) or of ZQ 4000 type (Waters) in positive electrospray ionization mode;
the NMR (nuclear magnetic resonance) spectra are produced on a Fourier transform spectrometer (Bruker) at a temperature of 300° C. (exchangeable protons not recorded);
s=singlet,
d=doublet,
m=multiplet,
br=broad signal
t=triplet,
q=quartet
DMSO-$d_6$=deuterated dimethyl sulphoxide,
CDCl$_3$=deuterated chloroform.

The mixtures of solvents are quantified in volumetric ratios.

The NMR spectra and mass spectra confirm the structures of the compounds obtained according to the examples below. In the examples which follow, the following abbreviations are used:
ACN: acetonitrile
AcOEt: ethyl acetate
AcOH: acetic acid
DBU: 1,8-diazabicyclo[5.4.0]undec-7-ene
DCM: dichloromethane
DCE: 1,2-dichloroethane
DIAD: diisopropyl azodicarboxylate
DIEA: diisopropylamine
DMF: N,N-dimethylformamide
EtOH: ethanol
HBTU: O-(benzotriazol-1-yl)-N,N,N',N'-tetramethyluronium hexafluorophosphate
IBCF: isobutyl chloroformate
MeOH: methanol
NaBH(OAc)$_3$: sodium triacetoxyborohydride
AT: ambient temperature
min: minute
THF: tetrahydrofuran
NEt$_3$: triethylamine
TFA: trifluoroacetic acid

EXAMPLES

The following examples describe the preparation of some compounds in accordance with the invention. These examples are not limiting and serve only to illustrate the present invention. The numbers of the compounds in the examples refer to those given in the table below, in which the chemical structures and the physical properties of a few compounds in accordance with the invention are illustrated.

Example 1

Compound No.°6

Preparation of {[3-(3,4-dimethoxybenzyl)-1-(1-formylpiperidin-4-yl)-2,4-dioxo-1,2,3,4-tetrahydroquinazolin-6-yl]oxy}acetonitrile

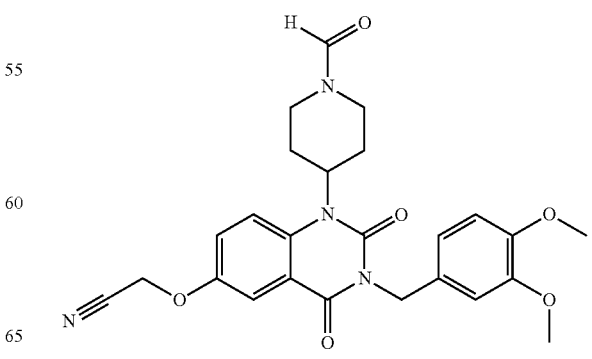

Stage 1.1

1,1-Dimethylethyl 4-{[4-(benzyloxy)-2-(methoxycarbonyl)phenyl]amino}piperidine-1-carboxylate

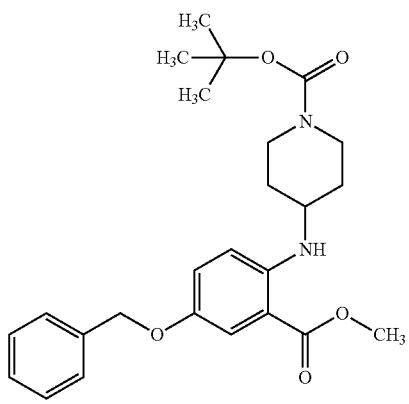 [SMILES: COC(=O)c1cc(OCc2ccccc2)ccc1NC1CCN(C(=O)OC(C)(C)C)CC1]

A mixture of 2 g of methyl 2-amino-5-(benzyloxy)benzoate, 3.1 g of 1,1-dimethylethyl 4-oxopiperidine-1-carboxylate and 3.29 g of NaBH(OAc)₃ in 10 ml of AcOH is irradiated under a microwave field (Biotage Initiator Sixty) at 110° C. for 20 min. The same reaction is repeated with two other lots of 2 g of methyl 2-amino-5-(benzyloxy)benzoate. The three reaction media are combined. The combined product is taken up in AcOEt. The organic phase is washed with water, with a saturated NH₄Cl solution and with a saturated NaHCO₃ solution, dried over Na₂SO₄ and filtered, and the solvent is evaporated under reduced pressure. The residue is chromatographed on silica gel, elution being carried out with an AcOEt/heptane mixture, (5/95, v/v) as far as (30170, v/v), to give 10.2 g of the expected product.

Stage 1.2

1,1-Dimethylethyl 4-{[4-(benzyloxy)-2-(methoxycarbonyl)phenyl][(2-methylpropoxy)carbonyl]amino}piperidine-1-carboxylate

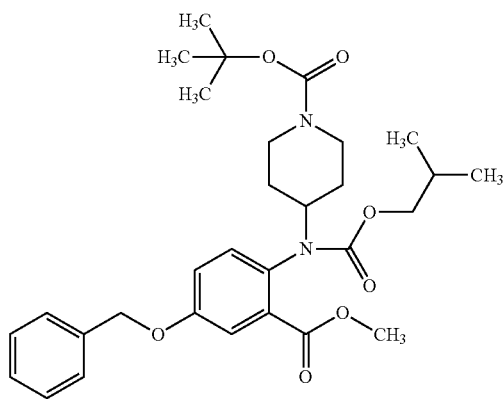 [SMILES: COC(=O)c1cc(OCc2ccccc2)ccc1N(C(=O)OCC(C)C)C1CCN(C(=O)OC(C)(C)C)CC1]

A mixture of 2 g of 1,1-dimethylethyl 4-{[4-(benzyloxy)-2-(methoxycarbonyl)phenyl]amino}piperidine-1-carboxylate obtained in stage 1.1, 0.87 ml of DIEA, 1.78 ml of IBCF and 1 g of NaOH in 10 ml of DCE is irradiated under a microwave field at 80° C. for 30 min. The same reaction is repeated with 4 other lots of 2 g of 1,1-dimethylethyl 4-{[4-(benzyloxy)-2-(methoxycarbonyl)phenyl]amino}piperidine-1-carboxylate. The 5 reaction media are combined. The combined product is taken up in AcOEt and filtered, and the filtrate is evaporated under reduced pressure. The residue is chromatographed on silica gel, elution being carried out with an AcOEt/heptane mixture, (10/90, v/v) as far as (50/50, v/v), to give 9.3 g of the expected product.

Stage 1.3

Sodium Salt of 5-(benzyloxy)-2-({1-[(1,1-dimethylethoxy)carbonyl]-piperidin-4-yl}[(2-methylpropoxy)carbonyl]amino)benzoic acid

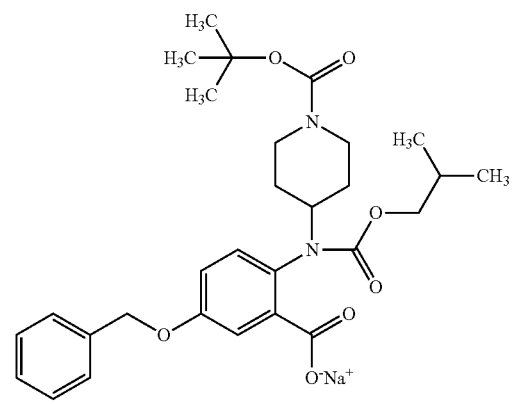

A mixture of 9.3 g of 1,1-dimethylethyl 4-{[4-(benzyloxy)-2-(methoxycarbonyl)phenyl][(2-methylpropoxy)carbonyl]amino}piperidine-1-carboxylate obtained in stage 1.2 and 34.4 ml of 2N NaOH in 57 ml of MeOH is heated at 100° C. for 3 h 00. The solution is evaporated under reduced pressure and DCM is added. Drying is carried out over Na₂SO₄, filtration is carried out and the solvent is evaporated under reduced pressure to give 8.7 g of the expected product.

Stage 1.4

1,1-Dimethylethyl 4-[{4-(benzyloxy)-2-[(3,4-dimethoxybenzyl)carbamoyl]phenyl}(isobutoxycarbonyl)amino]piperidine-1-carboxylate

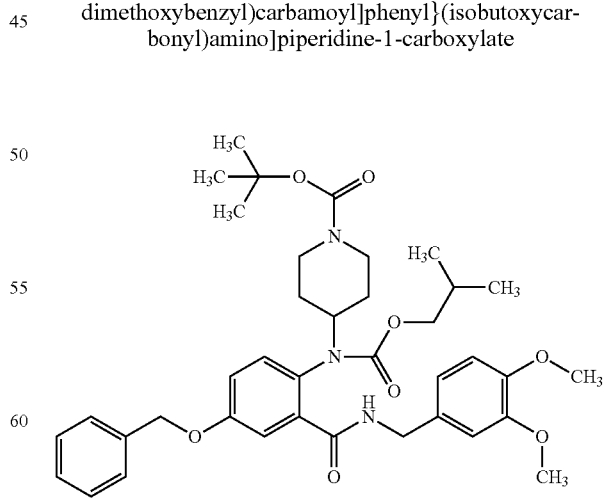

A mixture of 6 g of sodium salt of 5-(benzyloxy)-2-({1-[(1,1-dimethylethoxy)carbonyl]piperidin-4-yl}[(2-methylpropoxy)carbonyl]amino)benzoic acid obtained in stage 1.3 and 4.42 g of DIEA in 250 ml of DMF is stirred at AT for 15 min. 6.48 g of HBTU are added and the mixture is left stirring for 30 min. 2.48 g of veratrylamine are added and the reaction mixture is stirred for 48 h 00. It is evaporated under reduced pressure, the residue is taken up in AcOEt, washed with a saturated NH₄Cl solution and with a saturated NaHCO₃ solution, dried over Na₂SO₄ and filtered, and the solvent is evaporated under reduced pressure. The residue is chromatographed on silica gel, elution being carried out with an AcOEt/heptane mixture, (20/80, v/v) as far as (60/40, v/v), to give 7.5 g of expected product.

Stage 1.5

1,1-Dimethylethyl 4-[6-(benzyloxy)-3-(3,4-dimethoxybenzyl)-2,4-dioxo-3,4-dihydroquinazolin-1(2H)-yl]piperidine-1-carboxylate

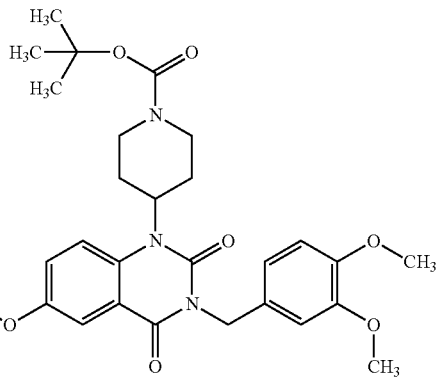

A mixture of 2.5 g of 1,1-dimethylethyl 4-[{4-(benzyloxy)-2-[(3,4-dimethoxybenzyl)carbamoyl]phenyl}(isobutoxycarbonyl)amino]piperidine-1-carboxylate obtained in stage 1.4 and 7.4 g of NaOH in 18.5 ml of DCE is irradiated under a microwave field at 110° C. for 30 min. The same reaction is repeated with 2 other lots of 2.5 g of 1,1-dimethylethyl 4-[{4-(benzyloxy)-2-[(3,4-dimethoxybenzyl)carbamoyl]phenyl}-(isobutoxycarbonyl)amino]piperidine-1-carboxylate. The 3 reaction media are combined. The combined product is taken up in DCM, washed with water, dried over Na₂SO₄ and filtered, and the solvent is evaporated under reduced pressure to give 6.6 g of expected product.

Stage 1.6

6-(Benzyloxy)-3-(3,4-dimethoxybenzyl)-1-(piperidin-4-yl)quinazoline-2,4(1H,3H)-dione

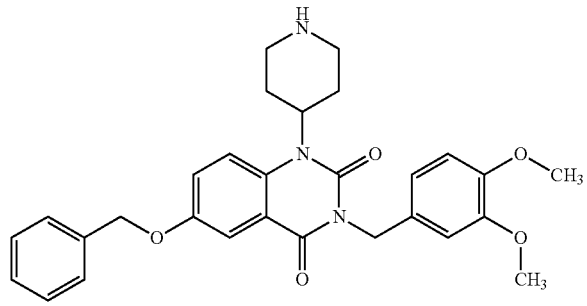 [SMILES: COc1ccc(Cn2c(=O)c3cc(OCc4ccccc4)ccc3n(C3CCNCC3)c2=O)cc1OC]

A mixture of 3.5 g of 1,1-dimethylethyl 4-[6-(benzyloxy)-3-(3,4-dimethoxybenzyl)-2,4-dioxo-3,4-dihydroquinazolin-1(2H)-yl]piperidine-1-carboxylate obtained in stage 1.5 and 25 ml of TFA in 50 ml of DCM is stirred at AT for 2 h 00. The mixture is neutralized with K₂CO₃. It is filtered and the filtrate is evaporated under reduced pressure. The residue is taken up in DCM and washed with a saturated NaHCO₃ solution and then with an 8% NaOH solution. The solution is dried over Na₂SO₄ and filtered, and the solvent is evaporated under reduced pressure to give 2.67 g of the expected product.

Stage 1.7

4-[6-(Benzyloxy)-3-(3,4-dimethoxybenzyl)-2,4-dioxo-3,4-dihydroquinazolin-1(2H)-yl]piperidine-1-carbaldehyde

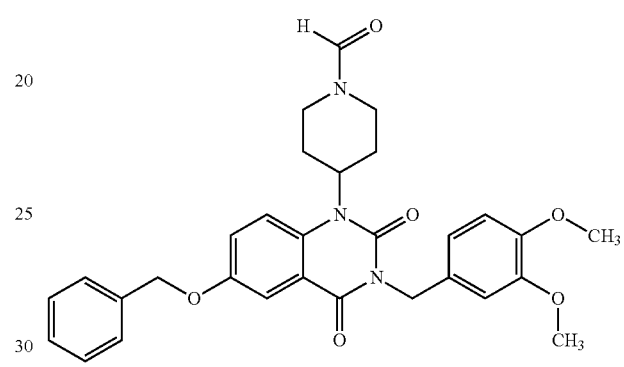

A mixture of 0.6 g of 6-(benzyloxy)-3-(3,4-dimethoxybenzyl)-1-(piperidin-4-yl)quinazoline-2,4(1H,3H)-dione obtained in stage 1.7 and 0.113 g of ammonium formate in 5 ml of ACN is irradiated under a microwave field at 140° C. for 1 h 00. The mixture is filtered and the filtrate is evaporated under reduced pressure to give 0.62 g of the expected product.

Stage 1.8

Compound No. 5

4-[3-(3,4-Dimethoxybenzyl)-6-hydroxy-2,4-dioxo-3,4-dihydroquinazolin-1(2H)-yl]piperidine-1-carbaldehyde

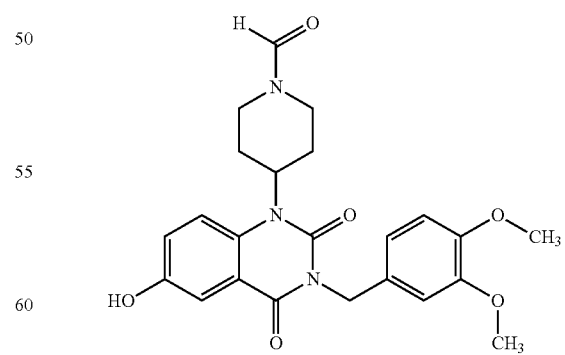

A mixture of 0.618 g of 4-[6-(benzyloxy)-3-(3,4-dimethoxybenzyl)-2,4-dioxo-3,4-dihydroquinazolin-1(2H)-yl]piperidine-1-carbaldehyde obtained in stage 1.7, 0.44 g of ammonium formate and 0.124 g of Pd/C (10%) in 10 ml of EtOH purged beforehand with nitrogen is irradiated under a microwave field at 80° C. for 2 h 00. The mixture is filtered and the filtrate is evaporated under reduced pressure to give 0.513 g of the expected product.

Stage 1.9

Compound No. 6

{[3-(3,4-Dimethoxybenzyl)-1-(1-formylpiperidin-4-yl)-2,4-dioxo-1,2,3,4-tetrahydroquinazolin-6-yl]oxy}acetonitrile

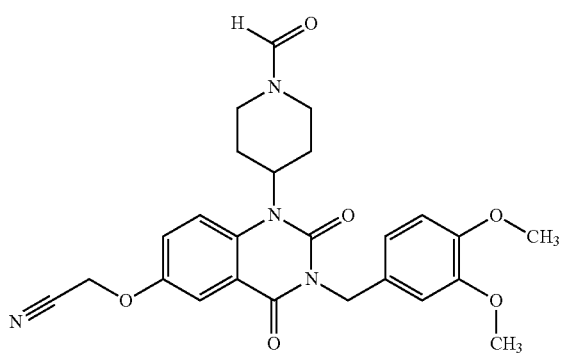 [SMILES: COc1ccc(Cn2c(=O)c3cc(OCC#N)ccc3n(C3CCN(C=O)CC3)c2=O)cc1OC]

0.17 g of 4-[3-(3,4-dimethoxybenzyl)-6-hydroxy-2,4-dioxo-3,4-dihydroquinazolin-1(2H)-yl]piperidine-1-carbaldehyde obtained in stage 1.8 and 0.25 g of Cs$_2$CO$_3$ in 3 ml of DMF are stirred for 15 min at AT. 0.056 g of bromoacetonitrile is added and the reaction mixture is subsequently irradiated under a microwave field at 100° C. for 15 min. It is filtered and evaporated under reduced pressure. The residue is chromatographed on silica gel, elution being carried out with an MeOH/DCM mixture, (1/99, v/v) as far as (4/96, v/v), to give 0.112 g of the expected product.

Example 2

Compound No. 3

Preparation of {[1-(1-acetylpiperidin-4-yl)-3-(3,4-dimethoxybenzyl)-2,4-dioxo-1,2,3,4-tetrahydroquinazolin-6-yl]oxy}acetonitrile

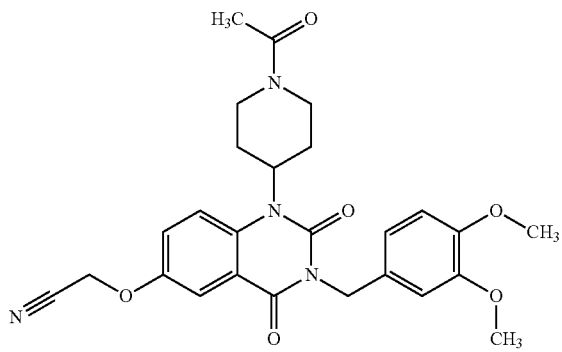 [SMILES: COc1ccc(Cn2c(=O)c3cc(OCC#N)ccc3n(C3CCN(C(C)=O)CC3)c2=O)cc1OC]

Stage 2.1

1-(1-Acetylpiperidin-4-yl)-6-(benzyloxy)-3-(3,4-dimethoxybenzyl)quinazoline-2,4(1H,3H)-dione

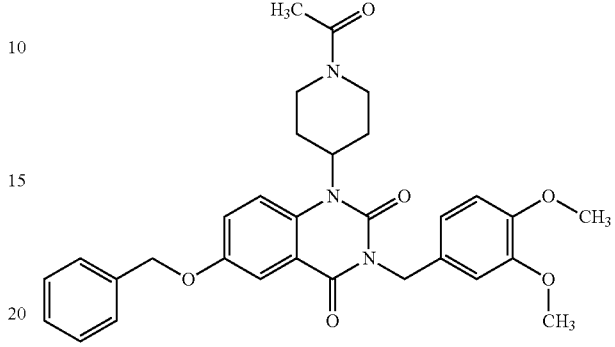

0.14 g of acetyl chloride is added to a mixture of 0.6 g of 6-(benzyloxy)-3-(3,4-dimethoxybenzyl)-1-(piperidin-4-yl)quinazoline-2,4(1H,3H)-dione obtained according to stage 1.6 and 0.24 g of NEt$_3$ in 10 ml of DCM cooled to 0° C. The mixture is stirred at AT overnight. It is washed twice with a saturated NH$_4$Cl solution and filtered, and then the filtrate is evaporated under reduced pressure to give 0.64 g of the expected product.

Stage 2.2

Compound No. 2

1-(1-Acetylpiperidin-4-yl)-3-(3,4-dimethoxybenzyl)-6-hydroxyquinazoline-2,4(1H,3H)-dione

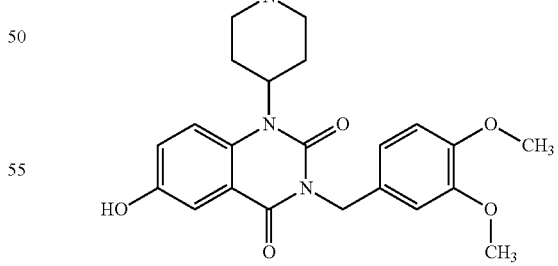

A mixture of 0.64 g of 1-(1-acetylpiperidin-4-yl)-6-(benzyloxy)-3-(3,4-dimethoxybenzyl)quinazoline-2,4(1H,3H)-dione obtained in stage 2.1, 0.44 g of ammonium formate and 0.125 g of Pd/C (10%) in 10 ml of EtOH purged beforehand with nitrogen is irradiated under a microwave field at 80° C. for 2 h 00. The mixture is filtered and the filtrate is evaporated under reduced pressure to give 0.48 g of the expected product.

Stage 2.3

Compound No. 3

{[1-(1-Acetylpiperidin-4-yl)-3-(3,4-dimethoxybenzyl)-2,4-dioxo-1,2,3,4-tetrahydroquinazolin-6-yl]oxy}acetonitrile

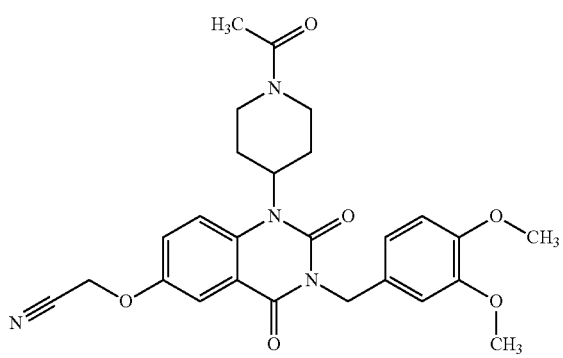 [SMILES: COc1ccc(Cn2c(=O)c3cc(OCC#N)ccc3n(C3CCN(C(C)=O)CC3)c2=O)cc1OC]

0.12 g of 1-(1-acetylpiperidin-4-yl)-3-(3,4-dimethoxybenzyl)-6-hydroxyquinazoline-2,4(1H,3H)-dione obtained in stage 2.2 and 0.172 g of $Cs_2CO_3$ in 3 ml of DMF are stirred for 15 min at AT. 0.038 g of bromoacetonitrile is added and the reaction mixture is subsequently irradiated under a microwave field at 100° C. for 15 min. It is filtered and the filtrate is evaporated under reduced pressure. The residue is chromatographed on silica gel, elution being carried out with an MeOH/DCM mixture, (1/99, v/v) as far as (4/96, v/v), to give 0.094 g of the expected product.

Example 3

Compound No. 34

Synthesis of 4-[3-(4-chlorobenzyl)-6-(2,2-difluoroethoxy)-2,4-dioxo-3,4-dihydroquinazolin-1(2H)-yl]piperidine-1-carbaldehyde

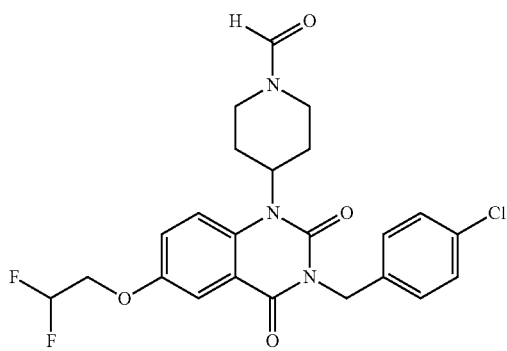 [SMILES: O=CN1CCC(n2c(=O)n(Cc3ccc(Cl)cc3)c(=O)c3cc(OCC(F)F)ccc32)CC1]

Stage 3.1

Methyl 5-(2,2-difluoroethoxy)-2-nitrobenzoate

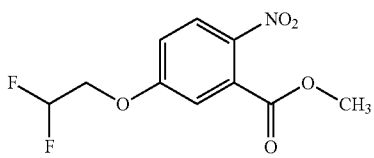

8.53 g of 2,2-difluoroethanol are added to a solution of 17.31 g of methyl 5-fluoro-2-nitrobenzoate, 9.64 g of $NEt_3$ and 32.71 g of 2,8,9-triisobutyl-2,5,8,9-tetraaza-1-phosphabicyclo[3.3.3]undecane in 250 ml of anhydrous THF. The mixture is stirred at AT for 30 min. The solvent is evaporated under reduced pressure. Water is added and extraction is carried out with AcOEt. The extract is washed with a 1N aqueous HCl solution, with water and then with a saturated NaCl solution. It is dried over $MgSO_4$ and filtered, and the solvent is evaporated under reduced pressure to give 21 g of the expected product.

Stage 3.2

Methyl 2-amino-5-(2,2-difluoroethoxy)benzoate

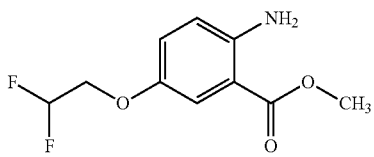 [SMILES: COC(=O)c1cc(OCC(F)F)ccc1[N+](=O)[O-]]

21 g of methyl 5-(2,2-difluoroethoxy)-2-nitrobenzoate obtained in stage 3.1 and 1 g of Pd/C (10%) in a mixture of 300 ml of AcOEt, 50 ml of EtOH and 5 ml of AcOH are stirred at AT under a hydrogen atmosphere for 24 h 00.

The mixture is filtered and evaporated under reduced pressure to give 18.6 g of the expected product.

Stage 3.3

1,1-Dimethylethyl 4-{[4-(2,2-difluoroethoxy)-2-(methoxycarbonyl)phenyl]amino}piperidine-1-carboxylate

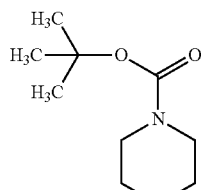
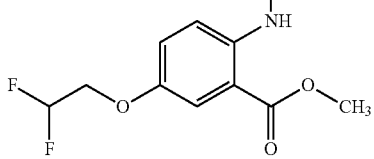

A mixture of 4 g of methyl 2-amino-5-(2,2-difluoroethoxy)benzoate and 6.88 g of 1,1-dimethylethyl 4-oxopiperidine-1-carboxylate obtained in stage 3.2 in 15 ml of AcOH is heated at 90° C. for 10 min. it is allowed to cool to AT and 7.3 g of NaBH(OAc)₃ are added. The mixture is left stirring at AT for 12 h 00. It is extracted with AcOEt and the extract is washed with a saturated K₂CO₃ solution and then with water. It is dried over MgSO₄, filtered and evaporated under reduced pressure to give 6.63 g of the expected product.

Stage 3.4

1,1-Dimethylethyl 4-{carbamoyl[4-(2,2-difluoroethoxy)-2-(methoxycarbonyl)-phenyl]amino}piperidine-1-carboxylate

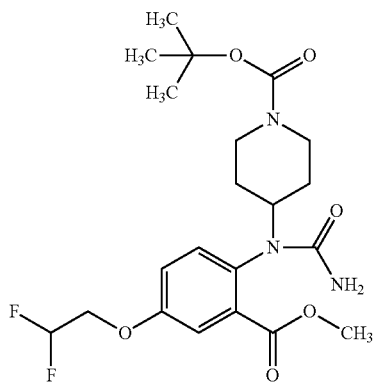 [SMILES: COC(=O)c1cc(OCC(F)F)ccc1N(C(N)=O)C1CCN(C(=O)OC(C)(C)C)CC1]

1.95 g of potassium isocyanate in solution of 4 ml of water are added to a solution of 6.63 g of 1,1-dimethylethyl 4-{[4-(2,2-difluoroethoxy)-2-(methoxycarbonyl)phenyl]amino}piperidine-1-carboxylate obtained in stage 3.3 in 40 ml of AcOH. The mixture is stirred at AT for 12 h 00. It is extracted with AcOEt and the extract is washed with a saturated K₂CO₃ solution and then with water. It is dried over MgSO₄, filtered and evaporated under reduced pressure to give 6.95 g of the expected product.

Stage 3.5

1,1-Dimethylethyl 4-[6-(2,2-difluoroethoxy)-2,4-dioxo-3,4-dihydroquinazolin-1(2H)-yl]piperidine-1-carboxylate

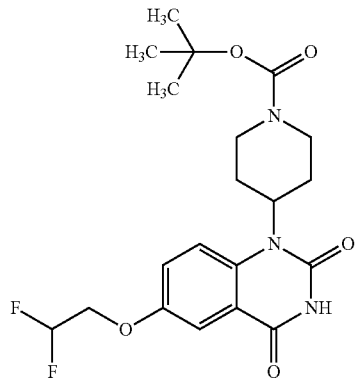 [SMILES: CC(C)(C)OC(=O)N1CCC(n2c(=O)[nH]c(=O)c3cc(OCC(F)F)ccc32)CC1]

2.5 g of 1,1-dimethylethyl 4-{carbamoyl[4-(2,2-difluoroethoxy)-2-(methoxycarbonyl)phenyl]amino}piperidine-1-carboxylate obtained in stage 3.4 in solution in a mixture of 10 ml of dioxane and 5 ml of a 1N aqueous NaOH solution are irradiated under a microwave field at 130° C. for 30 min. Extraction is carried out with AcOEt and the extract is neutralized with a 1N aqueous HCl solution, washed with water, dried over MgSO₄, filtered and evaporated under reduced pressure. The residue obtained is triturated in an AcOEt/pentane mixture to give the expected product. The same reaction is reproduced with 2 other lots of 2.5 g of 1,1-dimethylethyl 4-{carbamoyl[4-(2,2-difluoroethoxy)-2-(methoxycarbonyl)phenyl]amino}piperidine-1-carboxylate obtained in stage 3.4 to give, in total, 5.63 g of expected product.

Stage 3.6

6-(2,2-Difluoroethoxy)-1-(piperidin-4-yl)quinazoline-2,4(1H,3H)-dione

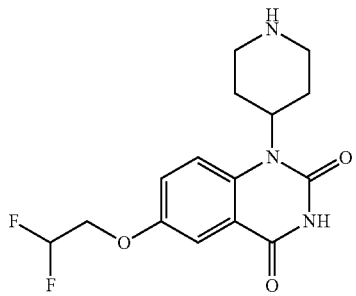 [SMILES: O=c1[nH]c(=O)n(C2CCNCC2)c2ccc(OCC(F)F)cc12]

A solution of 5.63 g of 1,1-dimethylethyl 4-[6-(2,2-difluoroethoxy)-2,4-dioxo-3,4-dihydroquinazolin-1(2H)-yl]piperidine-1-carboxylate obtained in stage 3.5 in 70 ml of formic acid is stirred at AT for 2 h 00. The solvent is evaporated under reduced pressure to give 6.13 g of the expected product in the form of the formic acid salt.

Stage 3.7

4-[6-(2,2-Difluoroethoxy)-2,4-dioxo-3,4-dihydroquinazolin-1(2H)-yl]piperidine-1-carbaldehyde

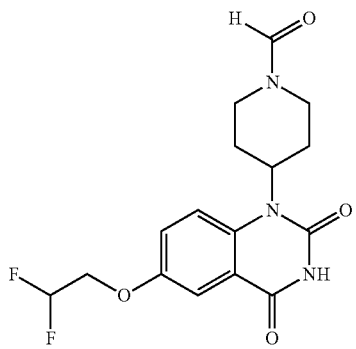 [SMILES: O=CN1CCC(n2c(=O)[nH]c(=O)c3cc(OCC(F)F)ccc32)CC1]

A mixture of 6.13 g of 6-(2,2-difluoroethoxy)-1-(piperidin-4-yl)quinazoline-2,4(1H,3H)-dione obtained in stage 3.6 and 3.12 g of ammonium formate in 28 ml of ACN and 28 ml of dioxane is irradiated under a microwave field at 140° C. for 1 h 00. The reaction mixture is run into water. The mixture is filtered and the precipitate is washed with water and then with ether to give 4.47 g of the expected product.

Stage 3.8

Compound No. 34

4-[3-(4-Chlorobenzyl)-6-(2,2-difluoroethoxy)-2,4-dioxo-3,4-dihydroquinazolin-1(2H)-yl]piperidine-1-carbaldehyde

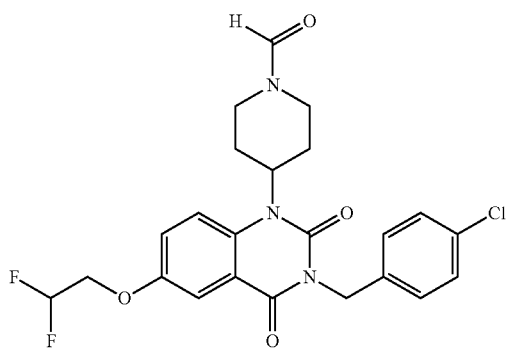 [SMILES: O=CN1CCC(n2c(=O)n(Cc3ccc(Cl)cc3)c(=O)c3cc(OCC(F)F)ccc32)CC1]

A mixture of 0.15 g of 4-[6-(2,2-difluoroethoxy)-2,4-dioxo-3,4-dihydroquinazolin-1(2H)-yl]piperidine-1-carbaldehyde obtained in stage 3.7, 0.096 g of 1-(bromomethyl)-4-chlorobenzene and 0.3 g of $Cs_2CO_3$ in 3 ml of DMF is stirred at AT for 1 h 00. AcOEt is added and washing is carried out with water and then with a saturated NaCl solution. The organic phase is dried over $MgSO_4$, filtered and evaporated under reduced pressure. The residue is chromatographed on silica gel, elution being carried out with AcOEt, to give 0.116 g of the expected product.

Example 4

Compound No. 49

Synthesis of 4-{3-[3-(cyclopentyloxy)-4-methoxybenzyl]-6-(2,2-difluoroethoxy)-2,4-dioxo-3,4-dihydroquinazolin-1(2H)-yl}piperidine-1-carbaldehyde

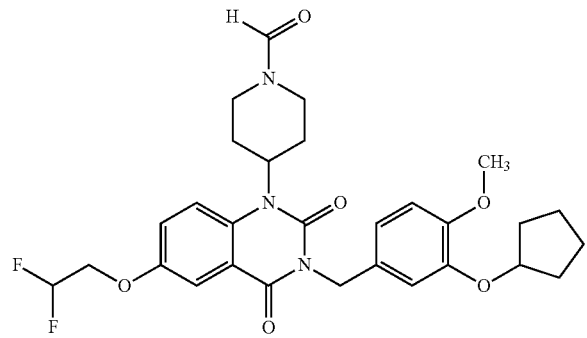 [SMILES: COc1ccc(Cn2c(=O)c3cc(OCC(F)F)ccc3n(C3CCN(C=O)CC3)c2=O)cc1OC1CCCC1]

0.172 g of DIAD is added to a solution of 0.15 g of 4-[6-(2,2-difluoroethoxy)-2,4-dioxo-3,4-dihydroquinazolin-1 (2H)-yl]piperidine-1-carbaldehyde obtained in stage 3.7, 0.142 g of [4-(cyclopentyloxy)-3-methoxyphenyl]methanol and 0.223 g of $PPh_3$ in 3 ml of anhydrous THF. The mixture is stirred at AT for 12 h 00 and then at 60° C. for 1 h 00. It is evaporated under reduced pressure and the residue is purified on silica gel, elution being carried out with AcOEt, to give 0.083 g of the expected product.

Example 5

Compound No. 20

Synthesis of N-{[3-(3,4-dimethoxybenzyl)-1-(1-formyl piperidin-4-yl)-2,4-dioxo-1,2,3,4-tetrahydroquinazolin-6-yl]methyl}acetamide

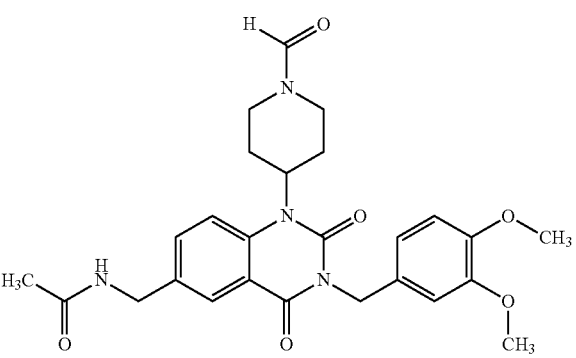 [SMILES: COc1ccc(Cn2c(=O)c3cc(CNC(C)=O)ccc3n(C3CCN(C=O)CC3)c2=O)cc1OC]

Stage 5.1

Methyl 2-amino-5-(({[(1,1-dimethylethoxy)carbonyl]amino}methyl)benzoate

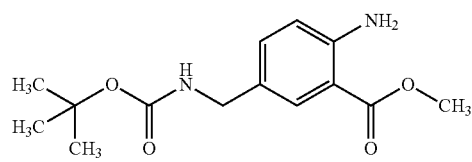 [SMILES: COC(=O)c1cc(CNC(=O)OC(C)(C)C)ccc1N]

A mixture of 0.273 g of methyl 5-{[(tert-butoxycarbonyl)amino]methyl}-2-nitrobenzoate, 0.166 g of ammonium formate and 0.094 g of Pd/C (10%) in 10 ml of EtOH purged beforehand with nitrogen is irradiated under a microwave field at 120° C. for 5 min. The mixture is filtered and the filtrate is evaporated under reduced pressure. The residue is chromatographed on silica gel, elution being carried out with an AcOEt/heptane mixture, (5/95, v/v) as far as (30/70, v/v), to give 0.2 g of the expected product.

Stage 5.2

Benzyl 4-{[4-({[(1,1-dimethylethoxy)carbonyl]amino}methyl)-2-(methoxycarbonyl)phenyl]amino}piperidine-1-carboxylate

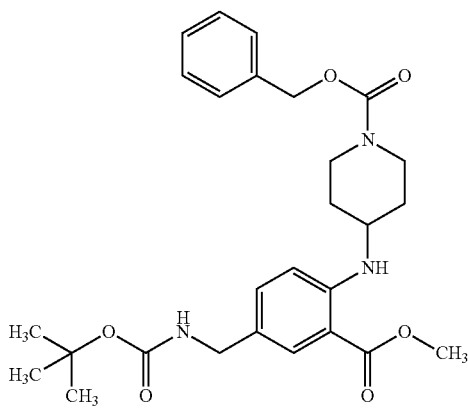 [SMILES: COC(=O)c1cc(CNC(=O)OC(C)(C)C)ccc1NC1CCN(C(=O)OCc2ccccc2)CC1]

A solution of 1.66 g of benzyl 4-oxopiperidine-1-carboxylate and 1 g of methyl 2-amino-5-({[(1,1-dimethylethoxy)carbonyl]amino}methyl)benzoate obtained in stage 5.1 in 20 ml of DCM is added dropwise at AT to a suspension of 2.04 g of NaBH(OAc)$_3$ in a mixture of 20 ml of DCM and 0.41 ml of AcOH. The mixture is stirred at AT for 15 h 00 and then a further 2.04 g of NaBH(OAc)$_3$ are added. After stirring for 6 h 00, 1.66 g of benzyl 4-oxopiperidine-1-carboxylate are added and the mixture is stirred at AT for 48 h 00. A saturated NaHCO$_3$ solution is added and extraction is carried out with DCM. The organic phase is washed with a saturated NaHCO$_3$ solution and twice with a saturated NH$_4$Cl solution. It is dried over Na$_2$SO$_4$ and filtered, and the filtrate is evaporated under reduced pressure. The residue is chromatographed on silica gel, elution being carried out with an AcOEt/heptane mixture, (5/95, v/v) as far as (40/60, v/v), to give 1.6 g of the expected product.

Stage 5.3

Benzyl 4-{[4-({[(1,1-dimethylethoxy)carbonyl]amino}methy)-2-(methoxycarbonyl)phenyl](ethoxycarbonyl)amino}piperidine-1-carboxylate

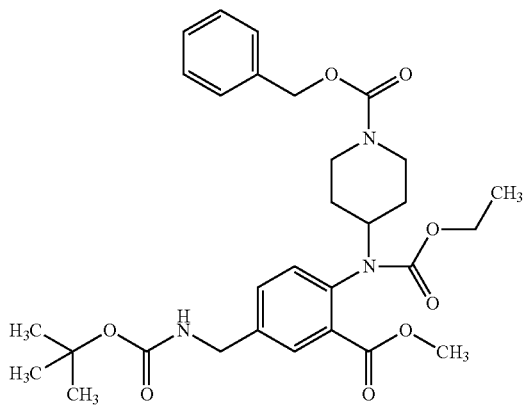 [SMILES: CCOC(=O)N(c1ccc(CNC(=O)OC(C)(C)C)cc1C(=O)OC)C1CCN(C(=O)OCc2ccccc2)CC1]

2.08 g of DIEA and then 1.745 g of ethyl chloroformate are added to a solution of 1.6 g of benzyl 4-{[4-({[(1,1-dimethylethoxy)carbonyl]amino}methyl)-2-(methoxycarbonyl)phenyl]amino}piperidine-1-carboxylate obtained in stage 5.2 in 11 ml of DCM. The mixture is stirred at AT for 4 days. It is evaporated under reduced pressure. The residue is taken up in 10 ml of pyridine (10 ml) and 0.7 g of ethyl chloroformate is added. The mixture is stirred at AT for 4 h 00. It is evaporated under reduced pressure. The residue is chromatographed on silica gel, elution being carried out with an AcOEt/heptane mixture, (10/90, v/v) as far as (30/70, v/v), to give 0.875 g of the expected product.

Stage 5.4

Benzyl 4-[3-(3,4-dimethoxybenzyl)-6-({[(1,1-dimethylethoxy)carbonyl]amino}-methyl)-2,4-dioxo-3,4-dihydroquinazolin-1(2H)-yl]piperidine-1-carboxylate

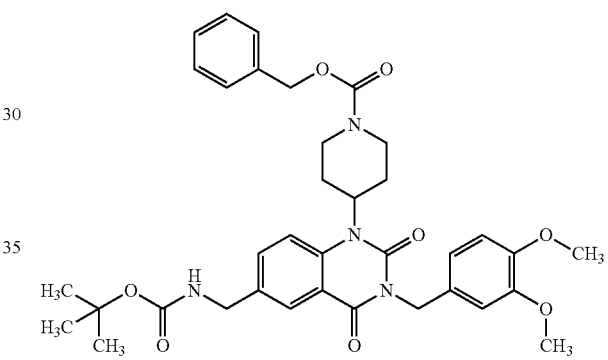

A mixture of 0.165 g of benzyl 4-{[4-({[(1,1-dimethylethoxy) carbonyl]amino}-methyl)-2-(methoxycarbonyl)phenyl](ethoxycarbonyl)amino}piperidine-1-carboxylate obtained in stage 5.3 and 0.028 g of LiOH in 5 ml of THF/H$_2$O (70/30) is stirred at AT for 15 h 00. The mixture is subsequently irradiated under a microwave field at 100° C. for 1 h 00. It is filtered and the filtrate is evaporated under reduced pressure. The residue is taken up in 5 ml of DMF. 0.108 g of DIEA is added and the mixture is stirred at AT for min. 0.159 g of HBTU is added and the mixture is stirred at AT for 30 min. 0.061 g of veratrylamine is subsequently added and the mixture is stirred at AT for 1 h 00. 0.5 ml of DBU is added and the mixture is stirred at AT for 48 h 00. It is evaporated under reduced pressure and the residue is taken up in AcOEt. The solution is washed 3 times with a saturated NH$_4$Cl solution and twice with water. It is dried over Na$_2$SO$_4$ and filtered, and the filtrate is evaporated under reduced pressure. The residue is chromatographed on silica gel, elution being carried out with an AcOEt/DCM mixture, (10/90, v/v) as far as (20/80, v/v), to give 0.104 g of the expected product.

Stage 5.5

Benzyl 4-[6-(aminomethyl)-3-(3,4-dimethoxybenzyl)-2,4-dioxo-3,4-dihydroquinazolin-1(2H)-yl]piperidine-1-carboxylate

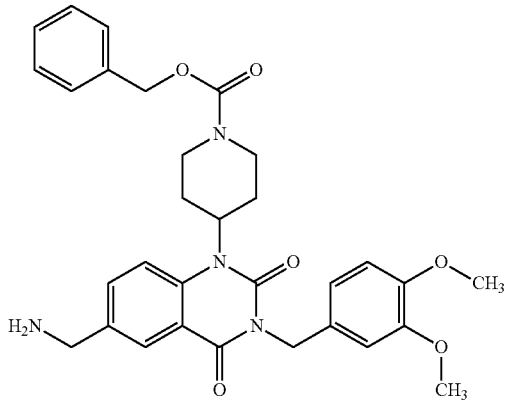 [SMILES: COc1ccc(Cn2c(=O)c3cc(CN)ccc3n(C3CCN(C(=O)OCc4ccccc4)CC3)c2=O)cc1OC]

A solution of 0.102 g of benzyl 4-[3-(3,4-dimethoxybenzyl)-6-({[(1,1-dimethylethoxy)carbonyl]amino}methyl)-2,4-dioxo-3,4-dihydroquinazolin-1(2H)-yl]piperidine-1-carboxylate obtained in stage 5.4 and 0.5 ml of TFA in 9.5 ml of DCM is stirred at AT for 2 h 00. A saturated NaHCO$_3$ solution is added. The organic phase is dried over Na$_2$SO$_4$ and filtered, and the filtrate is evaporated under reduced pressure to give 0.09 g of the expected product.

Stage 5.6

Benzyl 4-{6-[(acetylamino)methyl]-3-(3,4-dimethoxybenzyl)-2,4-dioxo-3,4-dihydroquinazolin-1(2H)-yl}piperidine-1-carboxylate

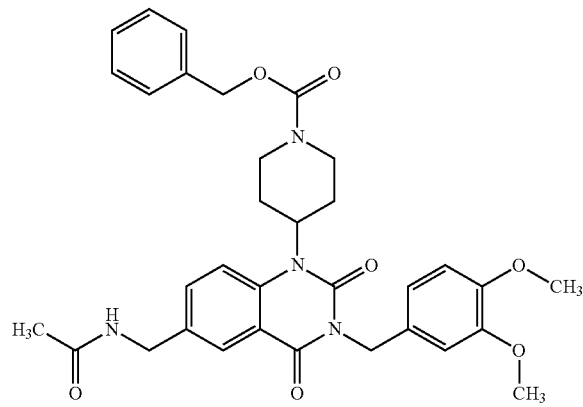 [SMILES: COc1ccc(Cn2c(=O)c3cc(CNC(C)=O)ccc3n(C3CCN(C(=O)OCc4ccccc4)CC3)c2=O)cc1OC]

0.049 g of acetic anhydride is added to a solution of 0.09 g of benzyl 4-[6-(aminomethyl)-3-(3,4-dimethoxybenzyl)-2,4-dioxo-3,4-dihydroquinazolin-1(2H)-yl]piperidine-1-carboxylate obtained in stage 5.5 and 0.09 ml of NEt$_3$ in 3 ml of DCM and the mixture is stirred at AT for 1 h 00. DCM is added and the solution is washed with a saturated NH$_4$Cl solution, then with a 1N HCl solution, then with a 2N NaOH solution and then with water. The organic phase is dried over Na$_2$SO$_4$ and filtered, and the filtrate is evaporated under reduced pressure to give 0.104 g of the expected product.

Stage 5.7

N-{[3-(3,4-Dimethoxybenzyl)-2,4-dioxo-1-(piperidin-4-yl)-1,2,3,4-tetrahydroquinazolin-6-yl]methyl}acetamide

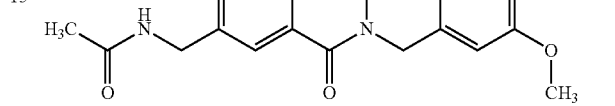

A mixture of 0.1 g of benzyl 4-{6-[(acetylamino)methyl]-3-(3,4-dimethoxybenzyl)-2,4-dioxo-3,4-dihydroquinazolin-1(2H)-yl}piperidine-1-carboxylate obtained in stage 5.6, 0.016 g of ammonium formate and 0.018 g of Pd/C (10%) in 2 ml of EtOH purged beforehand with nitrogen is irradiated under a microwave field at 800° C. for 30 min. The mixture is filtered and the filtrate is evaporated under reduced pressure to give 0.077 g of the expected product.

Stage 5.8

Compound No. 20

N-{[3-(3,4-Dimethoxybenzyl)-1-(1-formylpiperidin-4-yl)-2,4-dioxo-1,2,3,4-tetrahydroquinazolin-6-yl]methyl}acetamide

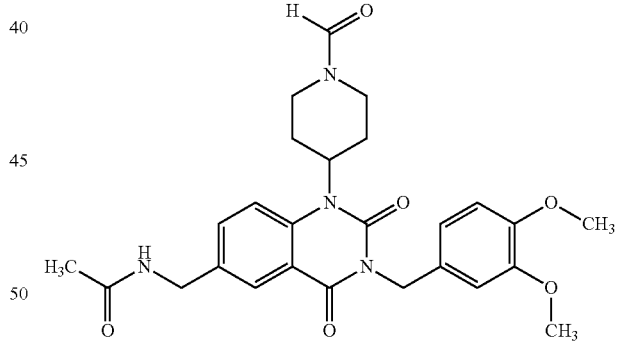

A mixture of 0.070 g of N-{[3-(3,4-dimethoxybenzyl)-2,4-dioxo-1-(piperidin-4-yl)-1,2,3,4-tetrahydroquinazolin-6-yl]methyl}acetamide obtained in stage 5.7 and 0.028 g of ammonium formate in 2 ml of ACN is irradiated under a microwave field at 140° C. for 1 h 00. The mixture is filtered and the filtrate is evaporated under reduced pressure. The residue is chromatographed on silica gel, elution being carried out with an MeOH/DCM mixture, (0.5/99.5, v/v) as far as (7/93, v/v), to give 0.035 g of the expected product.

The chemical structures and the physical properties of compounds corresponding to the general formula (I) according to the invention, and also of some of their intermediates (in particular compounds 32, 55, 120 and 257), are illustrated in the following table.

| COMPOUND No. | STRUCTURE | NOMENCLATURE | NMR or MASS |
|---|---|---|---|
| 1 | 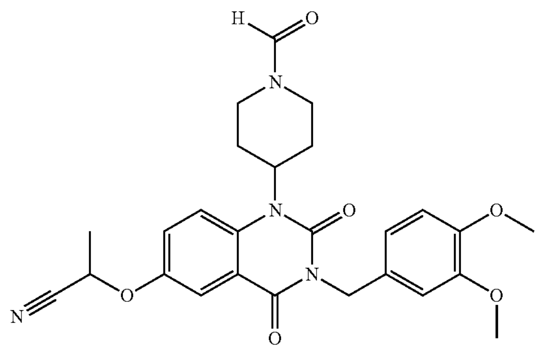 [SMILES: COc1ccc(Cn2c(=O)c3cc(OC(C)C#N)ccc3n(C3CCN(C=O)CC3)c2=O)cc1OC] | 2-{[3-(3,4-dimethoxybenzyl)-1-(1-formylpiperidin-4-yl)-2,4-dioxo-1,2,3,4-tetrahydro-quinazolin-6-yl]oxy}propanenitrile | $^1$H NMR (500 MHz, DMSO-d$_6$) δ ppm 1.71 (d, 3H) 1.79 (brdd, 2H) 2.41 (dq, 1H) 2.53 (dq, 1H) 2.80 (td, 1H) 3.25 (t, 1H) 3.70 (s, 3H) 3.71 (s, 3H) 3.80 (d, 1H) 4.31 (d, 1H) 4.77 (brs, 1H) 5.03 (s, 2H) 5.60 (q, 1H) 6.83 (dd, 1H) 6.85 (d, 1H) 6.98 (s, 1H) 7.51 (dd, 1H) 7.74 (d, 1H) 7.84 (d, 1H) 8.03 (s, 1H) |
| 2 | 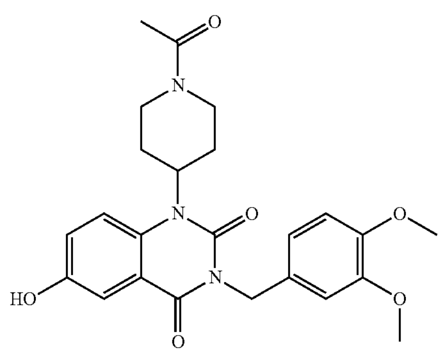 [SMILES: COc1ccc(Cn2c(=O)c3cc(O)ccc3n(C3CCN(C(C)=O)CC3)c2=O)cc1OC] | 1-(1-acetylpiperidin-4-yl)-3-(3,4-dimethoxybenzyl)-6-hydroxyquinazoline-2,4(1H,3H)-dione | $^1$H NMR (500 MHz, DMSO-d$_6$) δ ppm 1.69 (d, 1H) 1.74 (d, 1H) 2.05 (s, 3H) 2.42 (dq, 1H) 2.57 (dq, 1H) 2.70 (t, 1H) 3.24 (t, 2H) 3.70 (br s, 3H) 3.71 (s, 3H) 3.92 (d,1 H) 4.51 (d, 1H) 4.69 (brs, 1H) 5.02 (s, 2H) 6.81 (dd, 1H) 6.86 (d, 1H) 6.97 (d, 1H) 7.21 (dd, 1H) 7.44 (d, 1H) 7.65 (d, 1H) 9.88 (brs, 1H) |
| 3 | 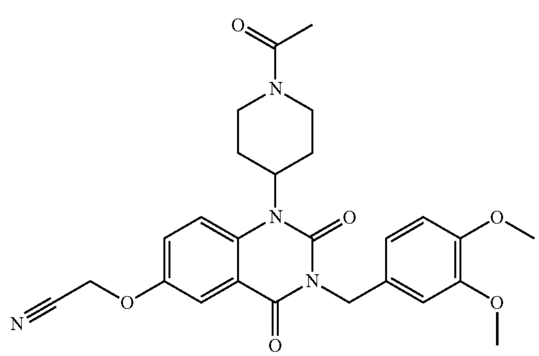 [SMILES: COc1ccc(Cn2c(=O)c3cc(OCC#N)ccc3n(C3CCN(C(C)=O)CC3)c2=O)cc1OC] | {[1-(1-acetylpiperidin-4-yl)-3-(3,4-dimethoxy-benzyl)-2,4-dioxo-1,2,3,4-tetrahydro-quinazolin-6-yl]oxy}acetonitrile | $^1$H NMR (500 MHz, DMSO-d$_6$) δ ppm 1.71 (d, 1H) 1.76 (d, 1H) 2.04 (s, 3H) 2.41 (dq, 1H) 2.56 (dq, 1H) 2.70 (t, 1H) 3.24 (t, 1H) 3.70 (s, 3H) 3.71 (s, 3H) 3.92 (d, 1H) 4.51 (d, 1H) 4.73 (brs, 1H) 5.04 (s, 2H) 5.29 (s, 2H) 6.82 (dd, 1H) 6.85 (d, 1H) 6.98 (d, 1H) 7.50 (dd, 1H) 7.70 (d, 1H) 7.83 (d, 1H) |
| 4 | 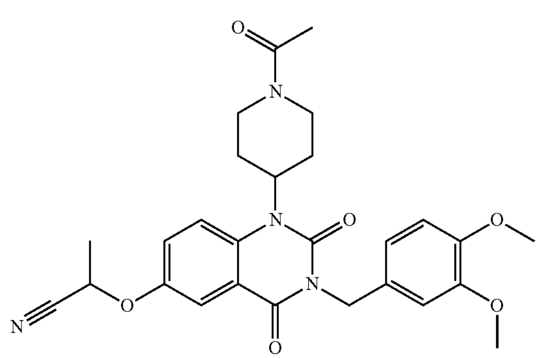 [SMILES: COc1ccc(Cn2c(=O)c3cc(OC(C)C#N)ccc3n(C3CCN(C(C)=O)CC3)c2=O)cc1OC] | 2-{[1-(1-acetylpiperidin-4-yl)-3-(3,4-dimethoxy-benzyl)-2,4-dioxo-1,2,3,4-tetrahydro-quinazolin-6-yl]oxy}propanenitrile | $^1$H NMR (500 MHz, DMSO-d$_6$) δ ppm 1.71 (d, 3H) 1.72 (d, 2H) 1.77 (d, 1H) 2.04 (s, 3H) 2.41 (qd, 1H) 2.56 (dq, 1H) 2.70 (d, 1H) 3.24 (t, 1H) 3.70 (s, 3H) 3.71 (s, 3H) 3.92 (d, 1H) 4.51 (d, 1H) 4.73 (brs, 1H) 5.03 (s, 2H) 5.60 (q, 1H) 6.83 (d, 1H) 6.85 (m, 1H) 6.98 (d, 1H) 7.51 (dd, 1H) 7.74 (d, 1H) 7.83 (d, 1H) |

-continued

| | | | |
|---|---|---|---|
| 5 | 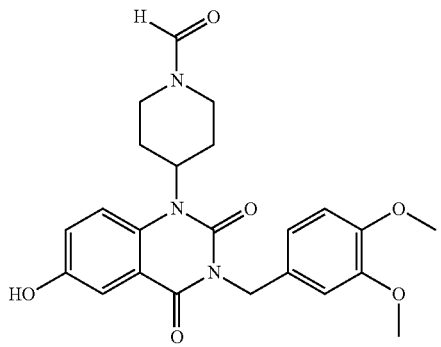 [SMILES: COc1ccc(Cn2c(=O)c3cc(O)ccc3n(C3CCN(C=O)CC3)c2=O)cc1OC] | 4-[3-(3,4-dimethoxy-benzyl)-6-hydroxy-2,4-dioxo-3,4-dihydroquinazolin-1(2H)-yl]piperidine-1-carbaldehyde | $^1$H NMR (500 MHz, DMSO-d$_6$) δ ppm 1.75 (d, 1H) 1.78 (d, 1H) 2.41 (qd, 1H) 2.53 (qd, 1H) 2.79 (td, 1H) 3.25 (td, 1H) 3.70 (s, 3H) 3.71 (s, 3H) 3.80 (d, 1H) 4.31 (d, 1H) 4.72 (brs, 1H) 5.02 (s, 2H) 6.82 (dd, 1H) 6.86 (d, 1H) 6.97 (d, 1H) 7.21 (dd, 1H) 7.44 (d, 1H) 7.66 (d, 1H) 8.03 (s, 1H) 9.85 (brs, 1H) |
| 6 | 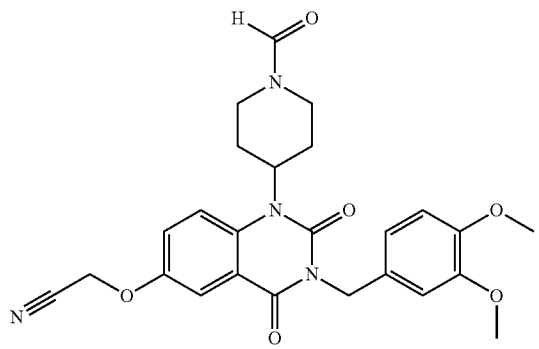 [SMILES: COc1ccc(Cn2c(=O)c3cc(OCC#N)ccc3n(C3CCN(C=O)CC3)c2=O)cc1OC] | {[3-(3,4-dimethoxy-benzyl)-1-(1-formyl-piperidin-4-yl)-2,4-dioxo-1,2,3,4-tetrahydroquinazolin-6-yl]oxy}acetonitrile | $^1$H NMR (500 MHz, DMSO-d$_6$) δ ppm 1.78 (d, 1H) 1.81 (d, 1H) 2.42 (qd, 1H) 2.54 (dt, 1H) 2.81 (td, 4H) 3.26 (dt, 1H) 3.71 (s, 3H) 3.72 (s, 3H) 3.81 (d, 1H) 4.32 (d, 1H) 4.77 (brs, 1H) 5.05 (s, 2H) 5.30 (s, 2H) 6.84 (dd, 1H) 6.87 (d, 1H) 6.99 (d, 1H) 7.51 (dd, 1H) 7.71 (d, 1H) 7.85 (d, 1H) 8.04 (s, 1H) |
| 7 | 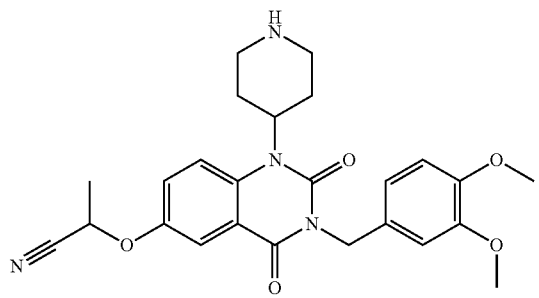 [SMILES: COc1ccc(Cn2c(=O)c3cc(OC(C)C#N)ccc3n(C3CCNCC3)c2=O)cc1OC] | 2-{[3-(3,4-dimethoxy-benzyl)-2,4-dioxo-1-(piperidin-4-yl)-1,2,3,4-tetrahydroquinazolin-6-yl]oxy}propanenitrile | $^1$H NMR (500 MHz, DMSO-d$_6$) δ ppm 1.69 (d, 3H) 1.75 (d, 2H) 2.65 (td, 2H) 2.87 (t, 2H) 3.21 (d, 2H) 3.69 (s, 3H) 3.70 (s, 3H) 4.68 (brs, 1H) 5.04 (s, 2H) 5.59 (q, 1H) 6.84 (m, 2H) 6.98 (d, 1H) 7.50 (dd, 1H) 7.73 (d, 1H) 7.80 (d, 1H) |
| 8 | 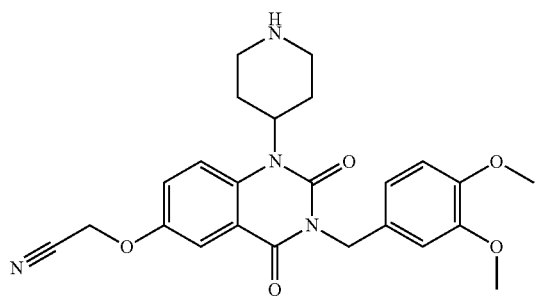 [SMILES: COc1ccc(Cn2c(=O)c3cc(OCC#N)ccc3n(C3CCNCC3)c2=O)cc1OC] | {[3-(3,4-dimethoxy-benzyl)-2,4-dioxo-1-(piperidin-4-yl)-1,2,3,4-tetrahydroquinazolin-6-yl]oxy}acetonitrile | $^1$H NMR (600 MHz, DMSO-d$_6$) δ ppm 1.77 (d, 2H) 2.67 (dt, 2H) 2.89 (t, 2H) 3.23 (d, 2H) 3.69 (s, 3H) 3.70 (s, 3H) 4.69 (brs, 1H) 5.05 (s, 2H) 5.28 (s, 2H) 6.84 (m, 2H) 6.99 (s, 1H) 7.49 (dd, 1H) 7.70 (d, 1H) 7.80 (d, 1H) |
| 9 | 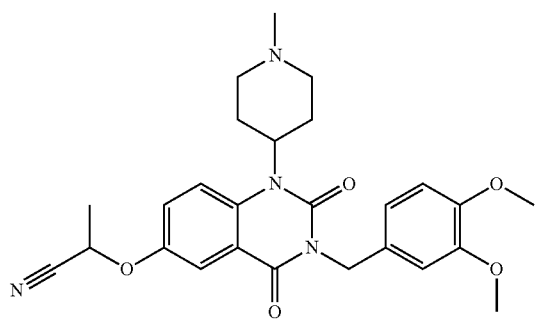 [SMILES: COc1ccc(Cn2c(=O)c3cc(OC(C)C#N)ccc3n(C3CCN(C)CC3)c2=O)cc1OC] | 2-{[3-(3,4-dimethoxy-benzyl)-1-(1-methyl-piperidin-4-yl)-2,4-dioxo-1,2,3,4-tetrahydroquinazolin-6-yl]oxy}propanenitrile | $^1$H NMR (500 MHz, DMSO-d$_6$) δ ppm 1.59 (d, 2H) 1.66 (d, 3H) 2.04 (t, 2H) 2.16 (s, 3H) 2.62 (dt, 2H) 2.82 (d, 2H) 3.66 (s, 3H) 3.67 (s, 3H) 4.43 (brs, 1H) 5.01 (s, 2H) 5.54 (q, 1H) 6.79 (m, 1H) 6.82 (d, 1H) 6.95 (d, 1H) 7.45 (dd, 1H) 7.68 (d, 1H) 7.70 (d, 1H) |

| | | | |
|---|---|---|---|
| 10 | 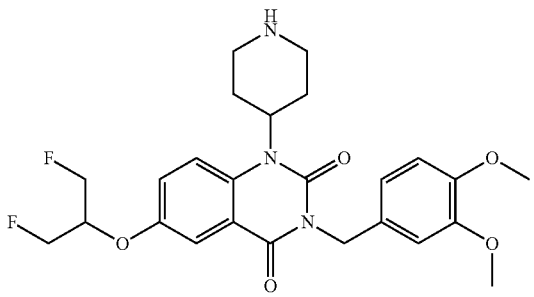 [SMILES: COc1ccc(Cn2c(=O)c3cc(OC(CF)CF)ccc3n(C3CCNCC3)c2=O)cc1OC] | 3-(3,4-dimethoxy-benzyl)-6-[2-fluoro-1-(fluoromethyl)ethoxy]-1-piperidin-4-ylquinazoline-2,4(1H,3H)-dione | $^1$H NMR (500 MHz, DMSO-d$_6$) δ ppm 1.85 (d, 2H) 2.78 (td, 2H) 3.04 (t, 2H) 3.33 (d, 2H) 3.71 (s, 6H) 4.61-4.82 (m, 4H) 5.04 (brt, 1H) 5.05 (s, 2H) 6.86 (m, 2H) 6.99 (s, 1H) 7.49 (dd, 1H) 7.68 (d, 1H) 7.76 (d, 1H) 8.05 (brs, 1H) |
| 11 | 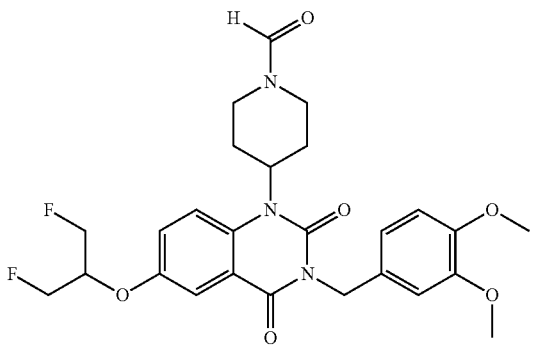 [SMILES: COc1ccc(Cn2c(=O)c3cc(OC(CF)CF)ccc3n(C3CCN(C=O)CC3)c2=O)cc1OC] | 4-[3-(3,4-dimethoxy-benzyl)-6-[2-fluoro-1-(fluoromethyl)ethoxy]-2,4-dioxo-3,4-dihydro-quinazolin-1(2H)-yl]piperidine-1-carbaldehyde | $^1$H NMR (500 MHz, DMSO-d$_6$) δ ppm 1.76 (d, 1H) 1.80 (d, 1H) 2.41 (qd, 1H) 2.53 (qd, 1H) 2.80 (td, 1H) 3.25 (dt, 1H) 3.70 (s, 6H) 3.80 (d, 1H) 4.31 (d, 1H) 4.61-4.83 (m, 5H) 5.02 (m, 1H) 5.03 (s, 2H) 6.83 (dd, 1H) 6.85 (d, 1H) 6.97 (d, 1H) 7.47 (dd, 1H) 7.67 (d, 1H) 7.77 (d, 1H) 8.03 (s, 1H) |
| 12 | 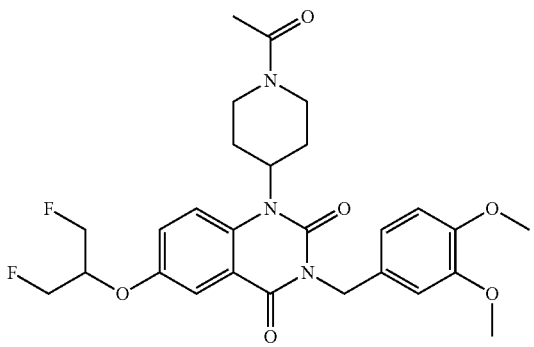 [SMILES: COc1ccc(Cn2c(=O)c3cc(OC(CF)CF)ccc3n(C3CCN(C(C)=O)CC3)c2=O)cc1OC] | 1-(1-acetylpiperidin-4-yl)-3-(3,4-dimethoxybenzyl)-6-[2-fluoro-1-(fluoromethyl)ethoxy]quinazoline-2,4(1H,3H)-dione | $^1$H NMR (500 MHz, DMSO-d$_6$) δ ppm 1.70 (d, 1H) 1.76 (d, 1H) 2.04 (s, 3H) 2.41 (dq, 1H) 2.56 (dq, 1H) 2.70 (t, 1H) 3.25 (t, 1H) 3.70 (s, 3H) 3.71 (s, 3H) 3.92 (d, 1H) 4.51 (d, 1H) 4.61-4.83 (m, 5H) 5.02 (m, 1H) 5.03 (s, 2H) 6.82 (dd, 1H) 6.85 (m, 1H) 6.97 (d, 1H) 7.47 (dd, 1H) 7.67 (d, 1H) 7.77 (d, 1H) |
| 13 | 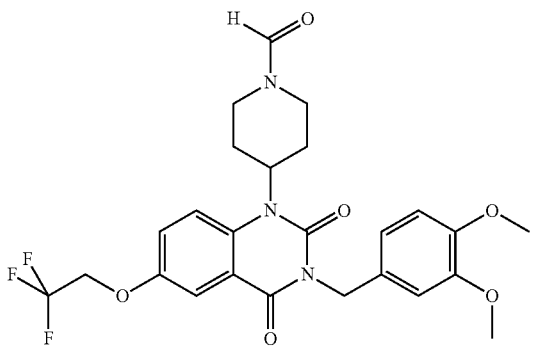 [SMILES: COc1ccc(Cn2c(=O)c3cc(OCC(F)(F)F)ccc3n(C3CCN(C=O)CC3)c2=O)cc1OC] | 4-[3-(3,4-dimethoxy-benzyl)-2,4-dioxo-6-(2,2,2-trifluoroethoxy)-3,4-dihydroquinazolin-1(2H)-yl]piperidine-1-carbaldehyde | $^1$H NMR (600 MHz, DMSO-d$_6$) δ ppm 1.75 (d, 1H) 1.79 (d, 1H) 2.40 (dq, 1H)) 2.52 (dq, 1H) 2.79 (td, 1H) 3.25 (td, 1H) 3.69 (s, 6H) 3.79 (d, 1H) 4.30 (d, 1H) 4.75 (brs, 1H) 4.88 (q, 2H) 5.02 (s, 2H) 6.82 (d, 1H) 6.85 (d, 1H) 6.97 (s, 1H) 7.49 (dd, 1H) 7.66 (d, 1H) 7.79 (d, 1H) 8.02 (s, 1H) |

| | | | |
|---|---|---|---|
| 14 | 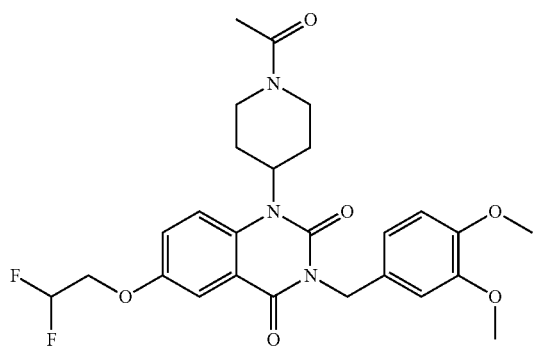 [SMILES: COc1ccc(Cn2c(=O)c3cc(OCC(F)F)ccc3n(C3CCN(C(C)=O)CC3)c2=O)cc1OC] | 1-(1-acetylpiperidin-4-yl)-6-(2,2-difluoro-ethoxy)-3-(3,4-dimethoxybenzyl)quinazoline-2,4(1H,3H)-dione | $^1$H NMR (500 MHz, DMSO-d$_6$) δ ppm 1.70 (d, 1H) 1.74 (d, 1H) 2.04 (s, 3H) 2.41 (qd, 1H) 2.56 (qd, 1H) 2.70 (t, 1H) 3.24 (t, 1H) 3.70 (s, 3H) 3.70 (s, 3H) 3.91 (d, 1H) 4.43 (td, 2 H) 4.50 (d, 1H) 4.73 (brs, 1H) 5.03 (s, 2H) 6.41 (tt, 1H) 6.82 (dd, 1H) 6.85 (d, 1H) 6.97 (d, 1H) 7.46 (dd, 1H) 7.60 (d, 1H) 7.79 (d, 1H) |
| 15 | 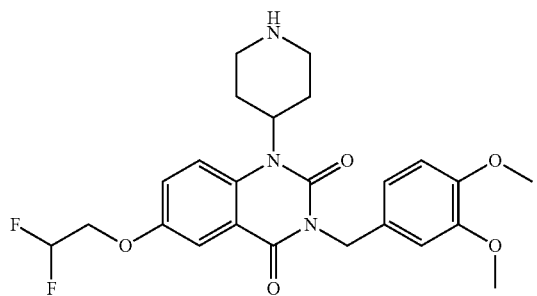 [SMILES: COc1ccc(Cn2c(=O)c3cc(OCC(F)F)ccc3n(C3CCNCC3)c2=O)cc1OC] | 6-(2,2-difluoroethoxy)-3-(3,4-dimethoxybenzyl)-1-(piperidin-4-yl)quinazoline-2,4(1H,3H)-dione | $^1$H NMR (500 MHz, DMSO-d$_6$) δ ppm 1.83 (d, 2H) 2.75 (td, 2H) 3.00 (t, 2H) 3.30 (d, 2H) 3.71 (s, 6H) 4.44 (td, 2H) 4.75 (b. s, 1H) 5.06 (s, 2H) 6.42 (tt, 1H) 6.83-6.89 (m, 2H) 7.00 (s, 1H) 7.48 (dd, 1H) 7.62 (d, 1H) 7.78 (d, 1H) |
| 16 | 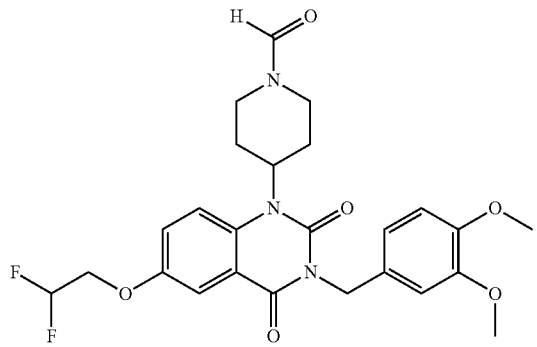 | 4-[6-(2,2-difluoro-ethoxy)-3-(3,4-dimethoxybenzyl)-2,4-dioxo-3,4-dihydroquinazolin-1(2H)-yl]piperidine-1-carbaldehyde | $^1$H NMR (500 MHz, DMSO-d$_6$) δ ppm 1.76 (d, 1H) 1.80 (d, 1H) 2.41 (qd, 1H) 2.53 (qd, 1H) 2.81 (td, 1H) 3.26 (td, 1H) 3.71 (s, 6H) 3.80 (d, 1H) 4.31 (d, 1H) 4.44 (td, 2H) 4.77 (brs, 1H) 5.04 (s, 2H) 6.42 (tt, 1H) 6.83 (m, 1H) 6.86 (d, 1H) 6.86 (d, 1H) 6.98 (d, 1H) 7.47 (dd, 1H) 7.61 (d, 1H) 7.80 (d, 1H) 8.03 (s, 1H) |
| 17 | 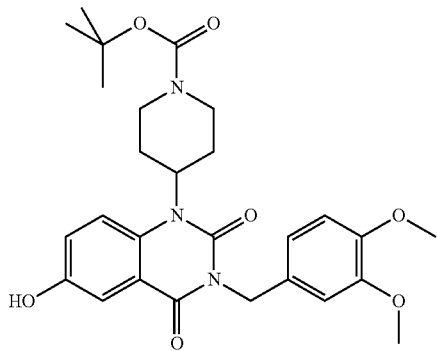 [SMILES: COc1ccc(Cn2c(=O)c3cc(O)ccc3n(C3CCN(C(=O)OC(C)(C)C)CC3)c2=O)cc1OC] | 1,1-dimethylethyl 4-[3-(3,4-dimethoxy-benzyl)-6-hydroxy-2,4-dioxo-3,4-dihydro-quinazolin-1(2H)-yl]piperidine-1-carboxylate | $^1$H NMR (500 MHz, DMSO-d$_6$) δ ppm 1.43 (s, 9H) 1.67 (d, 2H) 2.48 (m, 2H) 2.92 (brs, 2H) 3.70 (s, 3H) 3.71 (s, 3H) 4.05 (br s, 2H) 4.61 (brs, 1H) 5.02 (s, 2H) 6.80 (dd, 1H) 6.86 (d, 1H) 6.97 (d, 1H) 7.20 (dd, 1H) 7.43 (d, 1H) 7.62 (d, 1H) 9.95 (brs, 1H) |

-continued

| | | | |
|---|---|---|---|
| 18 | 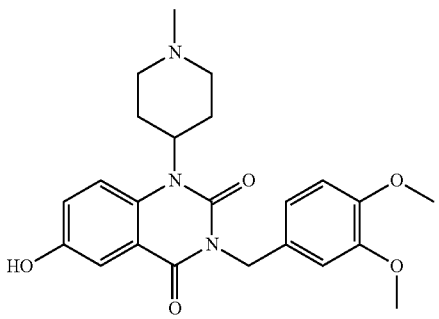 [SMILES: COc1ccc(Cn2c(=O)c3cc(O)ccc3n(C3CCN(C)CC3)c2=O)cc1OC] | 3-(3,4-dimethoxy-benzyl)-6-hydroxy-1-(1-methylpiperidin-4-yl)quinazoline-2,4(1H,3H)-dione | $^1$H NMR (500 MHz, DMSO-$d_6$) δ ppm 1.60 (d, 2H) 2.06 (td, 2H) 2.19 (s, 3H) 2.65 (qd, 2H) 2.85 (d, 2H) 3.70 (s, 3H) 3.71 (s, 3H) 4.43 (br. s, 1H) 5.02 (s, 2H) 6.81 (m, 1H) 6.85 (d, 1H) 6.98 (d, 1H) 7.19 (dd, 1H) 7.41 (d, 1H) 7.55 (d, 1H) 9.82 (s, 1H) |
| 19 | 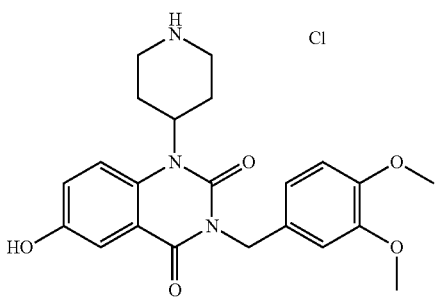 [SMILES: COc1ccc(Cn2c(=O)c3cc(O)ccc3n(C3CCNCC3)c2=O)cc1OC ; Cl] | 3-(3,4-dimethoxy-benzyl)-6-hydroxy-1-(piperidin-4-yl)quinazoline-2,4-(1H,3H)dione hydrochloride | $^1$H NMR (500 MHz, DMSO-$d_6$) δ ppm 1.86 (d, 2H) 2.83 (m, 2H) 3.12 (t, 2H) 3.37 (m, 2H) 3.70 (s, 6H) 4.76 (brs, 1H) 5.03 (s, 2H) 6.83 (dd, 1H) 6.85 (d, 1H) 6.98 (d, 1H) 7.21 (dd, 1H) 7.44 (d, 1H) 7.70 (d, 1H) 8.70 (brs, 2H) 9.91 (s, 1H) |
| 20 | 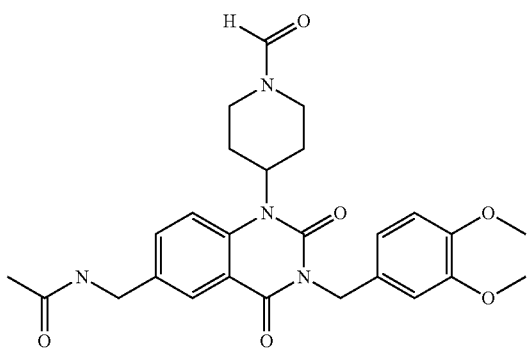 [SMILES: COc1ccc(Cn2c(=O)c3cc(CNC(C)=O)ccc3n(C3CCN(C=O)CC3)c2=O)cc1OC] | N-{[3-(3,4-dimethoxy-benzyl)-1-(1-formyl-piperidin-4-yl)-2,4-dioxo-1,2,3,4-tetra-hydroquinazolin-6-yl]methyl}acetamide | $^1$H NMR (500 MHz, DMSO-$d_6$) δ ppm 1.75 (d, 1H) 1.78 (d, 1H) 1.86 (s, 3H) 2.40 (qd, 1H) 2.53 (qd, 1H) 2.79 (t, 1H) 3.25 (t, 1H) 3.69 (s, 3H) 3.70 (s, 3H) 3.80 (d, 1H) 4.29 (d, 2H) 4.31 (d., 1H) 4.77 (brs, 1H) 5.02 (s, 2H) 6.80 (dd, 1H) 6.85 (d, 1H) 6.96 (d, 1H) 7.65 (dd, 1H) 7.76 (d, 1H) 7.96 (d, 1H) 8.02 (s, 1H) 8.46 (t, 1H) |
| 21 | 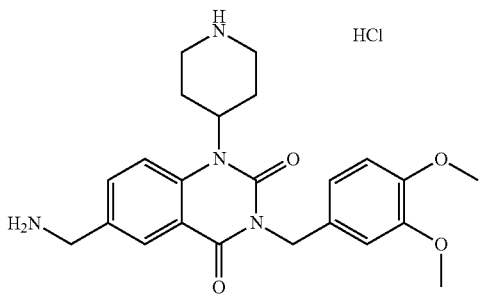 [SMILES: COc1ccc(Cn2c(=O)c3cc(CN)ccc3n(C3CCNCC3)c2=O)cc1OC ; Cl] | 6-(aminomethyl)-3-(3,4-dimethoxybenzyl)-1-(piperidin-4-yl)quinazoline-2,4(1H,3H)-dione hydrochloride | $^1$H NMR (500 MHz, DMSO-$d_6$) δ ppm 1.89 (d, 2H) 2.83-2.92 (m, 2H) 3.16 (brs, 2H) 3.38-3.42 (m, 2H) 3.71 (s, 6H) 4.13 (brs, 2H) 4.82-4.97 (m, 1H) 5.07 (s, 2H) 6.83-6.88 (m, 2H) 7.00 (s, 1H) 7.91-7.99 (m, 2H) 8.24 (s, 1H) 8.42 (br s, 3H) 9.16 (brs, 1H) |
| 22 | 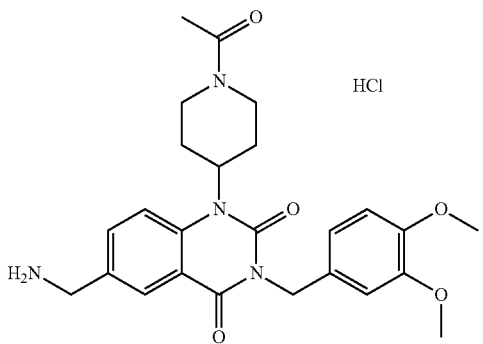 [SMILES: COc1ccc(Cn2c(=O)c3cc(CN)ccc3n(C3CCN(C(C)=O)CC3)c2=O)cc1OC ; Cl] | 1-(1-acetylpiperidin-4-yl)-6-(aminomethyl)-3-(3,4-dimethoxybenzyl)quinazoline-2,4(1H,3H)-dione hydrochloride | $^1$H NMR (500 MHz, DMSO-$d_6$) δ ppm 1.67-1.79 (m, 2H) 2.05 (s, 3H) 2.36-2.47 (m, 1H) 2.51-2.61 (m, 1H) 2.73 (t, 1H) 3.27 (t, 1H) 3.71 (s, 6H) 3.93 (d, 1H) 4.11-4.15 (m, 2H) 4.52 (d, 1H) 4.78 (brs, 1H) 5.05 (s, 2H) 6.82 (d, 1H) 6.86 (d, 1H) 6.98 (s, 1H) 7.87 (s, 2H) 8.24 (s, 1H) 8.32 (brs, 3H) |

| # | Structure | Name | 1H NMR |
|---|---|---|---|
| 23 | 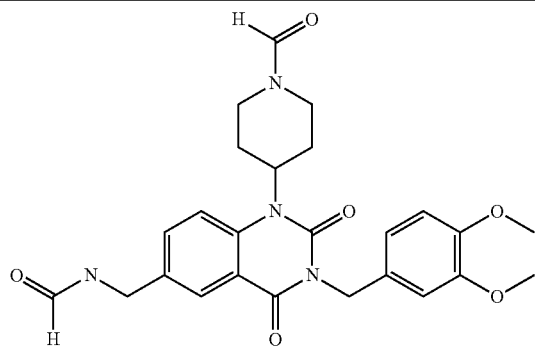 | N-{[3-(3,4-dimethoxy-benzyl)-1-(1-formyl-piperidin-4-yl)-2,4-dioxo-1,2,3,4-tetra-hydroquinazolin-6-yl]methyl}formamide | $^1$H NMR (500 MHz, DMSO-d$_6$) δ ppm 1.73-1.83 (m, 2H) 2.36-2.45 (m., 1H) 2.48-2.57 (m, 1H) 2.77-2.84 (m, 1H) 3.23-3.29 (m, 1H) 3.70 (s, 1H) 3.71 (s, 3H) 3.81 (d, 1H) 4.31 (d, 1H) 4.37 (d, 2H) 4.77 (brs, 1H) 5.04 (s, 2H) 6.82 (dd, 1H) 6.86 (d, 1H) 6.98 (d, 1H) 7.67 (dd, 1H) 7.78 (d, 1H) 7.99 (d, 1H) 8.03 (s, 1H) 8.16 (s, 1H) 8.62 (t, 1H) |
| 24 | 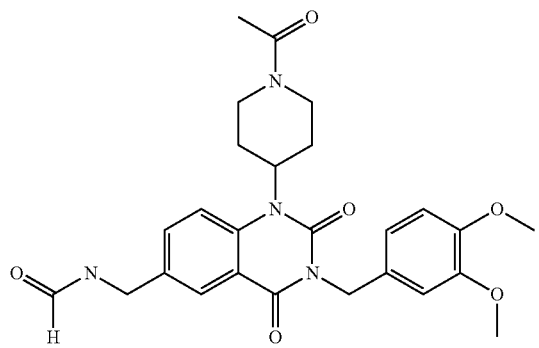 [SMILES: COc1ccc(Cn2c(=O)c3cc(CNC=O)ccc3n(C3CCN(C(C)=O)CC3)c2=O)cc1OC] | N-{[1-(1-acetylpiperidin-4-yl)-3-(3,4-dimethoxy-benzyl)-2,4-dioxo-1,2,3,4-tetrahydro-quinazolin-6-yl]methyl}formamide | $^1$H NMR (500 MHz, DMSO-d$_6$) δ ppm 1.67-1.78 (m, 2H) 2.05 (s, 3H) 2.35-2.48 (m, 1H) 2.53-2.62 (m, 1H) 2.72 (t, 1H) 3.25 (t, 1H) 3.70 (s, 3H) 3.71 (s, 3H) 3.93 (d, 1H) 4.37 (d, 2H) 4.52 (d, 1H) 4.75 (brs, 1H) 5.04 (s, 2H) 6.82 (dd, 1H) 6.86 (d, 1H) 6.98 (d, 1H) 7.67 (dd, 1H) 7.78 (d, 1H) 7.99 (d, 1H) 8.16 (s, 1H) 8.63 (t, 1H) |
| 25 | 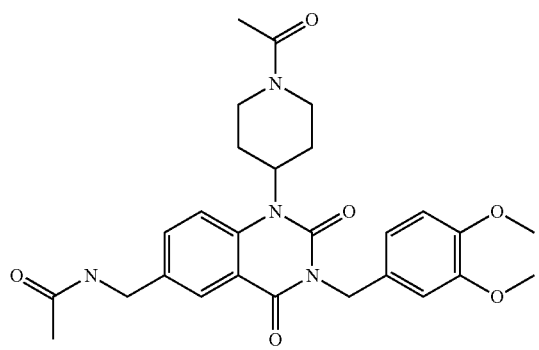 [SMILES: COc1ccc(Cn2c(=O)c3cc(CNC(C)=O)ccc3n(C3CCN(C(C)=O)CC3)c2=O)cc1OC] | N-{[1-(1-acetylpiperidin-4-yl)-3-(3,4-dimethoxy-benzyl)-2,4-dioxo-1,2,3,4-tetrahydro-quinazolin-6-yl]methyl}acetamide | $^1$H NMR (500 MHz, DMSO-d$_6$) δ ppm 1.63-1.81 (m, 2H) 1.87 (s, 3H) 2.05 (s, 3H) 2.32-2.42 (m, 1H) 2.54-2.63 (m, 1H) 2.71 (dt, 1H) 3.25 (dt, 1H) 3.70 (s, 3H) 3.71 (s, 3H) 3.93 (d, 1H) 4.30 (d, 2H) 4.52 (d, 1H) 4.76 (brs, 1H) 5.04 (s, 2H) 6.81 (dd, 1H) 6.86 (d, 1H) 6.97 (d, 1H) 7.65 (dd, 1H) 7.76 (d, 1H) 7.97 (d, 1H) 8.47 (t, 1H) |
| 26 | 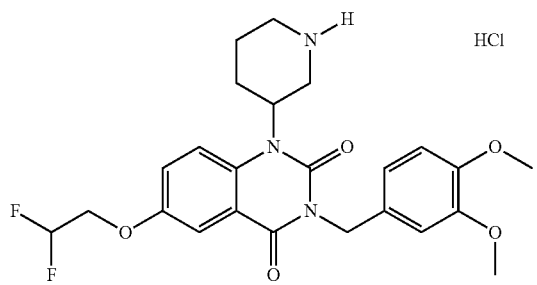 [SMILES: COc1ccc(Cn2c(=O)c3cc(OCC(F)F)ccc3n(C3CCCNC3)c2=O)cc1OC ; Cl] | 6-(2,2-difluoroethoxy)-3-(3,4-dimethoxybenzyl)-1-(piperidin-3-yl)quinazoline-2,4-(1H,3H)-dione hydrochloride | $^1$H NMR (600 MHz, DMSO-d$_6$) δ ppm 1.86-1.97 (m, 3H) 2.54-2.62 (m, 1H) 2.85-2.92 (m, 1H) 3.31-3.35 (m, 1H) 3.37-3.42 (m, 1H) 3.71 (s, 3H) 3.72 (s, 3H) 3.73-3.78 (m, 1H) 3.76 (t, 1H) 4.45 (td, 2H) 4.87 (br s, 1H) 5.05 (s, 2H) 6.41 (tt, 1H) 6.83-6.88 (m, 2H) 6.99 (s, 1H) 7.52 (dd, 1H) 7.63 (d, 1H) 7.72 (d, 1H) 8.95 (brs, 1H) |
| 27 | 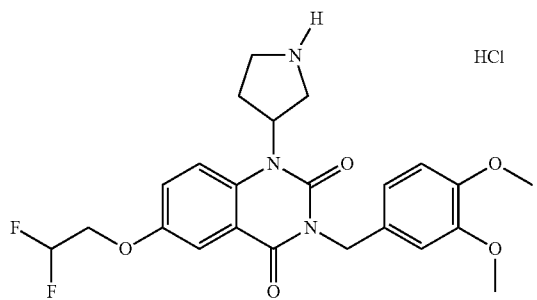 [SMILES: COc1ccc(Cn2c(=O)c3cc(OCC(F)F)ccc3n(C3CCNC3)c2=O)cc1OC ; Cl] | 6-(2,2-difluoroethoxy)-3-(3,4-dimethoxy-benzyl)-1-(pyrrolidin-3-yl)quinazoline-2,4(1H,3H)-dione hydrochloride | $^1$H NMR (500 MHz, DMSO-d$_6$) δ ppm 2.25-2.32 (m, 1H) 2.42-2.48 (m, 1H) 3.11-3.19 (m, 1H) 3.38-3.45 (m, 1H) 3.58-3.64 (m, 1H) 3.65-3.72 (m, 1H) 3.73 (s, 3H) 3.71 (s, 3H) 4.45 (td, 2H) 5.05-5.12 (m, 2H) 5.47-5.54 (m, 1H) 6.42 (tt, 1H) 6.82-6.88 (m, 2H) 7.01 (s, 1H) 7.55 (dd, 1H) 7.62 (d, 1H) 7.71 (d, 1H) 8.87 (brs, 1H) |

| # | Structure | Name | NMR |
|---|---|---|---|
| 28 | 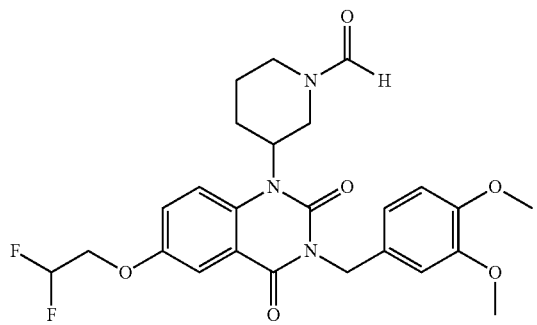 [SMILES: COc1ccc(Cn2c(=O)c3cc(OCC(F)F)ccc3n(C3CCCN(C=O)C3)c2=O)cc1OC] | 3-[6-(2,2-difluoroethoxy)-3-(3,4-dimethoxybenzyl)-2,4-dioxo-3,4-dihydroquinazolin-1(2H)-yl]piperidine-1-carbaldehyde | $^1$H NMR (600 MHz, DMSO-$d_6$) mixture of two isomers δ ppm 1.52-1.62 (m, 0.5H) 1.64-1.73 (m, 0.5H) 1.75-1.84 (m, 1H) 1.84-1.90 (m, 1H) 2.54-2.67 (m, 1.5H) 3.05 (t, 0.5H) 3.59 (t, 0.5H) 3.70 (s, 3.5H) 3.70 (s, 3H) 3.77 (dd, 0.5H) 4.06 (t, 0.5H) 4.17-4.27 (m, 1H) 4.31 (brs, 0.5H) 4.42 (td, 2H) 4.44 (brs, 0.5H) 5.04 (s, 2H) 6.38 (tt, 1H) 6.80-6.84 (m, 1H) 6.84-6.88 (m, 1H) 6.98 (brs, 1H) 7.43 (td, 1H) 7.60 (brs, 1H) 7.62 (d, 0.5H) 7.79 (d, 0.5H) 7.99 (s, 0.5H) 8.09 (s, 0.5H) |
| 29 | 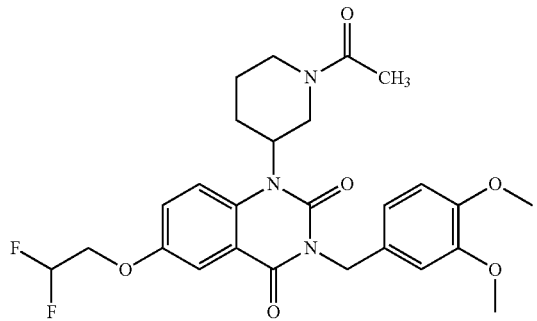 [SMILES: COc1ccc(Cn2c(=O)c3cc(OCC(F)F)ccc3n(C3CCCN(C(C)=O)C3)c2=O)cc1OC] | 1-(1-acetylpiperidin-3-yl)-6-(2,2-difluoro-ethoxy)-3-(3,4-dimethoxybenzyl)quinazoline-2,4(1H,3H)-dione | $^1$H NMR (500 MHz, DMSO-$d_6$) mixture of two isomers δ ppm 1.55-1.65 (m, 0.5H) 1.67-1.89 (m, 2.5H) 1.99 (s, 1.5H) 2.06 (s, 1.5H) 2.52-2.65 (m, 1H) 3.06 (t, 0.5H) 3.30-3.37 (m, 0.5H) 3.52 (t, 0.5H) 3.70 (s, 3H) 3.71 (s, 3H) 3.52 (t, 0.5H) 3.84 (d, 0.5H) 3.91 (d, 0.5H) 4.09 (t, 0.5H) 4.28 (brs, 0.5H) 4.39-4.48 (m, 3H) 4.49 (brs, 0.5H) 5.05 (d, 2H) 6.41 (tt, 1H) 6.81-6.89 (m, 2H) 6.99 (d, 1H) 7.44-7.48 (m, 1H) 7.59-7.62 (m, 1H) 7.64 (d, 0.5H) 7.82 (d, 0.5H) |
| 30 | 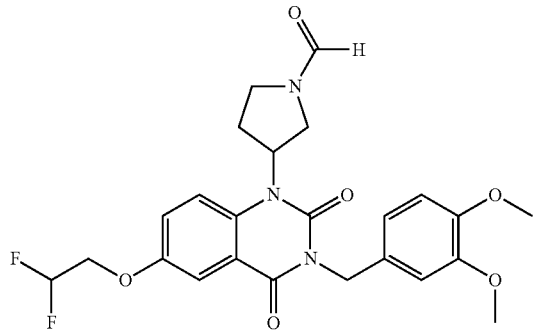 [SMILES: COc1ccc(Cn2c(=O)c3cc(OCC(F)F)ccc3n(C3CCN(C=O)C3)c2=O)cc1OC] | 3-[6-(2,2-difluoroethoxy)-3-(3,4-dimethoxybenzyl)-2,4-dioxo-3,4-dihydroquinazolin-1(2H)-yl]pyrrolidine-1-carbaldehyde | $^1$H NMR (500 MHz, DMSO-$d_6$) mixture of two isomers δ ppm 2.18-2.27 (m, 1H) 2.36-2.46 (m, 1H) 3.41-3.48 (m, 0.5H) 3.53-3.60 (m, 0.5H) 3.63-3.73 (m, 1.5H) 3.85-3.95 (m, 1.5H) 4.43 (td, 2H) 5.06 (s, 2H) 5.38-5.45 (m, 0.5H) 5.46-5.54 (m, 0.5H) 6.41 (tt, 1H) 6.82-6.88 (m, 2H) 7.00 (s, 1H) 7.46-7.51 (m, 1H) 7.61 (d, 1H) 7.66 (d, 0.5H) 7.72 (d, 0.5H) 8.16 (s, 0.5H) 8.20 (s, 0.5H) |
| 31 | 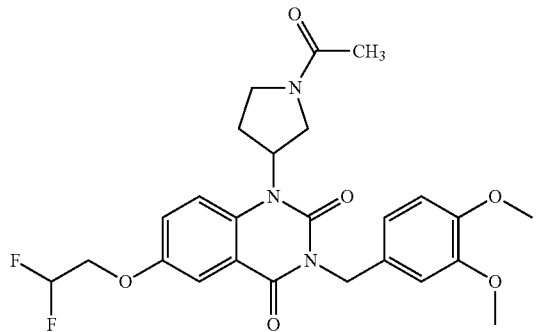 [SMILES: COc1ccc(Cn2c(=O)c3cc(OCC(F)F)ccc3n(C3CCN(C(C)=O)C3)c2=O)cc1OC] | 1-(1-acetylpyrrolidin-3-yl)-6-(2,2-difluoro-ethoxy)-3-(3,4-dimethoxybenzyl)quinazoline-2,4(1H,3H)-dione | $^1$H NMR (500 MHz, DMSO-$d_6$) mixture of two isomers δ ppm 1.98 (s, 1.5H) 2.04 (s, 1.5H) 2.17-2.25 (m, 0.5H) 2.27-2.35 (m, 0.5H) 2.57-2.66 (m, 1H) 3.40-3.45 (m, 0.5H) 3 56-3.61 (m, 0.5H) 3.70-3.78 (m, 7.5H) 3.82-3.95 (m, 1.5H) 4.48 (td, 2H) 5.10 (d, 2H) 5.45-5.58 (m, 1H) 6.46 (tt, 1H) 6.87-6.92 (m, 2H) 7.05 (dd, 1H) 7.53 (td, 1H) 7.66 (t, 1H) 7.72 (dd, 1H) |

| | | | |
|---|---|---|---|
| 32 | 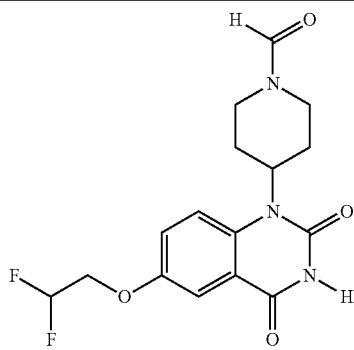 | 4-[6-(2,2-difluoro-ethoxy)-2,4-dioxo-3,4-dihydroquinazolin-1(2H)-yl]piperidine-1-carbaldehyde | ¹H NMR (600 MHz, DMSO-d₆) δ ppm 1.72-1.82 (m, 2H) 2.35-2.44 (m, 1H) 2.47-2.55 (m, 1H) 2.79 (td, 1H) 3.25 (td, 1H) 3.80 (d, 1H) 4.32 (d, 1H) 4.42 (td, 2H) 4.71 (brs, 1H) 6.40 (tt, 1H) 7.43 (dd, 1H) 7.55 (d, 1H) 7.74 (d, 1H) 8.03 (s, 1H) |
| 33 | 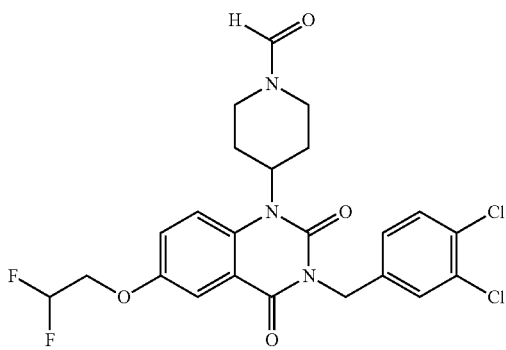 [SMILES: O=CN1CCC(n2c(=O)n(Cc3ccc(Cl)c(Cl)c3)c(=O)c3cc(OCC(F)F)ccc32)CC1] | 4-[3-(3,4-dichloro-benzyl)-6-(2,2-difluoroethoxy)-2,4-dioxo-3,4-dihydroquinazolin-1(2H)-yl]piperidine-1-carbaldehyde | ¹H NMR (500 MHz, DMSO-d₆) δ ppm 1.80 (dd, 2H) 2.32-2.43 (m, 1H) 2.44-2.52 (m, 1H) 2.80 (td, 1H) 3.26 (dt, 1H) 3.80 (brd, 1H) 4.31 (br d, 1H) 4.44 (td, 2H) 4.78 (brs, 1H) 5.09 (s, 2H) 6.41 (tt, 1H) 7.30 (dd, 1H) 7.49 (dd, 1H) 7.58 (d, 1H) 7.60 (d, 1H) 7.62 (d, 1H) 7.81 (d, 1H) 8.03 (s, 1H) |
| 34 | 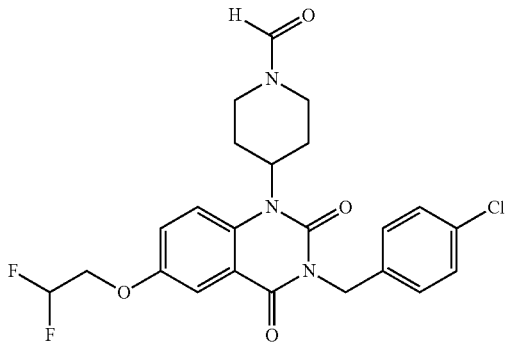 [SMILES: O=CN1CCC(n2c(=O)n(Cc3ccc(Cl)cc3)c(=O)c3cc(OCC(F)F)ccc32)CC1] | 4-[3-(4-chlorobenzyl)-6-(2,2-difluoroethoxy)-2,4-dioxo-3,4-dihydroquinazolin-1(2H)-yl]piperidine-1-carbaldehyde | ¹H NMR (500 MHz, DMSO-d6) δ ppm 1.72-1.83 (m, 2H) 2.32-2.44 (m, 1 H) 2.45-2.53 (m, 1H) 2.80 (dt, 1H) 3.25-3.30 (dt, 1H) 3.80 (d, 1H) 4.30 (d, 1H) 4.44 (td, 2H) 4.78 (brs, 1H) 5.09 (s, 2H) 6.42 (tt, 1H) 7.32-7.40 (m, 4H) 7.48 (dd, 1H) 7.61 (d, 1H) 7.81 (d, 1H) 8.03 (s, 1H) |
| 35 | 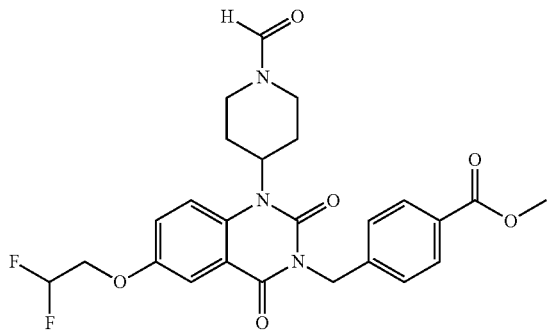 [SMILES: COC(=O)c1ccc(Cn2c(=O)c3cc(OCC(F)F)ccc3n(C3CCN(C=O)CC3)c2=O)cc1] | Methyl 4-{[6-(2,2-difluoroethoxy)-1-(1-formylpiperidin-4-yl)-2,4-dioxo-1,4-dihydro-quinazolin-3(2H)-yl]methyl}benzoate | ¹H NMR (500 MHz, DMSO-d₆) δ ppm 1.78 (dd, 1H) 2.33-2.42 (m, 1H) 2.44-2.52 (m, 1H) 2.80 (dt, 1H) 3.26 (dt, 1H) 3.79 (brd, 1H) 3.84 (s, 3H) 4.30 (brd, 1H) 4.45 (td, 2H) 4.79 (brs, 1H) 5.18 (s, 2H) 6.42 (tt, 1H) 7.43 (d, 2H) 7.49 (dd, 1H) 7.62 (d, 1H) 7.83 (d, 1H) 7.91 (d, 2H) 8.02 (s, 1H) |

| | | | |
|---|---|---|---|
| 36 | 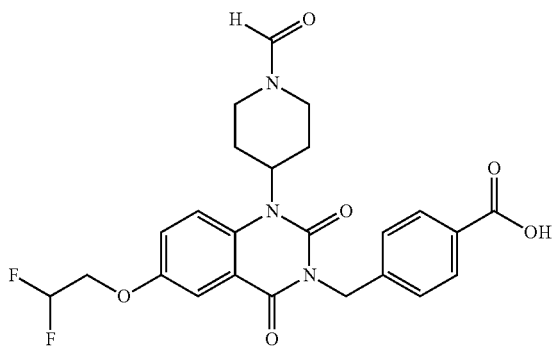 [SMILES: O=CN1CCC(n2c(=O)n(Cc3ccc(C(=O)O)cc3)c(=O)c3cc(OCC(F)F)ccc32)CC1] | 4-{[6-(2,2-difluoro-ethoxy)-1-(1-formylpiperidin-4-yl)-2,4-dioxo-1,4-dihydroquinazolin-3(2H)-yl]methyl} benzoic acid | $^1$H NMR (500 MHz, DMSO-d$_6$) δ ppm 1.79 (dd, 2H) 2.38 (qd, 1H) 2.49 (qd, 1H) 2.80 (dt, 1H) 3.26 (dt, 1H) 3.79 (d, 1H) 4.31 (d, 1H) 4.45 (td, 2H) 4.79 (brs, 1H) 5.17 (s, 2H) 6.42 (tt, 1H) 7.40 (d, 2H) 7.49 (dd, 1H) 7.62 (d, 1H) 7.83 (d, 1H) 7.88 (d, 2H) 8.02 (s, 1H) 12.94 (brs, 1H) |
| 37 | 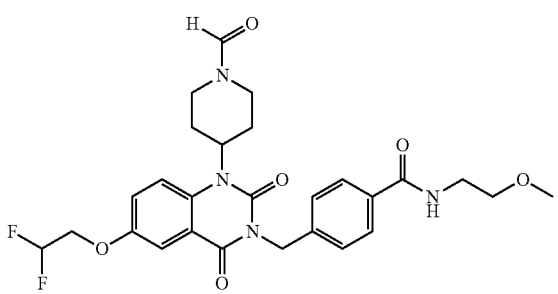 [SMILES: COCCNC(=O)c1ccc(Cn2c(=O)c3cc(OCC(F)F)ccc3n(C3CCN(C=O)CC3)c2=O)cc1] | 4-{[6-(2,2-difluoro-ethoxy)-1-(1-formylpiperidin-4-yl)-2,4-dioxo-1,4-dihydroquinazolin-3(2H)-yl]methyl}-N-(2-methoxyethyl) benzamide | $^1$H NMR (500 MHz, DMSO-d$_6$) δ ppm 1.72-1.82 (m, 2H) 2.32-2.42 (m, 1H) 2.44-2.54 (m, 1H) 2.75-2.83 (m, 1H) 3.21-3.29 (m, 4H) 3.37-3.45 (m, 4H) 3.77 (br. d., 1H) 4.29 (br. d., 1H) 4.44 (td, 2H) 4.78 (br. s., 1H) 5.14 (s, 2H) 6.41 (tt, 1H) 7.35 (m, 2H) 7.48 (dd, 1H) 7.61 (d, 1H) 7.77 (m, 2H) 7.81 (d, 1H) 8.01 (s, 1H) 8.47 (t, 1H) |
| 38 | 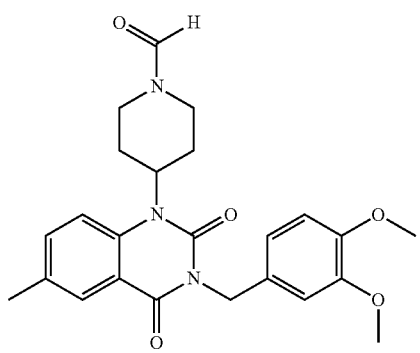 | 4-[3-(3,4-dimethoxy-benzyl)-6-methyl-2,4-dioxo-3,4-dihydroquinazolin-1(2H)-yl]piperidine-1-carbaldehyde | $^1$H NMR (500 MHz, DMSO-d$_6$) δ ppm 1.76 (dd, 2H) 2.37 (s, 3H) 2.39-2.42 (m, 1H) 2.50-2.54 (m, 1H) 2.77-2.82 (m, 1H) 3.19-3.30 (m, 1H) 3.70 (s, 6H) 3.79 (d, 1H) 4.30 (d, 1H) 4.76 (brs, 1H) 5.02 (s, 2H) 6.82 (dd, 1H) 6.85 (d, 1H) 6.97 (d, 1H) 7.60 (dd, 1H) 7.71 (d, 1H) 7.89 (s, 1H) 8.03 (s, 1H) |
| 39 | 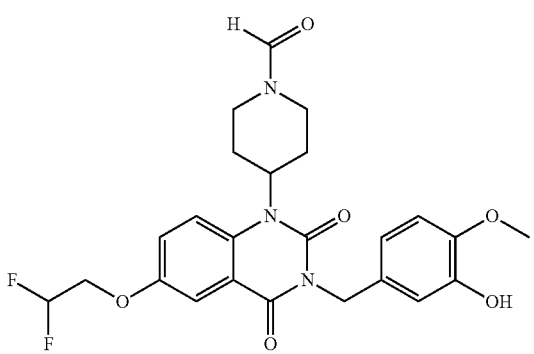 [SMILES: COc1ccc(Cn2c(=O)c3cc(OCC(F)F)ccc3n(C3CCN(C=O)CC3)c2=O)cc1O] | 4-[6-(2,2-difluoro-ethoxy)-3-(3-hydroxy-4-methoxybenzyl)-2,4-dioxo-3,4-dihydro-quinazolin-1(2H)-yl]piperidine-1-carbaldehyde | $^1$H NMR (500 MHz, DMSO-d$_6$) δ ppm 1.70-1.80 (m, 2H) 2.35-1.45 (m, 1H) 2.47-2.56 (m, 1H) 2.80 (dt, 1H) 3.25 (dt, 1H) 3.70 (s, 3H) 3.79 (brd, 1H) 4.30 (brd, 1H) 4.43 (td, 2H) 4.77 (brs, 1H) 4.96 (s, 2H) 6.41 (tt, 1H) 6.73 (d, 1H) 6.78-6.82 (m, 2H) 7.46 (dd, 1H) 7.60 (d, 1H) 7.79 (d, 1H) 8.03 (s, 1H) 8.95 (s, 1H) |
| 40 | 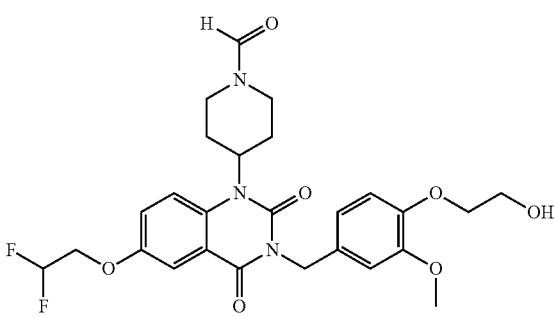 [SMILES: COc1cc(Cn2c(=O)c3cc(OCC(F)F)ccc3n(C3CCN(C=O)CC3)c2=O)ccc1OCCO] | 4-[6-(2,2-difluoro-ethoxy)-3-[3-(2-hydroxyethoxy)-4-methoxybenzyl]-2,4-dioxo-3,4-dihydroquinazolin-1(2H)-yl]piperidine-1-carbaldehyde | $^1$H NMR (600 MHz, DMSO-d6) δ ppm 1.76 (dd, 2H) 2.35-2.45 (m, 1H) 2.50-2.54 (m, 1H) 2.79 (dt, 1H) 3.25 (dt, 1H) 3.68 (dt, 2H) 3.70 (s, 3H) 3.79 (brd, 1H) 3.90 (t, 2H) 4.30 (brd, 1H) 4.42 (td, 2H) 4.75 (brs, 1H) 4.77 (t, 1H) 5.01 (s, 2H) 6.39 (tt, 1H) 6.85 (m, 2H) 6.97 (s, 1H) 7.45 (dd, 1H) 7.60 (d, 1H) 7.77 (d, 1H) 8.02 (s, 1H) |

| | | | |
|---|---|---|---|
| 41 | 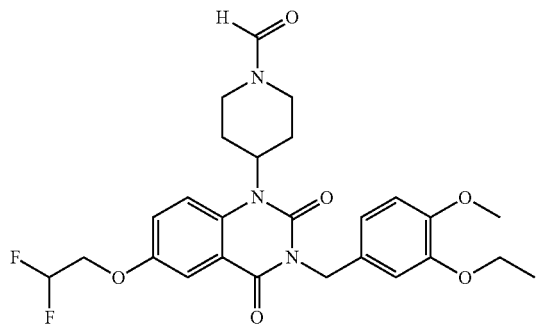 [SMILES: CCOc1cc(Cn2c(=O)c3cc(OCC(F)F)ccc3n(C3CCN(C=O)CC3)c2=O)ccc1OC] | 4-[6-(2,2-difluoro-ethoxy)-3-(3-ethoxy-4-methoxy-benzyl)-2,4-dioxo-3,4-dihydroquinazolin-1(2H)-yl]piperidine-1-carbaldehyde | ¹H NMR (600 MHz, DMSO-d₆) δ ppm 1.29 (t, 3H) 1.76 (dd, 2H) 2.33-2.45 (m, 1H) 2.50-2.56 (m, 1H) 2.76-2.82 (m, 1H) 3.21-3.31 (m, 1H) 3.70 (s, 3H) 3.79 (brd, 1H) 3.94 (q, 2H) 4.30 (brd, 1H) 4.41 (dt, 2H) 4.75 (brs, 1H) 5.01 (s, 2H) 6.39 (tt, 1H) 6.81-6.86 (m, 2H) 6.96 (s, 1H) 7.45 (dd, 1H) 7.60 (d, 1H) 7.77 (d, 1H) 8.02 (s, 1H) |
| 42 | 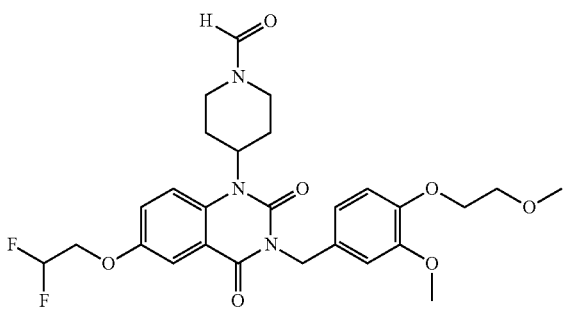 [SMILES: COCCOc1ccc(Cn2c(=O)c3cc(OCC(F)F)ccc3n(C3CCN(C=O)CC3)c2=O)cc1OC] | 4-[6-(2,2-difluoro-ethoxy)-3-[4-methoxy-3-(2-methoxyethoxy)benzyl]-2,4-dioxo-3,4-dihydro-quinazolin-1(2H)-yl]piperidine-1-carbaldehyde | ¹H NMR (600 MHz, DMSO-d₆) δ ppm 1.69-1.82 (m, 2H) 2.35-2.45 (m, 1H) 2.45-2.55 (m, 1H) 2.78 (t, 1H) 3.21-3.28 (m, 1H) 3.61 (brs, 2H) 3.70 (s, 3H) 3.78 (d, 1H) 4.00 (brs, 2H) 4.30 (d, 1H) 4.42 (t, 2H) 4.75 (brs, 1H) 5.01 (s, 2H) 6.39 (t, 1H) 6.82-6.88 (m, 2H) 6.97 (s, 1H) 7.45 (d, 1H) 7.59 (s, 1H) 7.77 (d, 1H) 8.02 (s, 1H) |
| 43 | 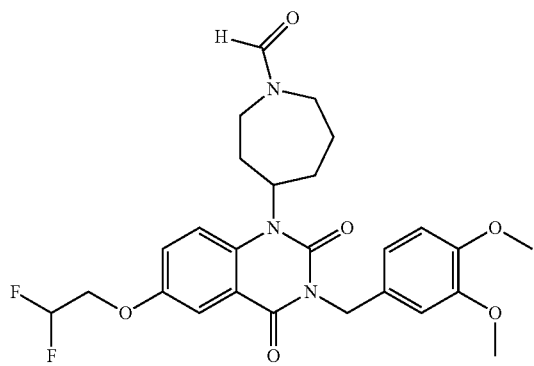 [SMILES: COc1ccc(Cn2c(=O)c3cc(OCC(F)F)ccc3n(C3CCCN(C=O)CC3)c2=O)cc1OC] | 4-[6-(2,2-difluoro-ethoxy)-3-(3,4-dimethoxybenzyl)-2,4-dioxo-3,4-dihydroquinazolin-1(2H)-yl]azepane-1-carbaldehyde | ¹H NMR (500 MHz, DMSO-d₆) mixture of two isomers δ ppm 1.72-1.81 (m, 1H) 1.85 (brd, 1H) 1.86-2.03 (m, 2H) 2.47 (brs, 2H) 3.30-3.40 (m, 1H) 3.42-3.52 (m, 1H) 3.58-3.64 (m, 2H) 3.70 (s, 3H) 3.71 (s, 3H) 4.42 (td, 2H) 4.45 (brs, 0.5H) 5.04 (brs, 2H) 5.21 (brs, 0.5H) 6.40 (tt, 1H) 6.78-6.83 (m, 1H) 6.86 (d, 1H) 6.98 (s, 1H) 7.38-7.48 (m, 1H) 7.59 (brs, 1H) 7.64-7.74 (m, 1H) 8.08 (brs, 0.5H) 8.12 (s, 0.5H) |
| 44 | 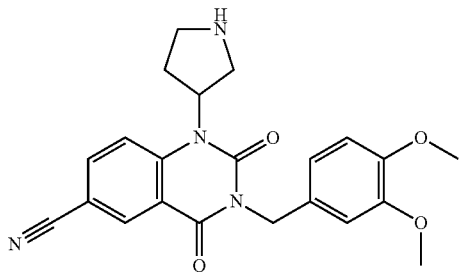 [SMILES: COc1ccc(Cn2c(=O)c3cc(C#N)ccc3n(C3CCNC3)c2=O)cc1OC] | 3-(3,4-dimethoxy-benzyl)-2,4-dioxo-1-(pyrrolidin-3-yl)-1,2,3,4-tetrahydro-quinazoline-6-carbonitrile | ¹H NMR (600 MHz, DMSO-d₆) δ ppm 1.96-2.09 (m, 2H) 2.78-2.84 (m, 1H) 3.05-3.12 (m, 2H) 3.18-3.27 (m, 1H) 3.70 (s, 3H) 3.71 (s, 3H) 5.04 (s, 2H) 5.47-5.53 (m, 1H) 6.83 (brs, 2H) 6.99 (s, 1H) 8.15 (dd, 1H) 8.20 (d, 1H) 8.47 (d, 1H) |
| 45 | 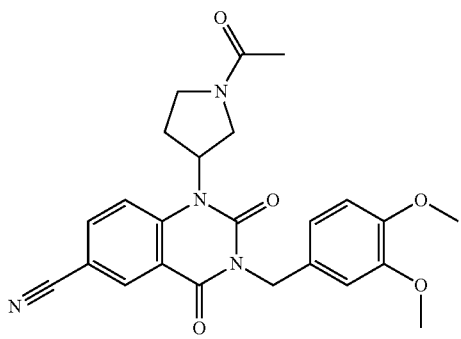 [SMILES: COc1ccc(Cn2c(=O)c3cc(C#N)ccc3n(C3CCN(C(C)=O)C3)c2=O)cc1OC] | 1-(1-acetylpyrrolidin-3-yl)-3-(3,4-dimethoxybenzyl)-2,4-dioxo-1,2,3,4-tetrahydro-quinazoline-6-carbonitrile | ¹H NMR (600 MHz, DMSO-d₆) mixture of two isomers δ ppm 1.91 (s, 1.5H) 1.98 (s, 1.5H) 2.14-2.22 (m, 0.5H) 2.25-2.32 (m, 0.5H) 2.43-2.50 (m, 0.5H) 2.52-2.58 (m, 0.5H) 3.31-3.39 (m, 0.5H) 3.50-3.55 (m, 0.5H) 3.63-3.73 (m, 7.5H) 3.79-3.87 (m, 1.5H) 5.00-5.06 (m, 2H) 5.43-5.55 (m, 1H) 6.82-6.90 (m, 2H) 6.98 (d, 1H) 7.84 (dd, 1H) 8.17 (dt, 1H) 8.43 (dd, 1H) |

| | | | |
|---|---|---|---|
| 46 | 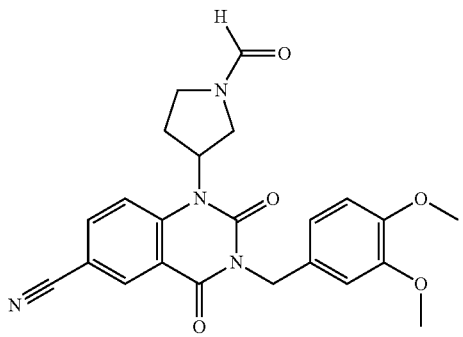 [SMILES: COc1ccc(Cn2c(=O)c3cc(C#N)ccc3n(C3CCN(C=O)C3)c2=O)cc1OC] | 3-(3,4-dimethoxy-benzyl)-1-(1-formylpyrrolidin-3-yl)-2,4-dioxo-1,2,3,4-tetrahydro-quinazoline-6-carbonitrile | $^1$H NMR (500 MHz, DMSO-$d_6$) mixture of two isomers δ ppm 2.19-2.27 (m, 1H) 2.36-2.43 (m, 1H) 3.43-3.47 (m, 0.4H) 3.53-3.59 (m, 0.6) 3.62-3.73 (m, 1.6H) 3.70 (s, 3H) 3.71 (s, 3H) 3.84-3.94 (m, 1.4H) 5.04 (s, 2H) 5.42-5.49 (m, 0.4H) 5.50-5.56 (m, 0.6H) 6.86 (s, 2H) 6.99 (s, 1H) 7.85 (d, 0.6H) 7.90 (d, 0.4H) 8.15-8.22 (m, 2H) 8.45 (s, 1H) |
| 47 | 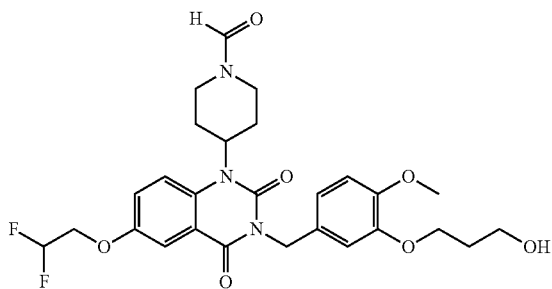 [SMILES: COc1ccc(Cn2c(=O)c3cc(OCC(F)F)ccc3n(C3CCN(C=O)CC3)c2=O)cc1OCCCO] | 4-[6-(2,2-difluoro-ethoxy)-3-[3-(3-hydroxypropoxy)-4-methoxybenzyl]-2,4-dioxo-3,4-dihydroquinazolin-1(2H)-yl]piperidine-1-carbaldehyde | $^1$H NMR (600 MHz, DMSO-$d_6$) δ ppm 1.72-1.79 (m, 2H) 1.82 (q, 2H) 2.36-2.44 (m, 1H) 2.49-2.55 (m, 1H) 2.78 (td, 1H) 3.25 (td, 1H) 3.51-3.54 (m, 2H) 3.70 (s, 3H) 3.76-3.80 (m, 1H) 3.95 (t, 2H) 4.28-4.32 (m, 1H) 4.41 (td, 2H) 4.47 (t, 1H) 4.75 (s, 1H) 5.01 (s, 2H) 6.39 (tt, 1H) 6.81-6.86 (m, 2H) 6.96-6.97 (m, 1H) 7.45 (dd, 1H) 7.59 (d, 1H) 7.77 (d, 1H) 8.02 (s, 1H) |
| 48 | 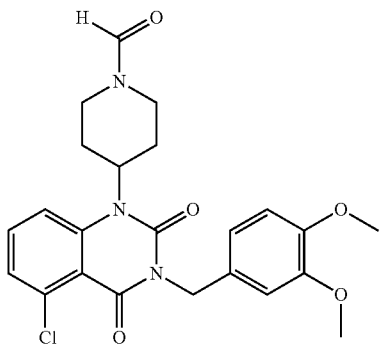 [SMILES: COc1ccc(Cn2c(=O)c3c(Cl)cccc3n(C3CCN(C=O)CC3)c2=O)cc1OC] | 4-[5-chloro-3-(3,4-dimethoxy benzyl)-2,4-dioxo-3,4-dihydro-quinazolin-1(2H)-yl]piperidine-1-carbaldehyde | $^1$H NMR (500 MHz, DMSO-$d_6$) δ ppm 1.78-1.88 (m, 2H) 2.34-2.44 (m, 1H) 2.46-2.56 (m, 1H) 2.80 (t, 1H) 3.25 (t, 1H) 3.71 (s, 6H) 3.80 (d, 1H) 4.31 (d, 1H) 4.71 (brs, 1H) 5.00 (s, 2H) 6.83 (d, 1H) 6.87 (d, 1H) 6.97 (s, 1H) 7.37 (d, 1H) 7.69 (dd, 1H) 7.77 (d, 1H) 8.03 (s, 1H) |
| 49 | 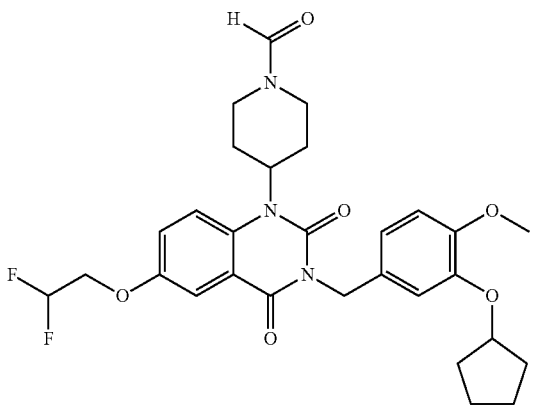 [SMILES: COc1ccc(Cn2c(=O)c3cc(OCC(F)F)ccc3n(C3CCN(C=O)CC3)c2=O)cc1OC1CCCC1] | 4-{3-[3-(cyclo-pentyloxy)-4-methoxybenzyl]-6-(2,2-difluoro-ethoxy)-2,4-dioxo-3,4-dihydroquinazolin-1(2H)-yl}-piperidine-1-carbaldehyde | $^1$H NMR (500 MHz, DMSO-$d_6$) δ ppm 1.5-1.6 (m, 2H) 1.63-1.71 (m, 3H) 1.68-1.78 (m, 1H) 1.78-1.98 (m, 3H) 2.35-2.46 (m, 1H) 2.47-2.57 (m, 1H) 2.79 (dt, 1H) 3.26 (dt, 1H) 3.69 (s, 3H) 3.79 (br. d., 1H) 4.30 (br. d., 1H) 4.43 (td, 2H) 4.66-4.70 (m, 1H) 4.76 (br. s., 1H) 5.01 (s, 2H) 6.41 (tt, 1H) 6.82-6.86 (m, 2H) 6.96 (s, 1H) 7.46 (dd, 1H) 7.6 (d, 1H) 7.80 (d, 1H) 8.03 (s, 1H) |

| | | | |
|---|---|---|---|
| 50 | 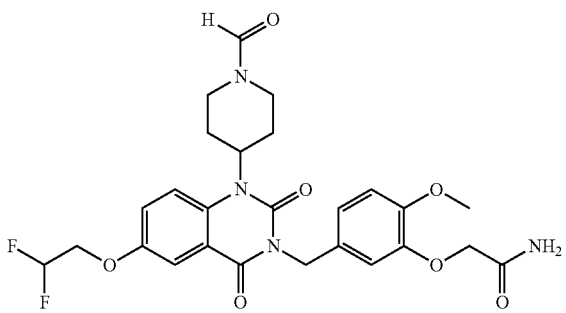 [SMILES: COc1ccc(Cn2c(=O)c3cc(OCC(F)F)ccc3n(C3CCN(C=O)CC3)c2=O)cc1OCC(N)=O] | 2-(5-{[6-(2,2-difluoro-ethoxy)-1-(1-formylpiperidin-4-yl)-2,4-dioxo-1,4-dihydroquinazolin-3(2H)-yl]-methyl}-2-methoxyphenoxy)-acetamide | $^1$H NMR (500 MHz, DMSO-d$_6$) δ ppm 1.72-1.82 (m, 2H) 2.35-2.45 (m, 1H) 2.46-2.56 (m, 1H) 2.79 (td, 1H) 3.25 (td, 1H) 3.74 (s, 3H) 3.79 (d, 1H) 4.31 (d, 1H) 4.35 (s, 2H) 4.43 (td, 2H) 4.76 (brs, 1H) 5.00 (s, 2H) 6.41 (tt, 1H) 6.88-6.95 (m, 3H) 7.31 (brs, 1H) 7.37 (brs, 1H) 7.46 (dd, 1H) 7.59 (d, 1H) 7.79 (d, 1H) 8.02 (s, 1H) |
| 51 | 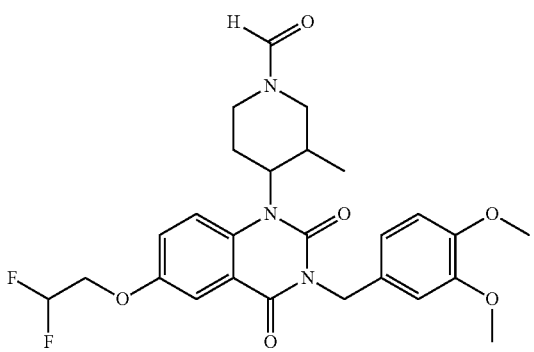 [SMILES: COc1ccc(Cn2c(=O)c3cc(OCC(F)F)ccc3n(C3CCN(C=O)CC3C)c2=O)cc1OC] | 4-[6-(2,2-difluoro-ethoxy)-3-(3,4-dimethoxybenzyl)-2,4-dioxo-3,4-dihydroquinazolin-1(2H)-yl]-3-methylpiperidine-1-carbaldehyde | $^1$H NMR (500 MHz, DMSO-d$_6$) mixture of two isomers δ ppm 0.92 (t, 3H) 1.72-1.82 (m, 1H) 2.23 (brs, 1H) 2.70-2.77 (m, 0.5H) 3.00-3.10 (m, 0.5H) 3.12-3.20 (m, 1.5H) 3.44 (d, 0.5H) 3.63 (dd, 0.5H) 3.69 (s, 6H) 3.80 (d, 0.5H) 4.04 (d, 0.5H) 4.29 (d, 0.5H) 4.43 (td, 2H) 4.62-4.70 (m, 1H) 5.03 (s, 2H) 6.41 (tt, 1H) 6.80 (dd, 1H) 6.85 (d, 1H) 6.97 (d, 1H) 7.46 (dd, 1H) 7.60 (d, 1H) 7.64 (dd, 1H) 7.97 (s, 0.5H) 8.11 (s, 0.5H) |
| 52 | 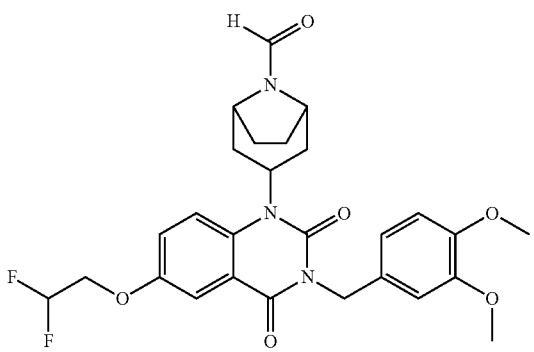 [SMILES: COc1ccc(Cn2c(=O)c3cc(OCC(F)F)ccc3n(C3CC4CCC(C3)N4C=O)c2=O)cc1OC] | 3-[6-(2,2-difluoro-ethoxy)-3-(3,4-dimethoxybenzyl)-2,4-dioxo-3,4-dihydroquinazolin-1(2H)-yl]-8-azabicyclo[3.2.1]octane-8-carbaldehyde | $^1$H NMR (600 MHz, DMSO-d$_6$) δ ppm 1.85-1.95 (m, 4H) 2.18 (t, 2H) 2.27-2.33 (m, 1H) 2.34-2.41 (m, 1H) 3.70 (s, 1H) 3.71 (s, 1H) 4.25-4.29 (m, 1H) 4.40 (td, 2H) 4.50-4.54 (m, 1H) 4.55 (br. s., 1H) 5.05 (s, 2H) 6.38 (tt, H) 6.80 (d, 1H) 6.85 (d, 1H) 6.98 (s, 1H) 7.45 (dd, 1H) 7.56 (d, 1H) 7.58 (d, 1H) 8.12 (s, 1H) |
| 53 | 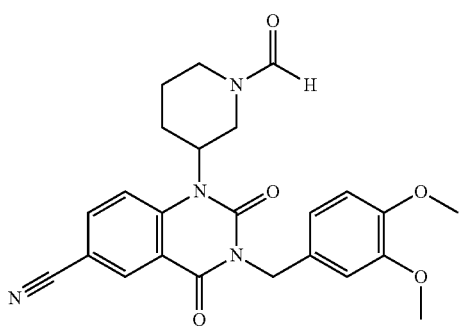 [SMILES: COc1ccc(Cn2c(=O)c3cc(C#N)ccc3n(C3CCCN(C=O)C3)c2=O)cc1OC] | 3-(3,4-dimethoxy-benzyl)-1-(1-formylpiperidin-3-yl)-2,4-dioxo-1,2,3,4-tetrahydro-quinazoline-6-carbonitrile | $^1$H NMR (500 MHz, DMSO-d$_6$) mixture of two isomers δ ppm 1.52-1.63 (m, 0.5H) 1.65-1.73 (m, 0.5H) 1.74-1.83 (m, 1H) 1.87-1.93 (m, 1H) 2.54-2.64 (m, 1.5H) 3.06 (dt, 0.5H) 3.57 (t, 0.5H) 3.70 (s, 3H) 3.71 (s, 3H) 3.79 (dd, 0.5H) 4.03 (t, 0.5H) 4.20 (d, 0.5H) 4.30 (d, 0.5H) 4.38 (brs, 0.5H) 4.53 (brs, 0.5H) 4.99-5.07 (m, 2H) 6.84-6.88 (m, 2H) 6.98 (s, 1H) 7.86 (d, 0.5H) 8.01 (d, 0.5H) 7.98 (s, 0.5H) 8.08 (s, 0.5H) 8.14-8.18 (m, 1H) 8.44 (s, 1H) |

| | | | |
|---|---|---|---|
| 54 | 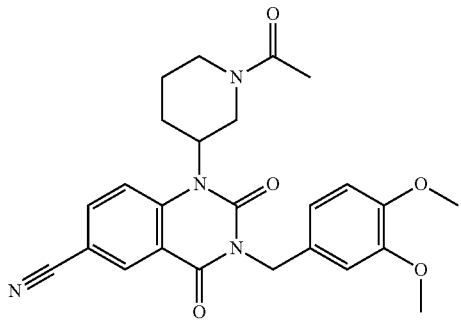 [SMILES: COc1ccc(Cn2c(=O)c3cc(C#N)ccc3n(C3CCCN(C(C)=O)C3)c2=O)cc1OC] | 1-(1-acetylpiperidin-3-yl)-3-(3,4-dimethoxybenzyl)-2,4-dioxo-1,2,3,4-tetrahydroquinazoline-6-carbonitrile | $^1$H NMR (500 MHz, DMSO-d$_6$) mixture of two isomers δ ppm 1.56-1.66 (m, 0.5H) 1.70-1.82 (m, 1.5H) 1.87 (brd, 1H) 1.97 (s, 1.5H) 2.05 (s, 1.5H) 2.54 (dd, 1H) 3.05 (brt, 0.5H) 3.48 (t, 0.5H) 3.70-3.72 (m, 6H) 3.83 (d, 0.5H) 3.94 (brd, 0.5H) 4.04 (t, 0.5H) 4.33 (brs, 0.5H) 4.45 (dd, 1H) 4.53 (brs, 0.5H) 4.99-5.07 (m, 2H) 6.83-6.87 (m, 2H) 6.98 (d, 1H) 7.84 (d, 0.5H) 8.02 (d, 0.5H) 8.16 (dt, 1H) 8.44 (dd, 1H) |
| 55 | 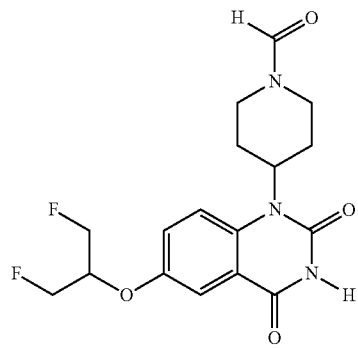 [SMILES: O=CN1CCC(n2c(=O)[nH]c(=O)c3cc(OC(CF)CF)ccc32)CC1] | 4-{6-[2-fluoro-1-(fluoromethyl)ethoxy]-2,4-dioxo-3,4-dihydroquinazolin-1(2H)-yl}piperidine-1-carbaldehyde | $^1$H NMR (600 MHz, DMSO-d$_6$) δ ppm 1.73-1.82 (m, 2H) 2.36-2.44 (m, 1H) 2.44-2.55 (m, 1H) 2.79 (td, 1H) 3.25 (td, 1H) 3.80 (brd, 1H) 4.32 (brd, 1H) 4.62-4.67 (m, 1H) 4.68-4.76 (m, 3H) 4.76-4.82 (m, 1H) 4.96-5.06 (m, 1H) 7.44 (dd, 1H) 7.61 (d, 1H) 7.73 (d, 1H) 8.03 (s, 1H) 11.46 (brs, 1H) |
| 56 | 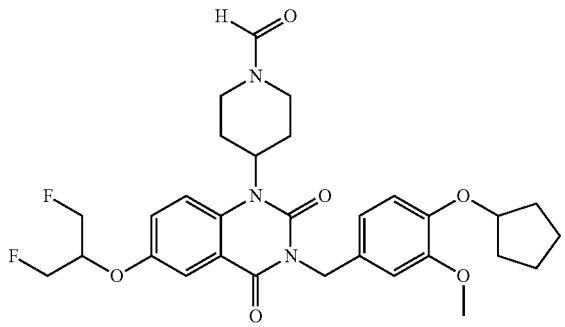 [SMILES: COc1cc(Cn2c(=O)c3cc(OC(CF)CF)ccc3n(C3CCN(C=O)CC3)c2=O)ccc1OC1CCCC1] | 4-{3-[4-(cyclopentyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | LCMS m/z [MH]+ 572 |
| 57 | 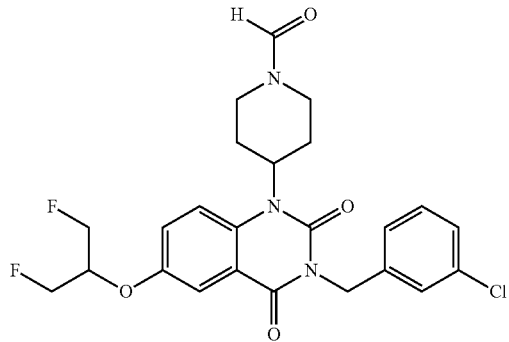 [SMILES: O=CN1CCC(n2c(=O)n(Cc3cccc(Cl)c3)c(=O)c3cc(OC(CF)CF)ccc32)CC1] | 4-[3-(3-chlorobenzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 492 |

-continued

| | | | |
|---|---|---|---|
| 58 | 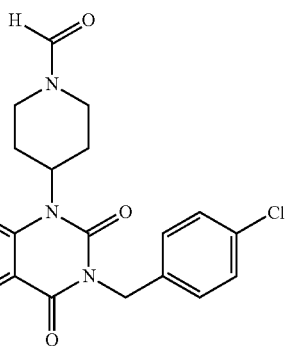 | 4-[3-(4-chlorobenzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 492 |
| 59 | 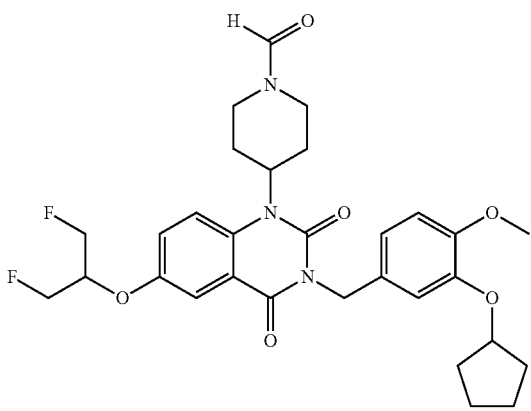 [SMILES: COc1ccc(Cn2c(=O)c3cc(OC(CF)CF)ccc3n(C3CCN(C=O)CC3)c2=O)cc1OC1CCCC1] | 4-{3-[3-(cyclopentyloxy)-4-methoxybenzyl]-6-[2-fluoro-1-(fluoromethyl)ethoxy]-2,4-dioxo-3,4-dihydroquinazolin-1(2H)-yl}piperidine-1-carbaldehyde | LCMS m/z [MH]+ 572 |
| 60 | 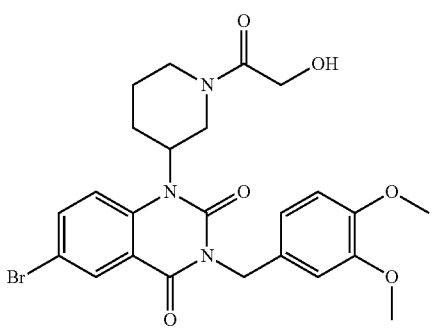 [SMILES: COc1ccc(Cn2c(=O)c3cc(Br)ccc3n(C3CCCN(C(=O)CO)C3)c2=O)cc1OC] | 6-bromo-3-(3,4-dimethoxybenzyl)-1-[1-(hydroxyacetyl)piperidin-3-yl]quinazoline-2,4(1H,3H)-dione | LCMS m/z [MH]+ 532 |
| 61 | 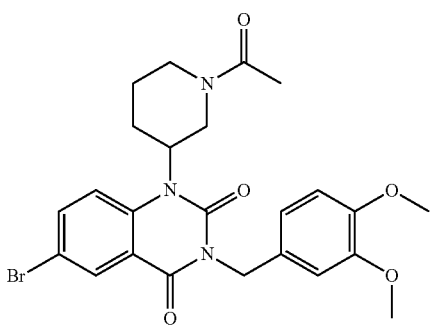 [SMILES: COc1ccc(Cn2c(=O)c3cc(Br)ccc3n(C3CCCN(C(C)=O)C3)c2=O)cc1OC] | 1-(1-acetylpiperidin-3-yl)-6-bromo-3-(3,4-dimethoxybenzyl)quinazoline-2,4(1H,3H)-dione | LCMS m/z [MH]+ 516 |

-continued

| | | | |
|---|---|---|---|
| 62 | 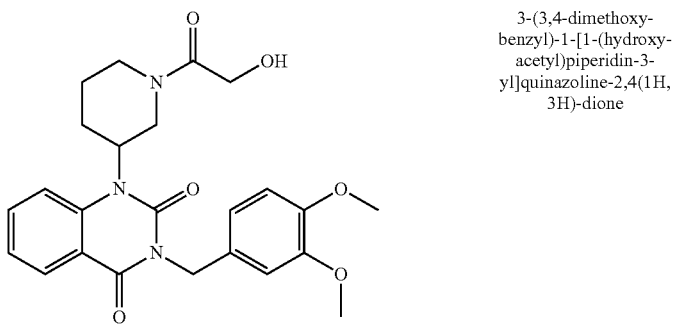 | 3-(3,4-dimethoxy-benzyl)-1-[1-(hydroxy-acetyl)piperidin-3-yl]quinazoline-2,4(1H,3H)-dione | LCMS m/z [MH]+ 454 |
| 63 | 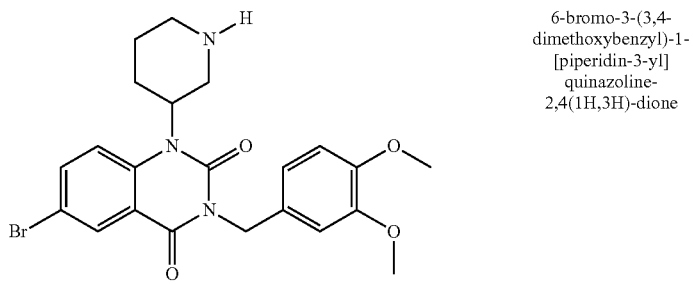 | 6-bromo-3-(3,4-dimethoxybenzyl)-1-[piperidin-3-yl]quinazoline-2,4(1H,3H)-dione | LCMS m/z [MH]+ 474 |
| 64 | 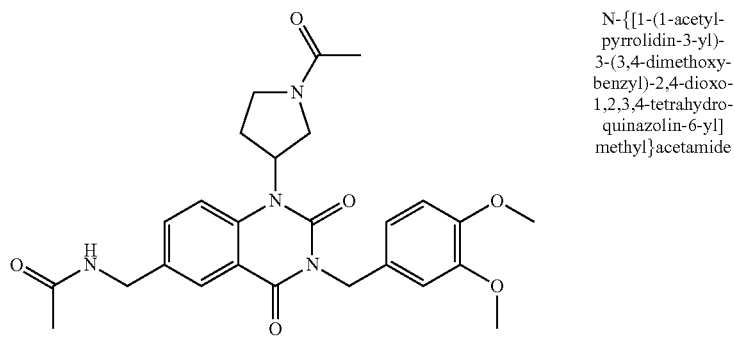 | N-{[1-(1-acetyl-pyrrolidin-3-yl)-3-(3,4-dimethoxy-benzyl)-2,4-dioxo-1,2,3,4-tetrahydro-quinazolin-6-yl]methyl}acetamide | LCMS m/z [MH]+ 495 |
| 65 | 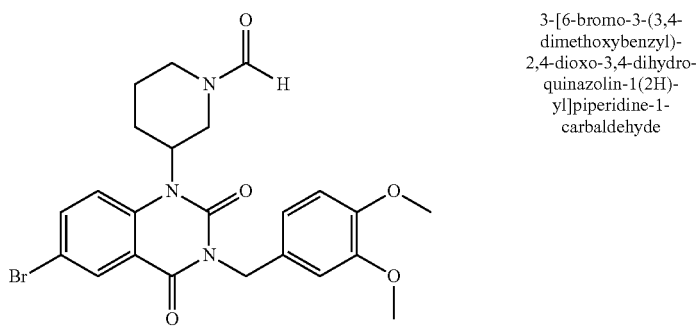 | 3-[6-bromo-3-(3,4-dimethoxybenzyl)-2,4-dioxo-3,4-dihydro-quinazolin-1(2H)-yl]piperidine-1-carbaldehyde | LCMS m/z [MH]+ 502 |
| 66 | 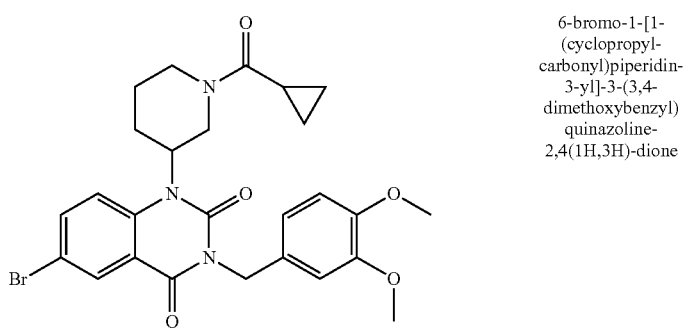 | 6-bromo-1-[1-(cyclopropyl-carbonyl)piperidin-3-yl]-3-(3,4-dimethoxybenzyl)quinazoline-2,4(1H,3H)-dione | LCMS m/z [MH]+ 542 |

| | | | |
|---|---|---|---|
| 67 | 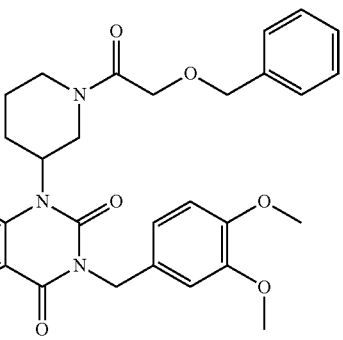 | 1-{1-[(benzyloxy)acetyl]piperidin-3-yl}-6-bromo-3-(3,4-dimethoxybenzyl)quinazoline-2,4(1H,3H)-dione | LCMS m/z [MH]+ 622 |
| 68 | 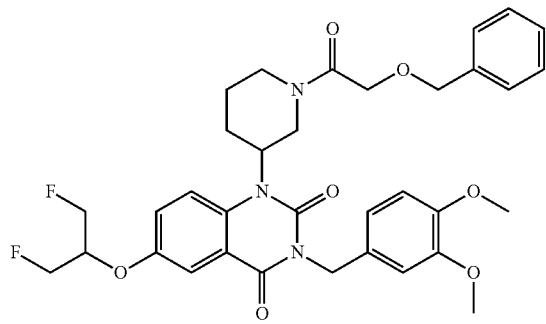 [SMILES: COc1ccc(Cn2c(=O)c3cc(OC(CF)CF)ccc3n(C3CCCN(C(=O)COCc4ccccc4)C3)c2=O)cc1OC] | 1-{1-[(benzyloxy)acetyl]piperidin-3-yl}-3-(3,4-dimethoxybenzyl)-6-[2-fluoro-1-(fluoromethyl)ethoxy]quinazoline-2,4(1H,3H)-dione | LCMS m/z [MH]+ 638 |
| 69 | 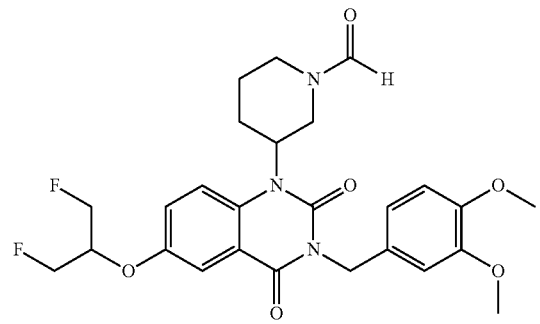 [SMILES: COc1ccc(Cn2c(=O)c3cc(OC(CF)CF)ccc3n(C3CCCN(C=O)C3)c2=O)cc1OC] | 3-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 518 |
| 70 | 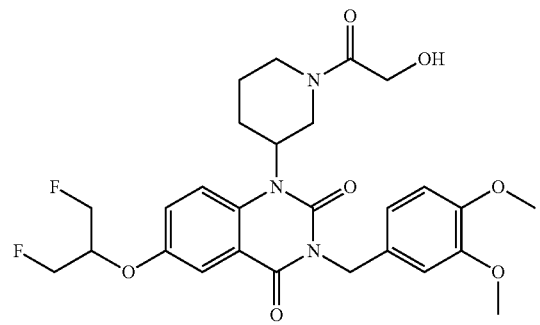 [SMILES: COc1ccc(Cn2c(=O)c3cc(OC(CF)CF)ccc3n(C3CCCN(C(=O)CO)C3)c2=O)cc1OC] | 3-(3,4-dimethoxybenzyl)-6-[2-fluoro-1-(fluoromethyl)ethoxy]-1-[1-(hydroxyacetyl)piperidin-3-yl]quinazoline-2,4(1H,3H)-dione | LCMS m/z [MH]+ 548 |
| 71 | 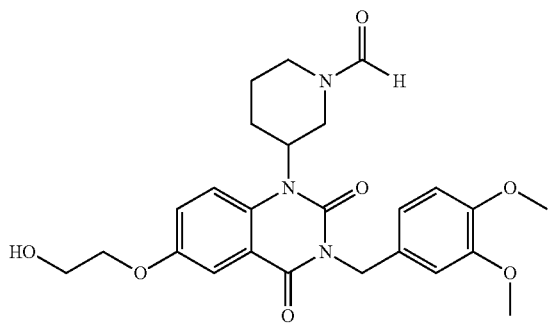 [SMILES: COc1ccc(Cn2c(=O)c3cc(OCCO)ccc3n(C3CCCN(C=O)C3)c2=O)cc1OC] | 3-[3-(3,4-dimethoxybenzyl)-6-(2-hydroxyethoxy)-2,4-dioxo-3,4-dihydroquinazolin-1(2H)-yl]piperidine-1-carbaldehyde | LCMS m/z [MH]+ 484 |

| | | | |
|---|---|---|---|
| 72 | 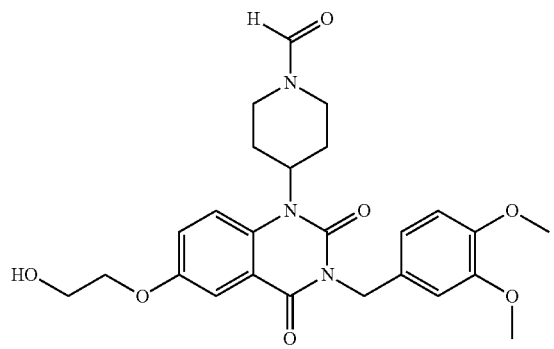 [SMILES: COc1ccc(Cn2c(=O)c3cc(OCCO)ccc3n(C3CCN(C=O)CC3)c2=O)cc1OC] | 4-[3-(3,4-dimethoxy-benzyl)-6-(2-hydroxyethoxy)-2,4-dioxo-3,4-dihydroquinazolin-1(2H)-yl]piperidine-1-carbaldehyde | LCMS m/z [MH]+ 484 |
| 73 | 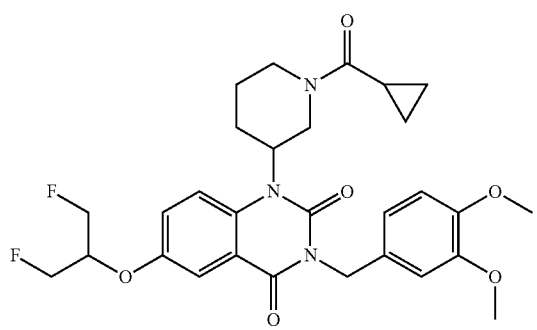 [SMILES: COc1ccc(Cn2c(=O)c3cc(OC(CF)CF)ccc3n(C3CCCN(C(=O)C4CC4)C3)c2=O)cc1OC] | 1-[1-(cyclopropyl-carbonyl)-piperidin-3-yl]-3-(3,4-dimethoxybenzyl)-6-[2-fluoro-1-(fluoromethyl)ethoxy]quinazoline-2,4(1H,3H)-dione | LCMS m/z [MH]+ 558 |
| 74 | 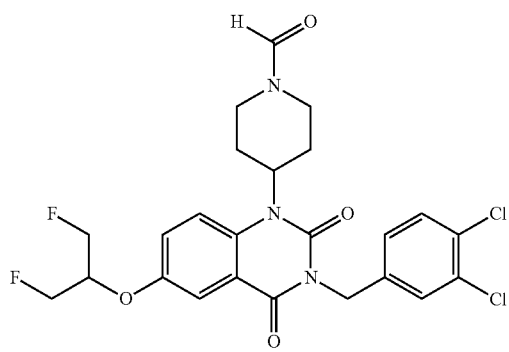 [SMILES: O=CN1CCC(n2c(=O)n(Cc3ccc(Cl)c(Cl)c3)c(=O)c3cc(OC(CF)CF)ccc32)CC1] | 4-[3-(3,4-dichloro-benzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 526 |
| 75 | 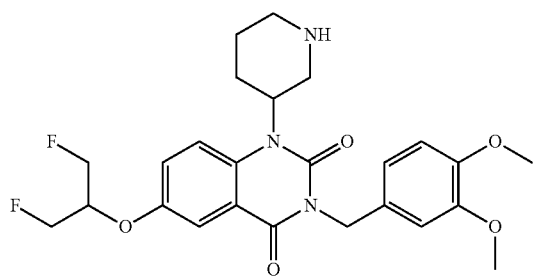 [SMILES: COc1ccc(Cn2c(=O)c3cc(OC(CF)CF)ccc3n(C3CCCNC3)c2=O)cc1OC] | 3-(3,4-dimethoxy-benzyl)-6-[2-fluoro-1-(fluoromethyl)ethoxy]-1-(piperidin-3-yl)quinazoline-2,4(1H,3H)-dione | LCMS m/z [MH]+ 490 |

| | | | |
|---|---|---|---|
| 76 | 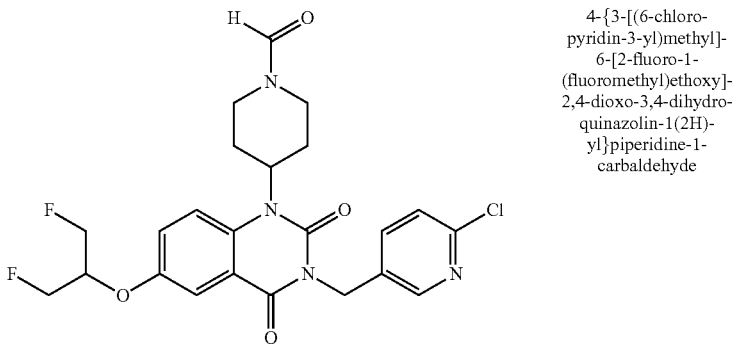 | 4-{3-[(6-chloro-pyridin-3-yl)methyl]-6-[2-fluoro-1-(fluoromethyl)ethoxy]-2,4-dioxo-3,4-dihydro-quinazolin-1(2H)-yl}piperidine-1-carbaldehyde | LCMS m/z [MH]+ 493 |
| 77 | 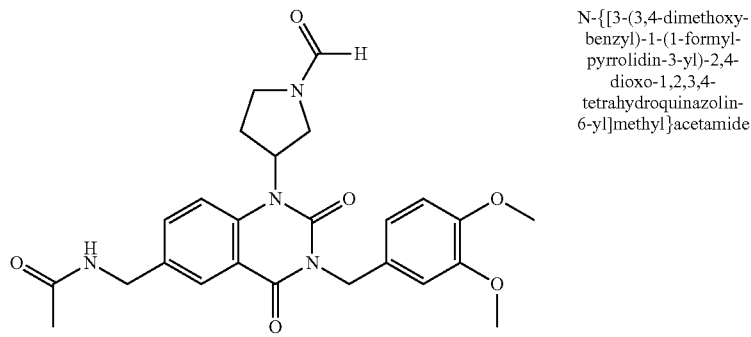 | N-{[3-(3,4-dimethoxy-benzyl)-1-(1-formyl-pyrrolidin-3-yl)-2,4-dioxo-1,2,3,4-tetrahydroquinazolin-6-yl]methyl}acetamide | LCMS m/z [MH]+ 481 |
| 78 | 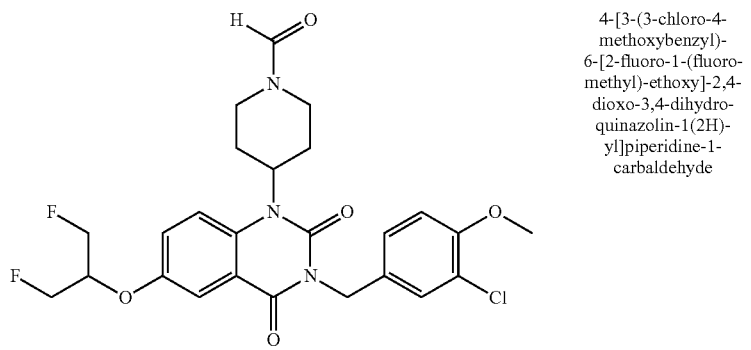 | 4-[3-(3-chloro-4-methoxybenzyl)-6-[2-fluoro-1-(fluoro-methyl)-ethoxy]-2,4-dioxo-3,4-dihydro-quinazolin-1(2H)-yl]piperidine-1-carbaldehyde | LCMS m/z [MH]+ 522 |
| 79 | 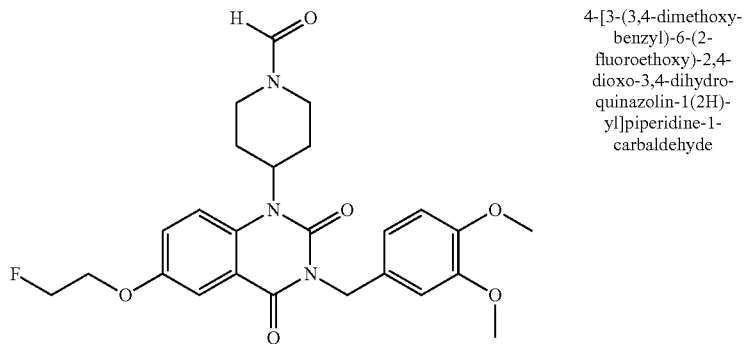 | 4-[3-(3,4-dimethoxy-benzyl)-6-(2-fluoroethoxy)-2,4-dioxo-3,4-dihydro-quinazolin-1(2H)-yl]piperidine-1-carbaldehyde | LCMS m/z [MH]+ 486 |
| 80 | 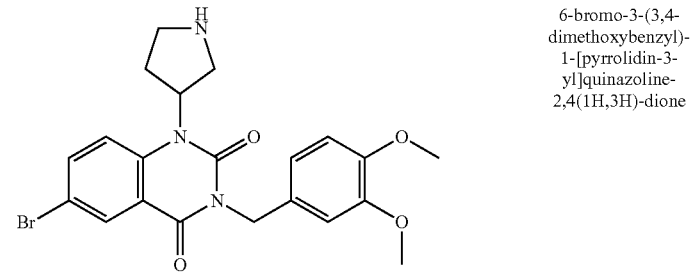 | 6-bromo-3-(3,4-dimethoxybenzyl)-1-[pyrrolidin-3-yl]quinazoline-2,4(1H,3H)-dione | LCMS m/z [MH]+ 460 |

-continued

| | | | |
|---|---|---|---|
| 81 | 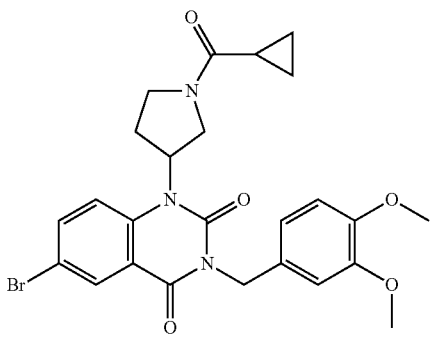 [SMILES: COc1ccc(Cn2c(=O)c3cc(Br)ccc3n(C3CCN(C(=O)C4CC4)C3)c2=O)cc1OC] | 6-bromo-1-[1-(cyclopropyl-carbonyl)pyrrolidin-3-yl]-3-(3,4-dimethoxybenzyl)quinazoline-2,4(1H,3H)-dione | LCMS m/z [MH]+ 528 |
| 82 | 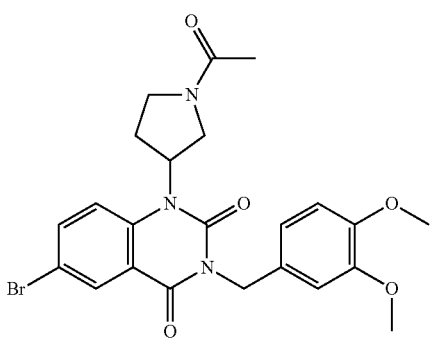 [SMILES: COc1ccc(Cn2c(=O)c3cc(Br)ccc3n(C3CCN(C(C)=O)C3)c2=O)cc1OC] | 1-(1-acetylpyrrolidin-3-yl)-6-bromo-3-(3,4-dimethoxybenzyl)-quinazoline-2,4(1H,3H)-dione | LCMS m/z [MH]+ 502 |
| 83 | 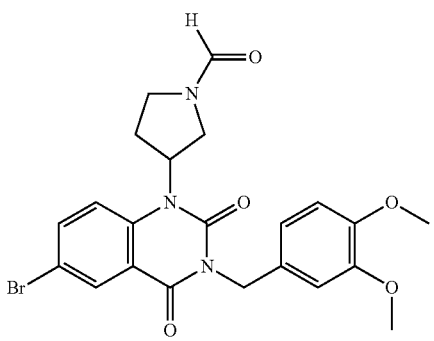 [SMILES: COc1ccc(Cn2c(=O)c3cc(Br)ccc3n(C3CCN(C=O)C3)c2=O)cc1OC] | 3-[6-bromo-3-(3,4-dimethoxy-benzyl)-2,4-dioxo-3,4-dihydroquinazolin-1(2H)-yl]pyrrolidine-1-carbaldehyde | LCMS m/z [MH]+ 488 |
| 84 | 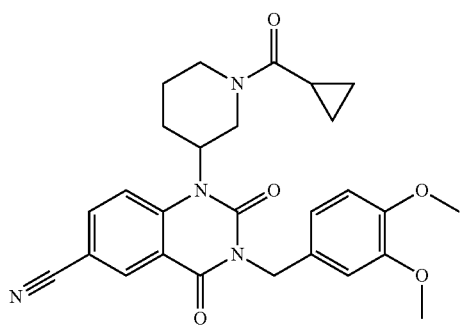 [SMILES: COc1ccc(Cn2c(=O)c3cc(C#N)ccc3n(C3CCCN(C(=O)C4CC4)C3)c2=O)cc1OC] | 1-[1-(cyclopropyl-carbonyl)-piperidin-3-yl]-3-(3,4-dimethoxybenzyl)-2,4-dioxo-1,2,3,4-tetrahydroquinazoline-6-carbonitrile | LCMS m/z [MH]+ 489 |
| 85 | 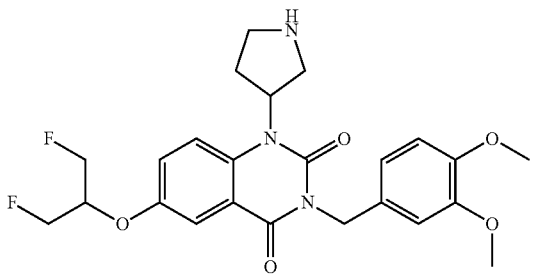 [SMILES: COc1ccc(Cn2c(=O)c3cc(OC(CF)CF)ccc3n(C3CCNC3)c2=O)cc1OC] | 3-(3,4-dimethoxy-benzyl)-6-[2-fluoro-1-(fluoromethyl)ethoxy]-1-(pyrrolidin-3-yl)quinazoline-2,4(1H,3H)-dione | LCMS m/z [MH]+ 476 |

| | | | |
|---|---|---|---|
| 86 | 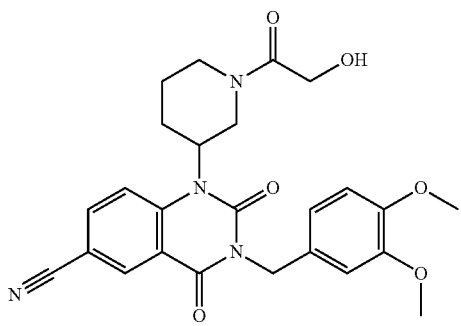 [SMILES: COc1ccc(Cn2c(=O)c3cc(C#N)ccc3n(C3CCCN(C(=O)CO)C3)c2=O)cc1OC] | 3-(3,4-dimethoxy-benzyl)-1-[1-(hydroxyacetyl)piperidin-3-yl]-2,4-dioxo-1,2,3,4-tetrahydroquinazoline-6-carbonitrile | LCMS m/z [MH]+ 479 |
| 87 | 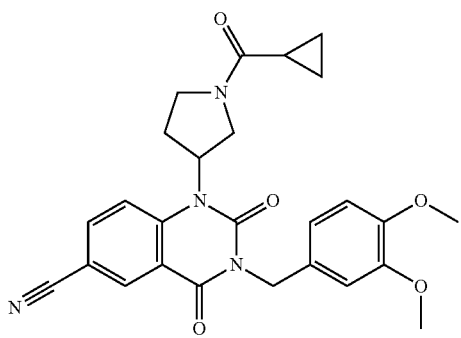 [SMILES: COc1ccc(Cn2c(=O)c3cc(C#N)ccc3n(C3CCN(C(=O)C4CC4)C3)c2=O)cc1OC] | 1-[1-(cyclopropyl-carbonyl)-pyrrolidin-3-yl]-3-(3,4-dimethoxybenzyl)-2,4-dioxo-1,2,3,4-tetrahydroquinazoline-6-carbonitrile | LCMS m/z [MH]+ 475 |
| 88 | 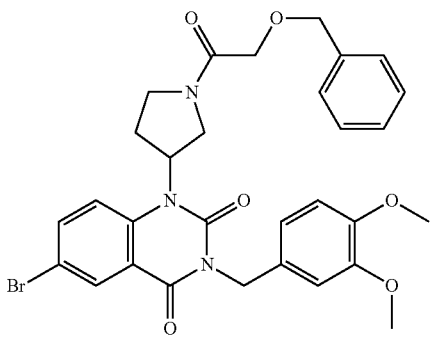 [SMILES: COc1ccc(Cn2c(=O)c3cc(Br)ccc3n(C3CCN(C(=O)COCc4ccccc4)C3)c2=O)cc1OC] | 1-{1-[(benzyloxy)acetyl]pyrrolidin-3-yl}-6-bromo-3-(3,4-dimethoxy-benzyl)quinazoline-2,4(1H,3H)-dione | LCMS m/z [MH]+ 608 |
| 89 | 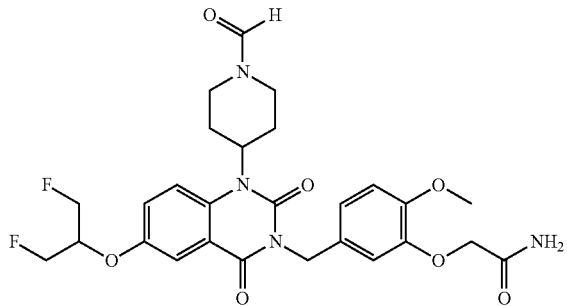 [SMILES: COc1ccc(Cn2c(=O)c3cc(OC(CF)CF)ccc3n(C3CCN(C=O)CC3)c2=O)cc1OCC(N)=O] | 2-[5-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]acetamide | LCMS m/z [MH]+ 561 |

| | | | |
|---|---|---|---|
| 90 | 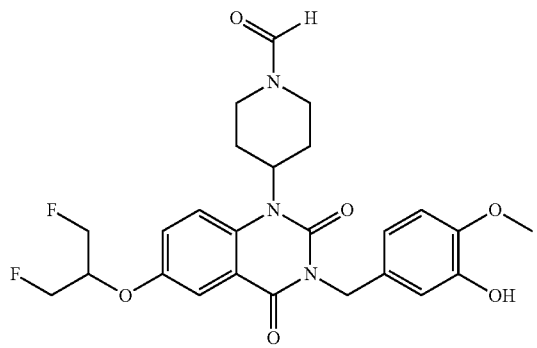 [SMILES: COc1ccc(Cn2c(=O)c3cc(OC(CF)CF)ccc3n(C3CCN(C=O)CC3)c2=O)cc1O] | 4-{6-[2-fluoro-1-(fluoromethyl)ethoxy]-3-(3-hydroxy-4-methoxybenzyl)-2,4-dioxo-3,4-dihydroquinazolin-1(2H)-yl}piperidine-1-carbaldehyde | LCMS m/z [MH]+ 504 |
| 91 | 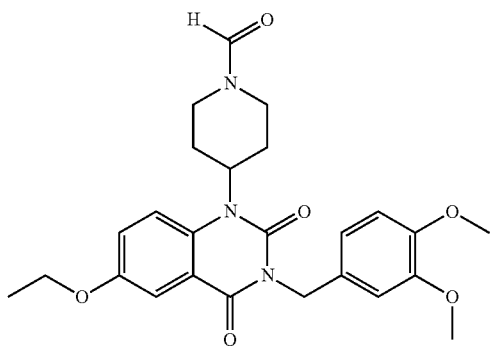 [SMILES: CCOc1ccc2c(c1)c(=O)n(Cc1ccc(OC)c(OC)c1)c(=O)n2C1CCN(C=O)CC1] | 4-[3-(3,4-dimethoxybenzyl)-6-ethoxy-2,4-dioxo-3,4-dihydroquinazolin-1(2H)-yl]piperidine-1-carbaldehyde | LCMS m/z [MH]+ 468 |
| 92 | 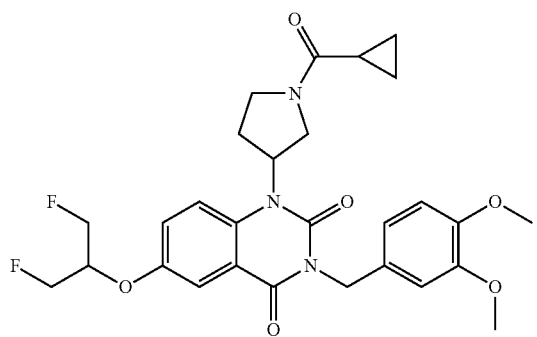 [SMILES: COc1ccc(Cn2c(=O)c3cc(OC(CF)CF)ccc3n(C3CCN(C(=O)C4CC4)C3)c2=O)cc1OC] | 1-[1-(cyclopropylcarbonyl)-pyrrolidin-3-yl]-3-(3,4-dimethoxybenzyl)-6-[2-fluoro-1-(fluoromethyl)ethoxy]quinazoline-2,4(1H,3H)-dione | LCMS m/z [MH]+ 544 |
| 93 | 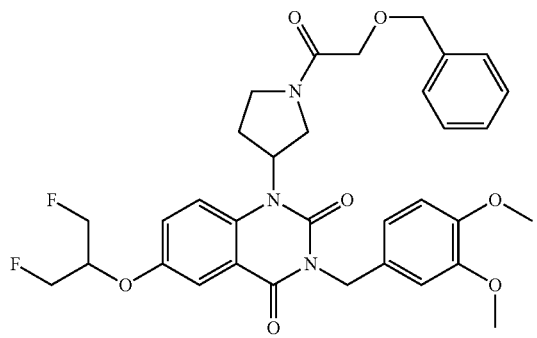 [SMILES: COc1ccc(Cn2c(=O)c3cc(OC(CF)CF)ccc3n(C3CCN(C(=O)COCc4ccccc4)C3)c2=O)cc1OC] | 1-{1-[(benzyloxy)acetyl]-pyrrolidin-3-yl}-3-(3,4-dimethoxybenzyl)-6-[2-fluoro-1-(fluoromethyl)ethoxy]quinazoline-2,4(1H,3H)-dione | LCMS m/z [MH]+ 624 |

| | | | |
|---|---|---|---|
| 94 | 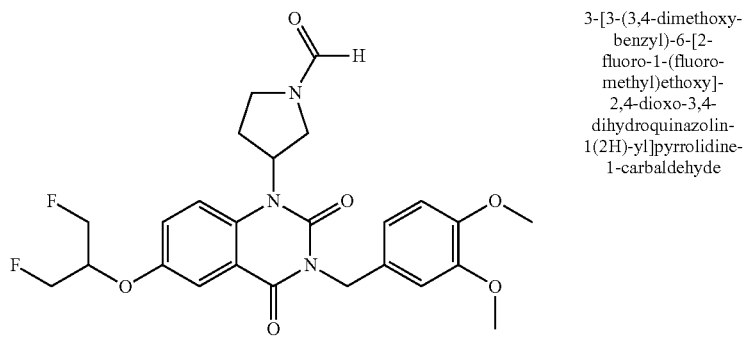 | 3-[3-(3,4-dimethoxy-benzyl)-6-[2-fluoro-1-(fluoro-methyl)ethoxy]-2,4-dioxo-3,4-dihydroquinazolin-1(2H)-yl]pyrrolidine-1-carbaldehyde | LCMS m/z [MH]+ 504 |
| 95 | 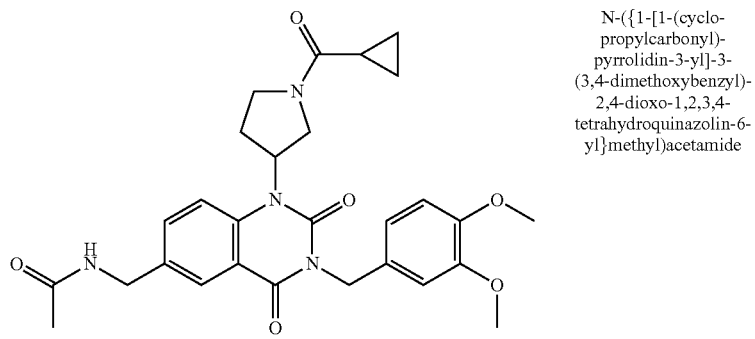 | N-({1-[1-(cyclo-propylcarbonyl)-pyrrolidin-3-yl]-3-(3,4-dimethoxybenzyl)-2,4-dioxo-1,2,3,4-tetrahydroquinazolin-6-yl}methyl)acetamide | LCMS m/z [MH]+ 521 |
| 96 | 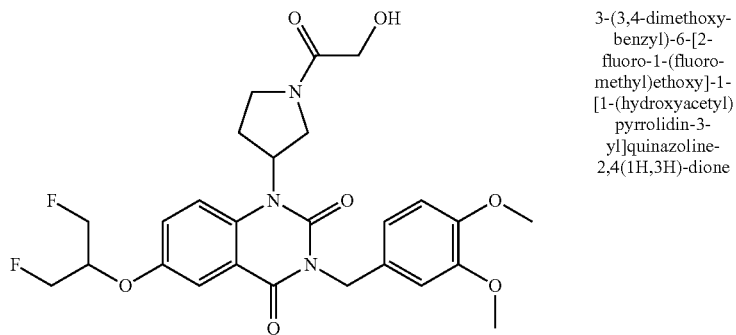 | 3-(3,4-dimethoxy-benzyl)-6-[2-fluoro-1-(fluoro-methyl)ethoxy]-1-[1-(hydroxyacetyl)pyrrolidin-3-yl]quinazoline-2,4(1H,3H)-dione | LCMS m/z [M + Na]+ 534 |
| 97 | 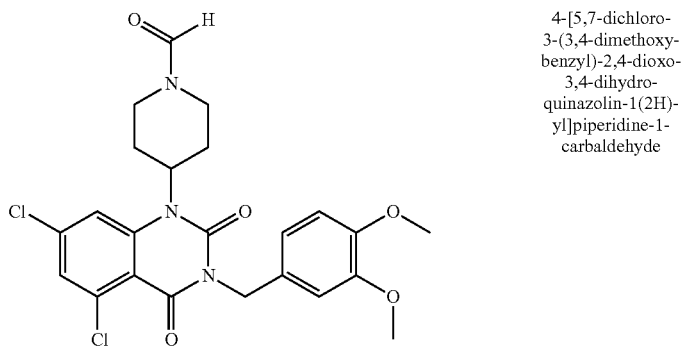 | 4-[5,7-dichloro-3-(3,4-dimethoxy-benzyl)-2,4-dioxo-3,4-dihydro-quinazolin-1(2H)-yl]piperidine-1-carbaldehyde | LCMS m/z [MH]+ 492 |

| | | | |
|---|---|---|---|
| 98 | 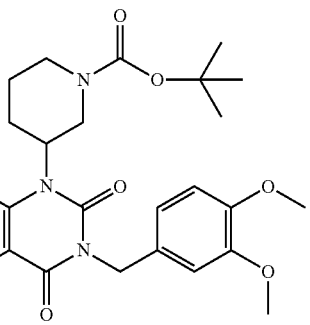 | 1,1-dimethylethyl 3-{6-[(acetylamino)methyl]-3-(3,4-dimethoxybenzyl)-2,4-dioxo-3,4-dihydroquinazolin-1(2H)-yl}piperidine-1-carboxylate | LCMS m/z [M + Na]+ 589 |
| 99 | 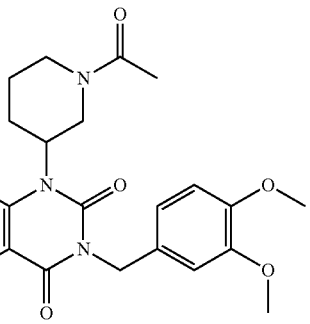 | N-{[3-(3,4-dimethoxy-benzyl)-1-(1-formylpiperidin-3-yl)-2,4-dioxo-1,2,3,4-tetrahydro-quinazolin-6-yl]methyl}acetamide | LCMS m/z [MH]+ 495 |
| 100 | 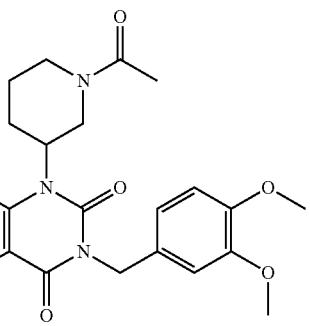 | N-{[1-(1-acetyl-piperidin-3-yl)-3-(3,4-dimethoxybenzyl)-2,4-dioxo-1,2,3,4-tetrahydroquinazolin-6-yl]methyl}acetamide | LCMS m/z [MH]+ 509 |
| 101 | 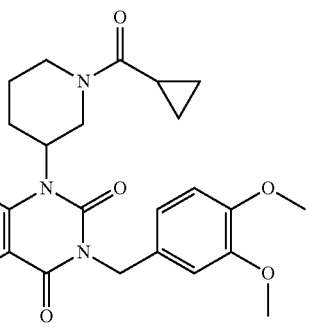 | N-({1-[1-(cyclo-propylcarbonyl)-piperidin-3-yl]-3-(3,4-dimethoxy-benzyl)-2,4-dioxo-1,2,3,4-tetrahydro-quinazolin-6-yl}methyl)acetamide | LCMS m/z [MH]+ 535 |
| 102 | 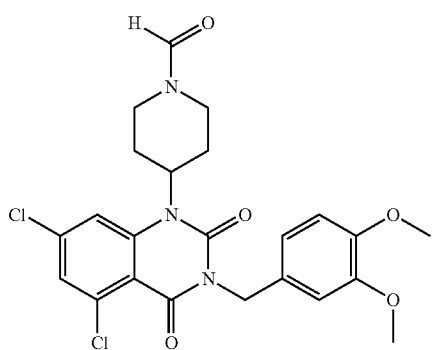 | 4-[7-chloro-3-(3,4-dimethoxybenzyl)-2,4-dioxo-3,4-dihydroquinazolin-1(2H)-yl]piperidine-1-carbaldehyde | LCMS m/z [MH]+ 458 |

| | | | |
|---|---|---|---|
| 103 | 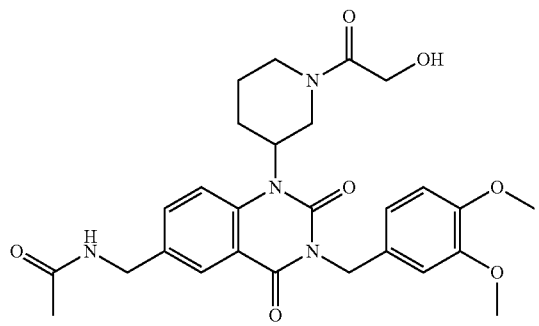 [SMILES: COc1ccc(Cn2c(=O)c3cc(CNC(C)=O)ccc3n(C3CCCN(C(=O)CO)C3)c2=O)cc1OC] | N-({3-(3,4-dimethoxy-benzyl)-1-[1-(hydroxy-acetyl)piperidin-3-yl]-2,4-dioxo-1,2,3,4-tetrahydro-quinazolin-6-yl}methyl)acetamide | LCMS m/z [MH]+ 525 |
| 104 | 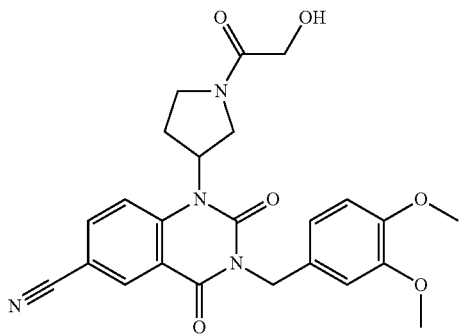 [SMILES: COc1ccc(Cn2c(=O)c3cc(C#N)ccc3n(C3CCN(C(=O)CO)C3)c2=O)cc1OC] | 3-(3,4-dimethoxy-benzyl)-1-[1-(hydroxyacetyl)pyrrolidin-3-yl]-2,4-dioxo-1,2,3,4-tetrahydro-quinazoline-6-carbonitrile | LCMS m/z [MH]+ 465 |
| 105 | 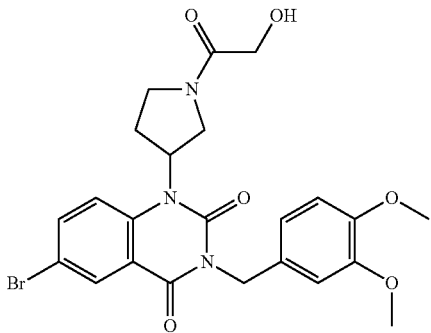 [SMILES: COc1ccc(Cn2c(=O)c3cc(Br)ccc3n(C3CCN(C(=O)CO)C3)c2=O)cc1OC] | 6-bromo-3-(3,4-dimethoxybenzyl)-1-[1-(hydroxyacetyl)pyrrolidin-3-yl]quinazoline-2,4(1H,3H)-dione | LCMS m/z [MH]+ 518 |
| 106 | 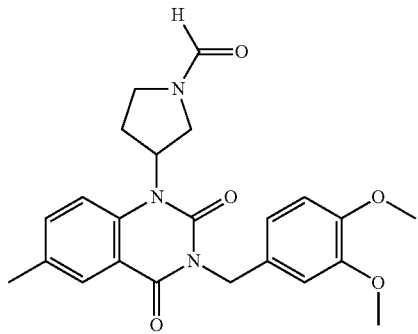 | 3-[3-(3,4-dimethoxy-benzyl)-6-methyl-2,4-dioxo-3,4-dihydroquinazolin-1(2H)-yl]pyrrolidine-1-carbaldehyde | LCMS m/z [MH]+ 424 |

| 107 | 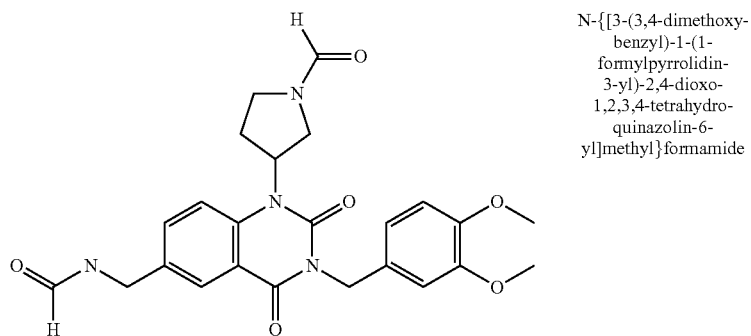 | N-{[3-(3,4-dimethoxy-benzyl)-1-(1-formylpyrrolidin-3-yl)-2,4-dioxo-1,2,3,4-tetrahydro-quinazolin-6-yl]methyl}formamide | LCMS m/z [MH]+ 467 |
| --- | --- | --- | --- |
| 108 | 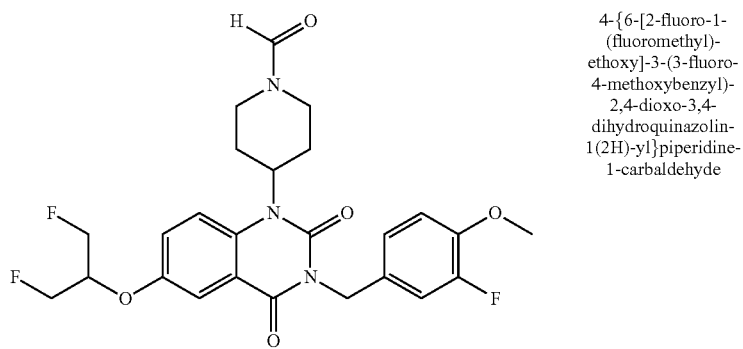 | 4-{6-[2-fluoro-1-(fluoromethyl)-ethoxy]-3-(3-fluoro-4-methoxybenzyl)-2,4-dioxo-3,4-dihydroquinazolin-1(2H)-yl}piperidine-1-carbaldehyde | LCMS m/z [MH]+ 506 |
| 109 | 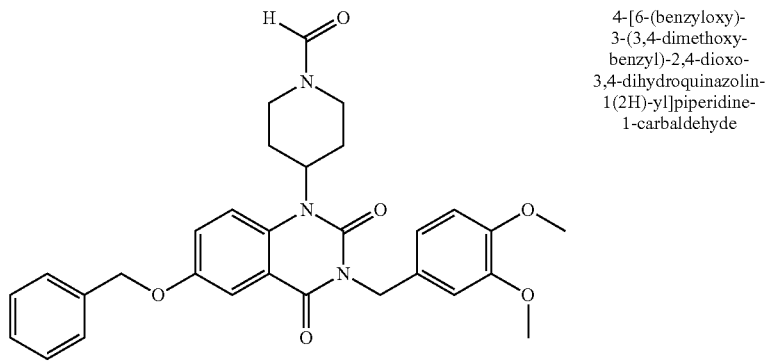 | 4-[6-(benzyloxy)-3-(3,4-dimethoxy-benzyl)-2,4-dioxo-3,4-dihydroquinazolin-1(2H)-yl]piperidine-1-carbaldehyde | LCMS m/z [MH]+ 530 |
| 110 | 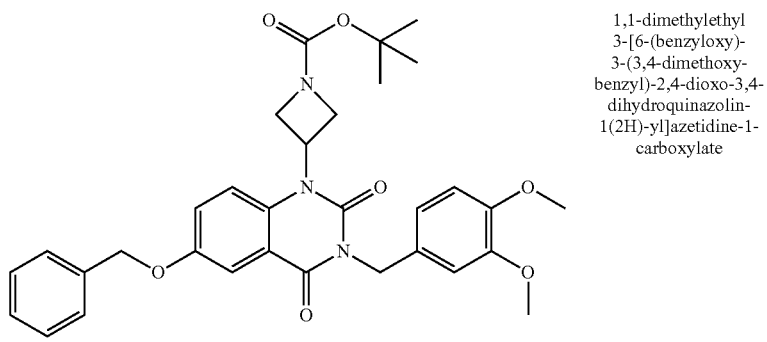 | 1,1-dimethylethyl 3-[6-(benzyloxy)-3-(3,4-dimethoxy-benzyl)-2,4-dioxo-3,4-dihydroquinazolin-1(2H)-yl]azetidine-1-carboxylate | LCMS m/z [MH]+ 574 |

| | | | |
|---|---|---|---|
| 111 | 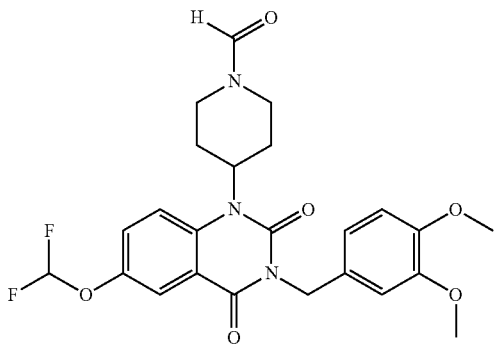 [SMILES: COc1ccc(Cn2c(=O)c3cc(OC(F)F)ccc3n(C3CCN(C=O)CC3)c2=O)cc1OC] | 4-[6-difluoromethoxy)-3-(3,4-dimethoxybenzyl)-2,4-dioxo-3,4-dihydroquinazolin-1(2H)-yl]piperidine-1-carbaldehyde | LCMS m/z [MH]+ 490 |
| 112 | 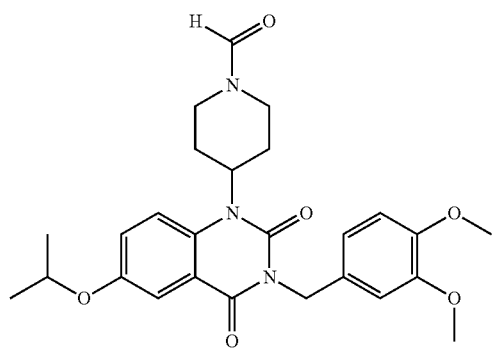 [SMILES: COc1ccc(Cn2c(=O)c3cc(OC(C)C)ccc3n(C3CCN(C=O)CC3)c2=O)cc1OC] | 4-[3-(3,4-dimethoxybenzyl)-6-(1-methylethoxy)-2,4-dioxo-3,4-dihydroquinazolin-1(2H)-yl]piperidine-1-carbaldehyde | LCMS m/z [MH]+ 482 |
| 113 | 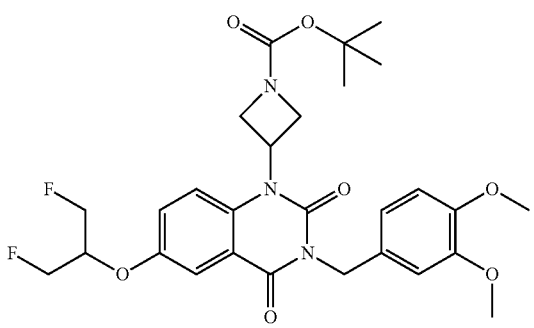 [SMILES: COc1ccc(Cn2c(=O)c3cc(OC(CF)CF)ccc3n(C3CN(C(=O)OC(C)(C)C)C3)c2=O)cc1OC] | 1,1-dimethylethyl 3-[3-(3,4-dimethoxybenzyl)-6-[2-fluoro-1-(fluoromethyl)ethoxy]-2,4-dioxo-3,4-dihydroquinazolin-1(2H)-yl]azetidine-1-carboxylate | LCMS m/z [MH]+ 562 |
| 114 | 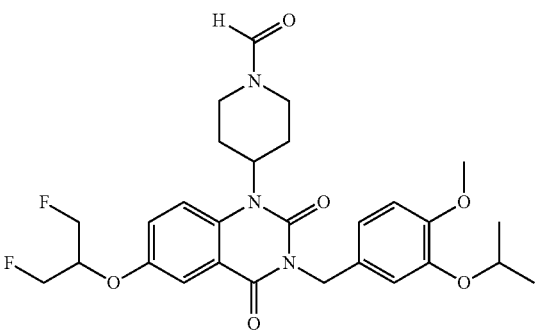 [SMILES: COc1ccc(Cn2c(=O)c3cc(OC(CF)CF)ccc3n(C3CCN(C=O)CC3)c2=O)cc1OC(C)C] | 4-{6-[2-fluoro-1-(fluoromethyl)ethoxy]-3-[4-methoxy-3-(1-methylethoxy)benzyl]-2,4-dioxo-3,4-dihydroquinazolin-1(2H)-yl}piperidine-1-carbaldehyde | LCMS m/z [MH]+ 546 |

| | | | |
|---|---|---|---|
| 115 | 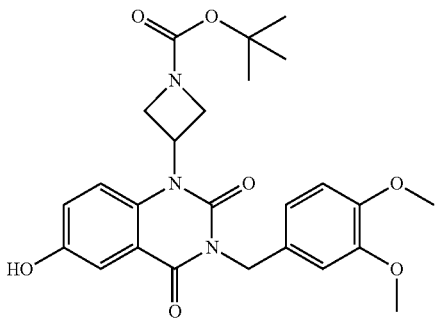 [SMILES: COc1ccc(Cn2c(=O)c3cc(O)ccc3n(C3CN(C(=O)OC(C)(C)C)C3)c2=O)cc1OC] | 1,1-dimethylethyl 3-[3-(3,4-dimethoxybenzyl)-6-hydroxy-2,4-dioxo-3,4-dihydroquinazolin-1(2H)-yl]azetidine-1-carboxylate | LCMS m/z [MH]+ 484 |
| 116 | 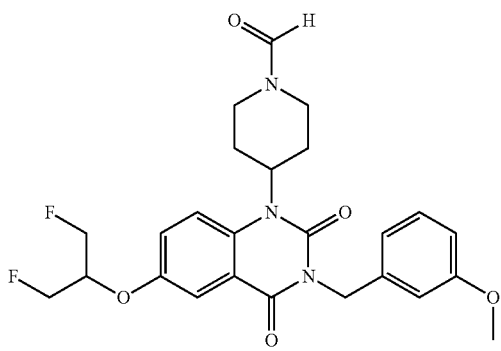 [SMILES: COc1cccc(Cn2c(=O)c3cc(OC(CF)CF)ccc3n(C3CCN(C=O)CC3)c2=O)c1] | 4-{6-[2-fluoro-1-(fluoromethyl)ethoxy]-3-(3-methoxybenzyl)-2,4-dioxo-3,4-dihydroquinazolin-1(2H)-yl}piperidine-1-carbaldehyde | LCMS m/z [MH]+ 488 |
| 117 | 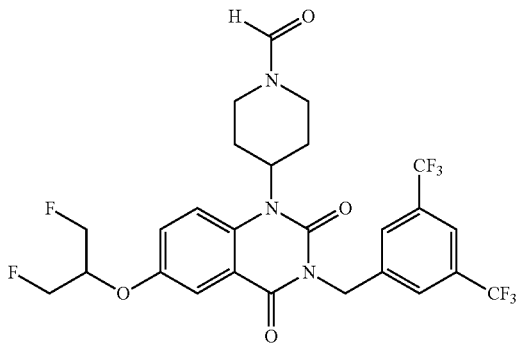 [SMILES: O=CN1CCC(n2c(=O)n(Cc3cc(C(F)(F)F)cc(C(F)(F)F)c3)c(=O)c3cc(OC(CF)CF)ccc32)CC1] | 4-{3-[3,5-bis(trifluoromethyl)benzyl]-6-[2-fluoro-1-(fluoromethyl)ethoxy]-2,4-dioxo-3,4-dihydroquinazolin-1(2H)-yl}piperidine-1-carbaldehyde | LCMS m/z [MH]+ 564 |
| 118 | 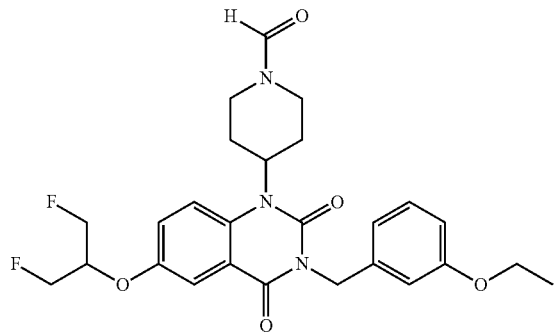 [SMILES: CCOc1cccc(Cn2c(=O)c3cc(OC(CF)CF)ccc3n(C3CCN(C=O)CC3)c2=O)c1] | 4-[3-(3-ethoxybenzyl)-6-[2-fluoro-1-(fluoromethyl)ethoxy]-2,4-dioxo-3,4-dihydroquinazolin-1(2H)-yl]piperidine-1-carbaldehyde | LCMS m/z [MH]+ 502 |

-continued

| COMPOUND No. | STRUCTURE | NOMENCLATURE | MASS LCUVMS MH+ |
|---|---|---|---|
| 119 | 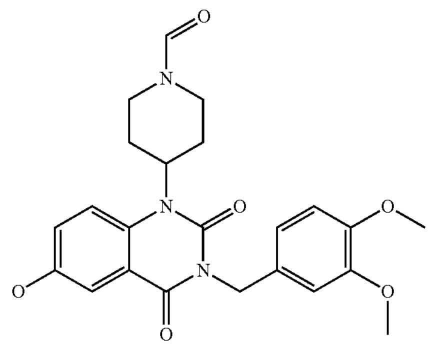 [SMILES: COc1ccc(Cn2c(=O)c3cc(O)ccc3n(C3CCN(C=O)CC3)c2=O)cc1OC] | 4-[3-(3,4-dimethoxybenzyl)-6-hydroxy-2,4-dioxo-3,4-dihydroquinazolin-1(2H)-yl]piperidine-1-carbaldehyde | 440 |
| 120 | 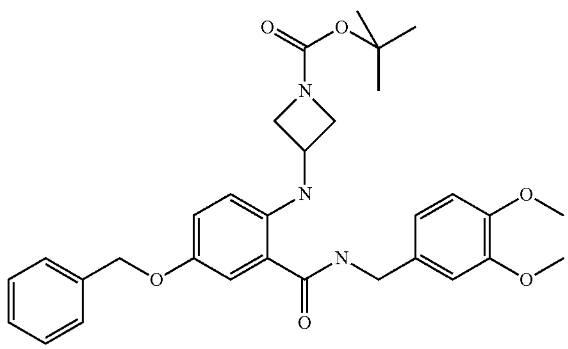 [SMILES: COc1ccc(CNC(=O)c2cc(OCc3ccccc3)ccc2NC2CN(C(=O)OC(C)(C)C)C2)cc1OC] | 1,1-dimethyl 3-({4-(benzyloxyl)-2-[(3,4-dimethoxybenzyl)carbamoyl]phenyl}amino)azetidine-1-carboxylate | 548 |
| 121 | 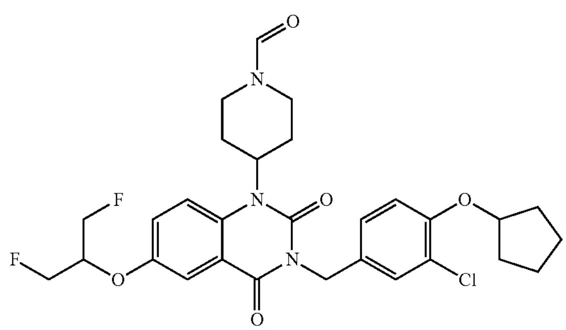 [SMILES: O=CN1CCC(n2c(=O)n(Cc3ccc(OC4CCCC4)c(Cl)c3)c(=O)c3cc(OC(CF)CF)ccc32)CC1] | 4-{3-[3-chloro-4-(cyclopentyloxy)benzyl]-6-[2-fluoro-1-(fluoromethyl)ethoxy]-2,4-dioxo-3,4-dihydroquinazolin-1(2H)-yl}piperidine-1-carbaldehyde | 576 |
| 122 | 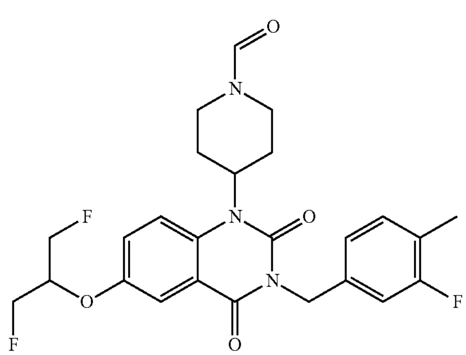 [SMILES: Cc1ccc(Cn2c(=O)c3cc(OC(CF)CF)ccc3n(C3CCN(C=O)CC3)c2=O)cc1F] | 4-{6-[2-fluoro-1-(fluoromethyl)ethoxy]-3-(3-fluoro-4-methylbenzyl)-2,4-dioxo-3,4-dihydroquinazolin-1(2H)-yl}piperidine-1-carbaldehyde | 490 |

| | | | |
|---|---|---|---|
| 123 | 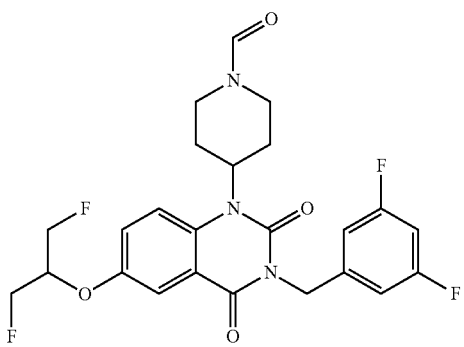 [SMILES: O=CN1CCC(n2c(=O)n(Cc3cc(F)cc(F)c3)c(=O)c3cc(OC(CF)CF)ccc32)CC1] | 4-[3-(3,5-difluorobenzyl)-6-[2-fluoro-1-(fluoromethyl)ethoxy]-2,4-dioxo-3,4-dihydroquinazolin-1(2H)-yl]piperidine-1-carbaldehyde | 494 |
| 124 | 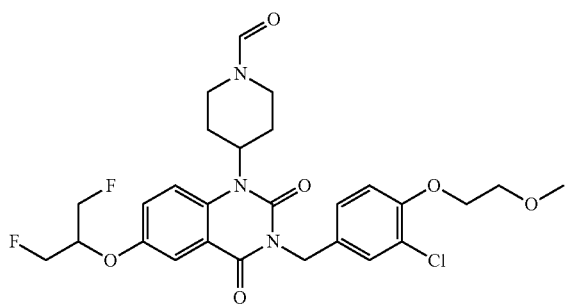 [SMILES: COCCOc1ccc(Cn2c(=O)c3cc(OC(CF)CF)ccc3n(C3CCN(C=O)CC3)c2=O)cc1Cl] | 4-{3-[3-chloro-4-(2-methoxyethoxy)benzyl]-6-[2-fluoro-1-(fluoromethyl)ethoxy]-2,4-dioxo-3,4-dihydroquinazolin-1(2H)-yl}piperidine-1-carbaldehyde | 566 |
| 125 | 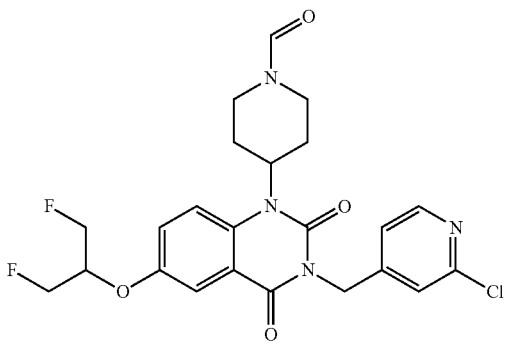 [SMILES: O=CN1CCC(n2c(=O)n(Cc3ccnc(Cl)c3)c(=O)c3cc(OC(CF)CF)ccc32)CC1] | 4-{3-[(2-chloropyridin-4-yl)methyl]-6-[2-fluoro-1-(fluoromethyl)ethoxy]-2,4-dioxo-3,4-dihydroquinazolin-1(2H)-yl}piperidine-1-carbaldehyde | 493 |
| 126 | 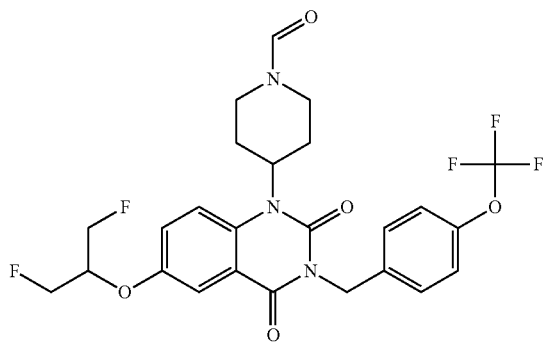 [SMILES: O=CN1CCC(n2c(=O)n(Cc3ccc(OC(F)(F)F)cc3)c(=O)c3cc(OC(CF)CF)ccc32)CC1] | 4-{6-[2-fluoro-1-(fluoromethyl)ethoxy]-2,4-dioxo-3-[4-(trifluoromethoxy)benzyl]-3,4-dihydroquinazolin-1(2H)-yl}piperidine-1-carbaldehyde | 542 |

-continued

| | | | |
|---|---|---|---|
| 127 | 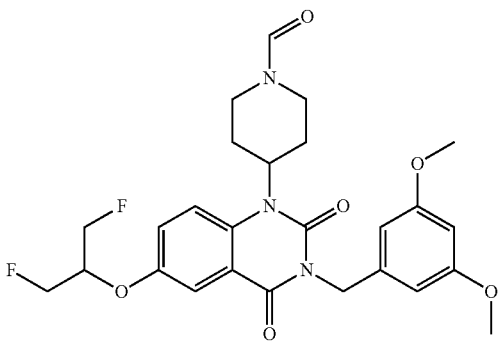 [SMILES: COc1cc(Cn2c(=O)c3cc(OC(CF)CF)ccc3n(C3CCN(C=O)CC3)c2=O)cc(OC)c1] | 4-[3-(3,5-dimethoxybenzyl)-6-[2-fluoro-1-(fluoromethyl)ethoxy]-2,4-dioxo-3,4-dihydroquinazolin-1(2H)-yl]piperidine-1-carbaldehyde | 518 |
| 128 | 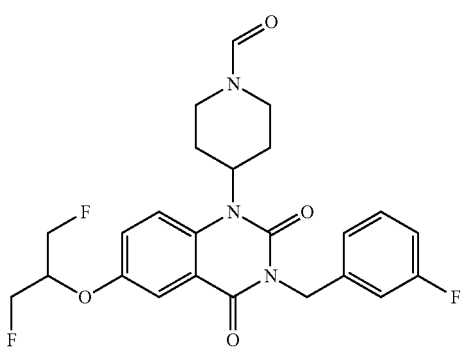 [SMILES: O=CN1CCC(n2c(=O)n(Cc3cccc(F)c3)c(=O)c3cc(OC(CF)CF)ccc32)CC1] | 4-[3-(3-fluorobenzyl)-6-[2-fluoro-1-(fluoromethyl)ethoxy]-2,4-dioxo-3,4-dihydroquinazolin-1(2H)-yl]piperidine-1-carbaldehyde | 476 |
| 129 | 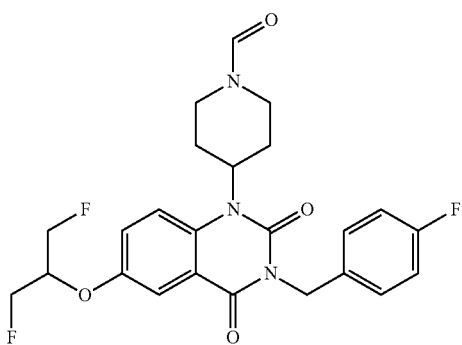 [SMILES: O=CN1CCC(n2c(=O)n(Cc3ccc(F)cc3)c(=O)c3cc(OC(CF)CF)ccc32)CC1] | 4-[3-(4-fluorobenzyl)-6-[2-fluoro-1-(fluoromethyl)ethoxy]-2,4-dioxo-3,4-dihydroquinazolin-1(2H)-yl]piperidine-1-carbaldehyde | 476 |
| 130 | 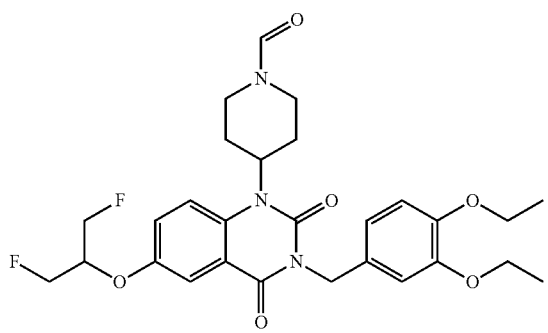 [SMILES: CCOc1ccc(Cn2c(=O)c3cc(OC(CF)CF)ccc3n(C3CCN(C=O)CC3)c2=O)cc1OCC] | 4-[3-(3,4-diethoxybenzyl)-6-[2-fluoro-1-(fluoromethyl)ethoxy]-2,4-dioxo-3,4-dihydroquinazolin-1(2H)-yl]piperidine-1-carbaldehyde | 546 |

| | | | |
|---|---|---|---|
| 131 | 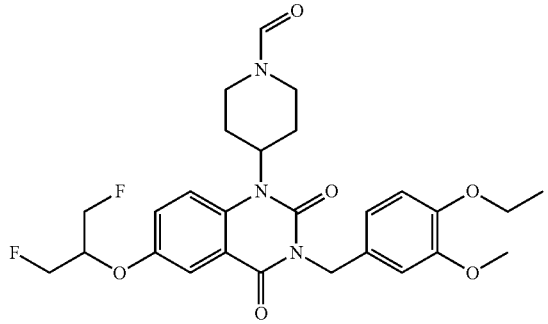 [SMILES: CCOc1ccc(Cn2c(=O)c3cc(OC(CF)CF)ccc3n(C3CCN(C=O)CC3)c2=O)cc1OC] | 4-[3-(4-ethoxy-3-methoxybenzyl)-6-[2-fluoro-1-(fluoromethyl)ethoxy]-2,4-dioxo-3,4-dihydroquinazolin-1(2H)-yl]piperidine-1-carbaldehyde | 532 |
| 132 | 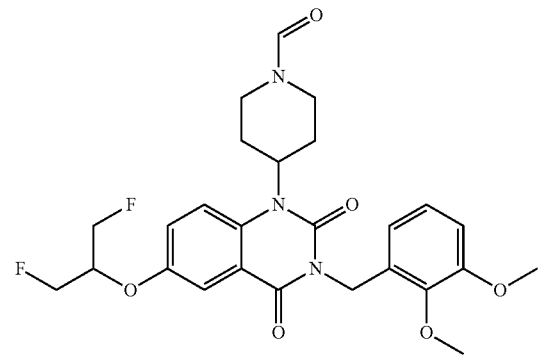 [SMILES: COc1cccc(Cn2c(=O)c3cc(OC(CF)CF)ccc3n(C3CCN(C=O)CC3)c2=O)c1OC] | 4-[3-(2,3-dimethoxybenzyl)-6-[2-fluoro-1-(fluoromethyl)ethoxy]-2,4-dioxo-3,4-dihydroquinazolin-1(2H)-yl]piperidine-1-carbaldehyde | 518 |
| 133 | 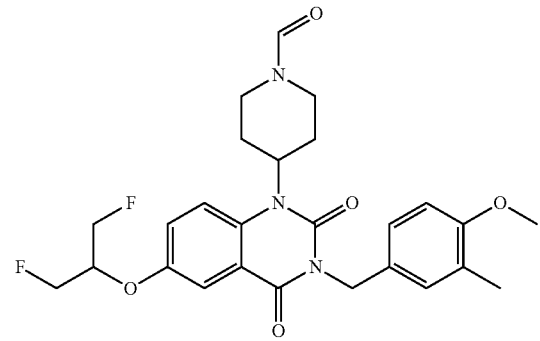 [SMILES: COc1ccc(Cn2c(=O)c3cc(OC(CF)CF)ccc3n(C3CCN(C=O)CC3)c2=O)cc1C] | 4-{6-[2-fluoro-1-(fluoromethyl)ethoxy]-3-(4-methoxy-3-methylbenzyl)-2,4-dioxo-3,4-dihydroquinazolin-1(2H)-yl}piperidine-1-carbaldehyde | 502 |
| 134 | 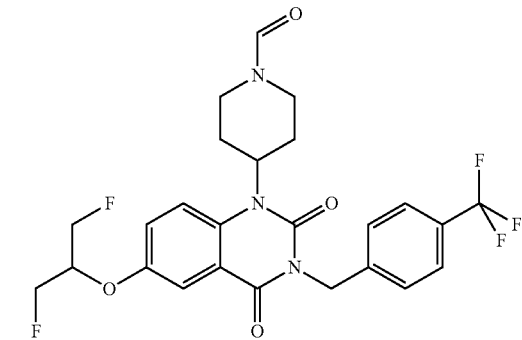 [SMILES: O=CN1CCC(n2c(=O)n(Cc3ccc(C(F)(F)F)cc3)c(=O)c3cc(OC(CF)CF)ccc32)CC1] | 4-{6-[2-fluoro-1-(fluoromethyl)ethoxy]-2,4-dioxo-3-[4-(trifluoromethyl)benzyl]-3,4-dihydroquinazolin-1(2H)-yl}piperidine-1-carbaldehyde | 526 |

-continued

| | | | |
|---|---|---|---|
| 135 | 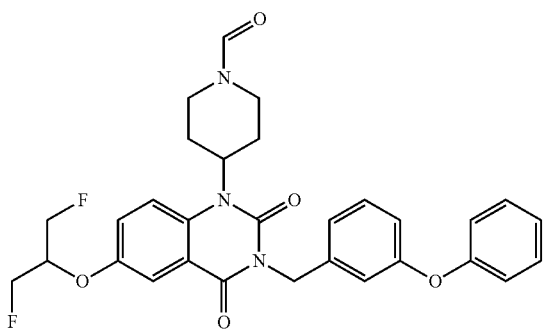 [SMILES: O=CN1CCC(n2c(=O)n(Cc3cccc(Oc4ccccc4)c3)c(=O)c3cc(OC(CF)CF)ccc32)CC1] | 4-{6-[2-fluoro-1-(fluoromethyl)ethoxy]-2,4-dioxo-3-(3-phenoxybenzyl)-3,4-dihydroquinazolin-1(2H)-yl}piperidine-1-carbaldehyde | 550 |
| 136 | 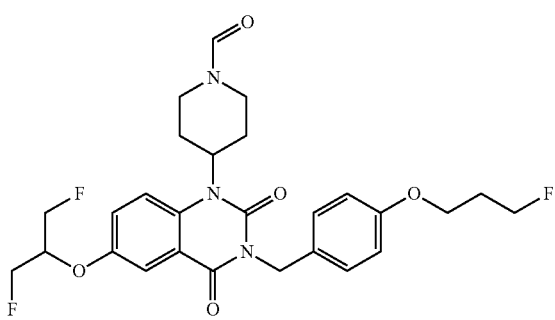 [SMILES: O=CN1CCC(n2c(=O)n(Cc3ccc(OCCCF)cc3)c(=O)c3cc(OC(CF)CF)ccc32)CC1] | 4-{6-[2-fluoro-1-(fluoromethyl)ethoxy]-3-[4-(3-fluoropropoxy)benzyl]-2,4-dioxo-3,4-dihydroquinazolin-1(2H)-yl}piperidine-1-carbaldehyde | 534 |
| 137 | 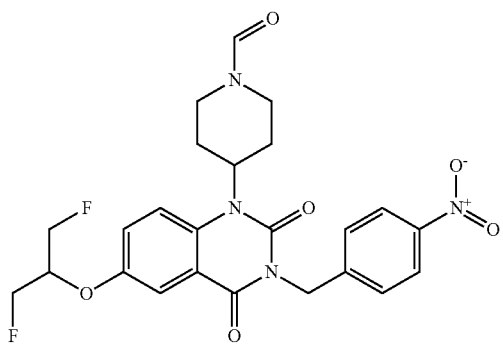 [SMILES: O=CN1CCC(n2c(=O)n(Cc3ccc([N+](=O)[O-])cc3)c(=O)c3cc(OC(CF)CF)ccc32)CC1] | 4-{6-[2-fluoro-1-(fluoromethyl)ethoxy]-3-(4-nitrobenzyl)-2,4-dioxo-3,4-dihydroquinazolin-1(2H)-yl}piperidine-1-carbaldehyde | 503 |
| 138 | 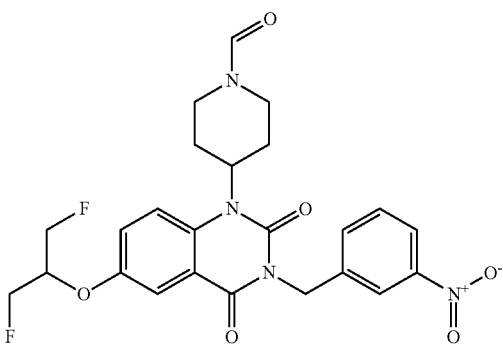 [SMILES: O=CN1CCC(n2c(=O)n(Cc3cccc([N+](=O)[O-])c3)c(=O)c3cc(OC(CF)CF)ccc32)CC1] | 4-{6-[2-fluoro-1-(fluoromethyl)ethoxy]-3-(3-nitrobenzyl)-2,4-dioxo-3,4-dihydroquinazolin-1(2H)-yl}piperidine-1-carbaldehyde | 503 |

| | | | |
|---|---|---|---|
| 139 | 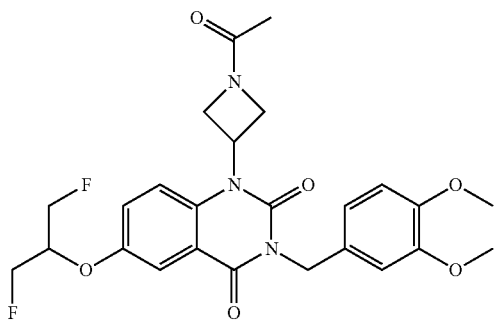 [SMILES: COc1ccc(Cn2c(=O)c3cc(OC(CF)CF)ccc3n(C3CN(C(C)=O)C3)c2=O)cc1OC] | 1-(1-acetylazetidin-3-yl)-3-(3,4-dimethoxybenzyl)-6-[2-fluoro-1-(fluoromethyl)ethoxy]quinazoline-2,4(1H,3H)-dione | 504 |
| 140 | 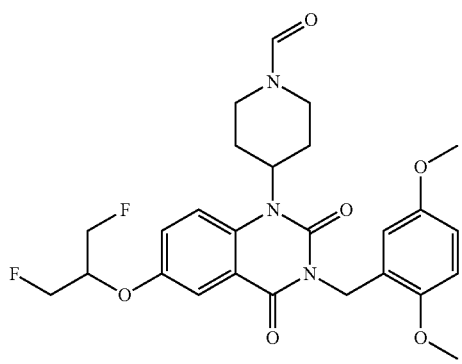 [SMILES: COc1ccc(OC)c(Cn2c(=O)c3cc(OC(CF)CF)ccc3n(C3CCN(C=O)CC3)c2=O)c1] | 4-[3-(2,5-dimethoxybenzyl)-6-[2-fluoro-1-(fluoromethyl)ethoxy]-2,4-dioxo-3,4-dihydroquinazolin-1(2H)-yl]piperidine-1-carbaldehyde | 518 |
| 141 | 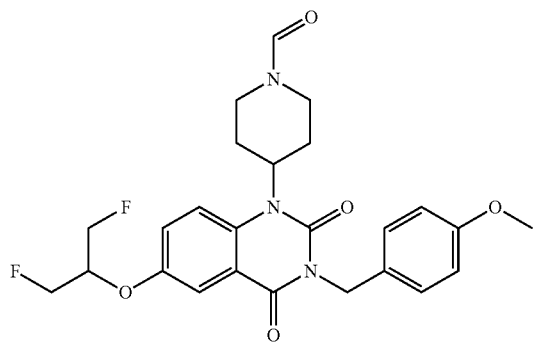 [SMILES: COc1ccc(Cn2c(=O)c3cc(OC(CF)CF)ccc3n(C3CCN(C=O)CC3)c2=O)cc1] | 4-{6-[2-fluoro-1-(fluoromethyl)ethoxy]-3-(4-methoxybenzyl)-2,4-dioxo-3,4-dihydroquinazolin-1(2H)-yl}piperidine-1-carbaldehyde | 488 |
| 142 | 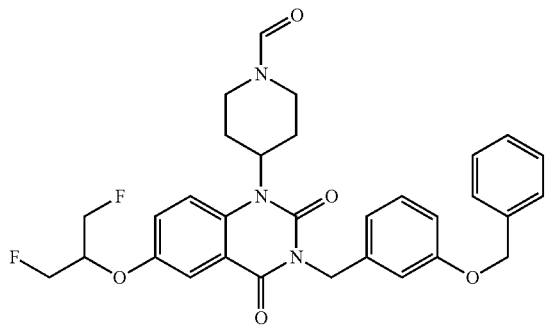 [SMILES: O=CN1CCC(n2c(=O)n(Cc3cccc(OCc4ccccc4)c3)c(=O)c3cc(OC(CF)CF)ccc32)CC1] | 4-{3-[3-(benzyloxy)benzyl]-6-[2-fluoro-1-(fluoromethyl)ethoxy]-2,4-dioxo-3,4-dihydroquinazolin-1(2H)-yl}piperidine-1-carbaldehyde | 564 |

| | | | |
|---|---|---|---|
| 143 | 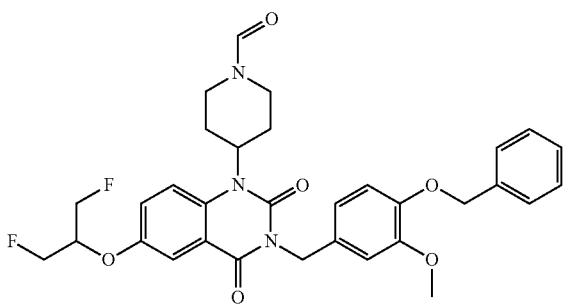 [SMILES: COc1cc(Cn2c(=O)c3cc(OC(CF)CF)ccc3n(C3CCN(C=O)CC3)c2=O)ccc1OCc1ccccc1] | 4-{3-[4-(benzyloxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | 594 |
| 144 | 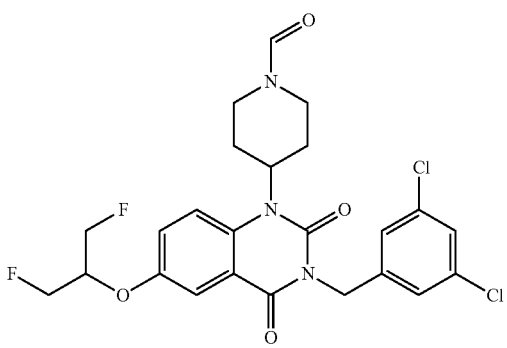 [SMILES: O=CN1CCC(n2c(=O)n(Cc3cc(Cl)cc(Cl)c3)c(=O)c3cc(OC(CF)CF)ccc32)CC1] | 4-[3-(3,5-dichlorobenzyl)-6-[2-fluoro-1-(fluoromethyl)ethoxy]-2,4-dioxo-3,4-dihydroquinazolin-1(2H)-yl]piperidine-1-carbaldehyde | 526 |
| 145 | 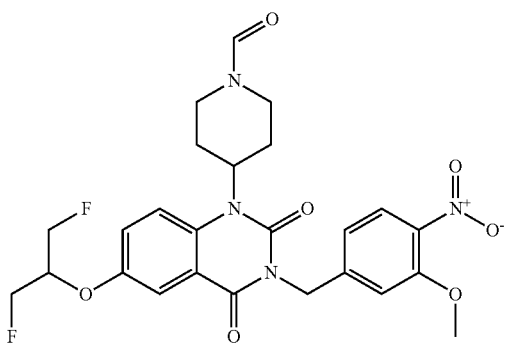 [SMILES: COc1cc(Cn2c(=O)c3cc(OC(CF)CF)ccc3n(C3CCN(C=O)CC3)c2=O)ccc1[N+](=O)[O-]] | 4-{6-[2-fluoro-1-(fluoromethyl)ethoxy]-3-(3-methoxy-3-nitrobenzyl)-2,4-dioxo-3,4-dihydroquinazolin-1(2H)-yl}piperidine-1-carbaldehyde | 533 |
| 146 | 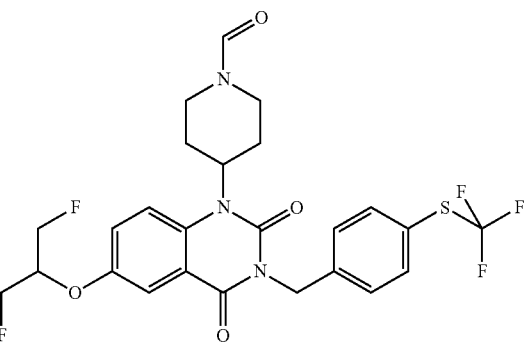 [SMILES: O=CN1CCC(n2c(=O)n(Cc3ccc(SC(F)(F)F)cc3)c(=O)c3cc(OC(CF)CF)ccc32)CC1] | 4-{6-[2-fluoro-1-(fluoromethyl)ethoxy]-2,4-dioxo-3-{4-[(trifluoromethyl)sulphanyl]benzyl}-3,4-dihydroquinazolin-1(2H)-yl}piperidine-1-carbaldehyde | 558 |

-continued

| | | | |
|---|---|---|---|
| 147 | 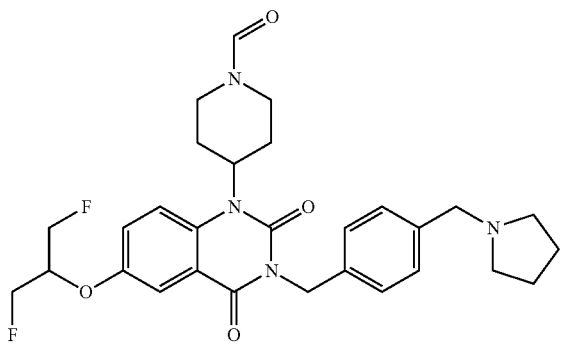 [SMILES: O=CN1CCC(n2c(=O)n(Cc3ccc(CN4CCCC4)cc3)c(=O)c3cc(OC(CF)CF)ccc32)CC1] | 4-{6-[2-fluoro-1-(fluoromethyl)ethoxy]-2,4-dioxo-3-[4-(pyrrolidin-1-ylmethyl)benzyl]-3,4-dihydroquinazolin-1(2H)-yl}piperidine-1-carbaldehyde | 541 |
| 148 | 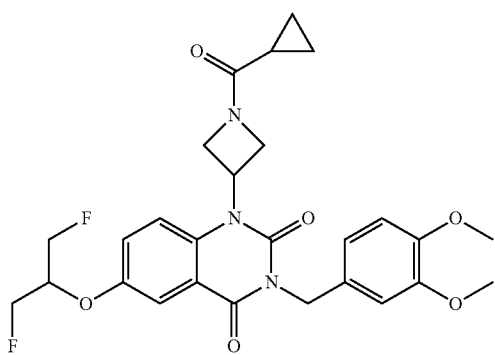 [SMILES: COc1ccc(Cn2c(=O)c3cc(OC(CF)CF)ccc3n(C3CN(C(=O)C4CC4)C3)c2=O)cc1OC] | 1-[1-(cyclopropylcarbonyl)azetidin-3-yl]-3-(3,4-dimethoxybenzyl)-6-[2-fluoro-1-(fluoromethyl)ethoxy]quinazoline-2,4(1H,3H)-dione | 530 |
| 149 | 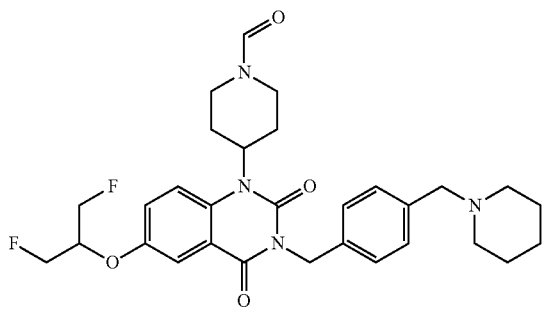 [SMILES: O=CN1CCC(n2c(=O)n(Cc3ccc(CN4CCCCC4)cc3)c(=O)c3cc(OC(CF)CF)ccc32)CC1] | 4-{6-[2-fluoro-1-(fluoromethyl)ethoxy]-2,4-dioxo-3-[4-(piperidin-1-ylmethyl)benzyl]-3,4-dihydroquinazolin-1(2H)-yl}piperidine-1-carbaldehyde | 555 |
| 150 | 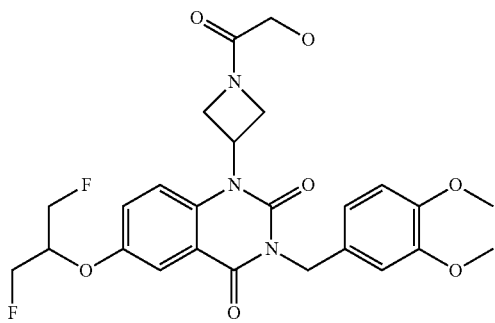 [SMILES: COc1ccc(Cn2c(=O)c3cc(OC(CF)CF)ccc3n(C3CN(C(=O)CO)C3)c2=O)cc1OC] | 3-(3,4-dimethoxybenzyl)-6-[2-fluoro-1-(fluoromethyl)ethoxy]-1-[1-(hydroxyacetyl)azetidin-3-yl]quinazoline-2,4(1H,3H)-dione | 520 |

| | | | |
|---|---|---|---|
| 151 | 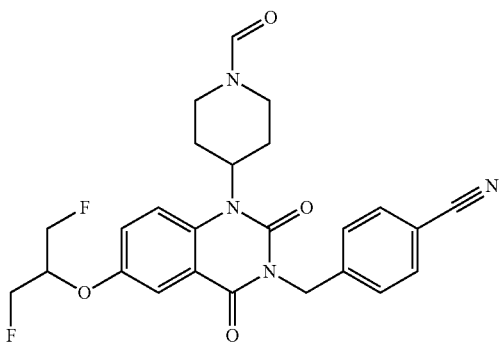 [SMILES: N#Cc1ccc(Cn2c(=O)c3cc(OC(CF)CF)ccc3n(C3CCN(C=O)CC3)c2=O)cc1] | 4-({6-[2-fluoro-1-(fluoromethyl)ethoxy]-1-(1-formylpiperidin-4-yl)-2,4-dioxo-1,4-dihydroquinazolin-3(2H)-yl}methyl)benzonitrile | 483 |
| 152 | 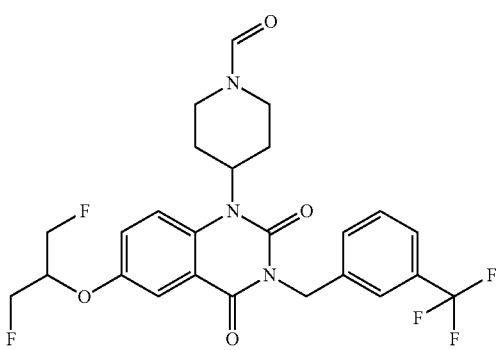 [SMILES: O=CN1CCC(n2c(=O)n(Cc3cccc(C(F)(F)F)c3)c(=O)c3cc(OC(CF)CF)ccc32)CC1] | 4-{6-[2-fluoro-1-(fluoromethyl)ethoxy]-2,4-dioxo-3-[3-(trifluoromethyl)benzyl]-3,4-dihydroquinazolin-1(2H)-yl}piperidine-1-carbaldehyde | 526 |
| 153 | 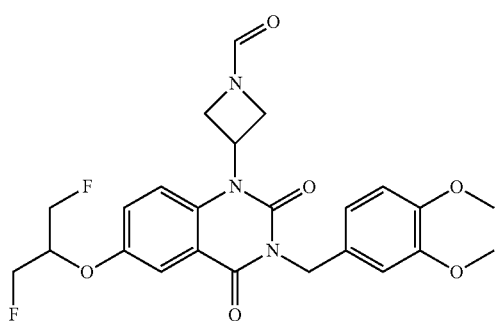 [SMILES: COc1ccc(Cn2c(=O)c3cc(OC(CF)CF)ccc3n(C3CN(C=O)C3)c2=O)cc1OC] | 3-[3-(3,4-dimethoxybenzyl)-6-[2-fluoro-1-(fluoromethyl)ethoxy]-2,4-dioxo-3,4-dihydroquinazolin-1(2H)-yl]azetidine-1-carbaldehyde | 490 |
| 154 | 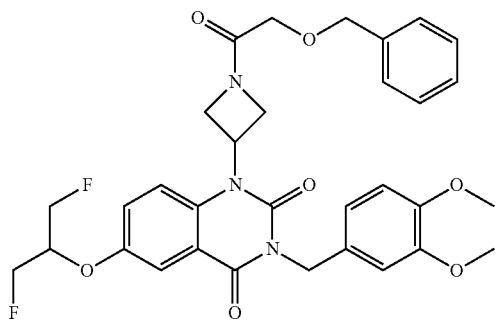 [SMILES: COc1ccc(Cn2c(=O)c3cc(OC(CF)CF)ccc3n(C3CN(C(=O)COCc4ccccc4)C3)c2=O)cc1OC] | 1-{1-[(benzyloxy)acetyl]azetidin-3-yl}-3-(3,4-dimethoxybenzyl)-6-[2-fluoro-1-(fluoromethyl)ethoxy]quinazoline-2,4-(1H,3H)-dione | 610 |

| | | | |
|---|---|---|---|
| 155 | 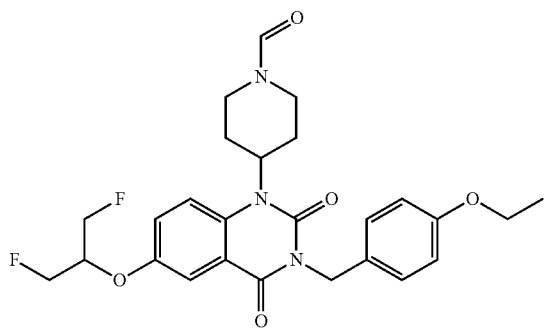 [SMILES: CCOc1ccc(Cn2c(=O)c3cc(OC(CF)CF)ccc3n(C3CCN(C=O)CC3)c2=O)cc1] | 4-[3-(4-ethoxybenzyl)-6-[2-fluoro-1-(fluoromethyl)ethoxy]-2,4-dioxo-3,4-dihydroquinazolin-1(2H)-yl]piperidine-1-carbaldehyde | 502 |
| 156 | 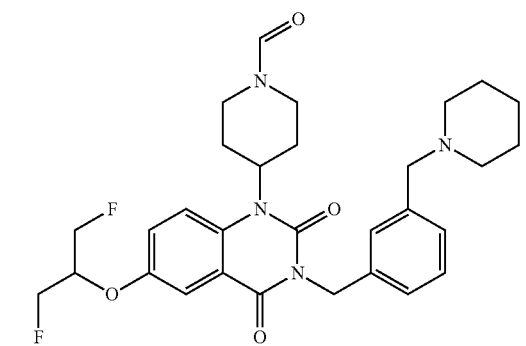 [SMILES: O=CN1CCC(n2c(=O)n(Cc3cccc(CN4CCCCC4)c3)c(=O)c3cc(OC(CF)CF)ccc32)CC1] | 4-{6-[2-fluoro-1-(fluoromethyl)ethoxy]-2,4-dioxo-3-[3-(piperidin-1-ylmethyl)benzyl]-3,4-dihydroquinazolin-1(2H)-yl}piperidine-1-carbaldehyde | 555 |
| 157 | 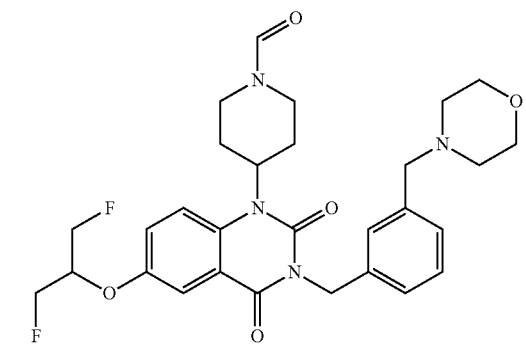 [SMILES: O=CN1CCC(n2c(=O)n(Cc3cccc(CN4CCOCC4)c3)c(=O)c3cc(OC(CF)CF)ccc32)CC1] | 4-{6-[2-fluoro-1-(fluoromethyl)ethoxy]-3-[3-(morpholin-4-ylmethyl)benzyl]-2,4-dioxo-3,4-dihydroquinazolin-1(2H)-yl}piperidine-1-carbaldehyde | 557 |
| 158 | 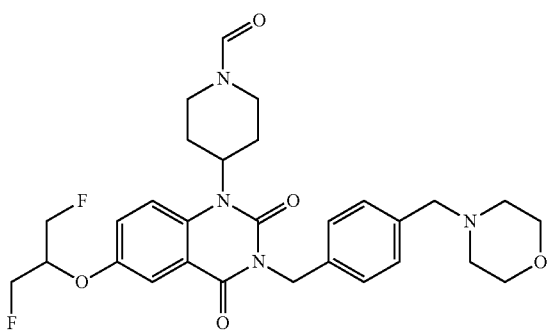 | 4-{6-[2-fluoro-1-(fluoromethyl)ethoxy]-3-[4-(morpholin-4-ylmethyl)benzyl]-2,4-dioxo-3,4-dihydroquinazolin-1(2H)-yl}piperidine-1-carbaldehyde | 557 |

| # | Structure | Name | MW |
|---|---|---|---|
| 159 | 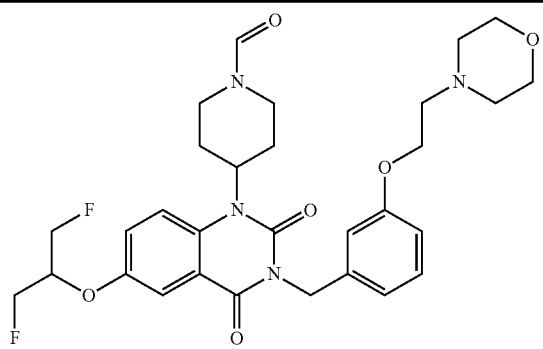 | 4-{6-[2-fluoro-1-(fluoromethyl)ethoxy]-3-[3-(2-(morpholin-4-yl)ethoxy)benzyl]-2,4-dioxo-3,4-dihydroquinazolin-1(2H)-yl}piperidine-1-carbaldehyde | 587 |
| 160 | 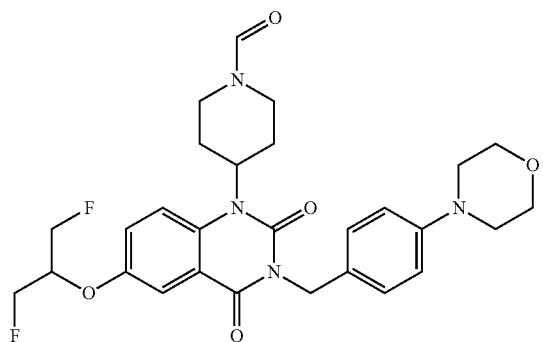 | 4-{6-[2-fluoro-1-(fluoromethyl)ethoxy]-3-(4-(morpholin-4-yl)benzyl)-2,4-dioxo-3,4-dihydroquinazolin-1(2H)-yl}piperidine-1-carbaldehyde | 543 |
| 161 | 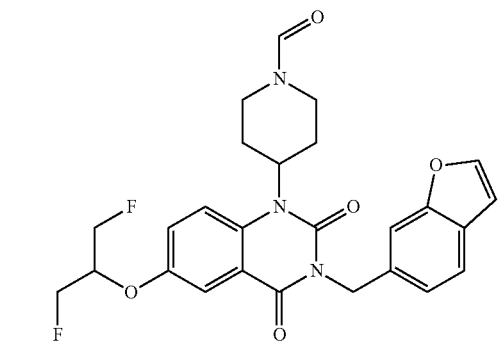 [SMILES: O=CN1CCC(n2c(=O)n(Cc3ccc4ccoc4c3)c(=O)c3cc(OC(CF)CF)ccc32)CC1] | 4-[3-(1-benzofur-6-ylmethyl)-6-[2-fluoro-1-(fluoromethyl)ethoxy]-2,4-dioxo-3,4-dihydroquinazolin-1(2H)-yl]piperidine-1-carbaldehyde | 498 |
| 162 | 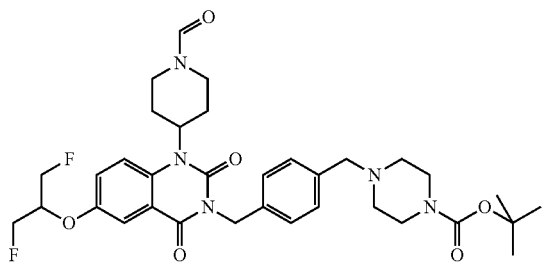 [SMILES: CC(C)(C)OC(=O)N1CCN(Cc2ccc(Cn3c(=O)c4cc(OC(CF)CF)ccc4n(C4CCN(C=O)CC4)c3=O)cc2)CC1] | 1,1-dimethylethyl 4-[4-({6-[2-fluoro-1-(fluoromethyl)ethoxy]-1-(1-formylpiperidin-4-yl)-2,4-dioxo-1,4-dihydroquinazolin-3(2H)-yl}methyl)benzyl]piperazine-1-carboxylate | 656 |
| 163 | 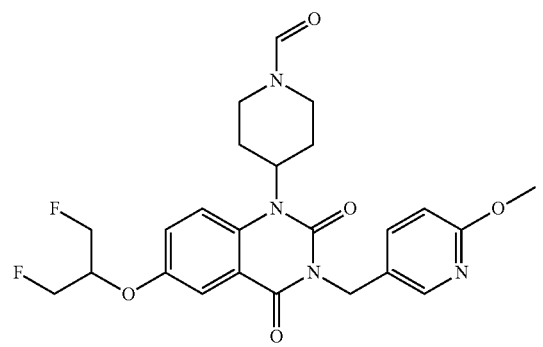 [SMILES: COc1ccc(Cn2c(=O)c3cc(OC(CF)CF)ccc3n(C3CCN(C=O)CC3)c2=O)cn1] | 4-{6-[2-fluoro-1-(fluoromethyl)ethoxy]-3-[(6-methoxypyridin-3-yl)methyl]-2,4-dioxo-3,4-dihydroquinazolin-1(2H)-yl}piperidine-1-carbaldehyde | 489 |

| | | | |
|---|---|---|---|
| 164 | 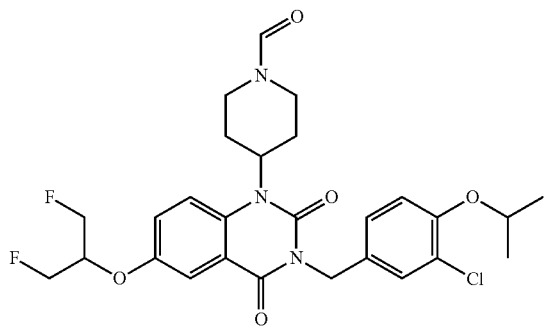 [SMILES: CC(C)Oc1ccc(Cn2c(=O)c3cc(OC(CF)CF)ccc3n(C3CCN(C=O)CC3)c2=O)cc1Cl] | 4-{3-[3-chloro-4-(1-methylethoxy) benzyl]-6-[2-fluoro-1-(fluoromethyl) ethoxy]-2,4-dioxo-3,4-dihydroquinazolin-1(2H)-yl}piperidine-1-carbaldehyde | 550 |
| 165 | 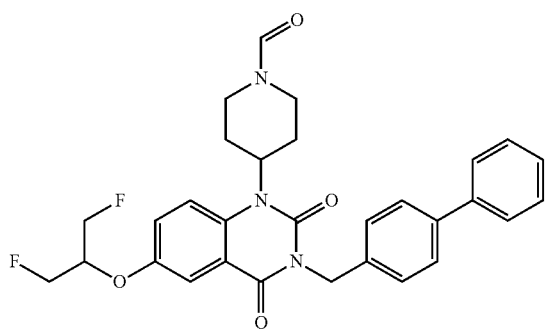 | 4-[3-(biphenyl-4-ylmethyl)-6-[2-fluoro-1-(fluoromethyl)ethoxy]-2,4-dioxo-3,4-dihydroquinazolin-1(2H)-yl]piperidine-1-carbaldehyde | 534 |
| 166 | 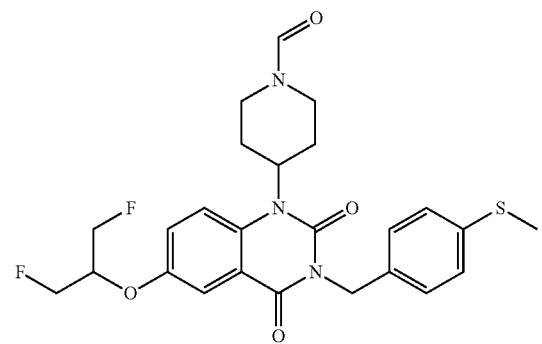 | 4-{6-[2-fluoro-1-(fluoromethyl)ethoxy]-3-[4-(methylsulphanyl)benzyl]-2,4-dioxo-3,4-dihydroquinazolin-1(2H)-yl}piperidine-1-carbaldehyde | 504 |
| 167 | 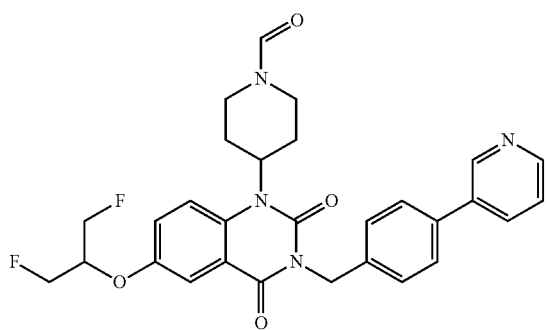 [SMILES: O=CN1CCC(n2c(=O)n(Cc3ccc(-c4cccnc4)cc3)c(=O)c3cc(OC(CF)CF)ccc32)CC1] | 4-{6-[2-fluoro-1-(fluoromethyl) ethoxy]-2,4-dioxo-3-(4-(pyridin-3-yl)benzyl)-3,4-dihydroquinazolin-1(2H)-yl}piperidine-1-carbaldehyde | 535 |

| | | | |
|---|---|---|---|
| 168 | 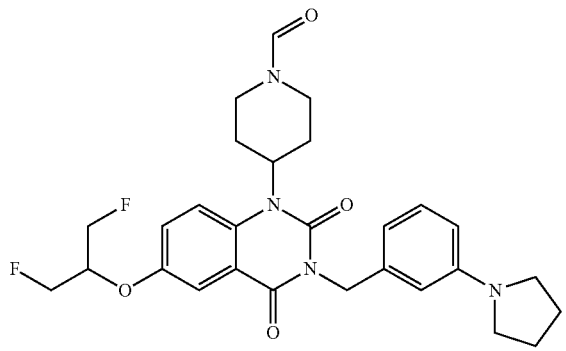 [SMILES: O=CN1CCC(n2c(=O)n(Cc3cccc(N4CCCC4)c3)c(=O)c3cc(OC(CF)CF)ccc32)CC1] | 4-{6-[2-fluoro-1-(fluoromethyl)ethoxy]-2,4-dioxo-3-(3-(pyrrolidin-1-yl)benzyl)-3,4-dihydroquinazolin-1(2H)-yl}piperidine-1-carbaldehyde | 527 |
| 169 | 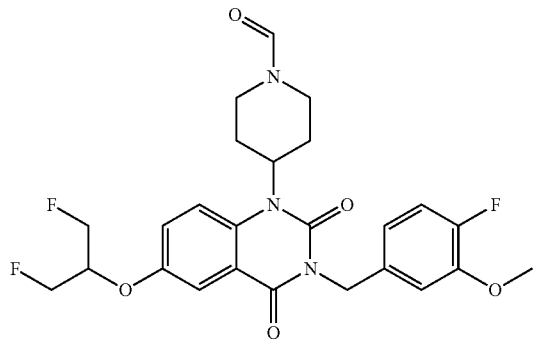 [SMILES: COc1cc(Cn2c(=O)c3cc(OC(CF)CF)ccc3n(C3CCN(C=O)CC3)c2=O)ccc1F] | 4-{6-[2-fluoro-1-(fluoromethyl)ethoxy]-3-(4-fluoro-3-methoxybenzyl)-2,4-dioxo-3,4-dihydroquinazolin-1(2H)-yl}piperidine-1-carbaldehyde | 506 |
| 170 | 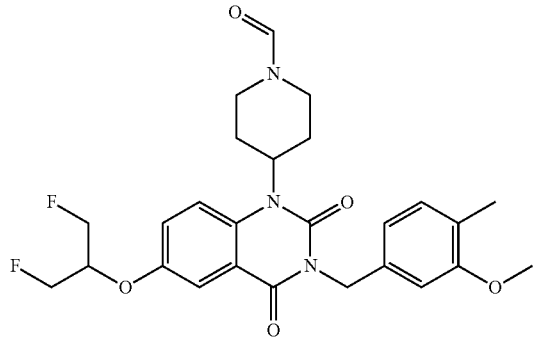 [SMILES: COc1cc(Cn2c(=O)c3cc(OC(CF)CF)ccc3n(C3CCN(C=O)CC3)c2=O)ccc1C] | 4-{6-[2-fluoro-1-(fluoromethyl)ethoxy]-3-(3-methoxy-4-methylbenzyl)-2,4-dioxo-3,4-dihydroquinazolin-1(2H)-yl}piperidine-1-carbaldehyde | 502 |
| 171 | 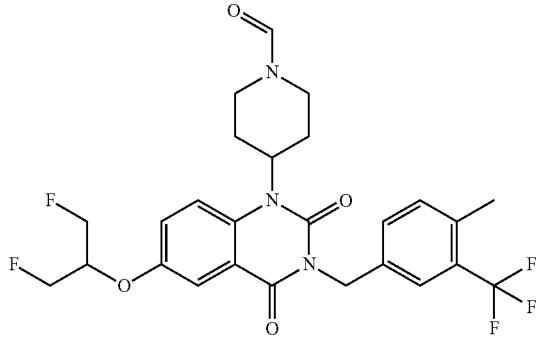 [SMILES: Cc1ccc(Cn2c(=O)c3cc(OC(CF)CF)ccc3n(C3CCN(C=O)CC3)c2=O)cc1C(F)(F)F] | 4-{6-[2-fluoro-1-(fluoromethyl)ethoxy]-3-[4-methyl-3-(trifluoromethyl)benzyl]-2,4-dioxo-3,4-dihydroquinazolin-1(2H)-yl}piperidine-1-carbaldehyde | 540 |

| | | | |
|---|---|---|---|
| 172 | 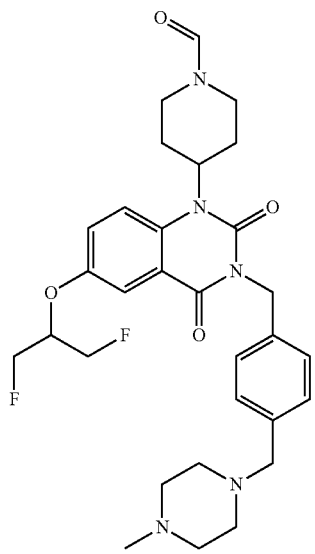 [SMILES: CN1CCN(Cc2ccc(Cn3c(=O)c4cc(OC(CF)CF)ccc4n(C4CCN(C=O)CC4)c3=O)cc2)CC1] | 4-{6-[2-fluoro-1-(fluoromethyl)ethoxy]-3-{4-[(4-methylpiperazin-1-yl)methyl]benzyl}-2,4-dioxo-3,4-dihydroquinazolin-1(2H)-yl}piperidine-1-carbaldehyde | 570 |
| 173 | 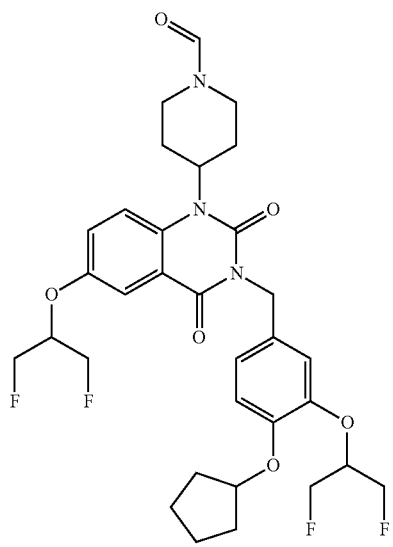 [SMILES: O=CN1CCC(n2c(=O)n(Cc3ccc(OC4CCCC4)c(OC(CF)CF)c3)c(=O)c3cc(OC(CF)CF)ccc32)CC1] | 4-[3-{4-(cyclopentyloxy)-3-[2-fluoro-1-(fluoromethyl)ethoxy]benzyl}-6-[2-fluoro-1-(fluoromethyl)ethoxy]-2,4-dioxo-3,4-dihydroquinazolin-1(2H)-yl]piperidine-1-carbaldehyde | 636 |
| 174 | 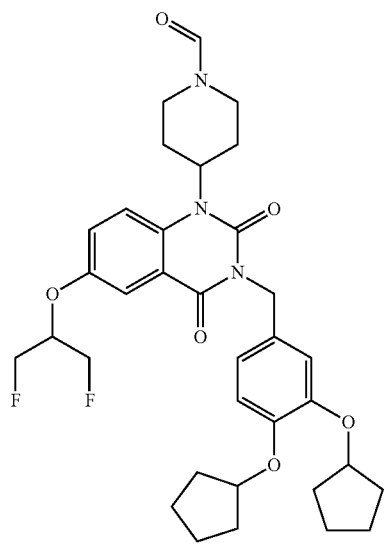 [SMILES: O=CN1CCC(n2c(=O)n(Cc3ccc(OC4CCCC4)c(OC4CCCC4)c3)c(=O)c3cc(OC(CF)CF)ccc32)CC1] | 3-[3,4-bis(cyclopentyloxy)benzyl]-1-(1-ethenylpiperidin-4-yl)-6-[2-fluoro-1-(fluoromethyl)ethoxy]quinazoline-2,4-(1H,3H)-dione | 626 |

| | | | |
|---|---|---|---|
| 175 | 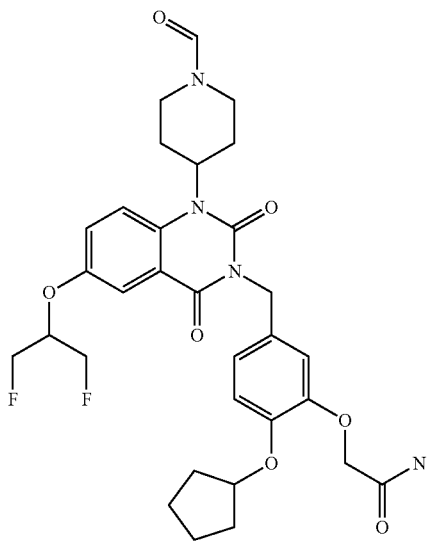 [SMILES: NC(=O)COc1cc(Cn2c(=O)c3cc(OC(CF)CF)ccc3n(C3CCN(C=O)CC3)c2=O)ccc1OC1CCCC1] | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]acetamide | 615 |
| 176 | 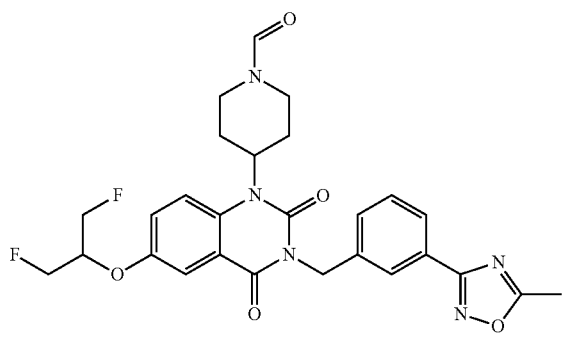 [SMILES: Cc1nc(-c2cccc(Cn3c(=O)c4cc(OC(CF)CF)ccc4n(C4CCN(C=O)CC4)c3=O)c2)no1] | 4-{6-[2-fluoro-1-(fluoromethyl)ethoxy]-3-[3-(5-methyl-1,2,4-oxadiazol-3-yl)benzyl]-2,4-dioxo-3,4-dihydroquinazolin-1(2H)-yl}piperidine-1-carbaldehyde | 540 |
| 177 | 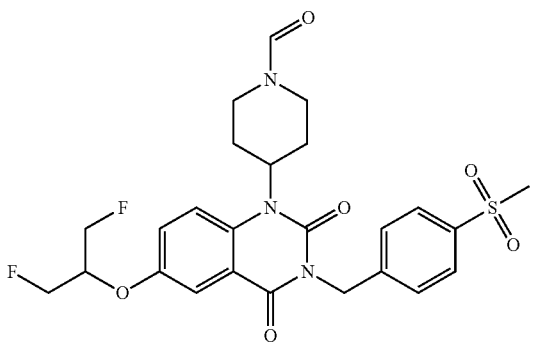 [SMILES: CS(=O)(=O)c1ccc(Cn2c(=O)c3cc(OC(CF)CF)ccc3n(C3CCN(C=O)CC3)c2=O)cc1] | 4-{6-[2-fluoro-1-(fluoromethyl)ethoxy]-3-[4-(methylsulphonyl)benzyl]-2,4-dioxo-3,4-dihydroquinazolin-1(2H)-yl}piperidine-1-carbaldehyde | 536 |
| 178 | 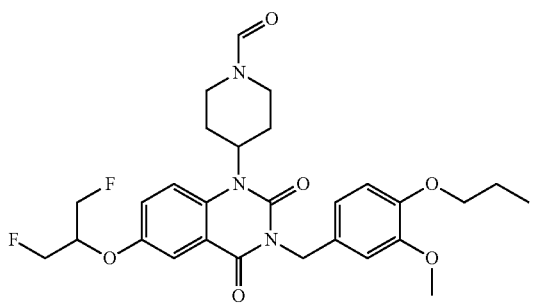 [SMILES: CCCOc1ccc(Cn2c(=O)c3cc(OC(CF)CF)ccc3n(C3CCN(C=O)CC3)c2=O)cc1OC] | 4-{6-[2-fluoro-1-(fluoromethyl)ethoxy]-3-(3-methoxy-4-propoxybenzyl)-2,4-dioxo-3,4-dihydroquinazolin-1(2H)-yl}piperidine-1-carbaldehyde | 546 |

| | | | |
|---|---|---|---|
| 179 | 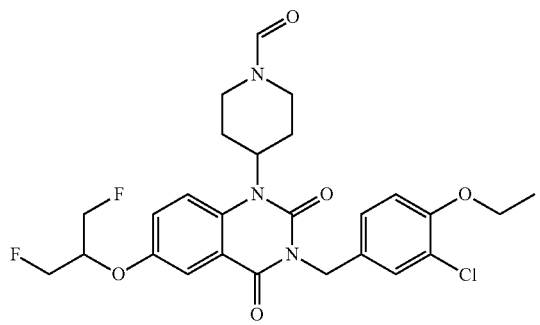 [SMILES: CCOc1ccc(Cn2c(=O)c3cc(OC(CF)CF)ccc3n(C3CCN(C=O)CC3)c2=O)cc1Cl] | 4-[3-(3-chloro-4-ethoxybenzyl)-6-[2-fluoro-1-(fluoromethyl)ethoxy]-2,4-dioxo-3,4-dihydroquinazolin-1(2H)-yl]piperidine-1-carbaldehyde | 536 |
| 180 | 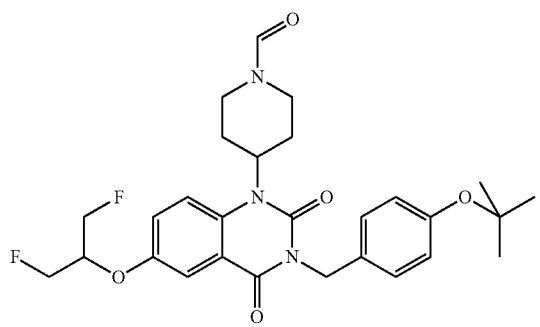 [SMILES: CC(C)(C)Oc1ccc(Cn2c(=O)c3cc(OC(CF)CF)ccc3n(C3CCN(C=O)CC3)c2=O)cc1] | 4-{3-[4-(1,1-dimethylethoxy)benzyl]-6-[2-fluoro-1-(fluoromethyl)ethoxy]-2,4-dioxo-3,4-dihydroquinazolin-1(2H)-yl}piperidine-1-carbaldehyde | 530 |
| 181 | 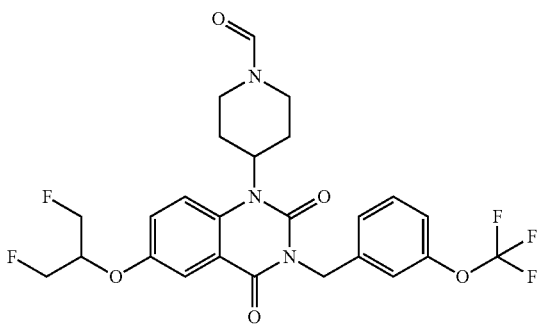 [SMILES: O=CN1CCC(n2c(=O)n(Cc3cccc(OC(F)(F)F)c3)c(=O)c3cc(OC(CF)CF)ccc32)CC1] | 4-{6-[2-fluoro-1-(fluoromethyl)ethoxy]-2,4-dioxo-3-[3-(trifluoromethoxy)benzyl]-3,4-dihydroquinazolin-1(2H)-yl}piperidine-1-carbaldehyde | 542 |
| 182 | 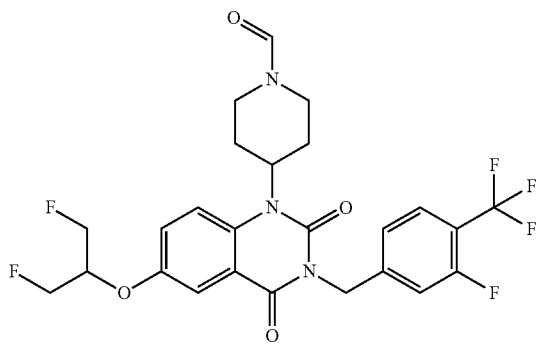 [SMILES: O=CN1CCC(n2c(=O)n(Cc3ccc(C(F)(F)F)c(F)c3)c(=O)c3cc(OC(CF)CF)ccc32)CC1] | 4-{6-fluoro-1-(fluoromethyl)ethoxy]-3-[3-fluoro-4-(trifluoromethyl)benzyl]-2,4-dioxo-3,4-dihydroquinazolin-1(2H)-yl}piperidine-1-carbaldehyde | 544 |

| # | Structure | Name | Value |
|---|---|---|---|
| 183 | 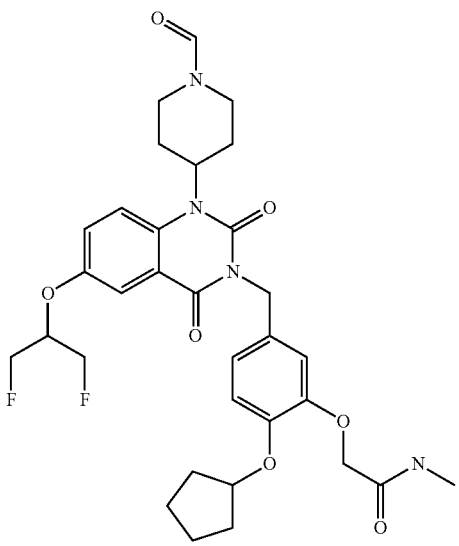 [SMILES: CNC(=O)COc1cc(Cn2c(=O)c3cc(OC(CF)CF)ccc3n(C3CCN(C=O)CC3)c2=O)ccc1OC1CCCC1] | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylacetamide | 629 |
| 184 | 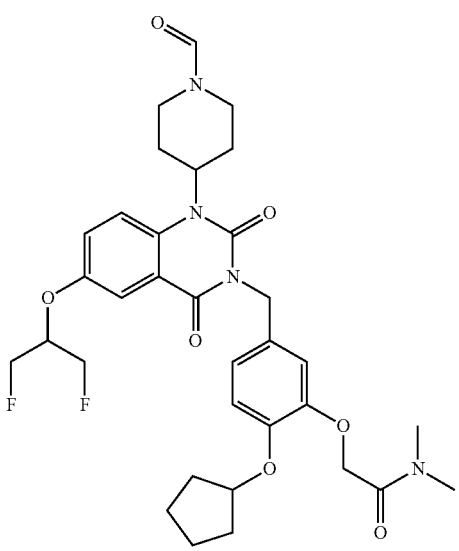 [SMILES: CN(C)C(=O)COc1cc(Cn2c(=O)c3cc(OC(CF)CF)ccc3n(C3CCN(C=O)CC3)c2=O)ccc1OC1CCCC1] | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N,N-dimethylacetamide | 643 |
| 185 | 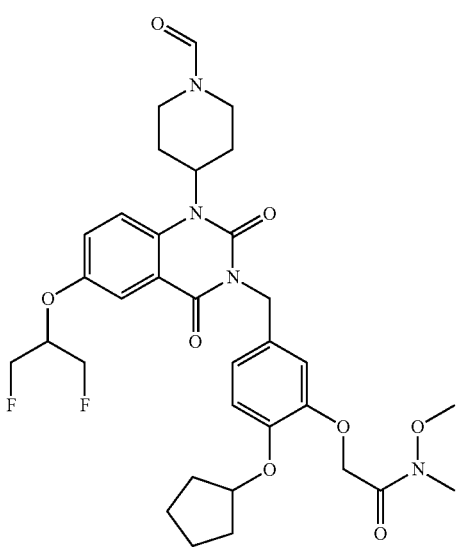 [SMILES: CON(C)C(=O)COc1cc(Cn2c(=O)c3cc(OC(CF)CF)ccc3n(C3CCN(C=O)CC3)c2=O)ccc1OC1CCCC1] | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methoxy-N-methylacetamide | 659 |

| # | Structure | Name | MW |
|---|---|---|---|
| 186 | 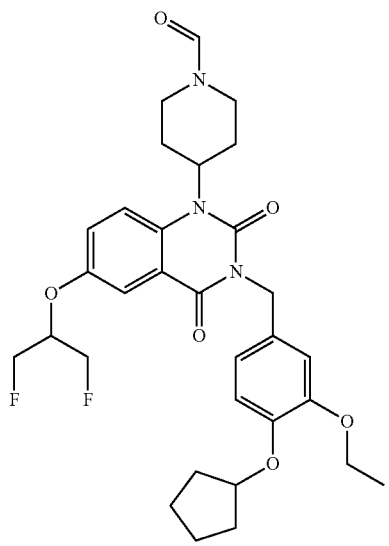 [SMILES: CCOc1cc(Cn2c(=O)c3cc(OC(CF)CF)ccc3n(C3CCN(C=O)CC3)c2=O)ccc1OC1CCCC1] | 4-{3-[4-(cyclopentyloxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde | 586 |
| 187 | 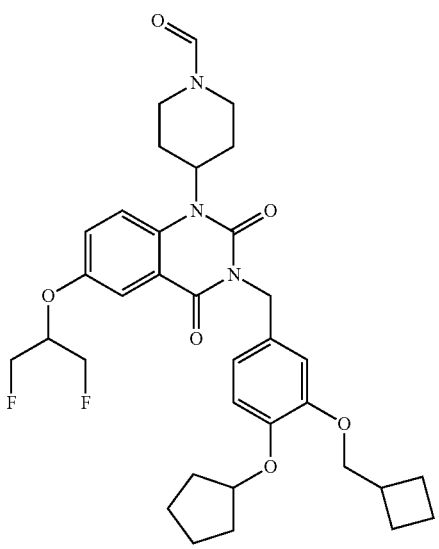 [SMILES: O=CN1CCC(n2c(=O)n(Cc3ccc(OC4CCCC4)c(OCC4CCC4)c3)c(=O)c3cc(OC(CF)CF)ccc32)CC1] | 4-{3-[3-(cyclobutylmethoxy)-4-(cyclopentyloxy)benzyl]-6-[2-fluoro-1-(fluoromethyl)ethoxy]-2,4-dioxo-3,4-dihydroquinazolin-1(2H)-yl}piperidine-1-carbaldehyde | 626 |
| 188 | 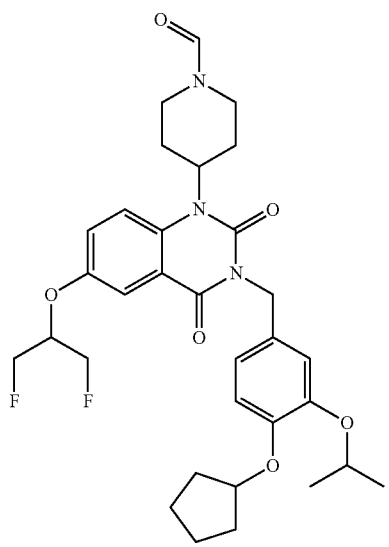 [SMILES: CC(C)Oc1cc(Cn2c(=O)c3cc(OC(CF)CF)ccc3n(C3CCN(C=O)CC3)c2=O)ccc1OC1CCCC1] | 4-{3-[4-(cyclopentyloxy)-3-(1-methylethoxy)benzyl]-6-[2-fluoro-1-(fluoromethyl)ethoxy]-2,4-dioxo-3,4-dihydroquinazolin-1(2H)-yl}piperidine-1-carbaldehyde | 600 |

| 189 | 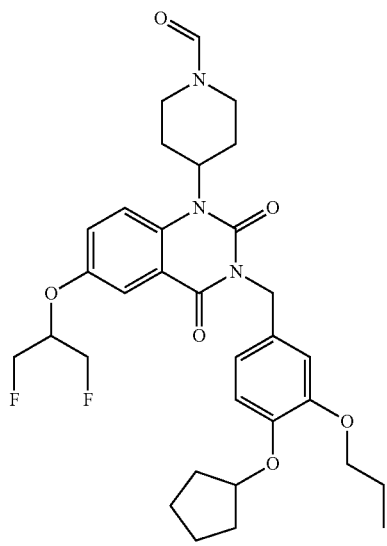 [SMILES: CCCOc1cc(Cn2c(=O)c3cc(OC(CF)CF)ccc3n(C3CCN(C=O)CC3)c2=O)ccc1OC1CCCC1] | 4-{3-[4-(cyclopentyloxy)-3-propoxybenzyl]-6-[2-fluoro-1-(fluoromethyl)ethoxy]-2,4-dioxo-3,4-dihydroquinazolin-1(2H)-yl}piperidine-1-carbaldehyde | 600 |
| 190 | 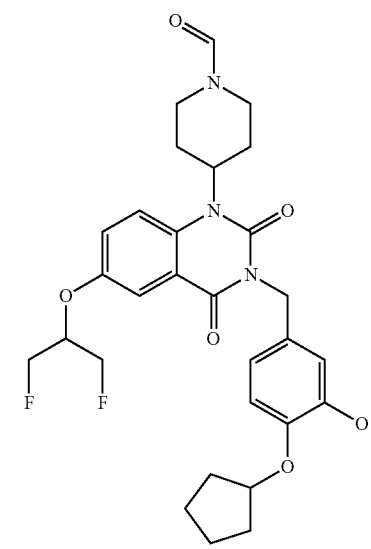 [SMILES: O=CN1CCC(n2c(=O)n(Cc3ccc(OC4CCCC4)c(O)c3)c(=O)c3cc(OC(CF)CF)ccc32)CC1] | 4-{3-[4-(cyclopentyloxy)-3-hydroxybenzyl]-6-[2-fluoro-1-(fluoromethyl)ethoxy]-2,4-dioxo-3,4-dihydroquinazolin-1(2H)-yl}piperidine-1-carbaldehyde | 558 |
| 191 | 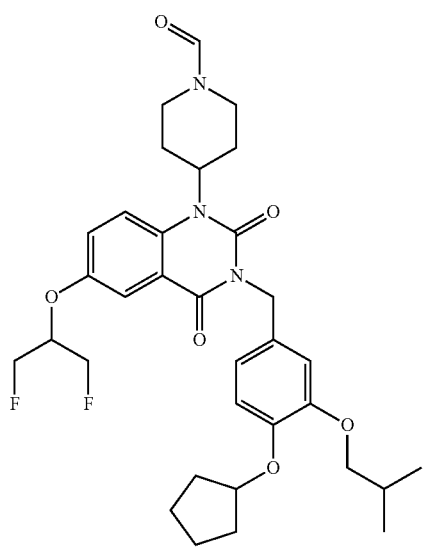 [SMILES: CC(C)COc1cc(Cn2c(=O)c3cc(OC(CF)CF)ccc3n(C3CCN(C=O)CC3)c2=O)ccc1OC1CCCC1] | 4-{3-[4-(cyclopentyloxy)-3-(2-methylpropoxy)benzyl]-6-[2-fluoro-1-(fluoromethyl)ethoxy]-2,4-dioxo-3,4-dihydroquinazolin-1(2H)-yl}piperidine-1-carbaldehyde | 614 |

| | | | |
|---|---|---|---|
| 192 | 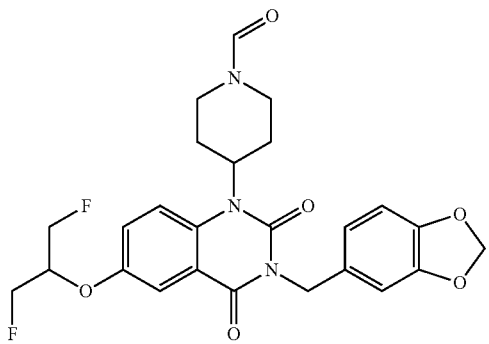 [SMILES: O=CN1CCC(n2c(=O)n(Cc3ccc4c(c3)OCO4)c(=O)c3cc(OC(CF)CF)ccc32)CC1] | 4-[3-(1,3-benzodioxol-5-ylmethyl)-6-[2-fluoro-1-(fluoromethyl)ethoxy]-2,4-dioxo-3,4-dihydroquinazolin-1(2H)-yl]piperidine-1-carbaldehyde | 502 |
| 193 | 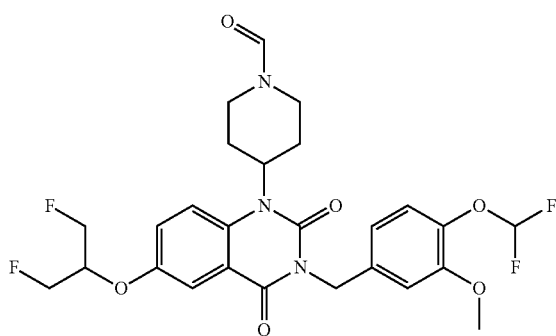 [SMILES: COc1cc(Cn2c(=O)c3cc(OC(CF)CF)ccc3n(C3CCN(C=O)CC3)c2=O)ccc1OC(F)F] | 4-{3-[4-(difluoromethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | 554 |
| 194 | 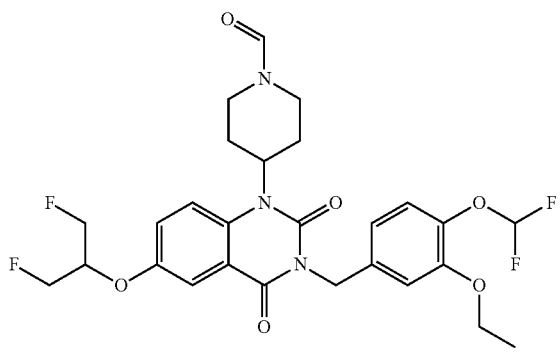 [SMILES: CCOc1cc(Cn2c(=O)c3cc(OC(CF)CF)ccc3n(C3CCN(C=O)CC3)c2=O)ccc1OC(F)F] | 4-{3-[4-(difluoromethoxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde | 568 |
| 195 | 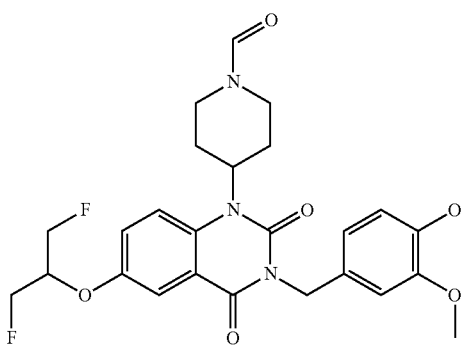 [SMILES: COc1cc(Cn2c(=O)c3cc(OC(CF)CF)ccc3n(C3CCN(C=O)CC3)c2=O)ccc1O] | 4-{6-[2-fluoro-1-(fluoromethyl)ethoxy]-3-(4-hydroxy-3-methoxybenzyl)-2,4-dioxo-3,4-dihydroquinazolin-1(2H)-yl}piperidine-1-carbaldehyde | 504 |

-continued

| | | |
|---|---|---|
| 196 | 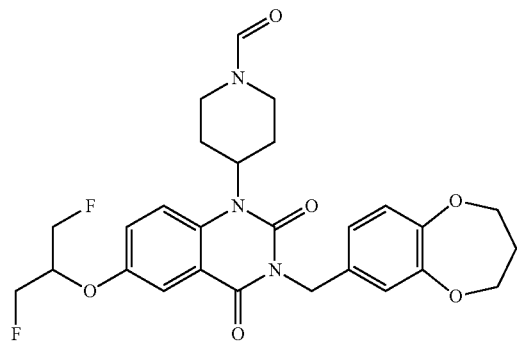 [SMILES: O=CN1CCC(n2c(=O)n(Cc3ccc4c(c3)OCCCO4)c(=O)c3cc(OC(CF)CF)ccc32)CC1] | 4-[3-(3,4-dihydro-2H-1,5-benzodioxepin-7-ylmethyl)-6-[2-fluoro-1-(fluoromethyl)ethoxy]-2,4-dioxo-3,4-dihydroquinazolin-1(2H)-yl]piperidine-1-carbaldehyde  530 |
| 197 | 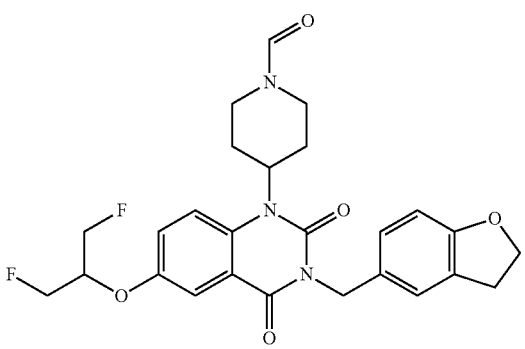 [SMILES: O=CN1CCC(n2c(=O)n(Cc3ccc4c(c3)CCO4)c(=O)c3cc(OC(CF)CF)ccc32)CC1] | 4-[3-(2,3-dihydro-1-benzofur-5-ylmethyl)-6-[2-fluoro-1-(fluoromethyl)ethoxy]-2,4-dioxo-3,4-dihydroquinazolin-1(2H)-yl]piperidine-1-carbaldehyde  500 |
| 198 | 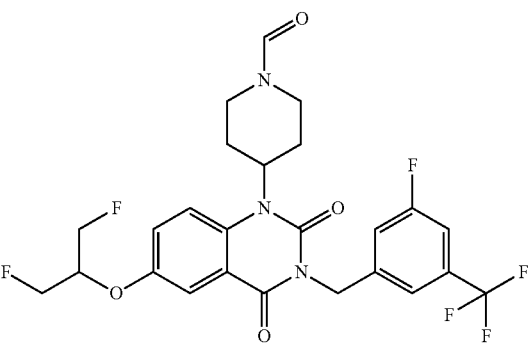 [SMILES: O=CN1CCC(n2c(=O)n(Cc3cc(F)cc(C(F)(F)F)c3)c(=O)c3cc(OC(CF)CF)ccc32)CC1] | 4-{6-[2-fluoro-1-(fluoromethyl)ethoxy]-3-[3-fluoro-5-(trifluoromethyl)benzyl]-2,4-dioxo-3,4-dihydroquinazolin-1(2H)-yl}piperidine-1-carbaldehyde  544 |
| 199 | 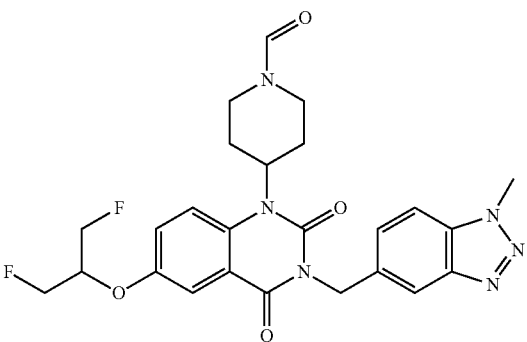 [SMILES: Cn1nnc2cc(Cn3c(=O)c4cc(OC(CF)CF)ccc4n(C4CCN(C=O)CC4)c3=O)ccc21] | 4-{6-[2-fluoro-1-(fluoromethyl)ethoxy]-3-[(1-methyl-1H-benzotriazol-5-yl)methyl]-2,4-dioxo-3,4-dihydroquinazolin-1(2H)-yl}piperidine-1-carbaldehyde  513 |

-continued

| | | | |
|---|---|---|---|
| 200 | 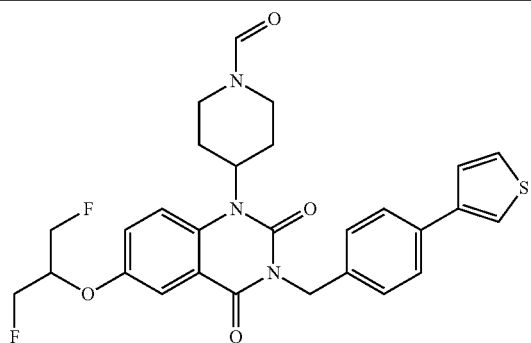 | 4-{6-[2-fluoro-1-(fluoromethyl)ethoxy]-2,4-dioxo-3-(4-(thiophen-3-yl)benzyl)-3,4-dihydroquinazolin-1(2H)-yl}piperidine-1-carbaldehyde | 540 |
| 201 | 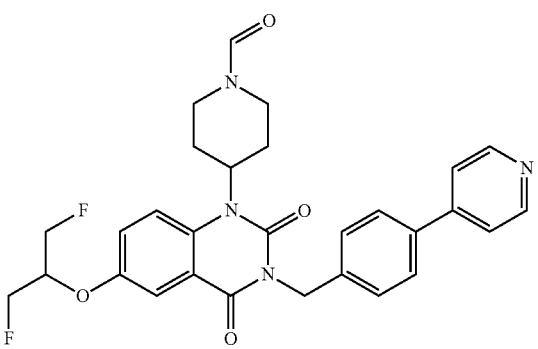 [SMILES: O=CN1CCC(n2c(=O)n(Cc3ccc(-c4ccncc4)cc3)c(=O)c3cc(OC(CF)CF)ccc32)CC1] | 4-{6-[2-fluoro-1-(fluoromethyl)ethoxy]-2,4-dioxo-3-(4-(pyridin-4-yl)benzyl)-3,4-dihydroquinazolin-1(2H)-yl}piperidine-1-carbaldehyde | 535 |
| 202 | 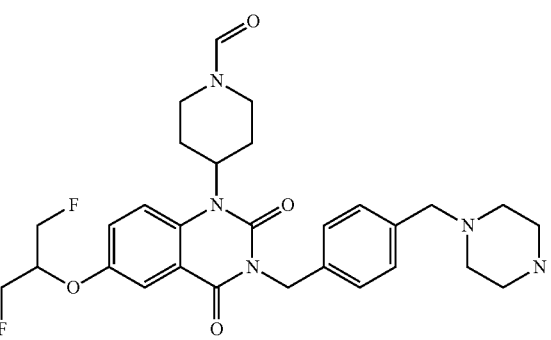 | 4-{6-[2-fluoro-1-(fluoromethyl)ethoxy]-2,4-dioxo-3-[4-(piperazin-1-ylmethyl)benzyl]-3,4-dihydroquinazolin-1(2H)-yl}piperidine-1-carbaldehyde | 555 |
| 203 | 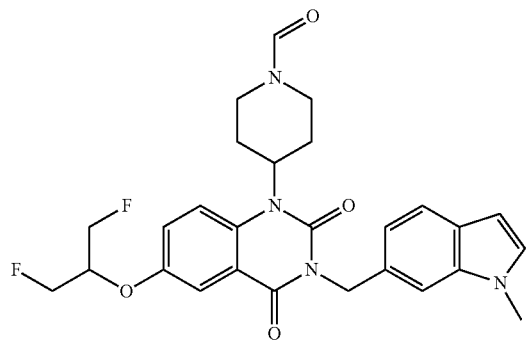 [SMILES: Cn1ccc2ccc(Cn3c(=O)c4cc(OC(CF)CF)ccc4n(C4CCN(C=O)CC4)c3=O)cc21] | 4-{6-[2-fluoro-1-(fluoromethyl)ethoxy]-3-[(1-methyl-1H-indol-6-yl)methyl]-2,4-dioxo-3,4-dihydroquinazolin-1(2H)-yl}piperidine-1-carbaldehyde | 511 |

| # | Structure | Name | MW |
|---|---|---|---|
| 204 | 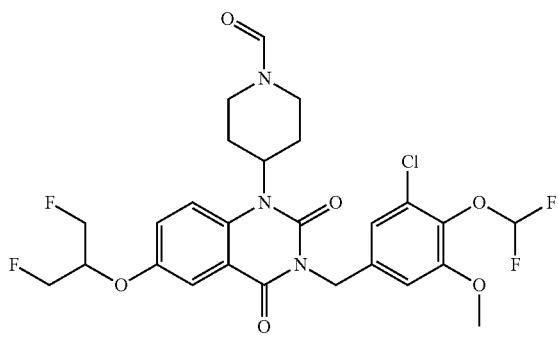 [SMILES: COc1cc(Cn2c(=O)c3cc(OC(CF)CF)ccc3n(C3CCN(C=O)CC3)c2=O)cc(Cl)c1OC(F)F] | 4-{3-[3-chloro-4-(difluoromethoxy)-5-methoxybenzyl]-6-[2-fluoro-1-(fluoromethyl)ethoxy]-2,4-dioxo-3,4-dihydroquinazolin-1(2H)-yl}piperidine-1-carbaldehyde | 588 |
| 205 | 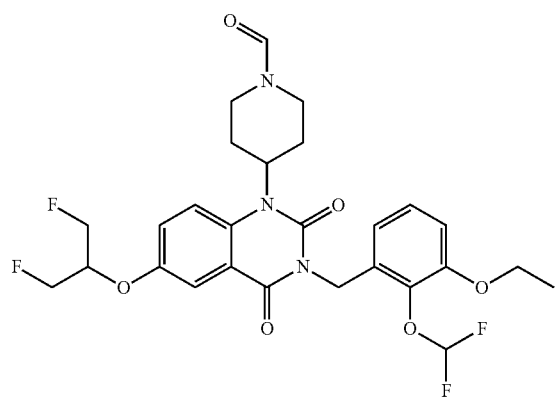 [SMILES: CCOc1cccc(Cn2c(=O)c3cc(OC(CF)CF)ccc3n(C3CCN(C=O)CC3)c2=O)c1OC(F)F] | 4-{3-[2-(difluoromethoxy)-3-ethoxybenzyl]-6-[2-fluoro-1-(fluoromethyl)ethoxy]-2,4-dioxo-3,4-dihydroquinazolin-1(2H)-yl}piperidine-1-carbaldehyde | 568 |
| 206 | 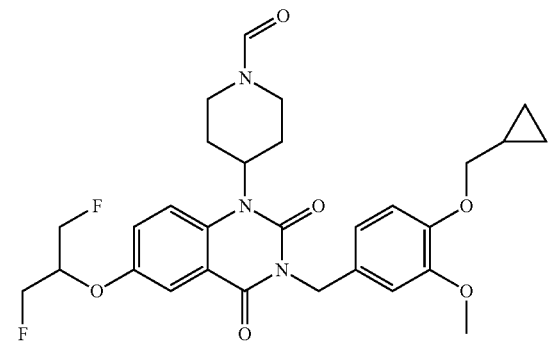 [SMILES: COc1cc(Cn2c(=O)c3cc(OC(CF)CF)ccc3n(C3CCN(C=O)CC3)c2=O)ccc1OCC1CC1] | 4-{3-[4-(cyclopropylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | 558 |
| 207 | 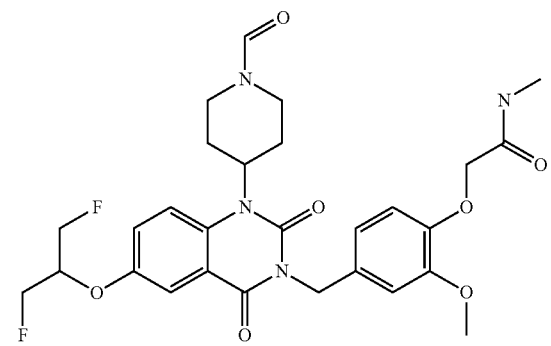 [SMILES: CNC(=O)COc1ccc(Cn2c(=O)c3cc(OC(CF)CF)ccc3n(C3CCN(C=O)CC3)c2=O)cc1OC] | 2-[4-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]-N-methylacetamide | 575 |

| # | Structure | Name | MW |
|---|---|---|---|
| 208 | 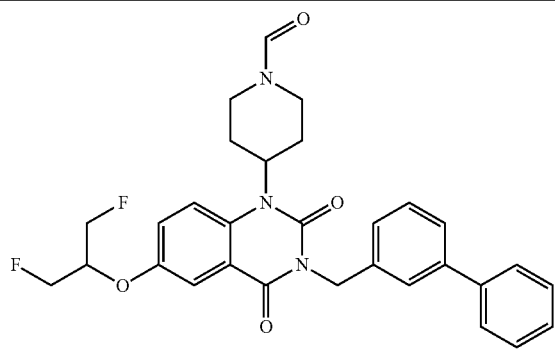 | 4-[3-(biphenyl-3-ylmethyl)-6-[2-fluoro-1-(fluoromethyl)ethoxy]-2,4-dioxo-3,4-dihydroquinazolin-1(2H)-yl]piperidine-1-carbaldehyde | 534 |
| 209 | 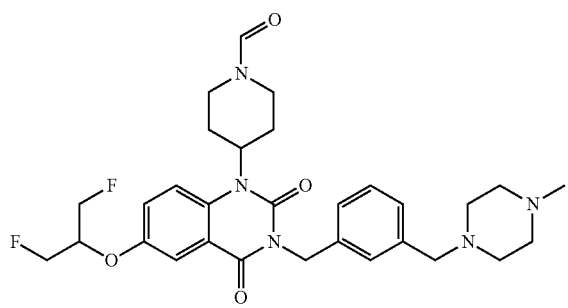 [SMILES: CN1CCN(Cc2cccc(Cn3c(=O)c4cc(OC(CF)CF)ccc4n(C4CCN(C=O)CC4)c3=O)c2)CC1] | 4-{6-[2-fluoro-1-(fluoromethyl)ethoxy]-3-{3-[(4-methylpiperazin-1-yl)methyl]benzyl}-2,4-dioxo-3,4-dihydroquinazolin-1(2H)-yl}piperidine-1-carbaldehyde | 570 |
| 210 | 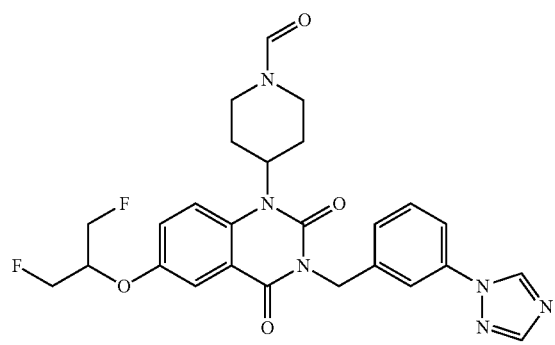 [SMILES: O=CN1CCC(n2c(=O)n(Cc3cccc(-n4cncn4)c3)c(=O)c3cc(OC(CF)CF)ccc32)CC1] | 4-{6-[2-fluoro-1-(fluoromethyl)ethoxy]-2,4-dioxo-3-[3-(1H-1,2,4-triazol-1-yl)benzyl]-3,4-dihydroquinazolin-1(2H)-yl}piperidine-1-carbaldehyde | 525 |
| 211 | 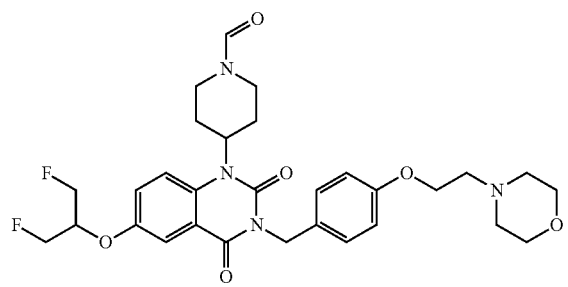 [SMILES: O=CN1CCC(n2c(=O)n(Cc3ccc(OCCN4CCOCC4)cc3)c(=O)c3cc(OC(CF)CF)ccc32)CC1] | 4-{6-[2-fluoro-1-(fluoromethyl)ethoxy]-3-[4-(2-(morpholin-4-yl)ethoxy]benzyl]-2,4-dioxo-3,4-dihydroquinazolin-1(2H)-yl}piperidine-1-carbaldehyde | 587 |
| 212 | 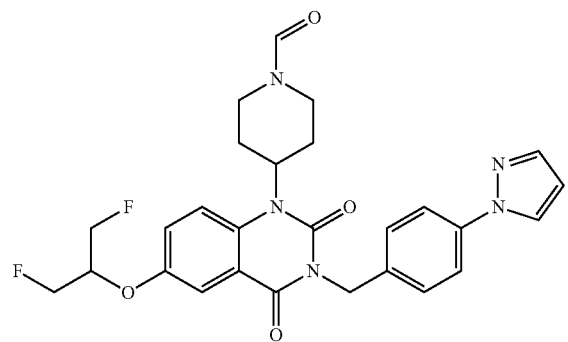 [SMILES: O=CN1CCC(n2c(=O)n(Cc3ccc(-n4cccn4)cc3)c(=O)c3cc(OC(CF)CF)ccc32)CC1] | 4-{6-[2-fluoro-1-(fluoromethyl)ethoxy]-2,4-dioxo-3-[4-(1H-pyrazol-1-yl)benzyl]-3,4-dihydroquinazolin-1(2H)-yl}piperidine-1-carbaldehyde | 524 |

| | | | |
|---|---|---|---|
| 213 | 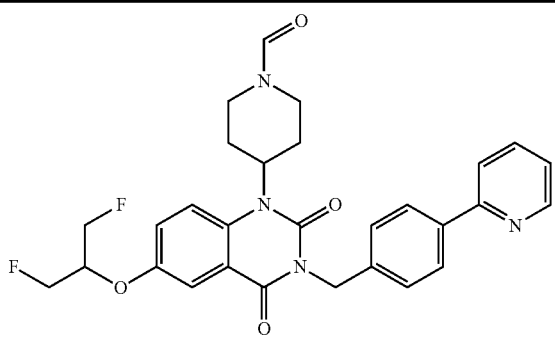 | 4-{6-[2-fluoro-1-(fluoromethyl)ethoxy]-2,4-dioxo-3-(4-(pyridin-2-yl)benzyl)-3,4-dihydroquinazolin-1(2H)-yl}piperidine-1-carbaldehyde | 535 |
| 214 | 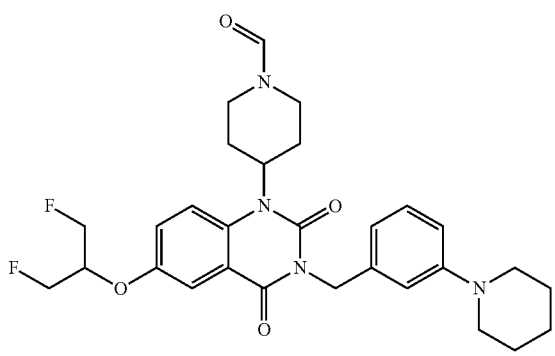 [SMILES: O=CN1CCC(n2c(=O)n(Cc3cccc(N4CCCCC4)c3)c(=O)c3cc(OC(CF)CF)ccc32)CC1] | 4-{6-[2-fluoro-1-(fluoromethyl)ethoxy]-2,4-dioxo-3-(3-(piperidin-1-yl)benzyl)-3,4-dihydroquinazolin-1(2H)-yl}piperidine-1-carbaldehyde | 541 |
| 215 | 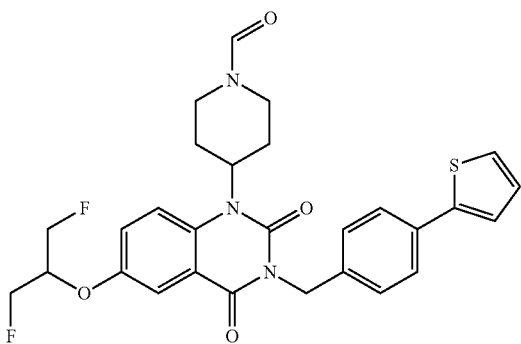 [SMILES: O=CN1CCC(n2c(=O)n(Cc3ccc(-c4cccs4)cc3)c(=O)c3cc(OC(CF)CF)ccc32)CC1] | 4-{6-[2-fluoro-1-(fluoromethyl)ethoxy]-2,4-dioxo-3-(4-(thiophen-2-yl)benzyl)-3,4-dihydroquinazolin-1(2H)-yl}piperidine-1-carbaldehyde | 540 |
| 216 | 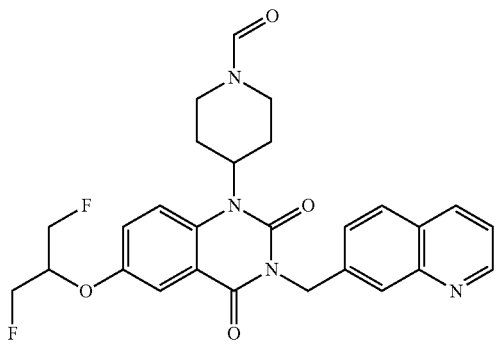 [SMILES: O=CN1CCC(n2c(=O)n(Cc3ccc4cccnc4c3)c(=O)c3cc(OC(CF)CF)ccc32)CC1] | 4-{6-[2-fluoro-1-(fluoromethyl)ethoxy]-2,4-dioxo-3-(quinolin-7-ylmethyl)-3,4-dihydroquinazolin-1(2H)-yl}piperidine-1-carbaldehyde | 509 |

| | | | |
|---|---|---|---|
| 217 | 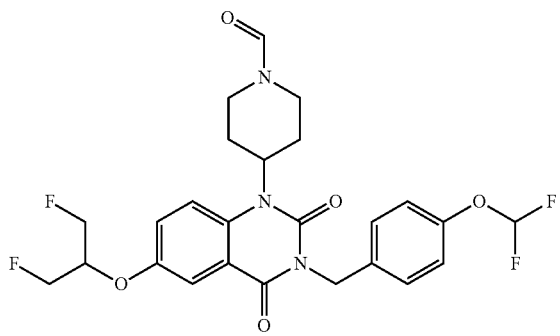 [SMILES: O=CN1CCC(n2c(=O)n(Cc3ccc(OC(F)F)cc3)c(=O)c3cc(OC(CF)CF)ccc32)CC1] | 4-{3-[4-(difluoromethoxy)benzyl]-6-[2-fluoro-1-(fluoromethyl)ethoxy]-2,4-dioxo-3,4-dihydroquinazolin-1(2H)-yl}piperidine-1-carbaldehyde | 524 |
| 218 | 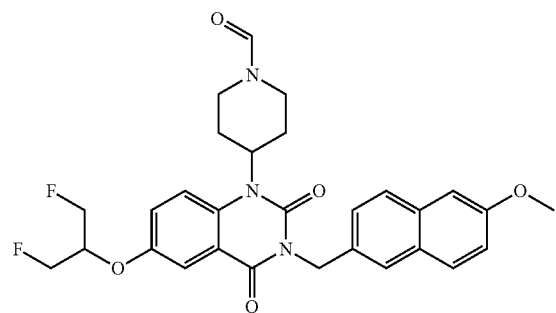 [SMILES: COc1ccc2cc(Cn3c(=O)c4cc(OC(CF)CF)ccc4n(C4CCN(C=O)CC4)c3=O)ccc2c1] | 4-{6-[2-fluoro-1-(fluoromethyl)ethoxy]-3-[(6-methoxynaphth-2-yl)methyl]-2,4-dioxo-3,4-dihydroquinazolin-1(2H)-yl}piperidine-1-carbaldehyde | 538 |
| 219 | 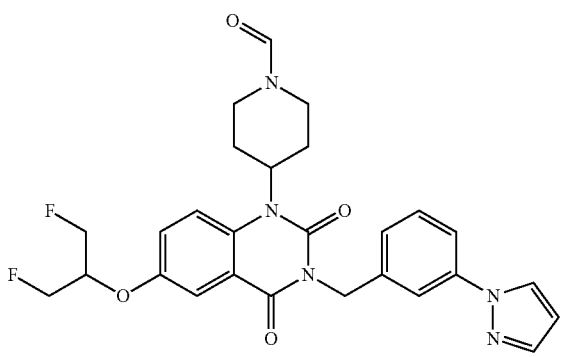 [SMILES: O=CN1CCC(n2c(=O)n(Cc3cccc(-n4cccn4)c3)c(=O)c3cc(OC(CF)CF)ccc32)CC1] | 4-{6-[2-fluoro-1-(fluoromethyl)ethoxy]-2,4-dioxo-3-[3-(1H-pyrazol-1-yl)benzyl]-3,4-dihydroquinazolin-1(2H)-yl}piperidine-1-carbaldehyde | 524 |
| 220 | 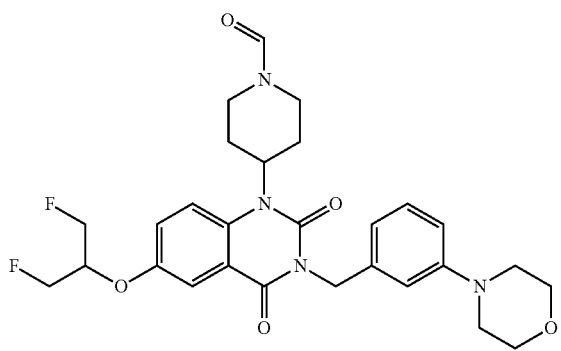 [SMILES: O=CN1CCC(n2c(=O)n(Cc3cccc(N4CCOCC4)c3)c(=O)c3cc(OC(CF)CF)ccc32)CC1] | 4-{6-[2-fluoro-1-(fluoromethyl)ethoxy]-3-(3-(morpholin-4-yl)benzyl)-2,4-dioxo-3,4-dihydroquinazolin-1(2H)-yl}piperidine-1-carbaldehyde | 543 |

-continued

| | | | |
|---|---|---|---|
| 221 | 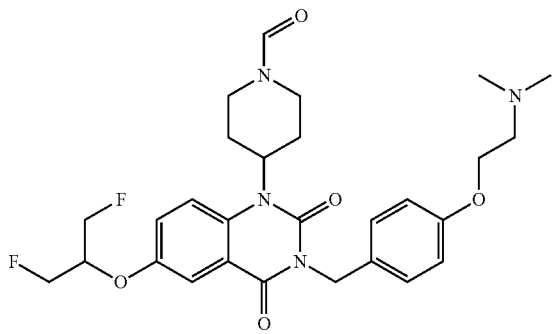 [SMILES: CN(C)CCOc1ccc(Cn2c(=O)c3cc(OC(CF)CF)ccc3n(C3CCN(C=O)CC3)c2=O)cc1] | 4-[3-{4-[2-(dimethylamino)ethoxy]benzyl}-6-[2-fluoro-1-(fluoromethyl)ethoxy]-2,4-dioxo-3,4-dihydroquinazolin-1(2H)-yl]piperidine-1-carbaldehyde | 545 |
| 222 | 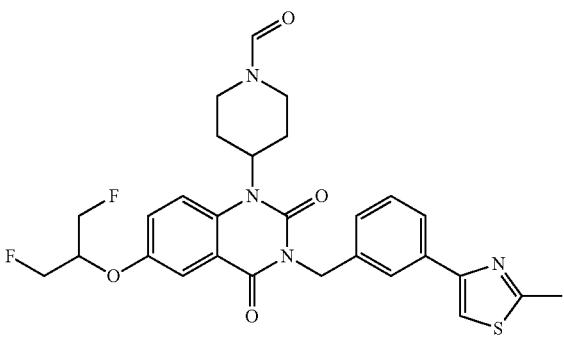 [SMILES: Cc1nc(-c2cccc(Cn3c(=O)c4cc(OC(CF)CF)ccc4n(C4CCN(C=O)CC4)c3=O)c2)cs1] | 4-{6-[2-fluoro-1-(fluoromethyl)ethoxy]-3-[3-(2-methyl-1,3-thiazol-4-yl)benzyl]-2,4-dioxo-3,4-dihydroquinazolin-1(2H)-yl}piperidine-1-carbaldehyde | 555 |
| 223 | 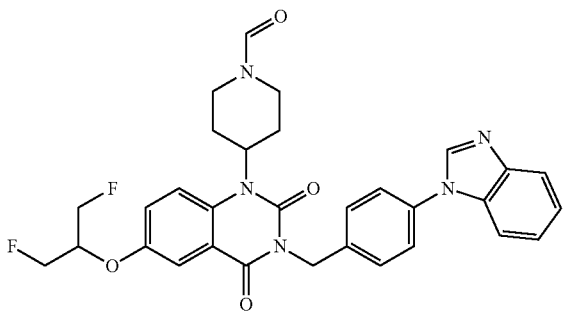 [SMILES: O=CN1CCC(n2c(=O)n(Cc3ccc(-n4cnc5ccccc54)cc3)c(=O)c3cc(OC(CF)CF)ccc32)CC1] | 4-{3-[4-(1H-benzimidazol-1-yl)benzyl]-6-[2-fluoro-1-(fluoromethyl)ethoxy]-2,4-dioxo-3,4-dihydroquinazolin-1(2H)-yl}piperidine-1-carbaldehyde | 574 |
| 224 | 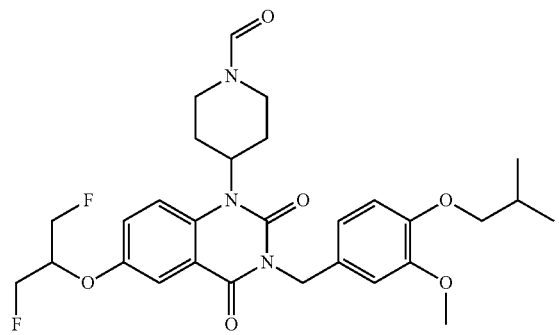 [SMILES: COc1cc(Cn2c(=O)c3cc(OC(CF)CF)ccc3n(C3CCN(C=O)CC3)c2=O)ccc1OCC(C)C] | 4-{6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde | 560 |
| 225 | 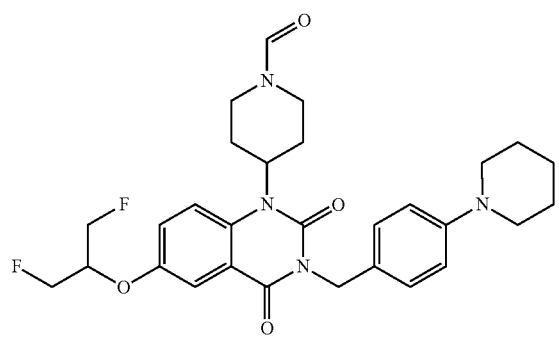 [SMILES: O=CN1CCC(n2c(=O)n(Cc3ccc(N4CCCCC4)cc3)c(=O)c3cc(OC(CF)CF)ccc32)CC1] | 4-{6-[2-fluoro-1-(fluoromethyl)ethoxy]-2,4-dioxo-3-(4-(piperidin-1-yl)benzyl)-3,4-dihydroquinazolin-1(2H)-yl}piperidine-1-carbaldehyde | 541 |

| | | | |
|---|---|---|---|
| 226 | 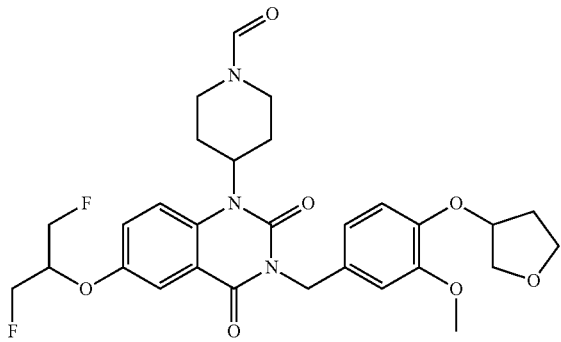 [SMILES: COc1cc(Cn2c(=O)c3cc(OC(CF)CF)ccc3n(C3CCN(C=O)CC3)c2=O)ccc1OC1CCOC1] | 4-{6-[2-fluoro-1-(fluoromethyl)ethoxy]-3-[3-methoxy-4-(tetrahydrofuran-3-yloxy)benzyl]-2,4-dioxo-3,4-dihydroquinazolin-1(2H)-yl}piperidine-1-carbaldehyde | 574 |
| 227 | 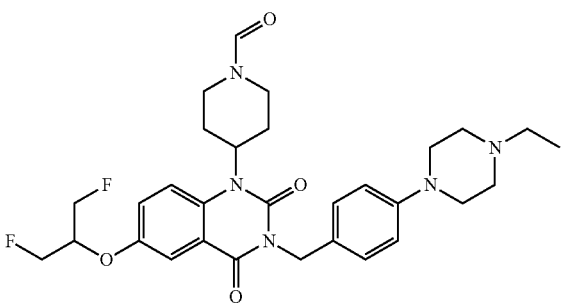 [SMILES: CCN1CCN(c2ccc(Cn3c(=O)c4cc(OC(CF)CF)ccc4n(C4CCN(C=O)CC4)c3=O)cc2)CC1] | 4-{3-[4-(4-ethylpiperazin-1-yl)benzyl]-6-[2-fluoro-1-(fluoromethyl)ethoxy]-2,4-dioxo-3,4-dihydroquinazolin-1(2H)-yl}piperidine-1-carbaldehyde | 570 |
| 228 | 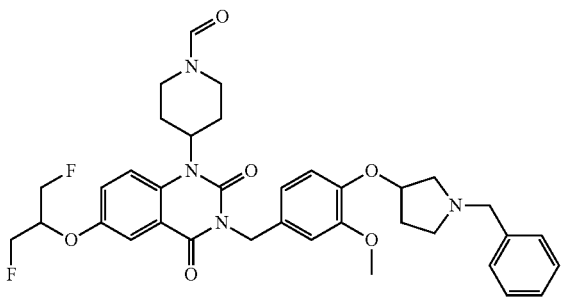 [SMILES: COc1cc(Cn2c(=O)c3cc(OC(CF)CF)ccc3n(C3CCN(C=O)CC3)c2=O)ccc1OC1CCN(Cc2ccccc2)C1] | 4-[3-{4-[(1-benzylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 663 |
| 229 | 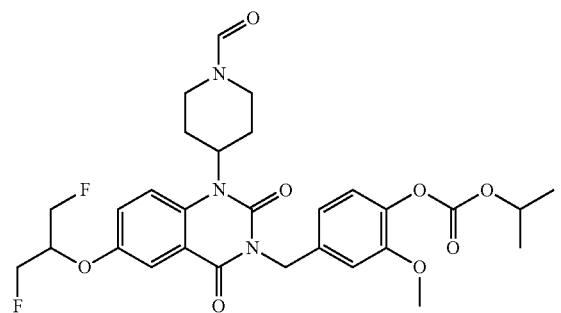 [SMILES: COc1cc(Cn2c(=O)c3cc(OC(CF)CF)ccc3n(C3CCN(C=O)CC3)c2=O)ccc1OC(=O)OC(C)C] | 4-({6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 1-methylethyl carbonate | 590 |
| 230 | 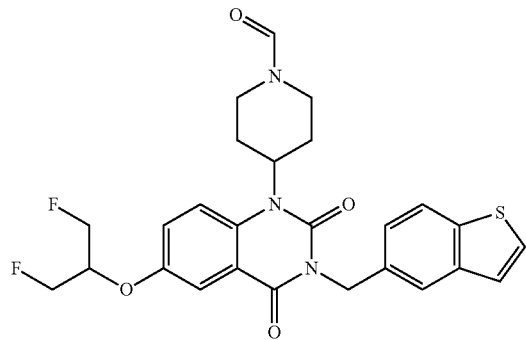 [SMILES: O=CN1CCC(n2c(=O)n(Cc3ccc4sccc4c3)c(=O)c3cc(OC(CF)CF)ccc32)CC1] | 4-[3-(1-benzothiophen-5-ylmethyl)-6-[2-fluoro-1-(fluoromethyl)ethoxy]-2,4-dioxo-3,4-dihydroquinazolin-1(2H)-yl]piperidine-1-carbaldehyde | 514 |

| | | | |
|---|---|---|---|
| 231 | 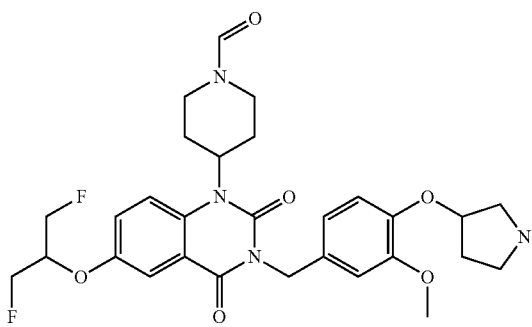 [SMILES: COc1cc(Cn2c(=O)c3cc(OC(CF)CF)ccc3n(C3CCN(C=O)CC3)c2=O)ccc1OC1CCNC1] | 4-{6-[2-fluoro-1-(fluoromethyl)ethoxy]-3-[3-methoxy-4-(pyrrolidin-3-yloxy)benzyl]-2,4-dioxo-3,4-dihydroquinazolin-1(2H)-yl}piperidine-1-carbaldehyde | 573 |
| 232 | 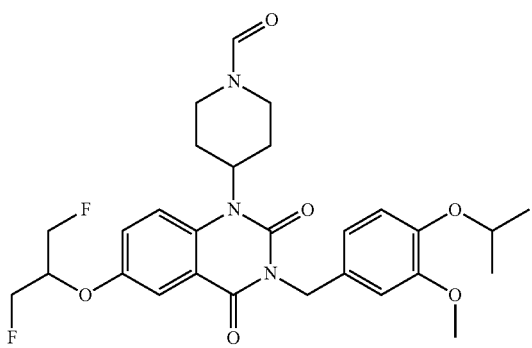 [SMILES: COc1cc(Cn2c(=O)c3cc(OC(CF)CF)ccc3n(C3CCN(C=O)CC3)c2=O)ccc1OC(C)C] | 4-{6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde | 546 |
| 233 | 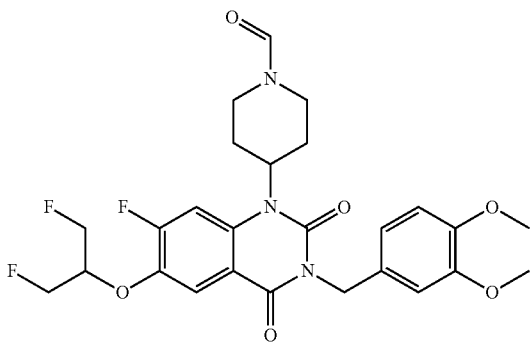 [SMILES: COc1ccc(Cn2c(=O)c3cc(OC(CF)CF)c(F)cc3n(C3CCN(C=O)CC3)c2=O)cc1OC] | 4-[3-(3,4-dimethoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde | 536 |
| 234 | 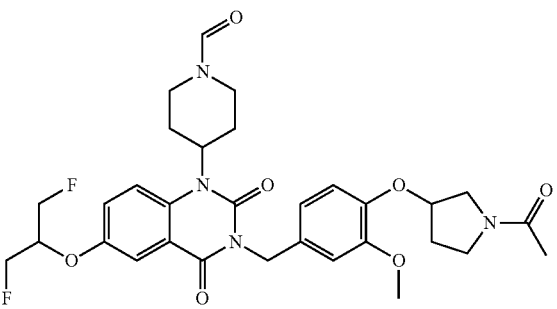 [SMILES: COc1cc(Cn2c(=O)c3cc(OC(CF)CF)ccc3n(C3CCN(C=O)CC3)c2=O)ccc1OC1CCN(C(C)=O)C1] | 4-[3-{4-[(1-acetylpyrrolidin-3-yl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 615 |

-continued

| | | | |
|---|---|---|---|
| 235 | 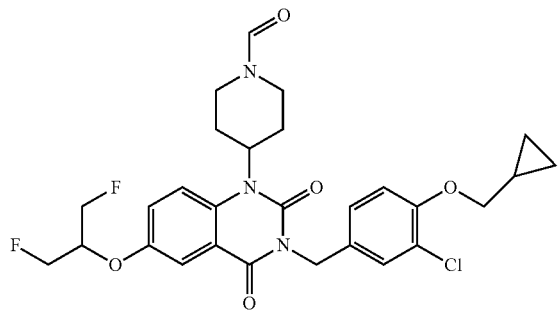 [SMILES: O=CN1CCC(n2c(=O)n(Cc3ccc(OCC4CC4)c(Cl)c3)c(=O)c3cc(OC(CF)CF)ccc32)CC1] | 4-{3-[3-chloro-4-(cyclopropylmethoxy)benzyl]-6-[2-fluoro-1-(fluoromethyl)ethoxy]-2,4-dioxo-3,4-dihydroquinazolin-1(2H)-yl}piperidine-1-carbaldehyde | 562 |
| 236 | 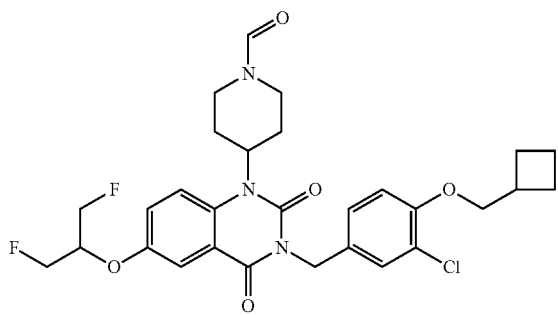 [SMILES: O=CN1CCC(n2c(=O)n(Cc3ccc(OCC4CCC4)c(Cl)c3)c(=O)c3cc(OC(CF)CF)ccc32)CC1] | 4-{3-[3-chloro-4-(cyclobutylmethoxy)benzyl]-6-[2-fluoro-1-(fluoromethyl)ethoxy]-2,4-dioxo-3,4-dihydroquinazolin-1(2H)-yl}piperidine-1-carbaldehyde | 576 |
| 237 | 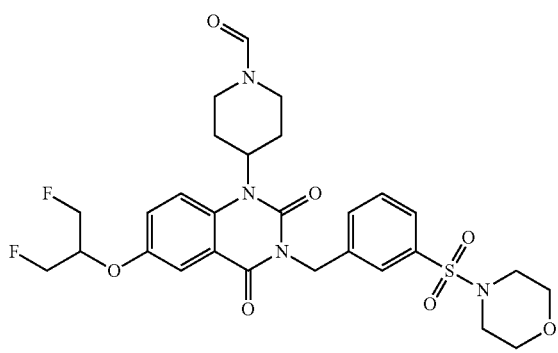 [SMILES: O=CN1CCC(n2c(=O)n(Cc3cccc(S(=O)(=O)N4CCOCC4)c3)c(=O)c3cc(OC(CF)CF)ccc32)CC1] | 4-{6-[2-fluoro-1-(fluoromethyl)ethoxy]-3-[3-(morpholin-4-ylsulphonyl)benzyl]-2,4-dioxo-3,4-dihydroquinazolin-1(2H)-yl}piperidine-1-carbaldehyde | 607 |
| 238 | 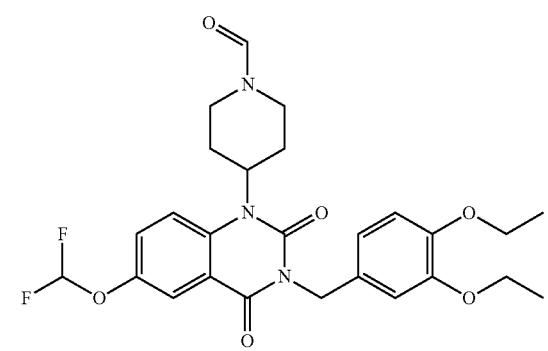 [SMILES: CCOc1ccc(Cn2c(=O)c3cc(OC(F)F)ccc3n(C3CCN(C=O)CC3)c2=O)cc1OCC] | 4-[3-(3,4-diethoxybenzyl)-6-(difluoromethoxy)-2,4-dioxo-3,4-dihydroquinazolin-1(2H)-yl]piperidine-1-carbaldehyde | 518 |
| 239 | 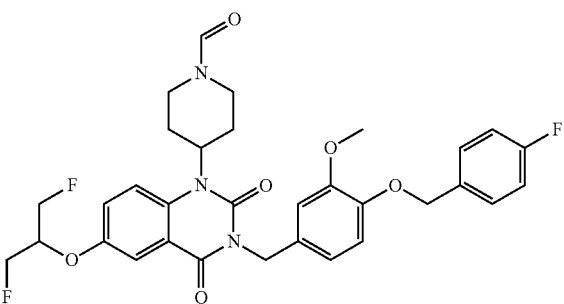 [SMILES: COc1cc(Cn2c(=O)c3cc(OC(CF)CF)ccc3n(C3CCN(C=O)CC3)c2=O)ccc1OCc1ccc(F)cc1] | 4-[3-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 612 |

| 240 | 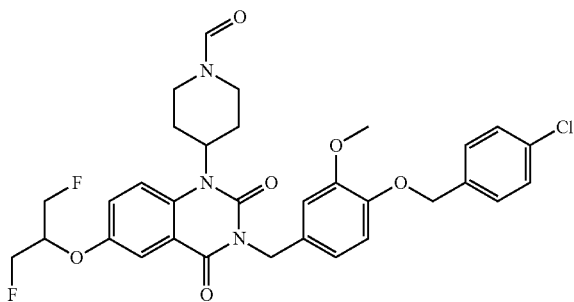 [SMILES: COc1cc(Cn2c(=O)c3cc(OC(CF)CF)ccc3n(C3CCN(C=O)CC3)c2=O)ccc1OCc1ccc(Cl)cc1] | 4-[3-{4-[(4-chlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 628 |
| 241 | 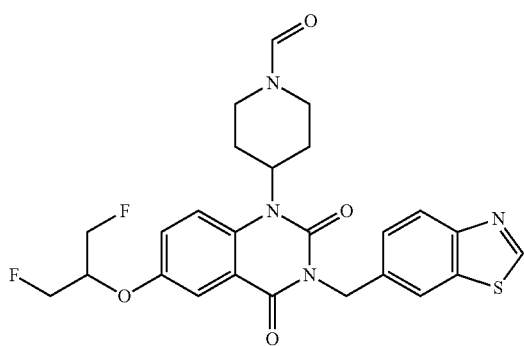 [SMILES: O=CN1CCC(n2c(=O)n(Cc3ccc4ncsc4c3)c(=O)c3cc(OC(CF)CF)ccc32)CC1] | 4-[3-(1,3-benzothiazol-6-ylmethyl)-6-[2-fluoro-1-(fluoromethyl)ethoxy]-2,4-dioxo-3,4-dihydroquinazolin-1(2H)-yl]piperidine-1-carbaldehyde | 515 |
| 242 | 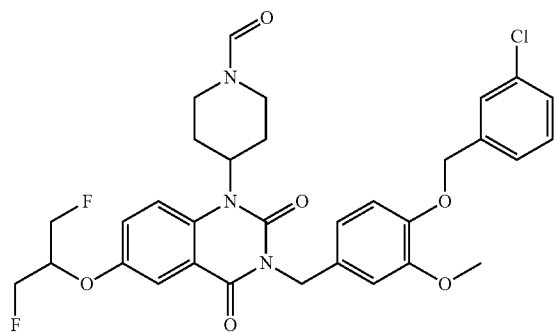 [SMILES: COc1cc(Cn2c(=O)c3cc(OC(CF)CF)ccc3n(C3CCN(C=O)CC3)c2=O)ccc1OCc1cccc(Cl)c1] | 4-[3-{4-[(3-chlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 628 |
| 243 | 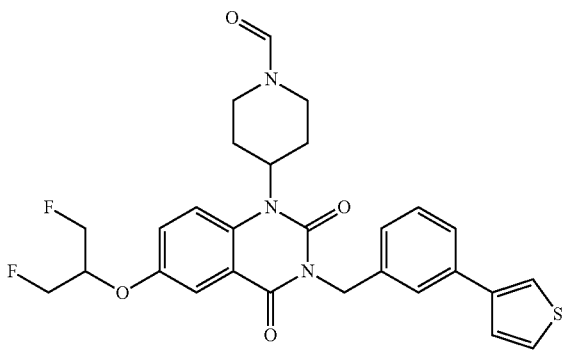 [SMILES: O=CN1CCC(n2c(=O)n(Cc3cccc(-c4ccsc4)c3)c(=O)c3cc(OC(CF)CF)ccc32)CC1] | 4-{6-[2-fluoro-1-(fluoromethyl)ethoxy]-2,4-dioxo-3-(3-(thiophen-3-yl)benzyl)-3,4-dihydroquinazolin-1(2H)-yl}piperidine-1-carbaldehyde | 540 |

| | | | |
|---|---|---|---|
| 244 | 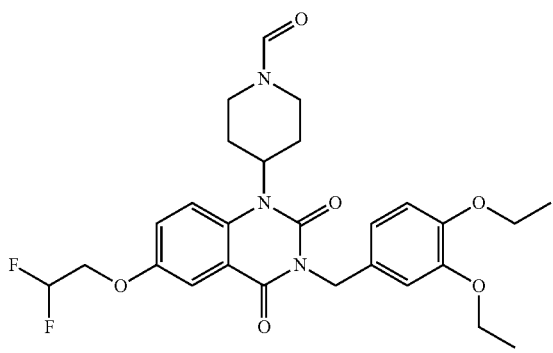 [SMILES: CCOc1ccc(Cn2c(=O)c3cc(OCC(F)F)ccc3n(C3CCN(C=O)CC3)c2=O)cc1OCC] | 4-[3-(3,4-diethoxybenzyl)-6-(2,2-difluoroethoxy)-2,4-dioxo-3,4-dihyroquinazolin-1(2H)-yl]piperidine-1-carbaldehyde | 532 |
| 245 | 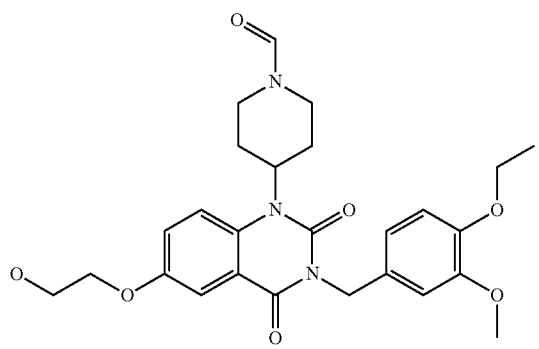 [SMILES: CCOc1ccc(Cn2c(=O)c3cc(OCCO)ccc3n(C3CCN(C=O)CC3)c2=O)cc1OC] | 4-[3-(4-ethoxy-3-methoxybenzyl)-6-(2-hydroxyethoxy)-2,4-dioxo-3,4-dihydroquinazolin-1(2H)-yl]piperidine-1-carbaldehyde | 498 |
| 246 | 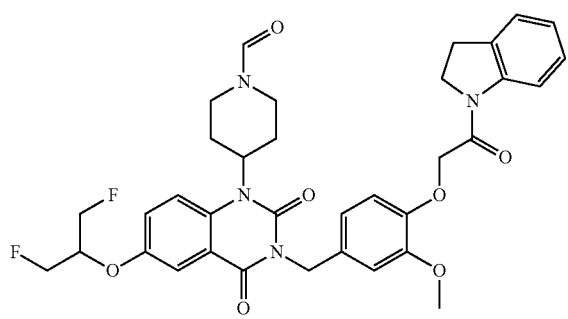 [SMILES: COc1cc(Cn2c(=O)c3cc(OC(CF)CF)ccc3n(C3CCN(C=O)CC3)c2=O)ccc1OCC(=O)N1CCc2ccccc21] | 4-[3-{4-[2-(2,3-dihydro-1H-indol-1-yl)-2-oxoethoxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 663 |
| 247 | 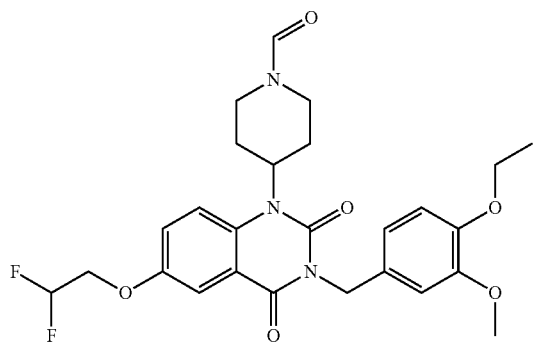 [SMILES: CCOc1ccc(Cn2c(=O)c3cc(OCC(F)F)ccc3n(C3CCN(C=O)CC3)c2=O)cc1OC] | 4-[6-(2,2-difluoroethoxy)-3-(4-ethoxy-3-methoxybenzyl)-2,4-dioxo-3,4-dihydroquinazolin-1(2H)-yl]piperidine-1-carbaldehyde | 518 |

| | | | |
|---|---|---|---|
| 248 | 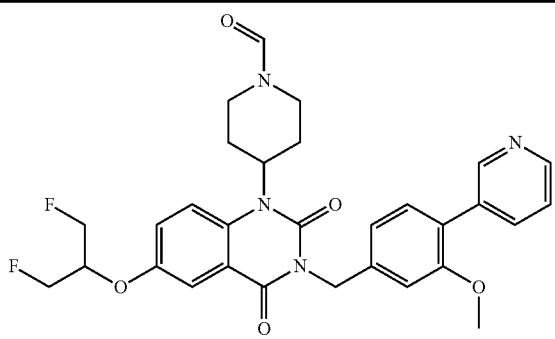 | 4-{6-[2-fluoro-1-(fluoromethyl)ethoxy]-3-(3-methoxy-4-(pyridin-3-yl)benzyl)-2,4-dioxo-3,4-dihydroquinazolin-1(2H)-yl}piperidine-1-carbaldehyde | 565 |
| 249 | 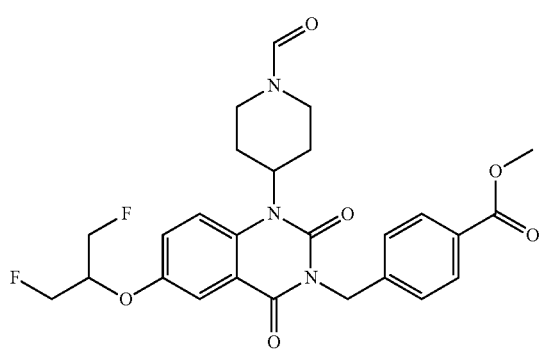 [SMILES: COC(=O)c1ccc(Cn2c(=O)c3cc(OC(CF)CF)ccc3n(C3CCN(C=O)CC3)c2=O)cc1] | methyl 4-({6-[2-fluoro-1-(fluoromethyl)ethoxy]-1-(1-formylpiperidin-4-yl)-2,4-dioxo-1,4-dihydroquinazolin-3(2H)-yl}methyl)benzoate | 516 |
| 250 | 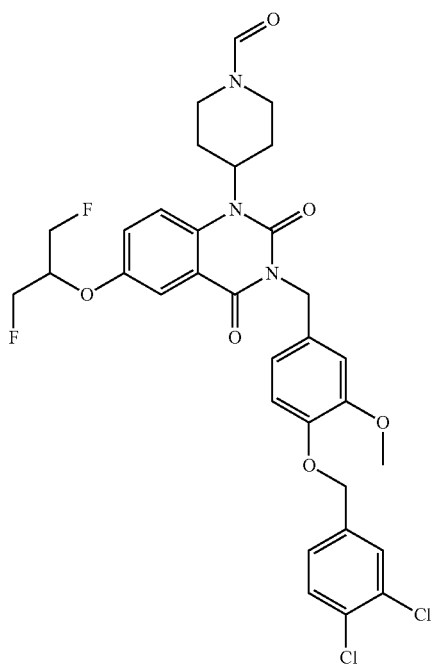 [SMILES: COc1cc(Cn2c(=O)c3cc(OC(CF)CF)ccc3n(C3CCN(C=O)CC3)c2=O)ccc1OCc1ccc(Cl)c(Cl)c1] | 4-[3-{4-[(3,4-dichlorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 662 |
| 251 | 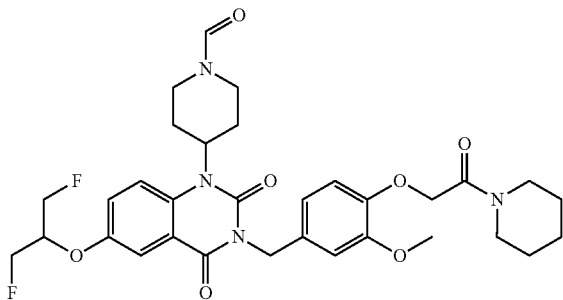 [SMILES: COc1cc(Cn2c(=O)c3cc(OC(CF)CF)ccc3n(C3CCN(C=O)CC3)c2=O)ccc1OCC(=O)N1CCCCC1] | 4-{6-[2-fluoro-1-(fluoromethyl)ethoxy]-3-[3-methoxy-4-(2-oxo-2-(piperidin-1-yl)ethoxy)benzyl]-2,4-dioxo-3,4-dihydroquinazolin-1(2H)-yl}piperidine-1-carbaldehyde | 629 |

-continued

| | | | |
|---|---|---|---|
| 252 | 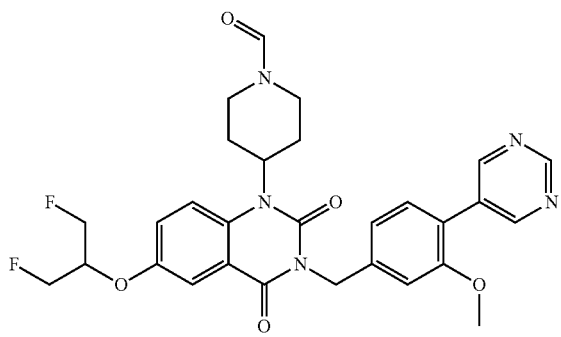 [SMILES: COc1cc(Cn2c(=O)c3cc(OC(CF)CF)ccc3n(C3CCN(C=O)CC3)c2=O)ccc1-c1cncnc1] | 4-{6-[2-fluoro-1-(fluoromethyl)ethoxy]-3-(3-methoxy-4-(pyrimidin-5-yl)benzyl)-2,4-dioxo-3,4-dihydroquinazolin-1(2H)-yl}piperidine-1-carbaldehyde | 566 |
| 253 | 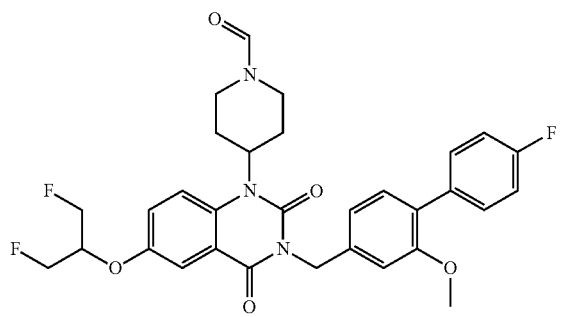 [SMILES: COc1cc(Cn2c(=O)c3cc(OC(CF)CF)ccc3n(C3CCN(C=O)CC3)c2=O)ccc1-c1ccc(F)cc1] | 4-{6-[2-fluoro-1-(fluoromethyl)ethoxy]-3-[(4'-fluoro-2-methoxybiphenyl-4-yl)methyl]-2,4-dioxo-3,4-dihydroquinazolin-1(2H)-yl}piperidine-1-carbaldehyde | 582 |
| 254 | 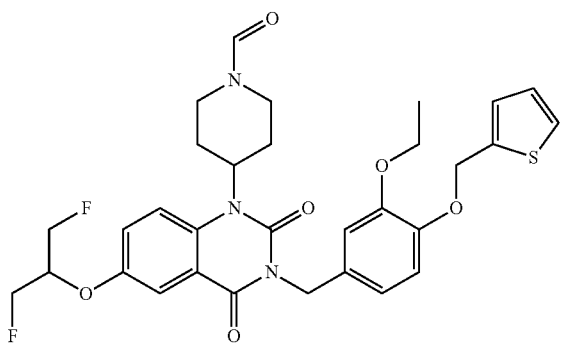 [SMILES: CCOc1cc(Cn2c(=O)c3cc(OC(CF)CF)ccc3n(C3CCN(C=O)CC3)c2=O)ccc1OCc1cccs1] | 4-{3-[3-ethoxy-4-(thiophen-2-ylmethoxy)benzyl]-6-[2-fluoro-1-(fluoromethyl)ethoxy]-2,4-dioxo-3,4-dihydroquinazolin-1(2H)-yl}piperidine-1-carbaldehyde | 614 |
| 255 | 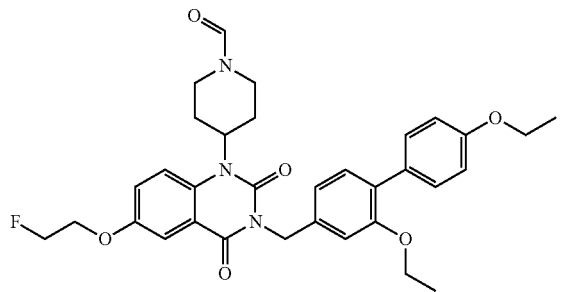 [SMILES: CCOc1ccc(-c2ccc(Cn3c(=O)c4cc(OCCF)ccc4n(C4CCN(C=O)CC4)c3=O)cc2OCC)cc1] | 4-[3-(3,4-diethoxybenzyl)-6-(2-fluoroethoxy)-2,4-dioxo-3,4-dihydroquinazolin-1(2H)-yl]piperidine-1-carbaldehyde | 514 |

| | | | |
|---|---|---|---|
| 256 | 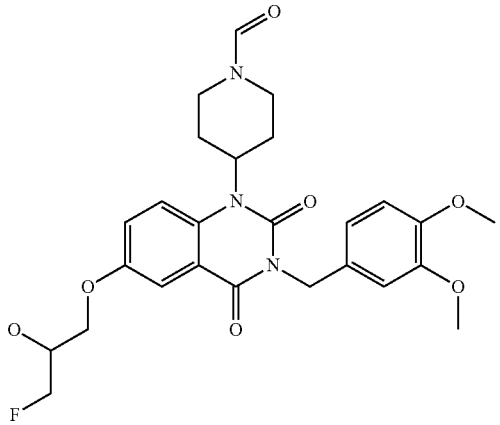 [SMILES: COc1ccc(Cn2c(=O)c3cc(OCC(O)CF)ccc3n(C3CCN(C=O)CC3)c2=O)cc1OC] | 4-[3-(3,4-dimethoxybenzyl)-6-(3-fluoro-2-hydroxypropoxy)-2,4-dioxo-3,4-dihydroquinazolin-1(2H)-yl]piperidine-1-carbaldehyde | 516 |
| 257 | 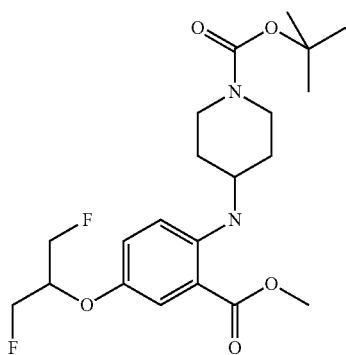 [SMILES: COC(=O)c1cc(OC(CF)CF)ccc1NC1CCN(C(=O)OC(C)(C)C)CC1] | 1,1-dimethylethyl 4-({4-[2-fluoro-1-(fluoromethyl)ethoxy]-2-(methoxycarbonyl)phenyl}amino)piperidine-1-carboxylate | 429 |
| 258 | 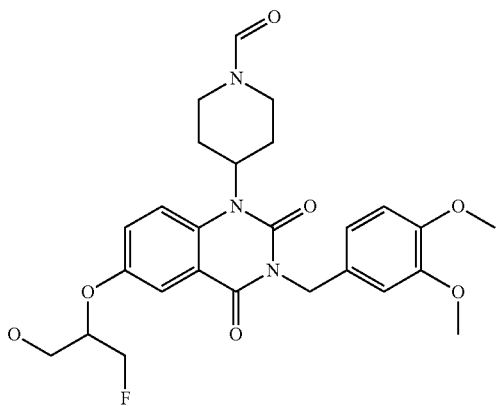 [SMILES: COc1ccc(Cn2c(=O)c3cc(OC(CO)CF)ccc3n(C3CCN(C=O)CC3)c2=O)cc1OC] | 4-[3-(3,4-dimethoxybenzyl)-6-[2-fluoro-1-(hydroxymethyl)ethoxy]-2,4-dioxo-3,4-dihydroquinazolin-1(2H)-yl}piperidine-1-carbaldehyde | 516 |
| 259 | 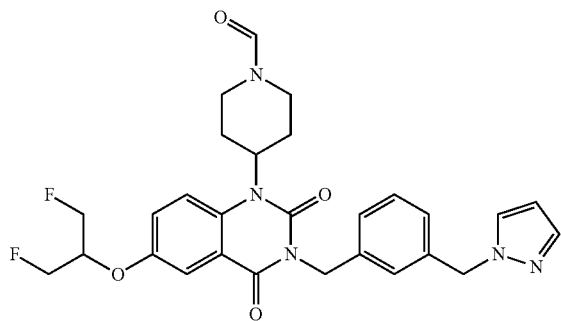 [SMILES: O=CN1CCC(n2c(=O)n(Cc3cccc(Cn4cccn4)c3)c(=O)c3cc(OC(CF)CF)ccc32)CC1] | 4-{6-[2-fluoro-1-(fluoromethyl)ethoxy]-2,4-dioxo-3-[3-(1H-pyrazol-1-ylmethyl)benzyl]-3,4-dihydroquinazolin-1(2H)-yl}piperidine-1-carbaldehyde | 538 |

| # | Structure | Name | Value |
|---|---|---|---|
| 260 | 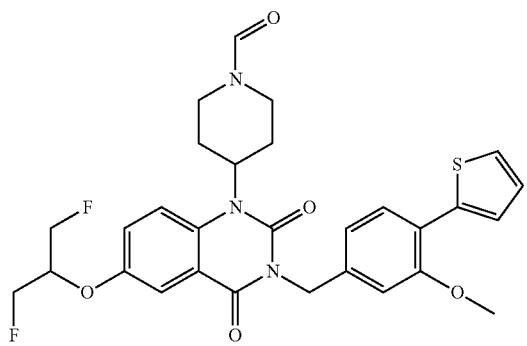 [SMILES: COc1cc(Cn2c(=O)c3cc(OC(CF)CF)ccc3n(C3CCN(C=O)CC3)c2=O)ccc1-c1cccs1] | 4-{6-[2-fluoro-1-(fluoromethyl)ethoxy]-3-(3-methoxy-4-(thiophen-2-yl)benzyl)-2,4-dioxo-3,4-dihydroquinazolin-1(2H)-yl}piperidine-1-carbaldehyde | 570 |
| 261 | 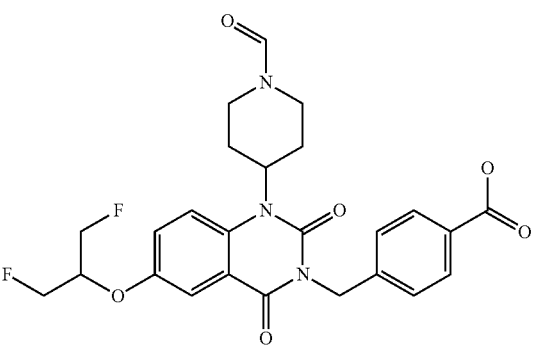 [SMILES: O=CN1CCC(n2c(=O)n(Cc3ccc(C(=O)O)cc3)c(=O)c3cc(OC(CF)CF)ccc32)CC1] | 4-({6-[2-fluoro-1-(fluoromethyl)ethoxy]-1-(1-formylpiperidin-4-yl)-2,4-dioxo-1,4-dihydroquinazolin-3(2H)-yl}methyl)benzoic acid | 502 |
| 262 | 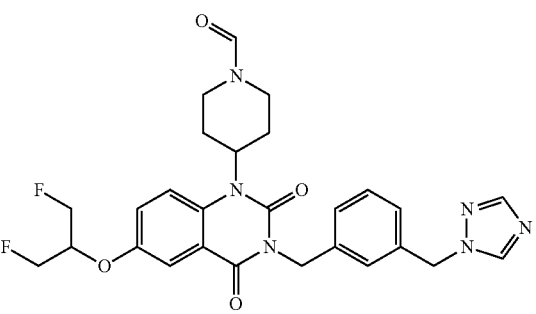 [SMILES: O=CN1CCC(n2c(=O)n(Cc3cccc(Cn4cncn4)c3)c(=O)c3cc(OC(CF)CF)ccc32)CC1] | 4-{6-[2-fluoro-1-(fluoromethyl)ethoxy]-2,4-dioxo-3-[2-(1H-1,2,4-triazol-1-ylmethyl)benzyl]-3,4-dihydroquinazolin-1(2H)-yl}piperidine-1-carbaldehyde | 539 |
| 263 | 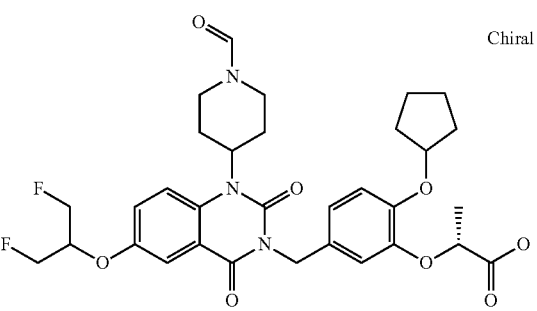 [SMILES: C[C@@H](Oc1cc(Cn2c(=O)c3cc(OC(CF)CF)ccc3n(C3CCN(C=O)CC3)c2=O)ccc1OC1CCCC1)C(=O)O] Chiral | (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid | 630 |
| 264 | 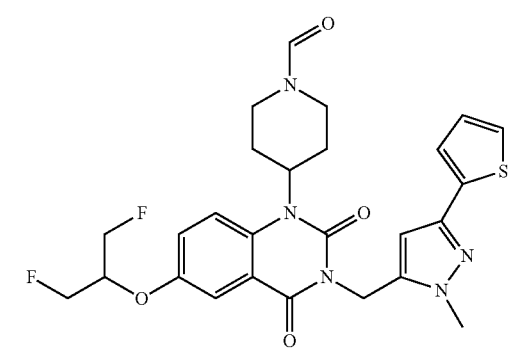 [SMILES: Cn1nc(-c2cccs2)cc1Cn1c(=O)c2cc(OC(CF)CF)ccc2n(C2CCN(C=O)CC2)c1=O] | 4-{6-[2-fluoro-1-(fluoromethyl)ethoxy]-3-[(1-methyl-3-(thiophen-2-yl)-1H-pyrazol-5-yl)methyl]-2,4-dioxo-3,4-dihydroquinazolin-1(2H)-yl}piperidine-1-carbaldehyde | 544 |

| 265 | 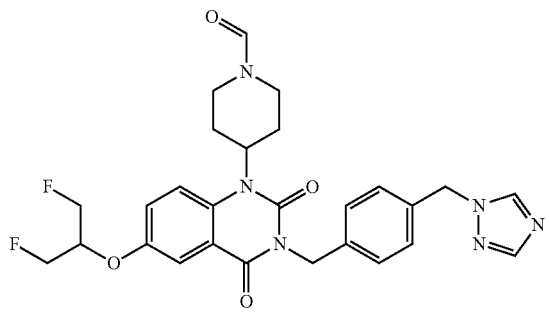 [SMILES: O=CN1CCC(n2c(=O)n(Cc3ccc(Cn4cncn4)cc3)c(=O)c3cc(OC(CF)CF)ccc32)CC1] | 4-{6-[2-fluoro-1-(fluoromethyl)ethoxy]-2,4-dioxo-3-[4-(1H-1,2,4-triazol-1-ylmethyl)benzyl]-3,4-dihydroquinazolin-1(2H)-yl}piperidine-1-carbaldehyde | 539 |
| 266 | 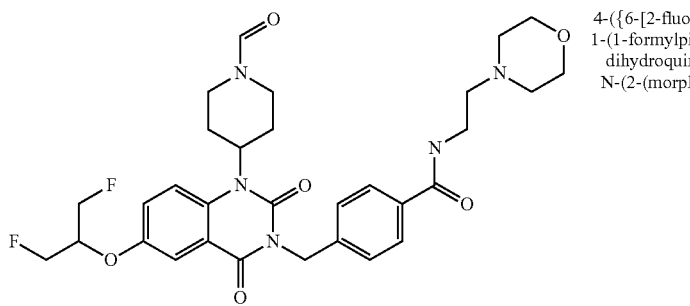 | 4-({6-[2-fluoro-1-(fluoromethyl)ethoxy]-1-(1-formylpiperidin-4-yl)-2,4-dioxo-1,4-dihydroquinazolin-3(2H)-yl}methyl)-N-(2-(morpholin-4-yl)ethyl)benzamide | 614 |
| 267 | 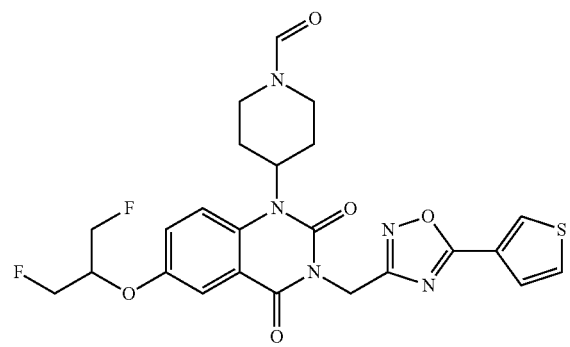 [SMILES: O=CN1CCC(n2c(=O)n(Cc3noc(-c4ccsc4)n3)c(=O)c3cc(OC(CF)CF)ccc32)CC1] | 4-{6-[2-fluoro-1-(fluoromethyl)ethoxy]-2,4-dioxo-3-[(5-(thiophen-3-yl)-1,2,4-oxadiazol-3-yl)methyl]-3,4-dihydroquinazolin-1(2H)-yl}piperidine-1-carbaldehyde | 532 |
| 268 | 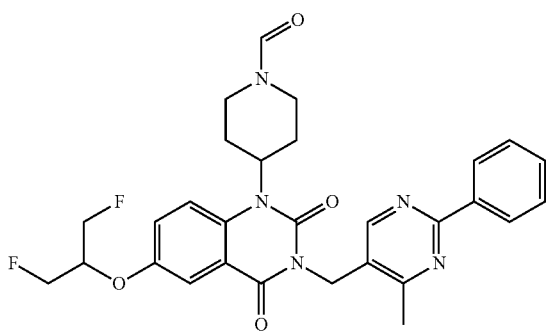 [SMILES: Cc1nc(-c2ccccc2)ncc1Cn1c(=O)c2cc(OC(CF)CF)ccc2n(C2CCN(C=O)CC2)c1=O] | 4-{6-[2-fluoro-1-(fluoromethyl)ethoxy]-3-[(4-methyl-2-phenylpyrimidin-5-yl)methyl]-2,4-dioxo-3,4-dihydroquinazolin-1(2H)-yl}piperidine-1-carbaldehyde | 550 |

-continued

| | | | |
|---|---|---|---|
| 269 | 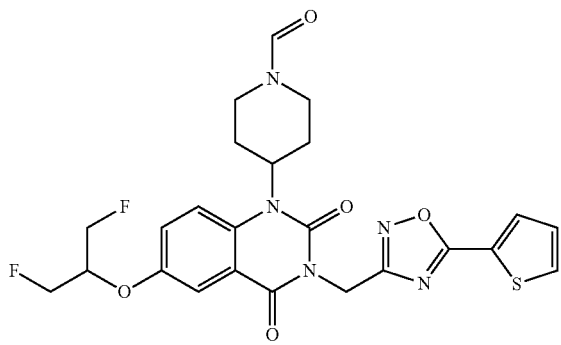 [SMILES: O=CN1CCC(n2c(=O)n(Cc3noc(-c4cccs4)n3)c(=O)c3cc(OC(CF)CF)ccc32)CC1] | 4-{6-[2-fluoro-1-(fluoromethyl)ethoxy]-2,4-dioxo-3-[(5-(thiophen-2-yl)-1,2,4-oxadiazol-3-yl)methyl]-3,4-dihydroquinazolin-1(2H)-yl}piperidine-1-carbaldehyde | 532 |
| 270 | 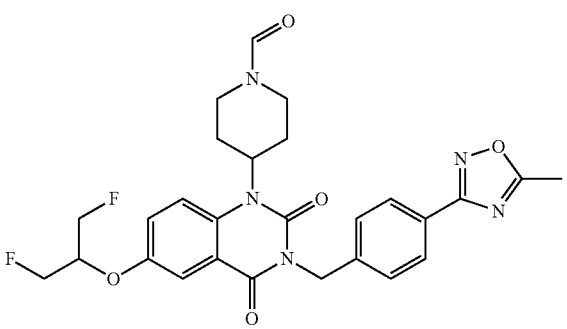 [SMILES: Cc1nc(-c2ccc(Cn3c(=O)c4cc(OC(CF)CF)ccc4n(C4CCN(C=O)CC4)c3=O)cc2)no1] | 4-{6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde | 540 |
| 271 | 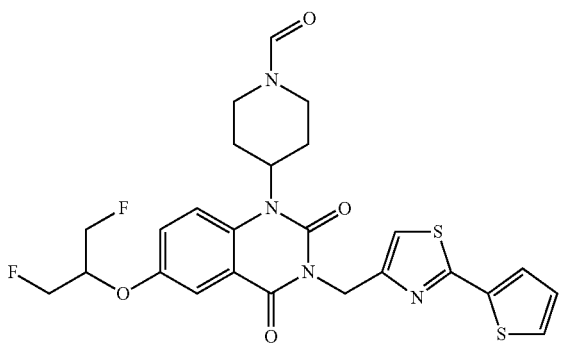 [SMILES: O=CN1CCC(n2c(=O)n(Cc3csc(-c4cccs4)n3)c(=O)c3cc(OC(CF)CF)ccc32)CC1] | 4-{6-[2-fluoro-1-(fluoromethyl)ethoxy]-2,4-dioxo-4-[(2-thiophen-2-yl)-1,3-thiazol-3-yl)methyl]-3,4-dihydroquinazolin-1(2H)-yl}piperidine-1-carbaldehyde | 547 |
| 272 | 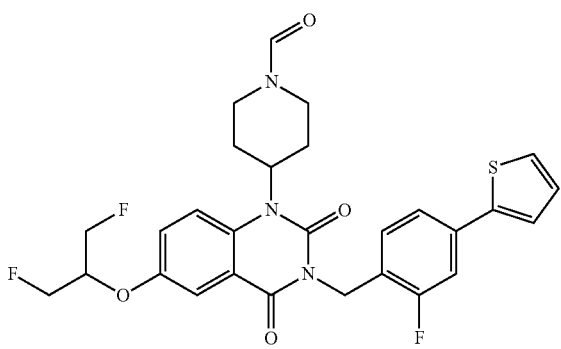 [SMILES: O=CN1CCC(n2c(=O)n(Cc3ccc(-c4cccs4)cc3F)c(=O)c3cc(OC(CF)CF)ccc32)CC1] | 4-{6-[2-fluoro-1-(fluoromethyl)ethoxy]-3-(2-fluoro-4-(thiophen-2-yl)benzyl)-2,4-dioxo-3,4-dihydroquinazolin-1(2H)-yl}piperidine-1-carbaldehyde | 558 |

| | | | |
|---|---|---|---|
| 273 | 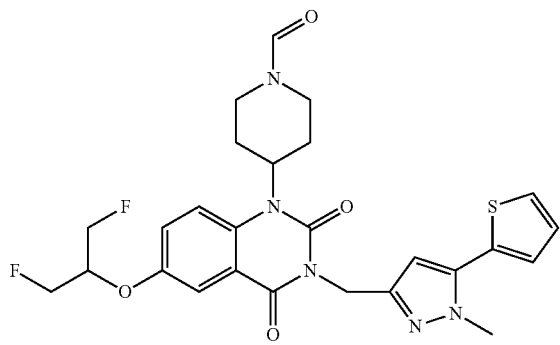 [SMILES: Cn1nc(Cn2c(=O)c3cc(OC(CF)CF)ccc3n(C3CCN(C=O)CC3)c2=O)cc1-c1cccs1] | 4-{6-[2-fluoro-1-(fluoromethyl)ethoxy]-3-[(1-methyl-5-(thiophen-2-yl)-1H-pyrazol-3-yl)methyl]-2,4-dioxo-3,4-dihydroquinazolin-1(2H)-yl}piperidine-1-carbaldehyde | 544 |
| 274 | 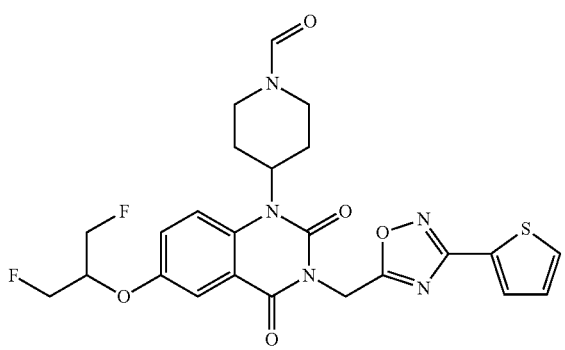 [SMILES: O=CN1CCC(n2c(=O)n(Cc3nc(-c4cccs4)no3)c(=O)c3cc(OC(CF)CF)ccc32)CC1] | 4-{6-[2-fluoro-1-(fluoromethyl)ethoxy]-2,4-dioxo-3-[(3-(thiophen-2-yl)-1,2,4-oxadiazol-5-yl)methyl]-3,4-dihydroquinazolin-1(2H)-yl}piperidine-1-carbaldehyde | 532 |
| 275 | 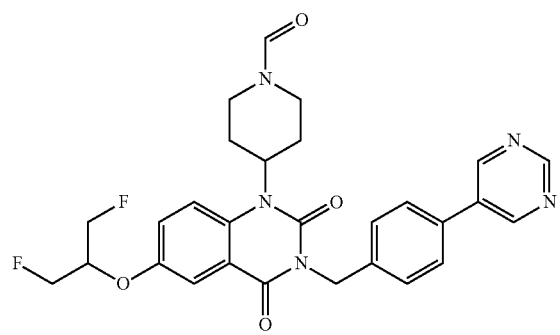 [SMILES: O=CN1CCC(n2c(=O)n(Cc3ccc(-c4cncnc4)cc3)c(=O)c3cc(OC(CF)CF)ccc32)CC1] | 4-{6-[2-fluoro-1-(fluoromethyl)ethoxy]-2,4-dioxo-3-(4-(pyrimidin-5-yl)benzyl)-3,4-dihydroquinazolin-1(2H)-yl}piperidine-1-carbaldehyde | 536 |
| 276 | 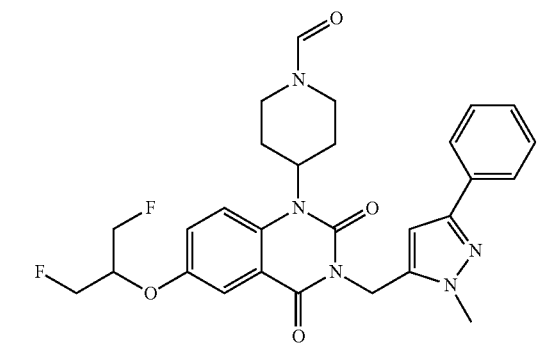 [SMILES: Cn1nc(-c2ccccc2)cc1Cn1c(=O)c2cc(OC(CF)CF)ccc2n(C2CCN(C=O)CC2)c1=O] | 4-{6-[2-fluoro-1-(fluoromethyl)ethoxy]-3-[(1-methyl-3-phenyl-1H-pyrazol-5-yl)methyl]-2,4-dioxo-3,4-dihydroquinazolin-1(2H)-yl}piperidine-1-carbaldehyde | 538 |

| | | | |
|---|---|---|---|
| 277 | 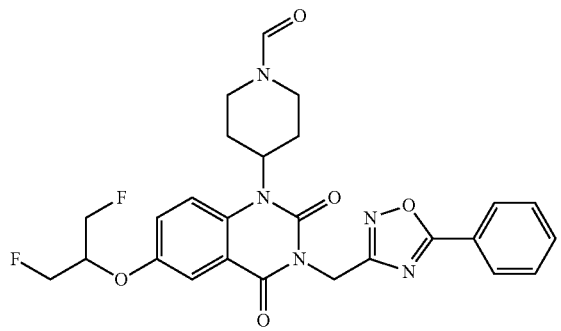 [SMILES: O=CN1CCC(n2c(=O)n(Cc3noc(-c4ccccc4)n3)c(=O)c3cc(OC(CF)CF)ccc32)CC1] | 4-{6-[2-fluoro-1-(fluoromethyl)ethoxy]-2,4-dioxo-3-[(5-phenyl-1,2,4-oxadiazol-3-yl)methyl]-3,4-dihydroquinazolin-1(2H)-yl}piperidine-1-carbaldehyde | 526 |
| 278 | 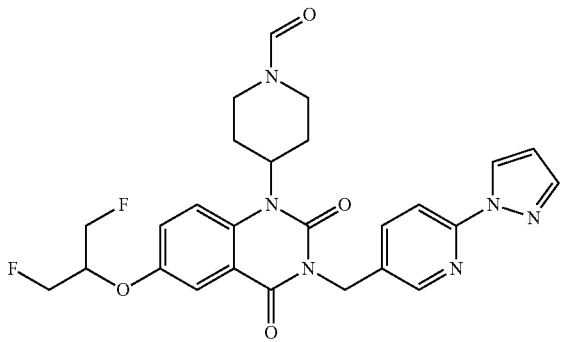 [SMILES: O=CN1CCC(n2c(=O)n(Cc3ccc(-n4cccn4)nc3)c(=O)c3cc(OC(CF)CF)ccc32)CC1] | 4-{6-[2-fluoro-1-(fluoromethyl)ethoxy]-2,4-dioxo-3-{[6-(1H-pyrazol-1-yl)pyridin-3-yl]methyl}-3,4-dihydroquinazolin-1(2H)-yl}piperidine-1-carbaldehyde | 525 |
| 279 | 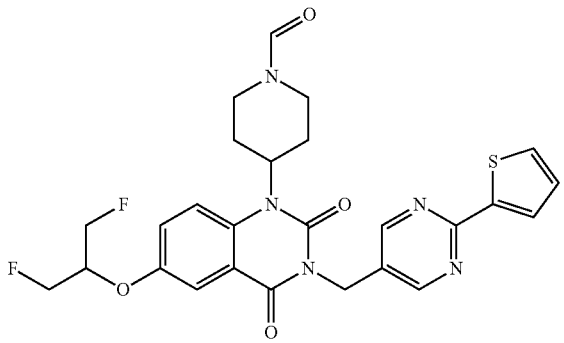 [SMILES: O=CN1CCC(n2c(=O)n(Cc3cnc(-c4cccs4)nc3)c(=O)c3cc(OC(CF)CF)ccc32)CC1] | 4-{6-[2-fluoro-1-(fluoromethyl)ethoxy]-2,4-dioxo-3-[(2-(thiophen-2-yl)pyrimidin-5-yl)methyl]-3,4-dihydroquinazolin-1(2H)-yl}piperidine-1-carbaldehyde | 542 |
| 280 | 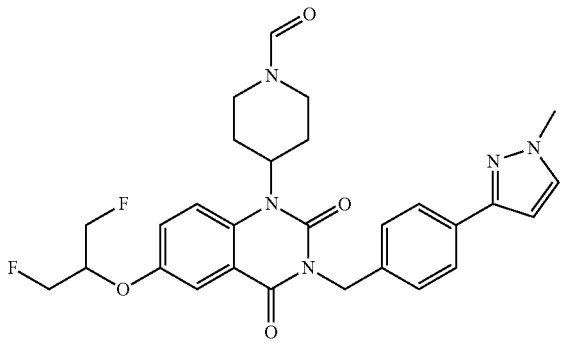 [SMILES: Cn1ccc(-c2ccc(Cn3c(=O)c4cc(OC(CF)CF)ccc4n(C4CCN(C=O)CC4)c3=O)cc2)n1] | 4-{6-[2-fluoro-1-(fluoromethyl)ethoxy]-3-[4-(1-methyl-1H-pyrazol-3-yl)benzyl]-2,4-dioxo-3,4-dihydroquinazolin-1(2H)-yl}piperidine-1-carbaldehyde | 538 |

-continued

| | | | |
|---|---|---|---|
| 281 | 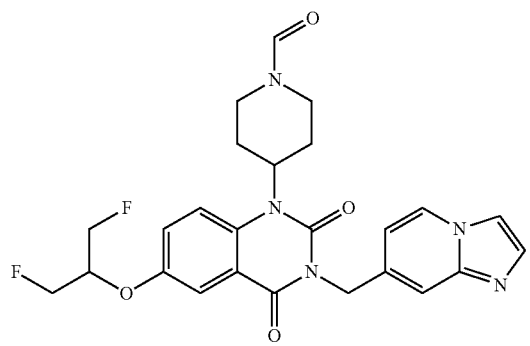 [SMILES: O=CN1CCC(n2c(=O)n(Cc3ccn4ccnc4c3)c(=O)c3cc(OC(CF)CF)ccc32)CC1] | 4-{6-[2-fluoro-1-(fluoromethyl)ethoxy]-3-(imidazo[1,2-a]pyridin-7-ylmethyl)-2,4-dioxo-3,4-dihydroquinazolin-1(2H)-yl}piperidine-1-carbaldehyde | 598 |
| 282 | 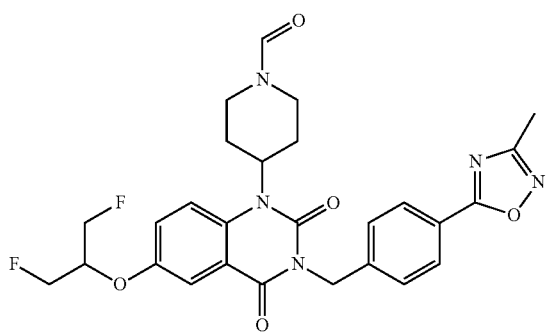 [SMILES: Cc1noc(-c2ccc(Cn3c(=O)c4cc(OC(CF)CF)ccc4n(C4CCN(C=O)CC4)c3=O)cc2)n1] | 4-{6-[2-fluoro-1-(fluoromethyl)ethoxy]-3-[4-(3-methyl-1,2,4-oxadiazol-5-yl)benzyl]-2,4-dioxo-3,4-dihydroquinazolin-1(2H)-yl}piperidine-1-carbaldehyde | 540 |
| 283 | 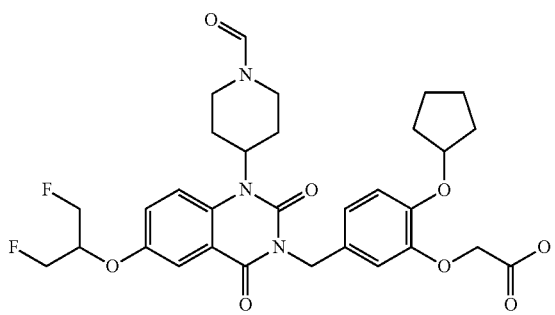 [SMILES: O=CN1CCC(n2c(=O)n(Cc3ccc(OC4CCCC4)c(OCC(=O)O)c3)c(=O)c3cc(OC(CF)CF)ccc32)CC1] | [2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]acetic acid | 616 |
| 284 | 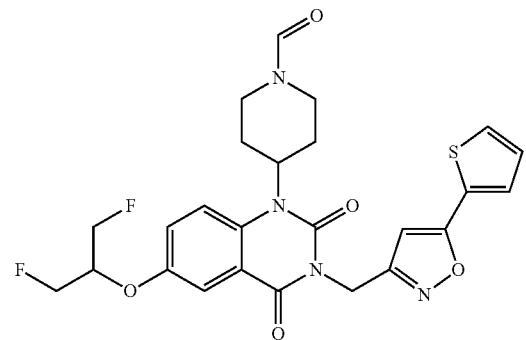 [SMILES: O=CN1CCC(n2c(=O)n(Cc3cc(-c4cccs4)on3)c(=O)c3cc(OC(CF)CF)ccc32)CC1] | 4-{6-[2-fluoro-1-(fluoromethyl)ethoxy]-2,4-dioxo-3-[(5-(thiophen-2-yl)isoxazol-3-yl)methyl]-3,4-dihydroquinazolin-1(2H)-yl}piperidine-1-carbaldehyde | 531 |

-continued

| | | | |
|---|---|---|---|
| 285 | 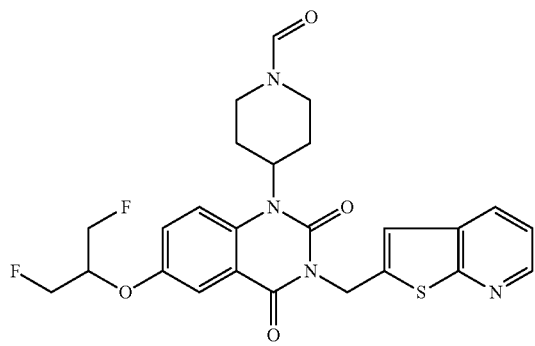 [SMILES: O=CN1CCC(n2c(=O)n(Cc3cc4cccnc4s3)c(=O)c3cc(OC(CF)CF)ccc32)CC1] | 4-{6-[2-fluoro-1-(fluoromethyl)ethoxy]-2,4-dioxo-3-(thieno[2,3-b]pyridin-2-ylmethyl)-3,4-dihydroquinazolin-1(2H)-yl}piperidine-1-carbaldehyde | 514 |
| 286 | 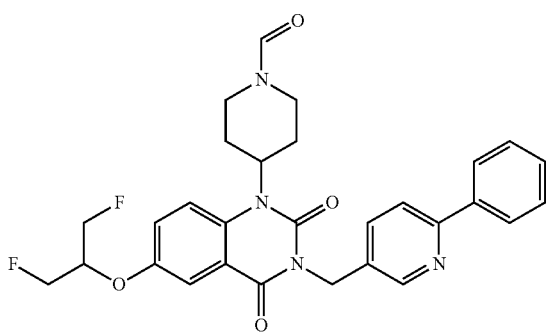 [SMILES: O=CN1CCC(n2c(=O)n(Cc3ccc(-c4ccccc4)nc3)c(=O)c3cc(OC(CF)CF)ccc32)CC1] | 4-{6-[2-fluoro-1-(fluoromethyl)ethoxy]-2,4-dioxo-3-[(6-phenylpyridin-3-yl)methyl]-3,4-dihydroquinazolin-1(2H)-yl}piperidine-1-carbaldehyde | 535 |
| 287 | 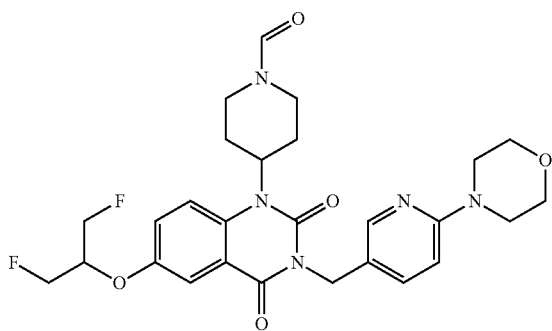 [SMILES: O=CN1CCC(n2c(=O)n(Cc3ccc(N4CCOCC4)nc3)c(=O)c3cc(OC(CF)CF)ccc32)CC1] | 4-{6-[2-fluoro-1-(fluoromethyl)ethoxy]-3-[(6-(morpholin-4-yl)pyridin-3-yl)methyl]-2,4-dioxo-3,4-dihydroquinazolin-1(2H)-yl}piperidine-1-carbaldehyde | 544 |
| 288 | 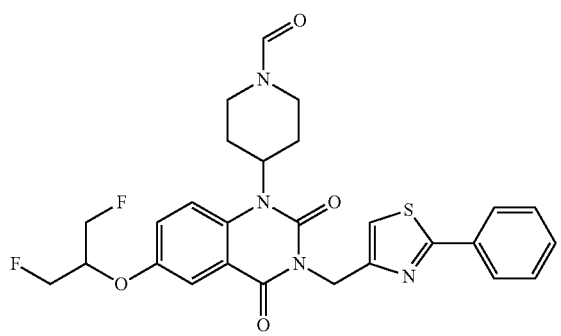 [SMILES: O=CN1CCC(n2c(=O)n(Cc3csc(-c4ccccc4)n3)c(=O)c3cc(OC(CF)CF)ccc32)CC1] | 4-{6-[2-fluoro-1-(fluoromethyl)ethoxy]-2,4-dioxo-3-[(2-phenyl-1,3-thiazol-4-yl)methyl]-3,4-dihydroquinazolin-1(2H)-yl}piperidine-1-carbaldehyde | 541 |

-continued

| | | | |
|---|---|---|---|
| 289 | 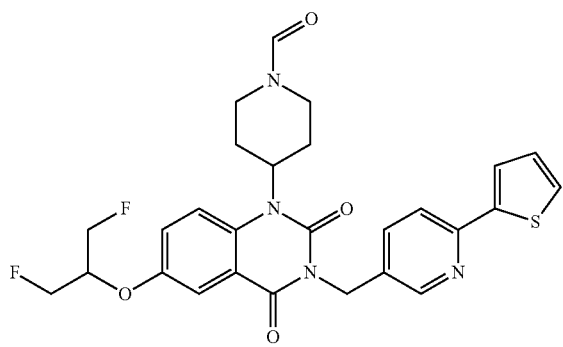 [SMILES: O=CN1CCC(n2c(=O)n(Cc3ccc(-c4cccs4)nc3)c(=O)c3cc(OC(CF)CF)ccc32)CC1] | 4-{6-[2-fluoro-1-(fluoromethyl)ethoxy]-2,4-dioxo-3-[(6-(thiophen-2-yl)pyridin-3-yl)methyl]-3,4-dihydroquinazolin-1(2H)-yl}piperidine-1-carbaldehyde | 541 |
| 290 | 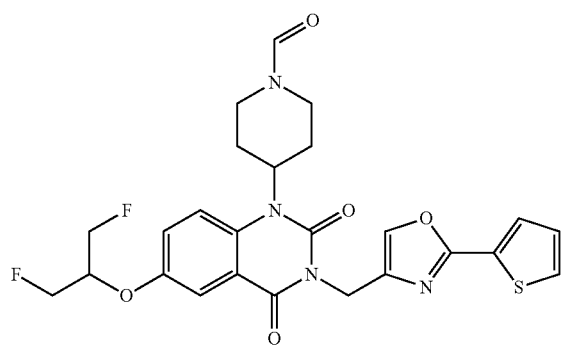 [SMILES: O=CN1CCC(n2c(=O)n(Cc3coc(-c4cccs4)n3)c(=O)c3cc(OC(CF)CF)ccc32)CC1] | 4-{6-[2-fluoro-1-(fluoromethyl)ethoxy]-2,4-dioxo-3-[(2-thiophen-2-yl)-1,3-oxazol-4-yl)methyl]-3,4-dihydroquinazolin-1(2H)-yl}piperidine-1-carbaldehyde | 531 |
| 291 | 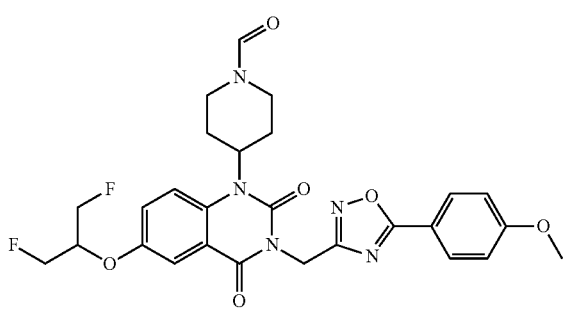 [SMILES: COc1ccc(-c2nc(Cn3c(=O)c4cc(OC(CF)CF)ccc4n(C4CCN(C=O)CC4)c3=O)no2)cc1] | 4-{6-[2-fluoro-1-(fluoromethyl)ethoxy]-3-{[5-(4-methoxyphenyl)-1,2,4-oxadiazol-3-yl]methyl}-2,4-dioxo-3,4-dihydroquinazolin-1(2H)-yl}piperidine-1-carbaldehyde | 556 |
| 292 | 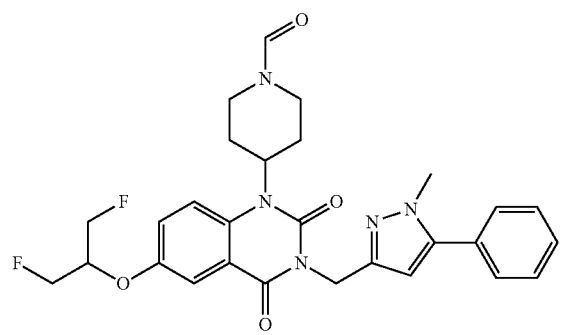 [SMILES: Cn1nc(Cn2c(=O)c3cc(OC(CF)CF)ccc3n(C3CCN(C=O)CC3)c2=O)cc1-c1ccccc1] | 4-{6-[2-fluoro-1-(fluoromethyl]ethoxy]-3-[(1-methyl-5-phenyl-1H-pyrazol-3-yl)methyl]-2,4-dioxo-3,4-dihydroquinazolin-1(2H)-yl} piperidine-1-carbaldehyde | 538 |

| | | | |
|---|---|---|---|
| 293 | 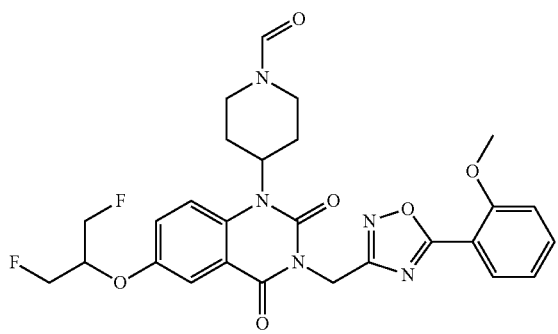 [SMILES: COc1ccccc1-c1nc(Cn2c(=O)c3cc(OC(CF)CF)ccc3n(C3CCN(C=O)CC3)c2=O)no1] | 4-{6-[2-fluoro-1-(fluoromethyl)ethoxy]-3-{[5-(2-methoxyphenyl)-1,2,4-oxadiazol-3-yl]methyl}-2,4-dioxo-3,4-dihydroquinazolin-1(2H)-yl}piperidine-1-carbaldehyde | 556 |
| 294 | 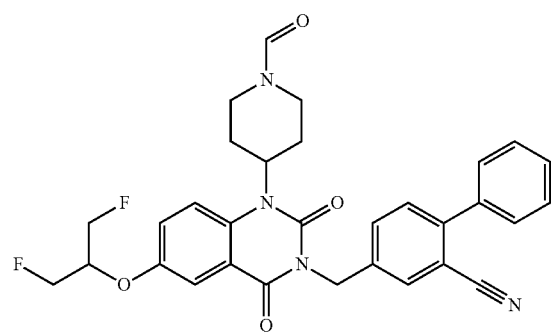 [SMILES: N#Cc1cc(Cn2c(=O)c3cc(OC(CF)CF)ccc3n(C3CCN(C=O)CC3)c2=O)ccc1-c1ccccc1] | 4-({6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile | 559 |
| 295 | 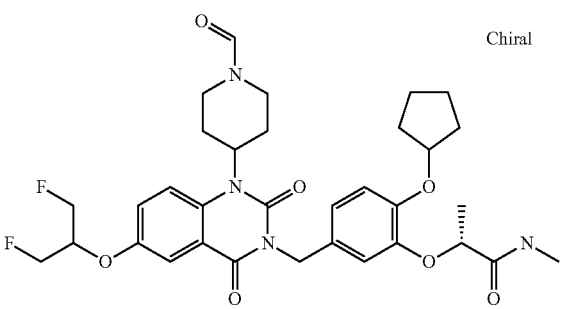 [SMILES: CNC(=O)[C@@H](C)Oc1cc(Cn2c(=O)c3cc(OC(CF)CF)ccc3n(C3CCN(C=O)CC3)c2=O)ccc1OC1CCCC1] Chiral | (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-methylpropanamide | 643 |
| 296 | 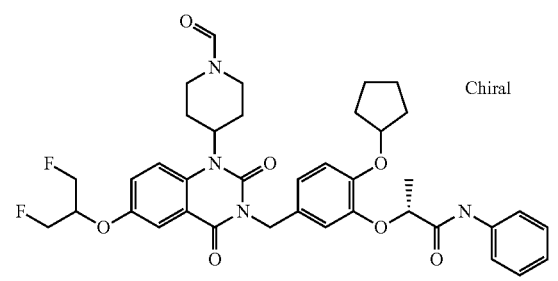 [SMILES: C[C@@H](Oc1cc(Cn2c(=O)c3cc(OC(CF)CF)ccc3n(C3CCN(C=O)CC3)c2=O)ccc1OC1CCCC1)C(=O)Nc1ccccc1] Chiral | (2R)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-phenylpropanamide | 705 |
| 297 | 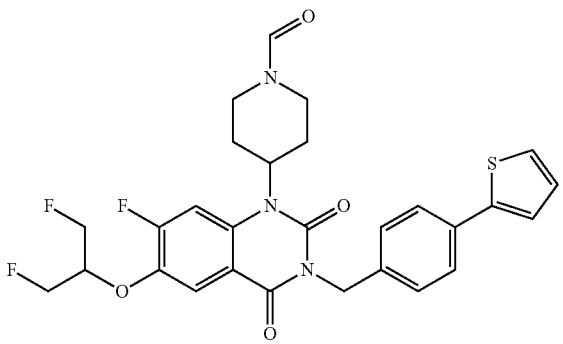 [SMILES: O=CN1CCC(n2c(=O)n(Cc3ccc(-c4cccs4)cc3)c(=O)c3cc(OC(CF)CF)c(F)cc32)CC1] | 4-{7-fluoro-6-[2-fluoro-1-(fluoromethyl)ethoxy]-2,4-dioxo-3-(4-(thiophen-2-yl)benzyl)-3,4-dihydroquinazolin-1(2H)-yl}piperidine-1-carbaldehyde | 558 |

| | | | |
|---|---|---|---|
| 298 | 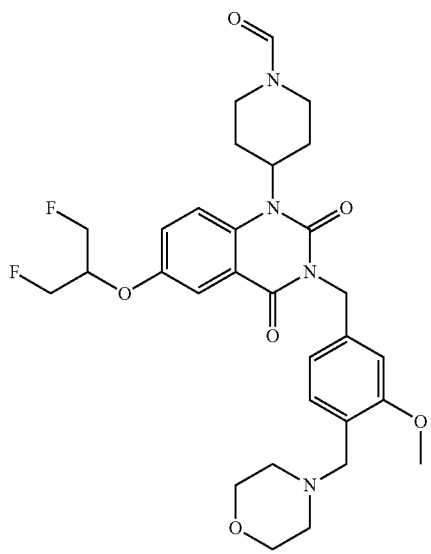 [SMILES: COc1cc(Cn2c(=O)c3cc(OC(CF)CF)ccc3n(C3CCN(C=O)CC3)c2=O)ccc1CN1CCOCC1] | 4-{6-[2-fluoro-1-(fluoromethyl)ethoxy]-3-[3-methoxy-4-(morpholin-4-ylmethyl)benzyl]-2,4-dioxo-3,4-dihydroquinazolin-1(2H)-yl}piperidine-1-carbaldehyde | 587 |
| 299 | 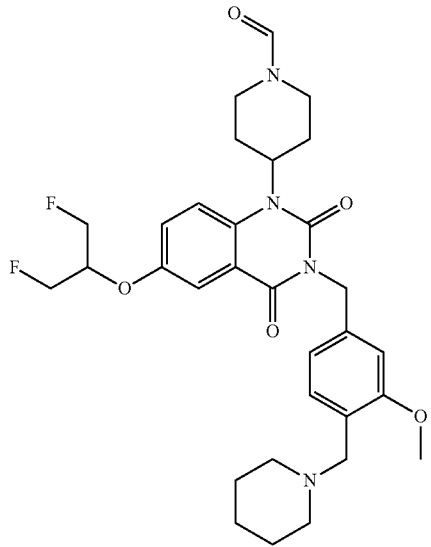 [SMILES: COc1cc(Cn2c(=O)c3cc(OC(CF)CF)ccc3n(C3CCN(C=O)CC3)c2=O)ccc1CN1CCCCC1] | 4-{6-[2-fluoro-1-(fluoromethyl)ethoxy]-3-[3-methoxy-4-(piperidin-1-ylmethyl)benzyl]-2,4-dioxo-3,4-dihydroquinazolin-1(2H)-yl}piperidine-1-carbaldehyde | 585 |
| 300 | 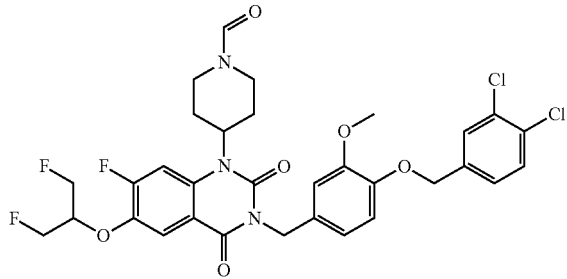 [SMILES: COc1cc(Cn2c(=O)c3cc(OC(CF)CF)c(F)cc3n(C3CCN(C=O)CC3)c2=O)ccc1OCc1ccc(Cl)c(Cl)c1] | 4-[3-{4-[(3,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |

| | | | |
|---|---|---|---|
| 301 | 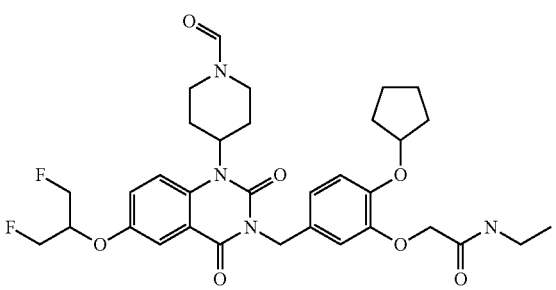 [SMILES: CCNC(=O)COc1cc(Cn2c(=O)c3cc(OC(CF)CF)ccc3n(C3CCN(C=O)CC3)c2=O)ccc1OC1CCCC1] | 2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]-N-ethylacetamide | 643 |
| 302 | 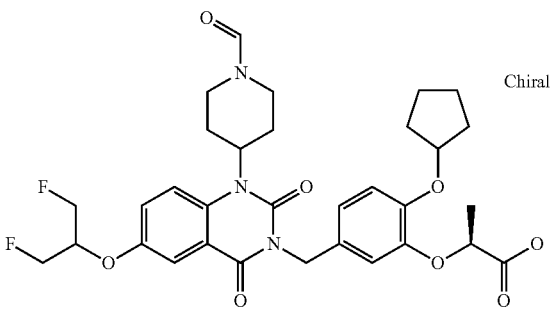 [SMILES: C[C@H](Oc1cc(Cn2c(=O)c3cc(OC(CF)CF)ccc3n(C3CCN(C=O)CC3)c2=O)ccc1OC1CCCC1)C(=O)O] Chiral | (2S)-2-[2-(cyclopentyloxy)-5-({6-[2-fluoro-1-(fluoromethyl)ethoxy]-1-(1-formylpiperidin-4-yl)-2,4-dioxo-1,4-dihydroquinazolin-3(2H)-yl}methyl)phenoxy]propanoic acid | 630 |
| 303 | 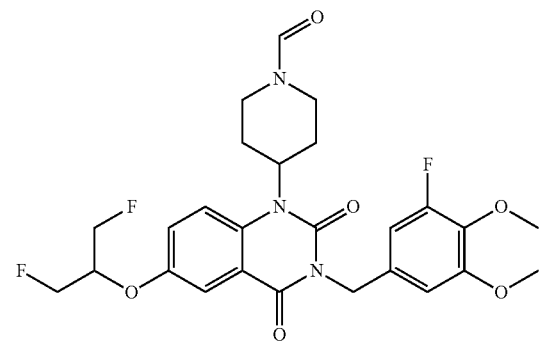 [SMILES: COc1cc(Cn2c(=O)c3cc(OC(CF)CF)ccc3n(C3CCN(C=O)CC3)c2=O)cc(F)c1OC] | 4-[3-(3-fluoro-4,5-dimethoxybenzyl)-6-[2-fluoro-1-(fluoromethyl)ethoxy]-2,4-dioxo-3,4-dihydroquinazolin-1(2H)-yl]piperidine-1-carbaldehyde | 536 |
| 304 | 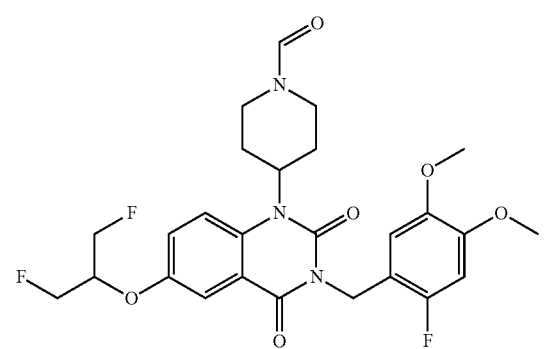 [SMILES: COc1cc(F)c(Cn2c(=O)c3cc(OC(CF)CF)ccc3n(C3CCN(C=O)CC3)c2=O)cc1OC] | 4-[3-(2-fluoro-4,5-dimethoxybenzyl)-6-[2-fluoro-1-(fluoromethyl)ethoxy]-2,4-dioxo-3,4-dihydroquinazolin-1(2H)-yl]piperidine-1-carbaldehyde | 536 |
| 305 | 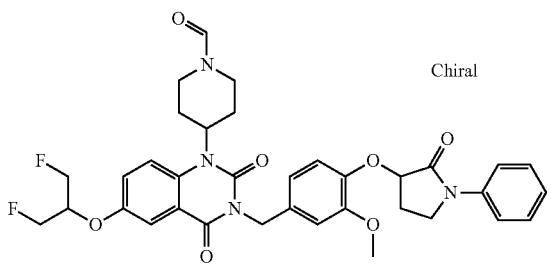 [SMILES: COc1cc(Cn2c(=O)c3cc(OC(CF)CF)ccc3n(C3CCN(C=O)CC3)c2=O)ccc1OC1CCN(c2ccccc2)C1=O] Chiral | 4-{6-[2-fluoro-1-(fluoromethyl)ethoxy]-3-(3-methoxy-4-{[(3R)-2-oxo-1-phenylpyrrolidin-3-yl]oxy}benzyl)-2,4-dioxo-3,4-dihydroquinazolin-1(2H)-yl}piperidine-1-carbaldehyde | 663 |

| | | | |
|---|---|---|---|
| 306 | 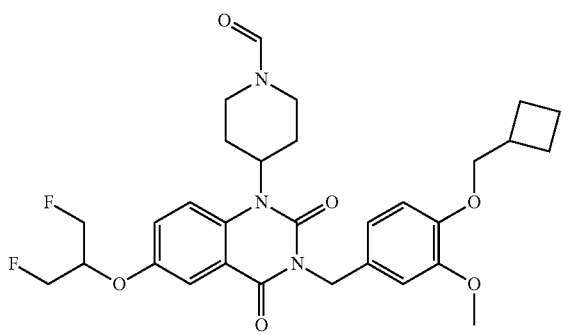 [SMILES: COc1cc(Cn2c(=O)c3cc(OC(CF)CF)ccc3n(C3CCN(C=O)CC3)c2=O)ccc1OCC1CCC1] | 4-{3-[4-(cyclobutylmethoxy)-3-methoxybenzyl]-6-[2-fluoro-1-(fluoromethyl)ethoxy]-2,4-dioxo-3,4-dihydroquinazolin-1(2H)-yl}piperidine-1-carbaldehyde | 572 |
| 307 | 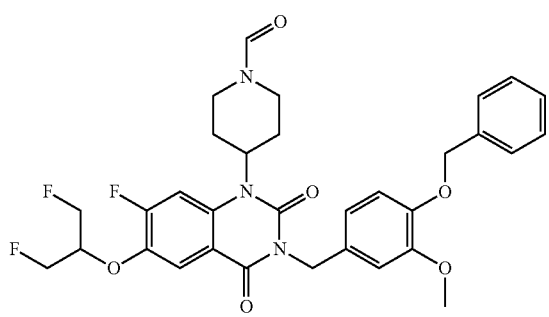 [SMILES: COc1cc(Cn2c(=O)c3cc(OC(CF)CF)c(F)cc3n(C3CCN(C=O)CC3)c2=O)ccc1OCc1ccccc1] | 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 612 |
| 308 | 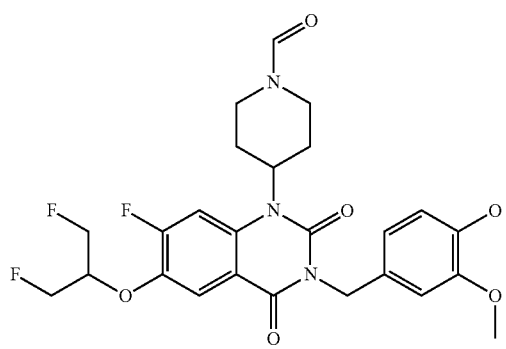 [SMILES: COc1cc(Cn2c(=O)c3cc(OC(CF)CF)c(F)cc3n(C3CCN(C=O)CC3)c2=O)ccc1O] | 4-{7-fluoro-6-[2-fluoro-1-(fluoromethyl)ethoxy]-3-(4-hydroxy-3-methoxybenzyl)-2,4-dioxo-3,4-dihydroquinazolin-1(2H)-yl}piperidine-1-carbaldehyde | 522 |
| 309 | 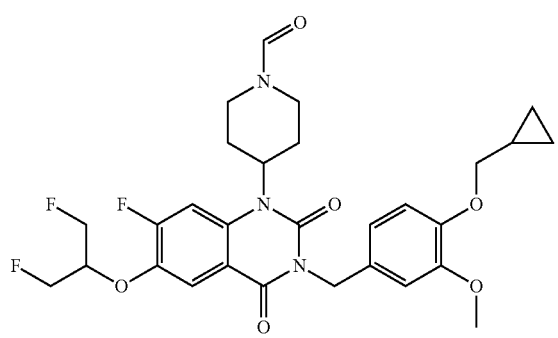 [SMILES: COc1cc(Cn2c(=O)c3cc(OC(CF)CF)c(F)cc3n(C3CCN(C=O)CC3)c2=O)ccc1OCC1CC1] | 4-{3-[2-(cyclopropylmethoxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 576 |
| 310 | 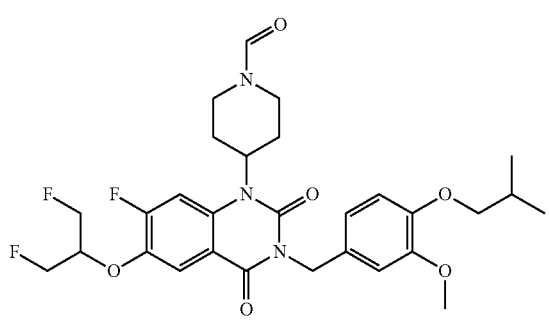 [SMILES: COc1cc(Cn2c(=O)c3cc(OC(CF)CF)c(F)cc3n(C3CCN(C=O)CC3)c2=O)ccc1OCC(C)C] | 4-{7-fluoro-6-[2-fluoro-1-(fluoromethyl)ethoxy]-3-[3-methoxy-4-(2-methylpropoxy)benzyl]-2,4-dioxo-3,4-dihydroquinazolin-1(2H)-yl}piperidine-1-carbaldehyde | 578 |

| | | | |
|---|---|---|---|
| 311 | 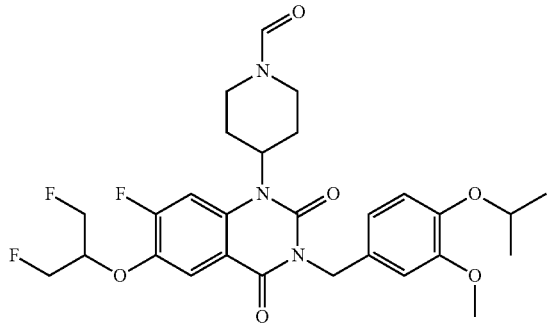 [SMILES: COc1cc(Cn2c(=O)c3cc(OC(CF)CF)c(F)cc3n(C3CCN(C=O)CC3)c2=O)ccc1OC(C)C] | 4-{7-fluoro-6-[2-fluoro-1-(fluoromethyl)ethoxy]-3-[3-methoxy-4-(1-methylethoxy)benzyl]-2,4-dioxo-3,4-dihydroquinazolin-1(2H)-yl}piperidine-1-carbaldehyde | 564 |
| 312 | 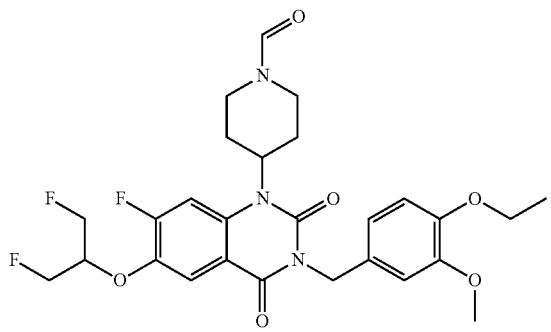 [SMILES: CCOc1ccc(Cn2c(=O)c3cc(OC(CF)CF)c(F)cc3n(C3CCN(C=O)CC3)c2=O)cc1OC] | 4-[3-(4-ethoxy-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde | 550 |
| 313 | 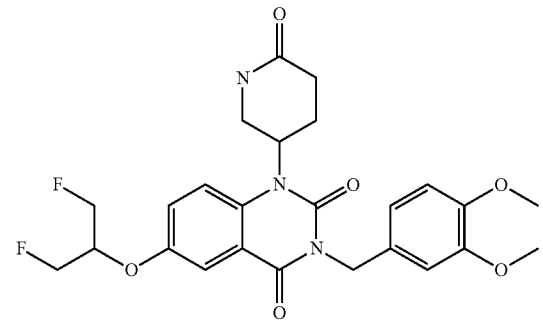 [SMILES: COc1ccc(Cn2c(=O)c3cc(OC(CF)CF)ccc3n(C3CCC(=O)NC3)c2=O)cc1OC] | 3-(3,4-dimethoxybenzyl)-6-[2-fluoro-1-(fluoromethyl)ethoxy]-1-(6-oxopiperidin-3-yl)quinazoline-2,4(1H,3H)-dione | 504 |
| 314 | 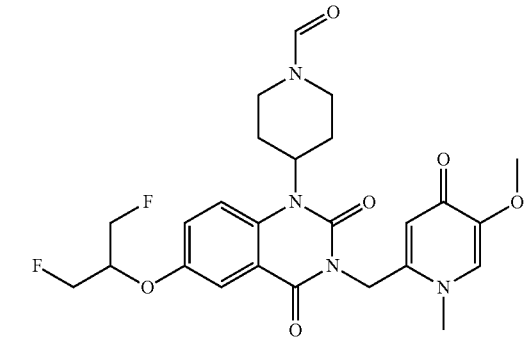 [SMILES: COc1cn(C)c(Cn2c(=O)c3cc(OC(CF)CF)ccc3n(C3CCN(C=O)CC3)c2=O)cc1=O] | 4-{6-[2-fluoro-1-(fluoromethyl)ethoxy]-3-[(5-methoxy-1-methyl-4-oxo-1,4-dihydropyridin-2-yl)methyl]-2,4-dioxo-3,4-dihydroquinazolin-1(2H)-yl}piperidine-1-carbaldehyde | 519 |

-continued

| | | | |
|---|---|---|---|
| 315 | 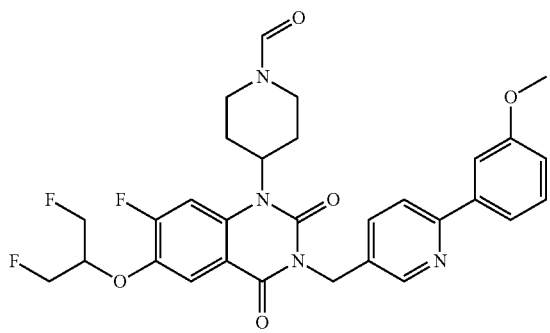 [SMILES: COc1cccc(-c2ccc(Cn3c(=O)c4cc(OC(CF)CF)c(F)cc4n(C4CCN(C=O)CC4)c3=O)cn2)c1] | 4-{7-fluoro-6-[2-fluoro-1-(fluoromethyl) ethoxy]-3-{[6-(3-methoxyphenyl) pyridin-3-yl]methyl}-2,4-dioxo-3,4-dihydroquinazolin-1(2H)-yl}piperidine-1-carbaldehyde | 583 |
| 316 | 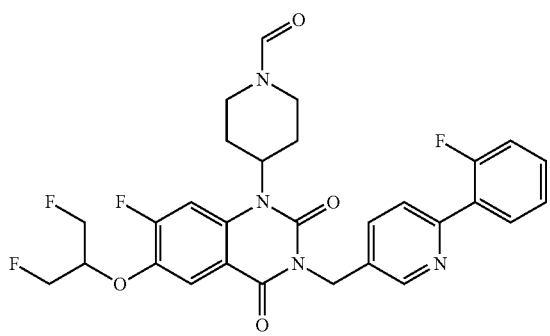 [SMILES: O=CN1CCC(n2c(=O)n(Cc3ccc(-c4ccccc4F)nc3)c(=O)c3cc(OC(CF)CF)c(F)cc32)CC1] | 4-{7-fluoro-6-[2-fluoro-1-(fluoromethyl) ethoxy]-3-{[6-(2-fluorophenyl)pyridin-3-yl]methyl}-2,4-dioxo-3,4-dihydroquinazolin-1(2H)-yl}piperidine-1-carbaldehyde | 571 |
| 317 | 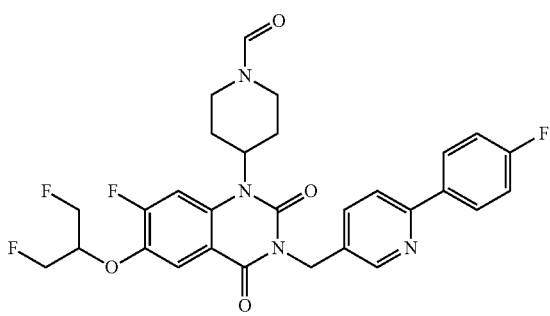 [SMILES: O=CN1CCC(n2c(=O)n(Cc3ccc(-c4ccc(F)cc4)nc3)c(=O)c3cc(OC(CF)CF)c(F)cc32)CC1] | 4-{7-fluoro-6-[2-fluoro-1-(fluoromethyl) ethoxy]-3-{[6-(4-fluorophenyl)pyridin-3-yl]methyl}-2,4-dioxo-3,4-dihydroquinazolin-1(2H)-yl}piperidine-1-carbaldehyde | 571 |
| 318 | 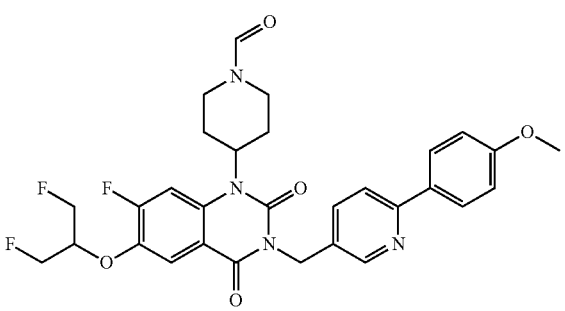 [SMILES: COc1ccc(-c2ccc(Cn3c(=O)c4cc(OC(CF)CF)c(F)cc4n(C4CCN(C=O)CC4)c3=O)cn2)cc1] | 4-{7-fluoro-6-[2-fluoro-1-(fluoromethyl) ethoxy]-3-{[6-(4-methoxyphenyl)pyridin-3-yl]methyl}-2,4-dioxo-3,4-dihydroquinazolin-1(2H)-yl}piperidine-1-carbaldehyde | 583 |
| 319 | 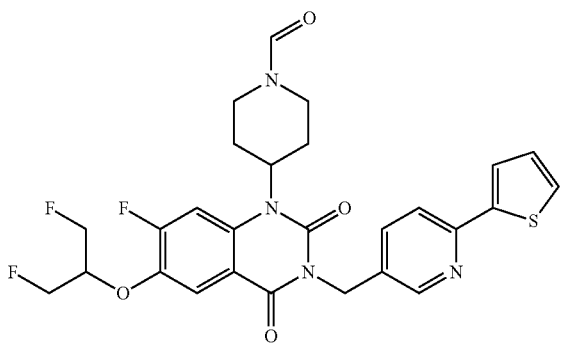 [SMILES: O=CN1CCC(n2c(=O)n(Cc3ccc(-c4cccs4)nc3)c(=O)c3cc(OC(CF)CF)c(F)cc32)CC1] | 4-{7-fluoro-6-[2-fluoro-1-(fluoromethyl) ethoxy]-2,4-dioxo-3-[(6-(thiophen-2-yl)pyridin-3-yl)methyl]-3,4-dihydroquinazolin-1(2H)-yl}piperidine-1-carbaldehyde | 559 |

| | | | |
|---|---|---|---|
| 320 | 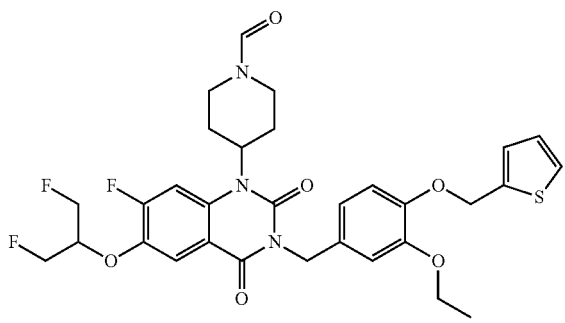 [SMILES: CCOc1cc(Cn2c(=O)c3cc(OC(CF)CF)c(F)cc3n(C3CCN(C=O)CC3)c2=O)ccc1OCc1cccs1] | 4-{3-[3-ethoxy-4-(thiophen-2-ylmethoxy) benzyl]-7-fluoro-6-[2-fluoro-1- (fluoromethyl)ethoxy]-2,4- dioxo-3,4-dihydroquinazolin-1(2H)- yl}piperidine-1-carbaldehyde | 632 |
| 321 | 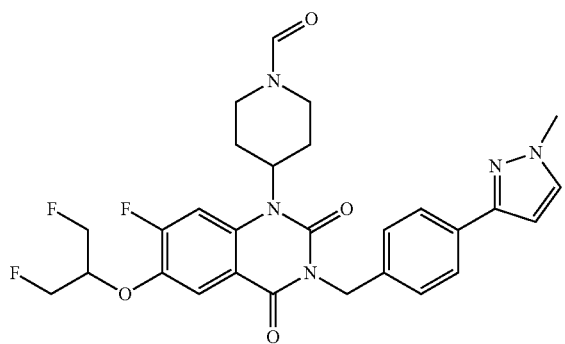 [SMILES: Cn1ccc(-c2ccc(Cn3c(=O)c4cc(OC(CF)CF)c(F)cc4n(C4CCN(C=O)CC4)c3=O)cc2)n1] | 4-{7-fluoro-6-[2-fluoro-1-(fluoromethyl) ethoxy]-3-[4-(1-methyl-1H-pyrazol-3-yl) benzyl]-2,4-dioxo-3,4-dihydroquinazolin- 1(2H)-yl}piperidine-1-carbaldehyde | 556 |
| 322 | 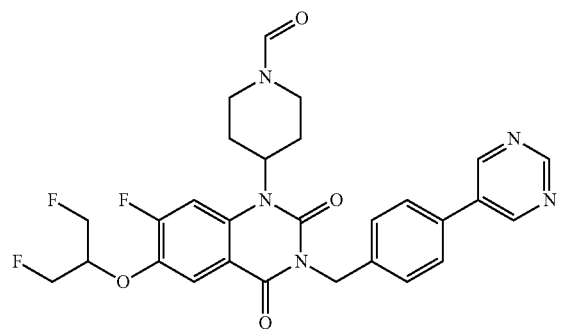 [SMILES: O=CN1CCC(n2c(=O)n(Cc3ccc(-c4cncnc4)cc3)c(=O)c3cc(OC(CF)CF)c(F)cc32)CC1] | 4-{7-fluoro-6-[2-fluoro-1-(fluoromethyl) ethoxy]-2,4-dioxo-3-(4-(pyrimidin-5-yl) benzyl)-3,4-dihydroquinazolin-1(2H)- yl}piperidine-1-carbaldehyde | 554 |
| 323 | 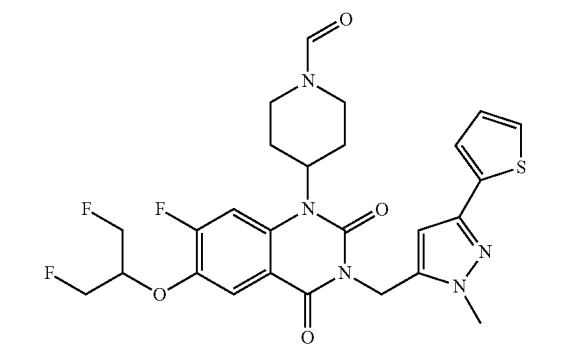 [SMILES: Cn1nc(-c2cccs2)cc1Cn1c(=O)c2cc(OC(CF)CF)c(F)cc2n(C2CCN(C=O)CC2)c1=O] | 4-{7-fluoro-6-[2-fluoro-1-(fluoromethyl) ethoxy]-3-[(1-methyl-3-(thiophen-2-yl)- 1H-pyrazol-5-yl)methyl]-2,4-dioxo-3,4- dihydroquinazolin-1(2H)-yl}piperidine- 1-carbaldehyde | 562 |
| 324 | 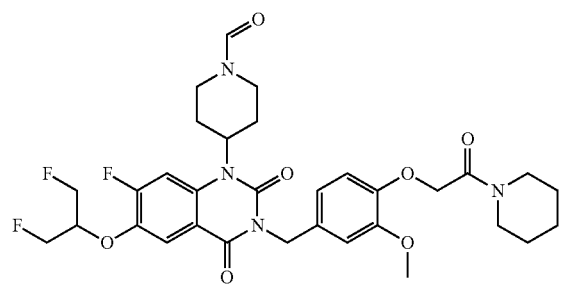 [SMILES: COc1cc(Cn2c(=O)c3cc(OC(CF)CF)c(F)cc3n(C3CCN(C=O)CC3)c2=O)ccc1OCC(=O)N1CCCCC1] | 4-{7-fluoro-6-[2-fluoro-1-(fluoromethyl) ethoxy]-3-[3-methoxy-4-(2-oxo-2- (piperidin-1-yl)ethoxy)benzyl]-2,4-dioxo- 3,4-dihydroquinazolin-1(2H)-yl} piperidine-1-carbaldehyde | 647 |

| | | | |
|---|---|---|---|
| 325 | 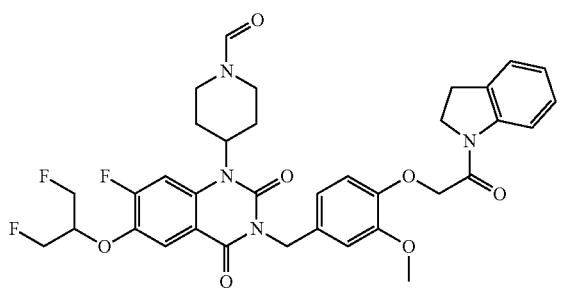 [SMILES: COc1cc(Cn2c(=O)c3cc(OC(CF)CF)c(F)cc3n(C3CCN(C=O)CC3)c2=O)ccc1OCC(=O)N1CCc2ccccc21] | 4-[3-{4-[2-(2,3-dihydro-1H-indol-1-yl)-2-oxoethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 681 |
| 326 | 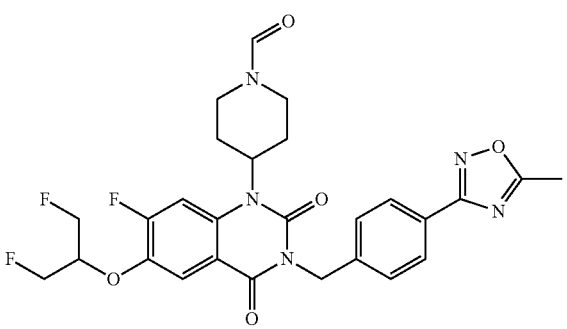 [SMILES: Cc1nc(-c2ccc(Cn3c(=O)c4cc(OC(CF)CF)c(F)cc4n(C4CCN(C=O)CC4)c3=O)cc2)no1] | 4-{7-fluoro-6-[2-fluoro-1-(fluoromethyl)ethoxy]-3-[4-(5-methyl-1,2,4-oxadiazol-3-yl)benzyl]-2,4-dioxo-3,4-dihydroquinazolin-1(2H)-yl}piperidine-1-carbaldehyde | 558 |
| 327 | 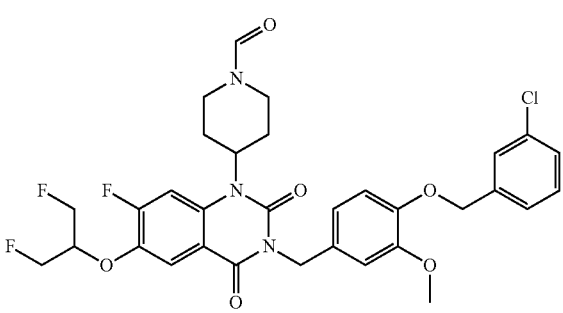 [SMILES: COc1cc(Cn2c(=O)c3cc(OC(CF)CF)c(F)cc3n(C3CCN(C=O)CC3)c2=O)ccc1OCc1cccc(Cl)c1] | 4-[3-{4-[(3-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 646 |
| 328 | 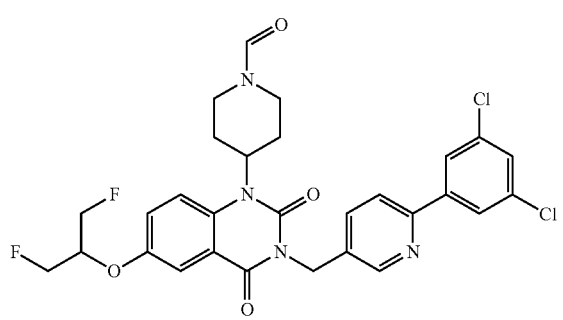 [SMILES: O=CN1CCC(n2c(=O)n(Cc3ccc(-c4cc(Cl)cc(Cl)c4)nc3)c(=O)c3cc(OC(CF)CF)ccc32)CC1] | 4-[3-{[6-(3,5-dichlorophenyl)pyridin-3-yl]methyl}-6-[2-fluoro-1-(fluoromethyl)ethoxy]-2,4-dioxo-3,4-dihydroquinazolin-1(2H)-yl]piperidine-1-carbaldehyde | 603 |
| 329 | 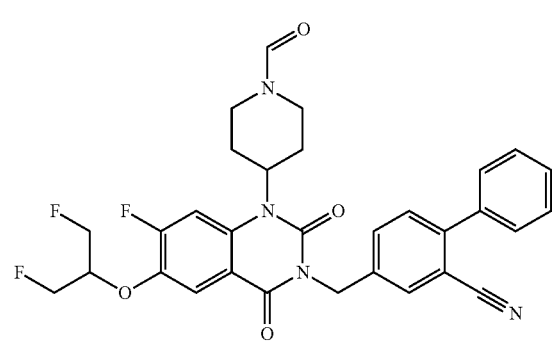 [SMILES: N#Cc1cc(Cn2c(=O)c3cc(OC(CF)CF)c(F)cc3n(C3CCN(C=O)CC3)c2=O)ccc1-c1ccccc1] | 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)biphenyl-2-carbonitrile | 577 |

| # | Structure | Name | MW |
|---|---|---|---|
| 330 | 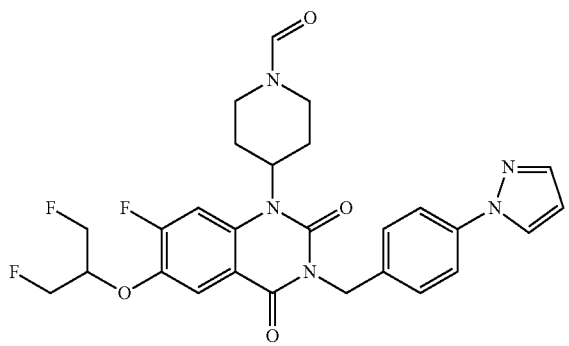 [SMILES: O=CN1CCC(n2c(=O)n(Cc3ccc(-n4cccn4)cc3)c(=O)c3cc(OC(CF)CF)c(F)cc32)CC1] | 4-{7-fluoro-6-[2-fluoro-1-(fluoromethyl) ethoxy]-2,4-dioxo-3-[4-(1H-pyrazol-1-yl) benzyl]-3,4-dihydroquinazolin-1(2H)-yl}piperidine-1-carbaldehyde | 542 |
| 331 | 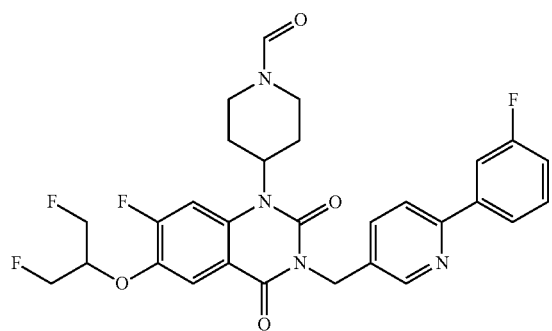 [SMILES: O=CN1CCC(n2c(=O)n(Cc3ccc(-c4cccc(F)c4)nc3)c(=O)c3cc(OC(CF)CF)c(F)cc32)CC1] | 4-{7-fluoro-6-[2-fluoro-1-(fluoromethyl) ethoxy]-3-{[6-(3-fluorophenyl)pyridin-3-yl]methyl}-2,4-dioxo-3,4-dihydroquinazolin-1(2H)-yl} piperidine-1-carbaldehyde | 571 |
| 332 | 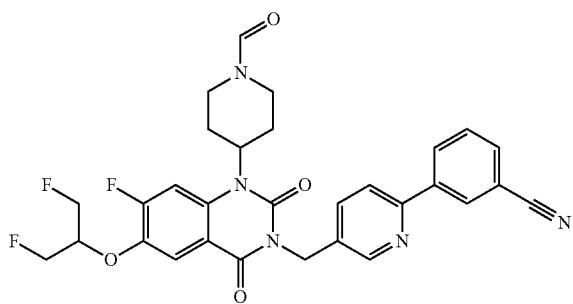 [SMILES: N#Cc1cccc(-c2ccc(Cn3c(=O)c4cc(OC(CF)CF)c(F)cc4n(C4CCN(C=O)CC4)c3=O)cn2)c1] | 3-[5-({7-fluoro-6-[2-fluoro-1-(fluoromethyl)ethoxy]-1-(1-formylpiperidin-4-yl)-2,4-dioxo-1,4-dihydroquinazolin-3(2H)-yl} methyl)pyridin-2-yl]benzonitrile | 578 |
| 333 | 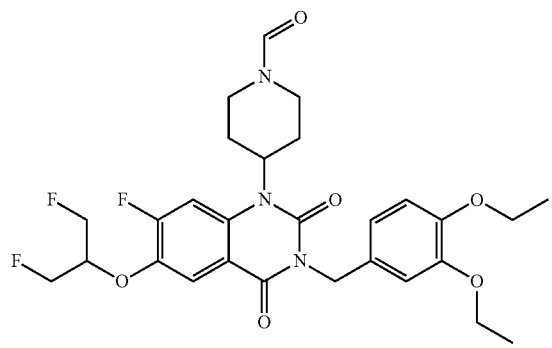 [SMILES: CCOc1ccc(Cn2c(=O)c3cc(OC(CF)CF)c(F)cc3n(C3CCN(C=O)CC3)c2=O)cc1OCC] | 4-[3-(3,4-diethoxybenzyl)-7-fluoro-6-[2-fluoro-1-(fluoromethyl)ethoxy]-2,4-dioxo-3,4-dihydroquinazolin-1(2H)-yl] piperidine-1-carbaldehyde | 564 |
| 334 | 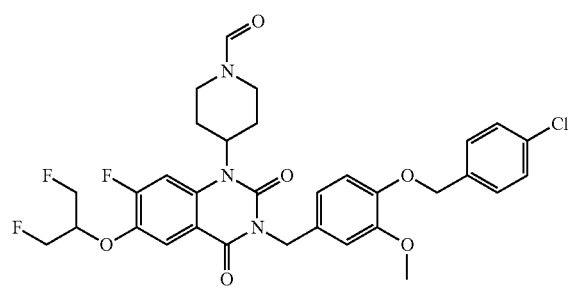 [SMILES: COc1cc(Cn2c(=O)c3cc(OC(CF)CF)c(F)cc3n(C3CCN(C=O)CC3)c2=O)ccc1OCc1ccc(Cl)cc1] | 4-[3-{4-[(4-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl] piperidine-1-carbaldehyde | 646 |

| | | | |
|---|---|---|---|
| 335 | 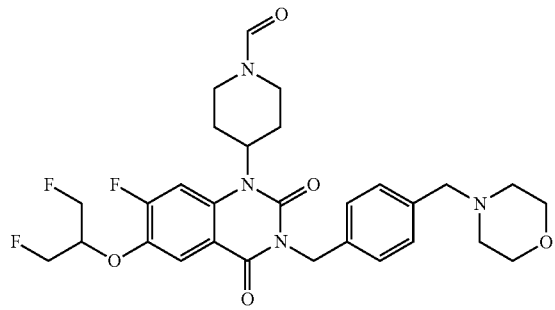 [SMILES: O=CN1CCC(n2c(=O)n(Cc3ccc(CN4CCOCC4)cc3)c(=O)c3cc(OC(CF)CF)c(F)cc32)CC1] | 4-{7-fluoro-6-[2-fluoro-1-(fluoromethyl) ethoxy]-3-[4-(morpholin-4-ylmethyl)benzyl]-2,4-dioxo-3,4-dihydroquinazolin-1(2H)-yl} piperidine-1-carbaldehyde | 575 |
| 336 | 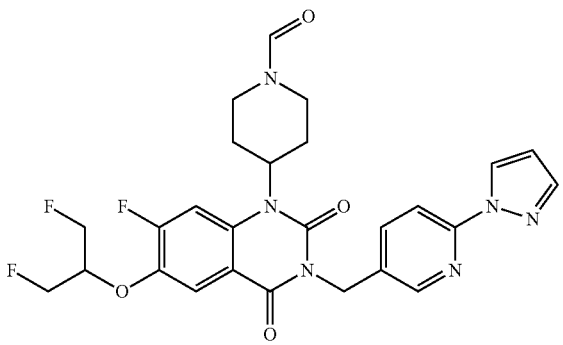 [SMILES: O=CN1CCC(n2c(=O)n(Cc3ccc(-n4cccn4)nc3)c(=O)c3cc(OC(CF)CF)c(F)cc32)CC1] | 4-{7-fluoro-6-[2-fluoro-1-(fluoromethyl) ethoxy]-2,4-dioxo-3-{[6-(1H-pyrazol-1-yl)pyridin-3-yl]methyl}-3,4-dihydroquinazolin-1(2H)-yl}piperidine-1-carbaldehyde | 543 |
| 337 | 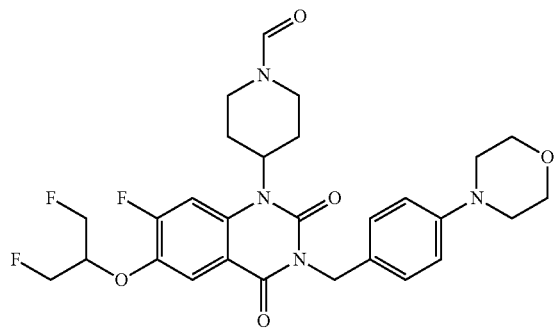 [SMILES: O=CN1CCC(n2c(=O)n(Cc3ccc(N4CCOCC4)cc3)c(=O)c3cc(OC(CF)CF)c(F)cc32)CC1] | 4-{7-fluoro-6-[2-fluoro-1-(fluoromethyl) ethoxy]-3-(4-(morpholin-4-yl)benzyl)-2,4-dioxo-3,4-dihydroquinazolin-1(2H)-yl}piperidine-1-carbaldehyde | 561 |
| 338 | 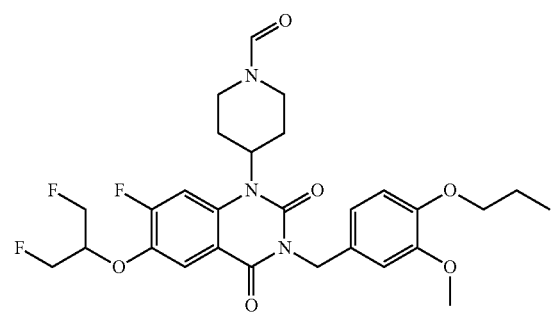 [SMILES: CCCOc1ccc(Cn2c(=O)c3cc(OC(CF)CF)c(F)cc3n(C3CCN(C=O)CC3)c2=O)cc1OC] | 4-{7-fluoro-6-[2-fluoro-1-(fluoromethyl) ethoxy]-3-(3-methoxy-4-propoxybenzyl)-2,4-dioxo-3,4-dihydroquinazolin-1(2H)-yl}piperidine-1-carbaldehyde | 564 |
| 339 | 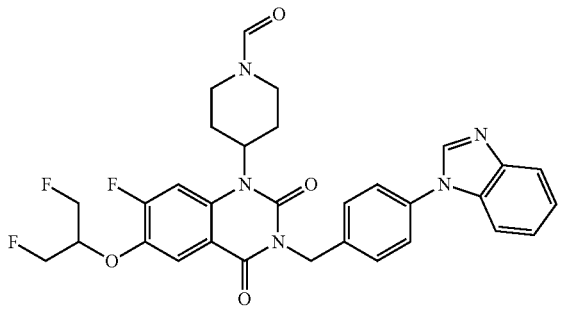 [SMILES: O=CN1CCC(n2c(=O)n(Cc3ccc(-n4cnc5ccccc54)cc3)c(=O)c3cc(OC(CF)CF)c(F)cc32)CC1] | 4-{3-[4-(1H-benzimidazol-1-yl)benzyl]-7-fluoro-6-[2-fluoro-1-(fluoromethyl) ethoxy]-2,4-dioxo-3,4-dihydroquinazolin-1(2H)-yl}piperidine-1-carbaldehyde | 592 |

-continued

| | | | |
|---|---|---|---|
| 340 | 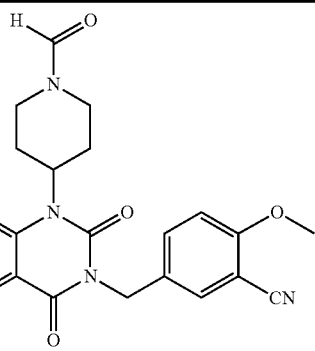 | 5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxybenzonitrile | 531 |
| 341 | 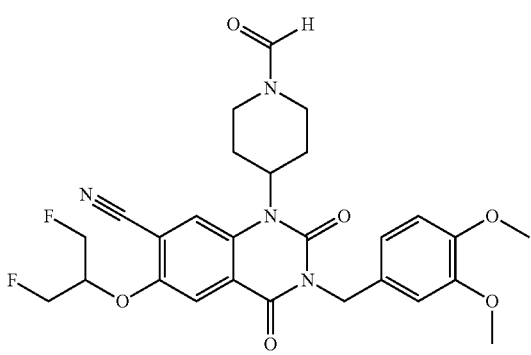 [SMILES: COc1ccc(Cn2c(=O)c3cc(OC(CF)CF)c(C#N)cc3n(C3CCN(C=O)CC3)c2=O)cc1OC] | 3-(3,4-dimethoxybenzyl)-6-[2-fluoro-1-(fluoromethyl)ethoxy]-1-(1-formylpiperidin-4-yl)-2,4-dioxo-1,2,3,4-tetrahydroquinazoline-7-carbonitrile | 543 |
| 342 | 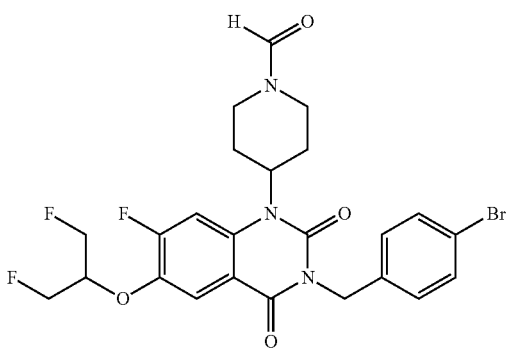 [SMILES: O=CN1CCC(n2c(=O)n(Cc3ccc(Br)cc3)c(=O)c3cc(OC(CF)CF)c(F)cc32)CC1] | 4-[3-(4-bromobenzyl)-7-fluoro-6-[2-fluoro-1-(fluoromethyl)ethoxy]-2,4-dioxo-3,4-dihydroquinazolin-1(2H)-yl]piperidine-1-carbaldehyde | 554 |
| 343 | 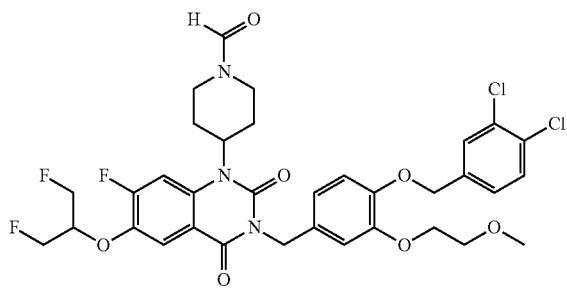 [SMILES: COCCOc1cc(Cn2c(=O)c3cc(OC(CF)CF)c(F)cc3n(C3CCN(C=O)CC3)c2=O)ccc1OCc1ccc(Cl)c(Cl)c1] | 4-[3-{4-[(3,4-dichlorobenzyl)oxy]-3-(2-methoxyethoxy)benzyl}-7-fluoro-6-[2-fluoro-1-(fluoromethyl)ethoxy]-2,4-dioxo-3,4-dihydroquinazolin-1(2H)-yl]piperidine-1-carbaldehyde | 724 |
| 344 | 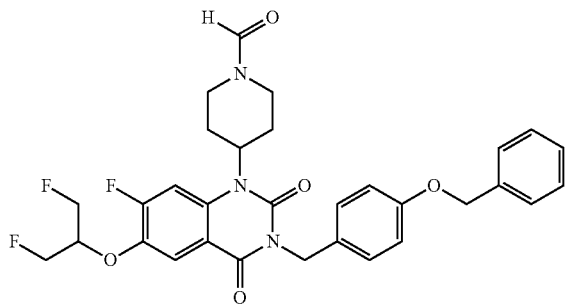 [SMILES: O=CN1CCC(n2c(=O)n(Cc3ccc(OCc4ccccc4)cc3)c(=O)c3cc(OC(CF)CF)c(F)cc32)CC1] | 4-{3-[4-(benzyloxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 582 |

| | | | |
|---|---|---|---|
| 345 | 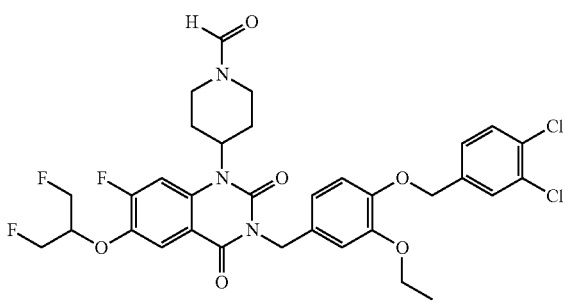 [SMILES: CCOc1cc(Cn2c(=O)c3cc(OC(CF)CF)c(F)cc3n(C3CCN(C=O)CC3)c2=O)ccc1OCc1ccc(Cl)c(Cl)c1] | 4-[3-{4-[(3,4-dichlorobenzyl)oxy]-3-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 694 |
| 346 | 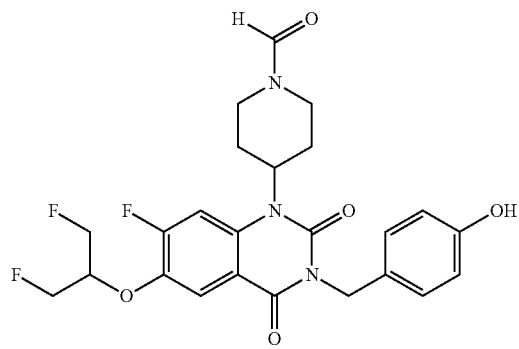 [SMILES: O=CN1CCC(n2c(=O)n(Cc3ccc(O)cc3)c(=O)c3cc(OC(CF)CF)c(F)cc32)CC1] | 4-{7-fluoro-6-[2-fluoro-1-(fluoromethyl)ethoxy]-3-(4-hydroxybenzyl)-2,4-dioxo-3,4-dihydroquinazolin-1(2H)-yl}piperidine-1-carbaldehyde | 492 |
| 347 | 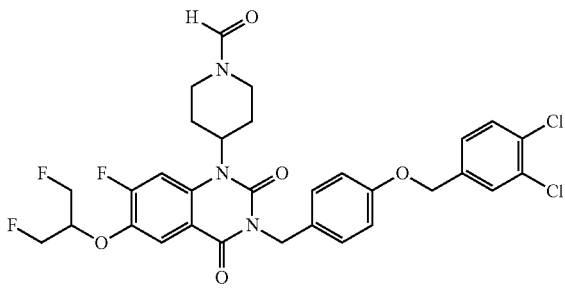 | 4-[3-{4-[(3,4-dichlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 650 |
| 348 | 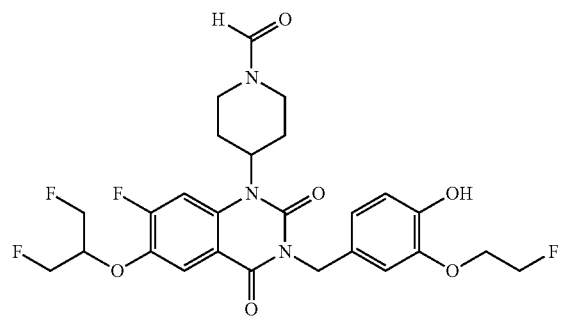 [SMILES: O=CN1CCC(n2c(=O)n(Cc3ccc(O)c(OCCF)c3)c(=O)c3cc(OC(CF)CF)c(F)cc32)CC1] | 4-{7-fluoro-3-[3-(2-fluoroethoxy)-4-hydroxybenzyl]-6-[2-fluoro-1-(fluoromethyl)ethoxy]-2,4-dioxo-3,4-dihydroquinazolin-1(2H)-yl}piperidine-1-carbaldehyde | 554 |
| 349 | 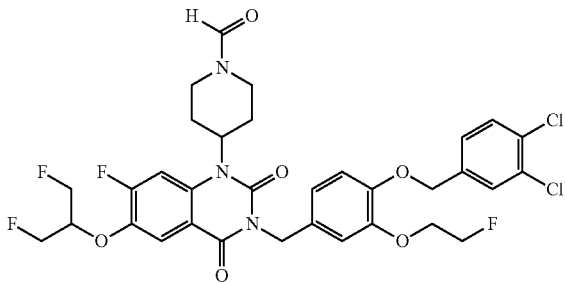 [SMILES: O=CN1CCC(n2c(=O)n(Cc3ccc(OCc4ccc(Cl)c(Cl)c4)c(OCCF)c3)c(=O)c3cc(OC(CF)CF)c(F)cc32)CC1] | 4-[3-{4-[(3,4-dichlorobenzyl)oxy]-3-(2-fluoroethoxy)benzyl}-7-fluoro-6-[2-fluoro-1-(fluoromethyl)ethoxy]-2,4-dioxo-3,4-dihydroquinazolin-1(2H)-yl]piperidine-1-carbaldehyde | 712 |

| | | | |
|---|---|---|---|
| 350 | | 4-[3-{4-[(2-chloro-4-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 664 |
| 351 | | 4-[3-{4-[(2,4-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |
| 352 | | 4-[3-{4-[(2-chloro-6-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 664 |
| 353 | | 4-[3-{4-[(2,6-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |
| 354 | | 4-[3-{4-[(2-chlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 646 |

| # | Structure | Name | Value |
|---|---|---|---|
| 355 | 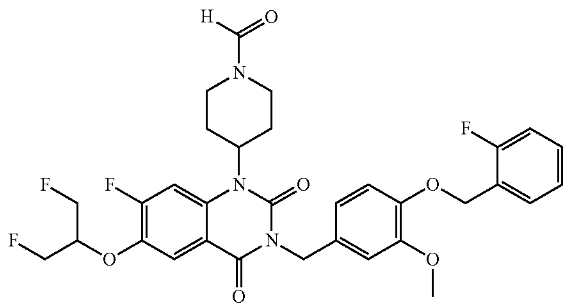 [SMILES: COc1cc(Cn2c(=O)c3cc(OC(CF)CF)c(F)cc3n(C3CCN(C=O)CC3)c2=O)ccc1OCc1ccccc1F] | 4-[7-fluoro-3-{4-[(2-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 630 |
| 356 | 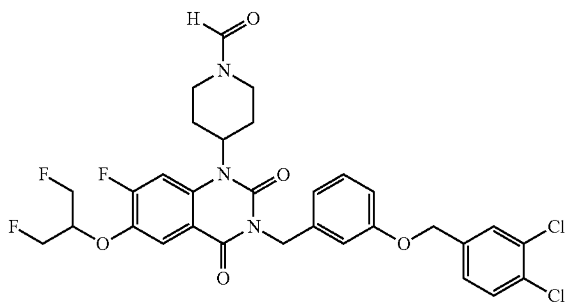 [SMILES: O=CN1CCC(n2c(=O)n(Cc3cccc(OCc4ccc(Cl)c(Cl)c4)c3)c(=O)c3cc(OC(CF)CF)c(F)cc32)CC1] | 4-[3-{3-[(3,4-dichlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 650 |
| 357 | 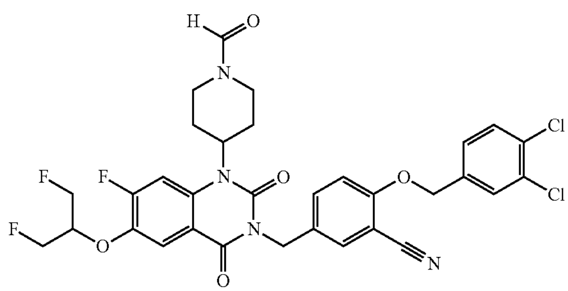 [SMILES: N#Cc1cc(Cn2c(=O)c3cc(OC(CF)CF)c(F)cc3n(C3CCN(C=O)CC3)c2=O)ccc1OCc1ccc(Cl)c(Cl)c1] | 2-[(3,4-dichlorobenzyl)oxy]-5-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)benzonitrile | 675 |
| 358 | 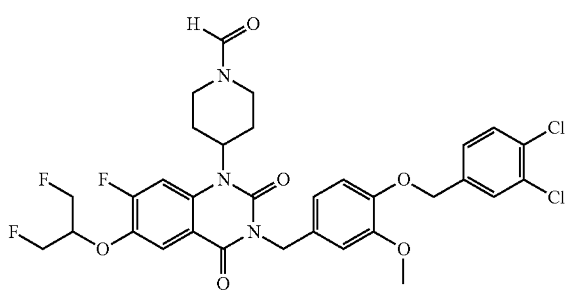 [SMILES: COc1cc(Cn2c(=O)c3cc(OC(CF)CF)c(F)cc3n(C3CCN(C=O)CC3)c2=O)ccc1OCc1ccc(Cl)c(Cl)c1] | 4-[3-{4-[(3,4-dichlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |
| 359 | 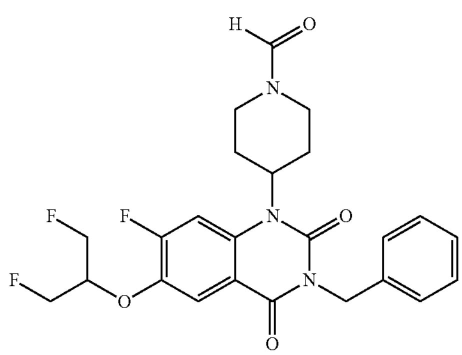 [SMILES: O=CN1CCC(n2c(=O)n(Cc3ccccc3)c(=O)c3cc(OC(CF)CF)c(F)cc32)CC1] | 4-{3-benzyl-7-fluoro-6-[2-fluoro-1-(fluoromethyl)ethoxy]-2,4-dioxo-3,4-dihydroquinazolin-1(2H)-yl}piperidine-1-carbaldehyde | 476 |

-continued

| | | | |
|---|---|---|---|
| 360 | 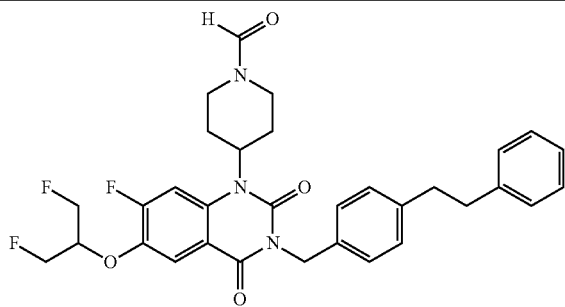 | 4-{7-fluoro-6-[2-fluoro-1-(fluoromethyl) ethoxy]-2,4-dioxo-3-[4-(2-phenylethyl) benzyl]-3,4-dihydroquinazolin-1(2H)-yl}piperidine-1-carbaldehyde | 580 |
| 361 | 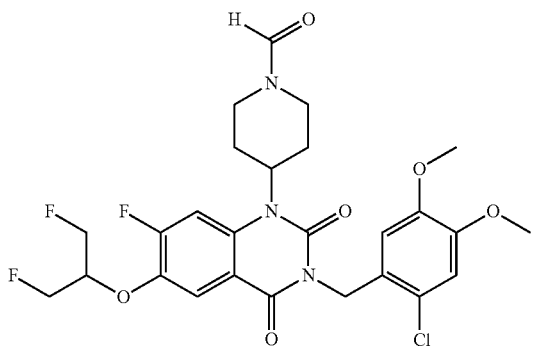 [SMILES: COc1cc(Cl)c(Cn2c(=O)c3cc(OC(CF)CF)c(F)cc3n(C3CCN(C=O)CC3)c2=O)cc1OC] | 4-[3-(2-chloro-4,5-dimethoxybenzyl)-6-[2-fluoro-1-(fluoromethyl)ethoxy]-2,4-dioxo-3,4-dihydroquinazolin-1(2H)-yl]piperidine-1-carbaldehyde | 552 |
| 362 | 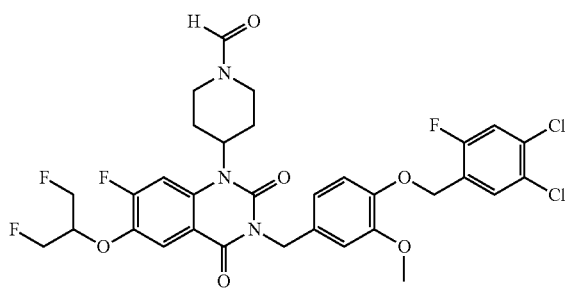 [SMILES: COc1cc(Cn2c(=O)c3cc(OC(CF)CF)c(F)cc3n(C3CCN(C=O)CC3)c2=O)ccc1OCc1cc(Cl)c(Cl)cc1F] | 4-[3-{4-[(4,5-dichloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 698 |
| 363 | 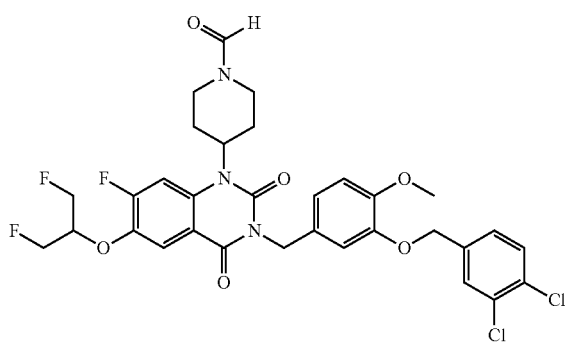 [SMILES: COc1ccc(Cn2c(=O)c3cc(OC(CF)CF)c(F)cc3n(C3CCN(C=O)CC3)c2=O)cc1OCc1ccc(Cl)c(Cl)c1] | 4-[3-{3-[(3,4-dichlorobenzyl)oxy]-4-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |
| 364 | 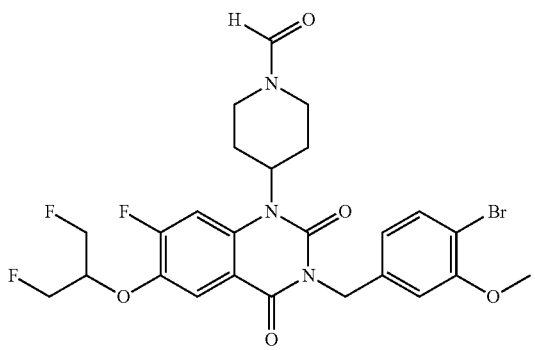 [SMILES: COc1cc(Cn2c(=O)c3cc(OC(CF)CF)c(F)cc3n(C3CCN(C=O)CC3)c2=O)ccc1Br] | 4-[3-(4-bromo-3-methoxybenzyl)-7-fluoro-6-[2-fluoro-1-(fluoromethyl) ethoxy]-2,4-dioxo-3,4-dihydroquinazolin-1(2H)-yl]piperidine-1-carbaldehyde | 584 |

| # | Structure | Name | Value |
|---|---|---|---|
| 365 | 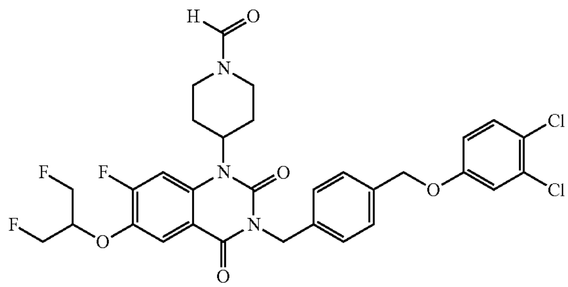 | 4-[3-{4-[(3,4-dichlorophenoxy)methyl]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 650 |
| 366 | 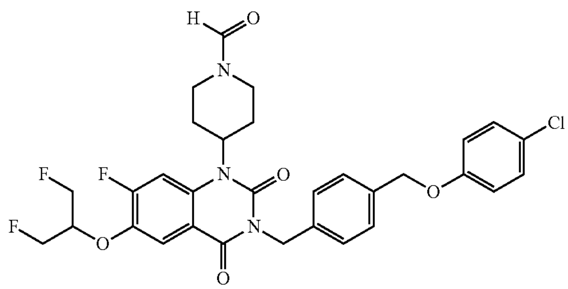 | 4-[3-{4-[(4-chlorophenoxy)methyl]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 616 |
| 367 | 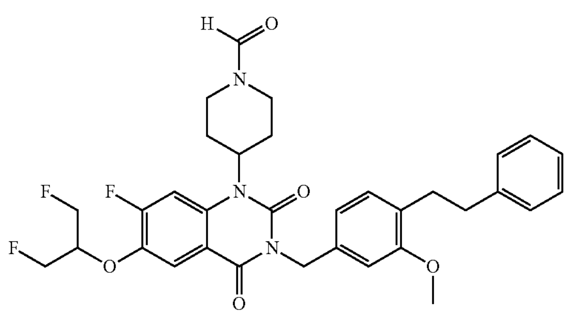 [SMILES: COc1cc(Cn2c(=O)c3cc(OC(CF)CF)c(F)cc3n(C3CCN(C=O)CC3)c2=O)ccc1CCc1ccccc1] | 4-{7-fluoro-6-[2-fluoro-1-(fluoromethyl)ethoxy]-3-[3-methoxy-4-(2-phenylethyl)benzyl]-2,4-dioxo-3,4-dihydroquinazolin-1(2H)-yl}piperidine-1-carbaldehyde | 610 |
| 368 | 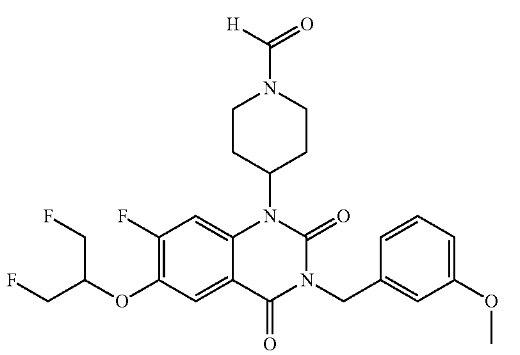 [SMILES: COc1cccc(Cn2c(=O)c3cc(OC(CF)CF)c(F)cc3n(C3CCN(C=O)CC3)c2=O)c1] | 4-{7-fluoro-6-[2-fluoro-1-(fluoromethyl)ethoxy]-3-(3-methoxybenzyl)-2,4-dioxo-3,4-dihydroquinazolin-1(2H)-yl}piperidine-1-carbaldehyde | 506 |
| 369 | 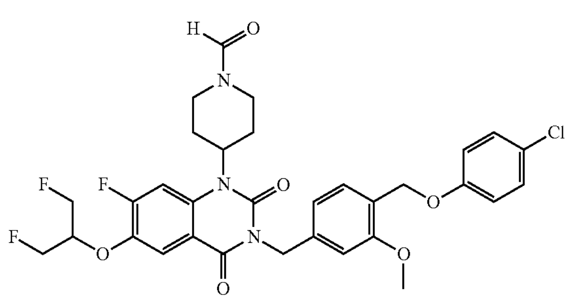 [SMILES: COc1cc(Cn2c(=O)c3cc(OC(CF)CF)c(F)cc3n(C3CCN(C=O)CC3)c2=O)ccc1COc1ccc(Cl)cc1] | 4-[3-{4-[(4-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 646 |

| | | | |
|---|---|---|---|
| 370 | 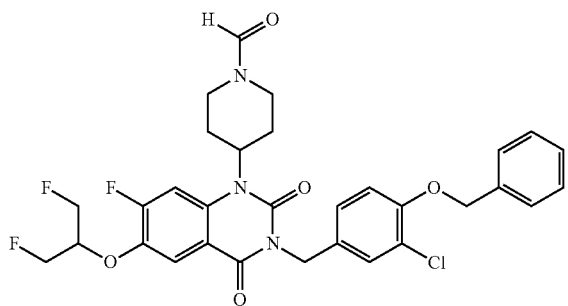 [SMILES: O=CN1CCC(n2c(=O)n(Cc3ccc(OCc4ccccc4)c(Cl)c3)c(=O)c3cc(OC(CF)CF)c(F)cc32)CC1] | 4-{3-[4-(benzyloxy)-3-chlorobenzyl]-7-fluoro-6-[2-fluoro-1-(fluoromethyl)ethoxy]-2,4-dioxo-3,4-dihydroquinazolin-1(2H)-yl}piperidine-1-carbaldehyde | 616 |
| 371 | 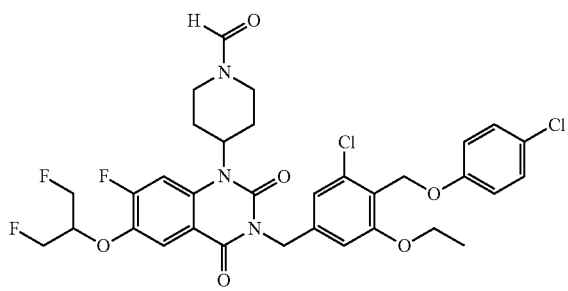 [SMILES: CCOc1cc(Cn2c(=O)c3cc(OC(CF)CF)c(F)cc3n(C3CCN(C=O)CC3)c2=O)cc(Cl)c1COc1ccc(Cl)cc1] | 4-[3-{3-chloro-4-[(4-chlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 694 |
| 372 | 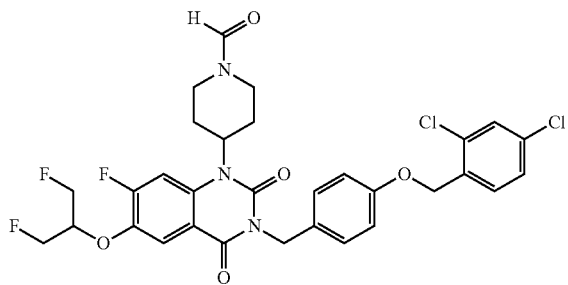 [SMILES: O=CN1CCC(n2c(=O)n(Cc3ccc(OCc4ccc(Cl)cc4Cl)cc3)c(=O)c3cc(OC(CF)CF)c(F)cc32)CC1] | 4-[3-{4-[(2,4-dichlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 650 |
| 373 | 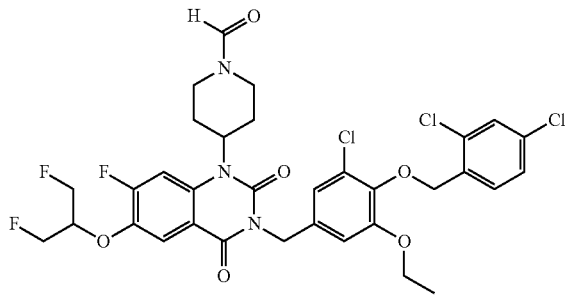 [SMILES: CCOc1cc(Cn2c(=O)c3cc(OC(CF)CF)c(F)cc3n(C3CCN(C=O)CC3)c2=O)cc(Cl)c1OCc1ccc(Cl)cc1Cl] | 4-[3-{3-chloro-4-[(2,4-dichlorobenzyl)oxy]-5-ethoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 728 |
| 374 | 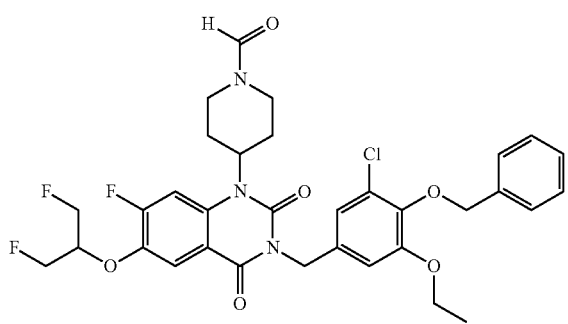 [SMILES: CCOc1cc(Cn2c(=O)c3cc(OC(CF)CF)c(F)cc3n(C3CCN(C=O)CC3)c2=O)cc(Cl)c1OCc1ccccc1] | 4-{3-[4-(benzyloxy)-3-chloro-5-ethoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 660 |

| | | | |
|---|---|---|---|
| 375 | 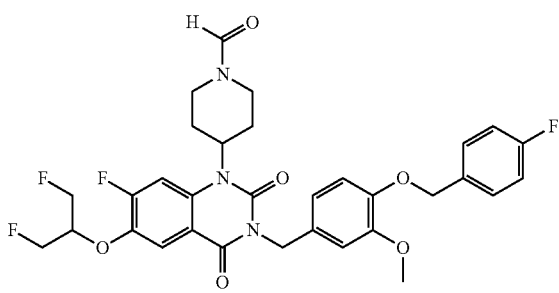 [SMILES: COc1cc(Cn2c(=O)c3cc(OC(CF)CF)c(F)cc3n(C3CCN(C=O)CC3)c2=O)ccc1OCc1ccc(F)cc1] | 4-[7-fluoro-4-{4-[(4-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 630 |
| 376 | 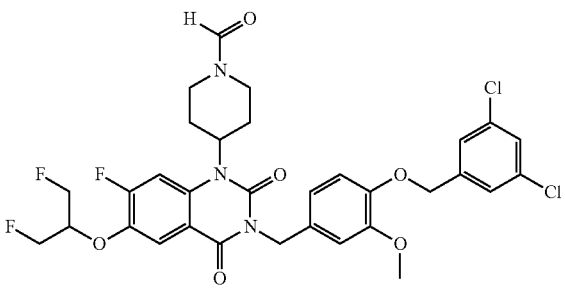 [SMILES: COc1cc(Cn2c(=O)c3cc(OC(CF)CF)c(F)cc3n(C3CCN(C=O)CC3)c2=O)ccc1OCc1cc(Cl)cc(Cl)c1] | 4-[3-{4-[(3,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |
| 377 | 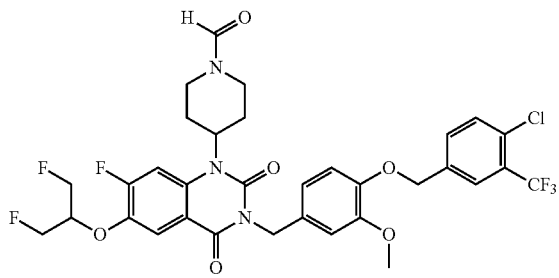 [SMILES: COc1cc(Cn2c(=O)c3cc(OC(CF)CF)c(F)cc3n(C3CCN(C=O)CC3)c2=O)ccc1OCc1ccc(Cl)c(C(F)(F)F)c1] | 4-[3-(4-{[4-chloro-3-(trifluoromethyl)benzyl]oxy}-3-methoxybenzyl)-7-fluoro-6-[2-fluoro-1-(fluoromethyl)ethoxy]-2,4-dioxo-3,4-dihydroquinazolin-1(2H)-yl]piperidine-1-carbaldehyde | 714 |
| 378 | 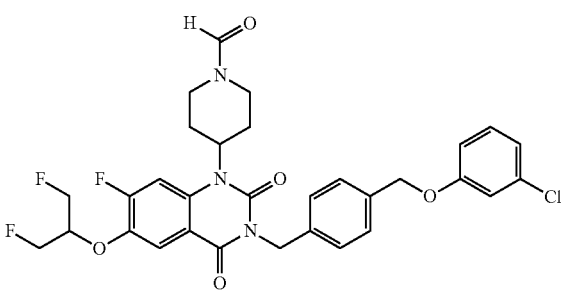 [SMILES: O=CN1CCC(n2c(=O)n(Cc3ccc(COc4cccc(Cl)c4)cc3)c(=O)c3cc(OC(CF)CF)c(F)cc32)CC1] | 4-[3-{4-[(3-chlorophenoxy)methyl]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 616 |
| 379 | 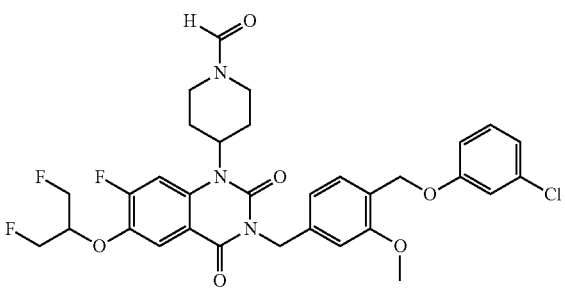 [SMILES: COc1cc(Cn2c(=O)c3cc(OC(CF)CF)c(F)cc3n(C3CCN(C=O)CC3)c2=O)ccc1COc1cccc(Cl)c1] | 4-[3-{4-[(3-chlorophenoxy)methyl]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 646 |

| | | | |
|---|---|---|---|
| 380 | 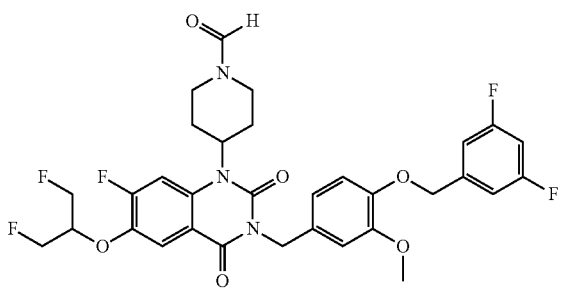 [SMILES: COc1cc(Cn2c(=O)c3cc(OC(CF)CF)c(F)cc3n(C3CCN(C=O)CC3)c2=O)ccc1OCc1cc(F)cc(F)c1] | 4-[3-{4-[(3,5-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 648 |
| 381 | 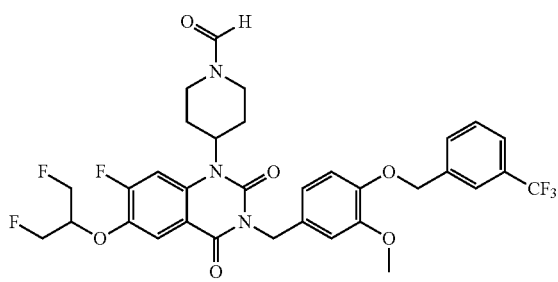 [SMILES: COc1cc(Cn2c(=O)c3cc(OC(CF)CF)c(F)cc3n(C3CCN(C=O)CC3)c2=O)ccc1OCc1cccc(C(F)(F)F)c1] | 4-{3-[4-(benzyloxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 680 |
| 382 | 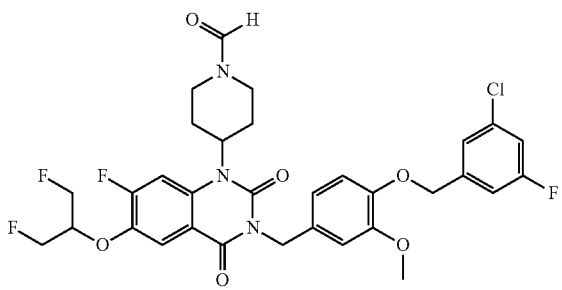 [SMILES: COc1cc(Cn2c(=O)c3cc(OC(CF)CF)c(F)cc3n(C3CCN(C=O)CC3)c2=O)ccc1OCc1cc(F)cc(Cl)c1] | 4-[3-{4-[(3-chloro-5-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 664 |
| 383 | 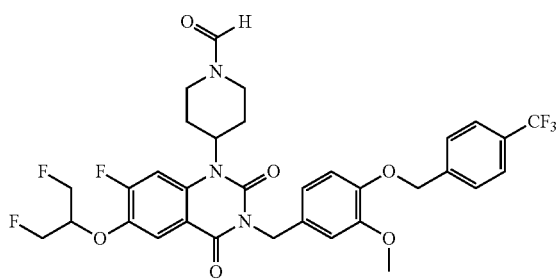 [SMILES: COc1cc(Cn2c(=O)c3cc(OC(CF)CF)c(F)cc3n(C3CCN(C=O)CC3)c2=O)ccc1OCc1ccc(C(F)(F)F)cc1] | 4-{7-fluoro-6-[2-fluoro-1-(fluoromethyl)ethoxy]-3-(3-methoxy-4-{[4-(trifluoromethyl)benzyl]oxy}benzyl)-2,4-dioxo-3,4-dihydroquinazolin-1(2H)-yl}piperidine-1-carbaldehyde | 680 |
| 384 | 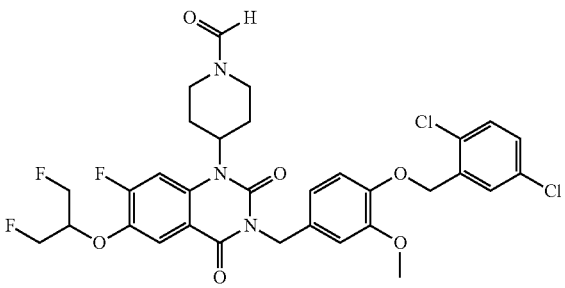 [SMILES: COc1cc(Cn2c(=O)c3cc(OC(CF)CF)c(F)cc3n(C3CCN(C=O)CC3)c2=O)ccc1OCc1cc(Cl)ccc1Cl] | 4-[3-{4-[(2,5-dichlorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 680 |

| | | | |
|---|---|---|---|
| 385 | 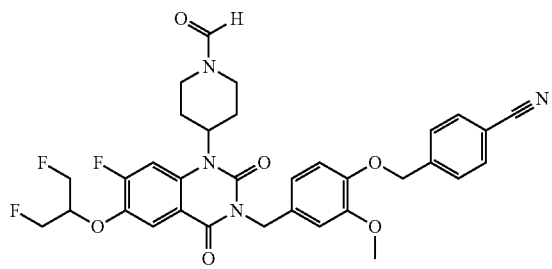 [SMILES: COc1cc(Cn2c(=O)c3cc(OC(CF)CF)c(F)cc3n(C3CCN(C=O)CC3)c2=O)ccc1OCc1ccc(C#N)cc1] | 4-{[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl}benzonitrile | 637 |
| 386 | 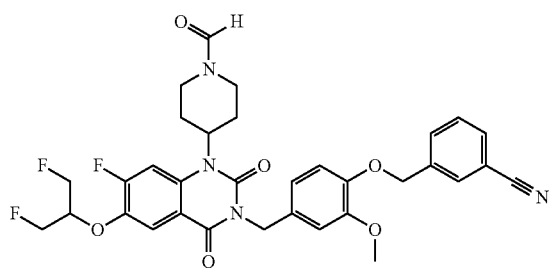 [SMILES: COc1cc(Cn2c(=O)c3cc(OC(CF)CF)c(F)cc3n(C3CCN(C=O)CC3)c2=O)ccc1OCc1cccc(C#N)c1] | 3-{[4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenoxy]methyl}benzonitrile | 637 |
| 387 | 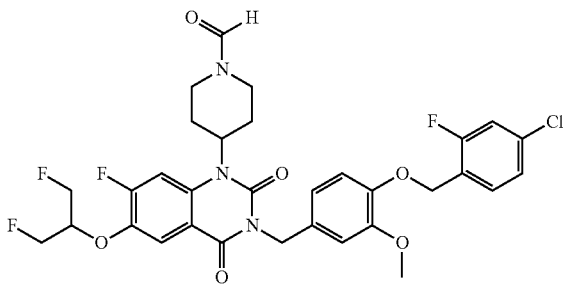 [SMILES: COc1cc(Cn2c(=O)c3cc(OC(CF)CF)c(F)cc3n(C3CCN(C=O)CC3)c2=O)ccc1OCc1ccc(Cl)cc1F] | 4-[3-{4-[(4-chloro-2-fluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 664 |
| 388 | 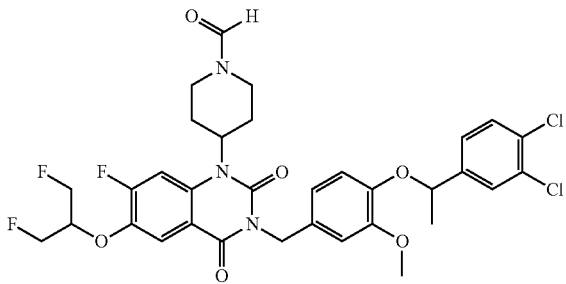 [SMILES: COc1cc(Cn2c(=O)c3cc(OC(CF)CF)c(F)cc3n(C3CCN(C=O)CC3)c2=O)ccc1OC(C)c1ccc(Cl)c(Cl)c1] | 4-[3-{4-[1-(3,4-dichlorophenyl)ethoxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 694 |
| 389 | 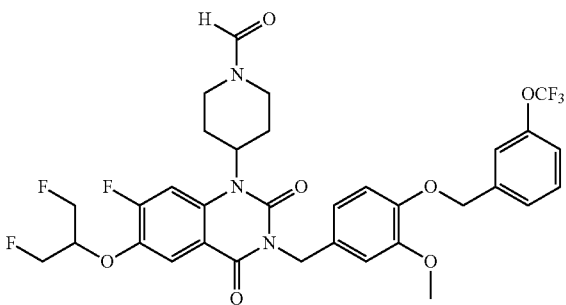 [SMILES: COc1cc(Cn2c(=O)c3cc(OC(CF)CF)c(F)cc3n(C3CCN(C=O)CC3)c2=O)ccc1OCc1cccc(OC(F)(F)F)c1] | 4-{7-fluoro-6-[2-fluoro-1-(fluoromethyl)ethoxy]-3-{4-[(3-hydroxybenzyl)oxy]-3-methoxybenzyl}-2,4-dioxo-3,4-dihydroquinazolin-1(2H)-yl}piperidine-1-carbaldehyde | 696 |

-continued

| | | | |
|---|---|---|---|
| 390 | 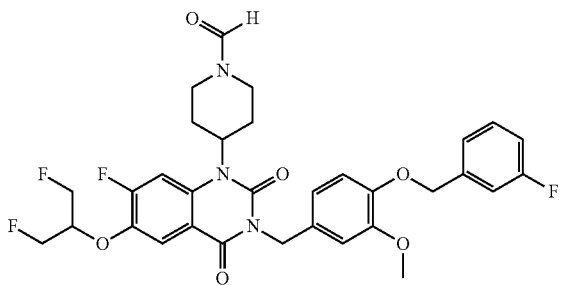 [SMILES: COc1cc(Cn2c(=O)c3cc(OC(CF)CF)c(F)cc3n(C3CCN(C=O)CC3)c2=O)ccc1OCc1cccc(F)c1] | 4-{7-fluoro-3-{4-[(3-fluorobenzyl)oxy]-3-methoxybenzyl}-6-[2-fluoro-1-(fluoromethyl)ethoxy]-2,4-dioxo-3,4-dihydroquinazolin-1(2H)-yl]piperidine-1-carbaldehyde | 630 |
| 391 | 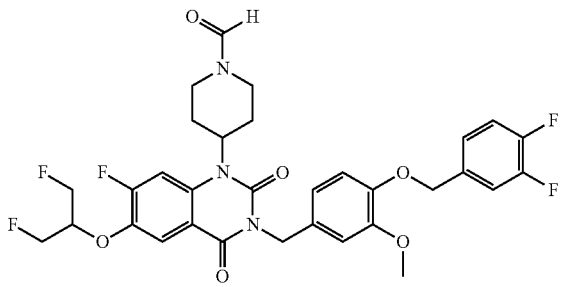 [SMILES: COc1cc(Cn2c(=O)c3cc(OC(CF)CF)c(F)cc3n(C3CCN(C=O)CC3)c2=O)ccc1OCc1ccc(F)c(F)c1] | 4-[3-{4-[(3,4-difluorobenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 648 |
| 392 | 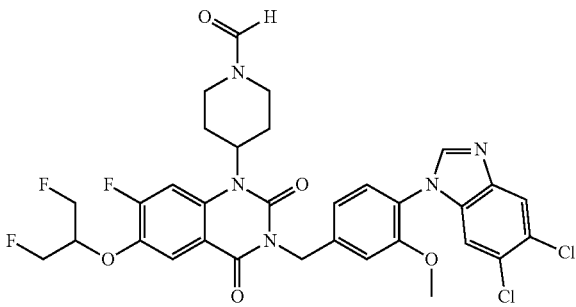 [SMILES: COc1cc(Cn2c(=O)c3cc(OC(CF)CF)c(F)cc3n(C3CCN(C=O)CC3)c2=O)ccc1-n1cnc2cc(Cl)c(Cl)cc21] | 4-{3-[4-(5,6-dichloro-1H-benzimidazol-1-yl)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 660 |
| 393 | 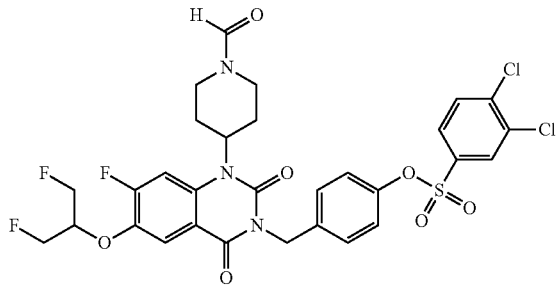 [SMILES: O=CN1CCC(n2c(=O)n(Cc3ccc(OS(=O)(=O)c4ccc(Cl)c(Cl)c4)cc3)c(=O)c3cc(OC(CF)CF)c(F)cc32)CC1] | 4-({7-fluoro-6-[2-fluoro-1-(fluoromethyl)ethoxy]-1-(1-formyl-piperidin-4-yl)-2,4-dioxo-1,4-dihydroquinazolin-3(2H)-yl}methyl)phenyl 3,4-dichlorobenzenesulphonate | 700 |
| 394 | 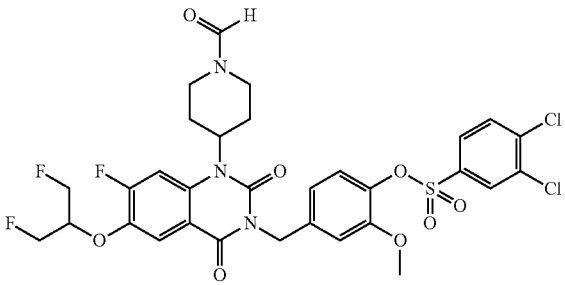 [SMILES: COc1cc(Cn2c(=O)c3cc(OC(CF)CF)c(F)cc3n(C3CCN(C=O)CC3)c2=O)ccc1OS(=O)(=O)c1ccc(Cl)c(Cl)c1] | 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 3,4-dichlorobenzenesulphonate | 730 |

| # | Structure | Name | MW |
|---|---|---|---|
| 395 | 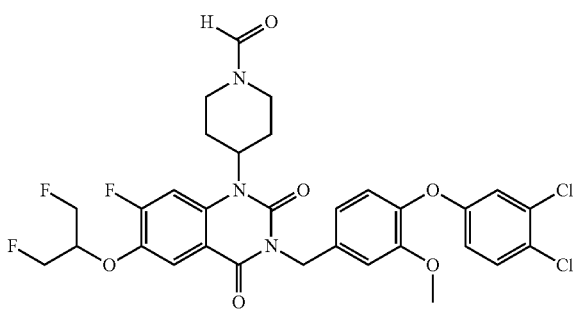 [SMILES: COc1cc(Cn2c(=O)c3cc(OC(CF)CF)c(F)cc3n(C3CCN(C=O)CC3)c2=O)ccc1Oc1ccc(Cl)c(Cl)c1] | 4-{3-[4-(3,4-dichlorophenoxy)-3-methoxybenzyl]-7-fluoro-6-[2-fluoro-1-(fluoromethyl)ethoxy]-2,4-dioxo-3,4-dihydroquinazolin-1(2H)-yl}piperidine-1-carbaldehyde | 666 |
| 396 | 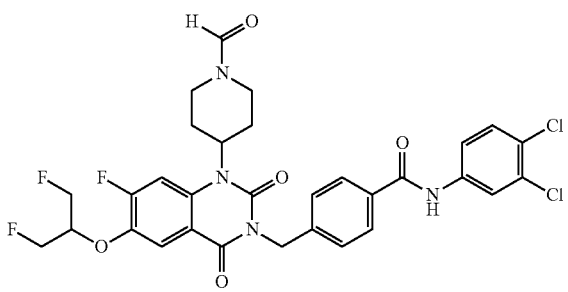 [SMILES: O=CN1CCC(n2c(=O)n(Cc3ccc(C(=O)Nc4ccc(Cl)c(Cl)c4)cc3)c(=O)c3cc(OC(CF)CF)c(F)cc32)CC1] | N-(3,4-dichlorophenyl)-4-({7-fluoro-6-[2-fluoro-1-(fluoromethyl)ethoxy]-1-(1-formylpiperidin-4-yl)-2,4-dioxo-3,4-dihydroquinazolin-3(2H)-yl}methyl)benzamide | 645 |
| 397 | 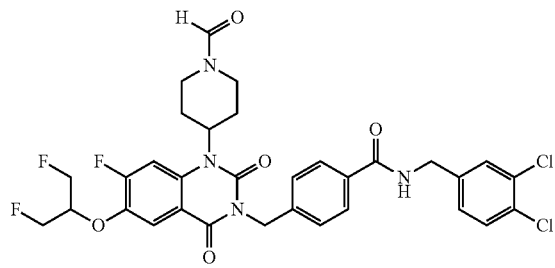 [SMILES: O=CN1CCC(n2c(=O)n(Cc3ccc(C(=O)NCc4ccc(Cl)c(Cl)c4)cc3)c(=O)c3cc(OC(CF)CF)c(F)cc32)CC1] | N-(3,4-dichlorobenzyl)-4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)benzamide | 659 |
| 398 | 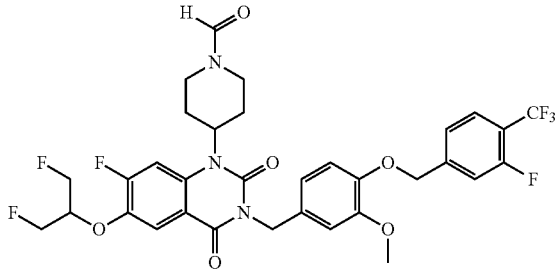 [SMILES: COc1cc(Cn2c(=O)c3cc(OC(CF)CF)c(F)cc3n(C3CCN(C=O)CC3)c2=O)ccc1OCc1ccc(C(F)(F)F)c(F)c1] | 4-{7-fluoro-6-[2-fluoro-1-(fluoromethyl)ethoxy]-3-(4-{[3-fluoro-4-(trifluoromethyl)benzyl]oxy}-3-methoxybenzyl)-2,4-dioxo-3,4-dihydroquinazolin-1(2H)-yl}piperidine-1-carbaldehyde | 698 |
| 399 | 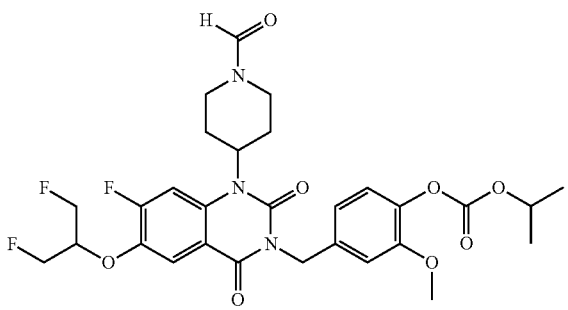 [SMILES: COc1cc(Cn2c(=O)c3cc(OC(CF)CF)c(F)cc3n(C3CCN(C=O)CC3)c2=O)ccc1OC(=O)OC(C)C] | 4-({7-fluoro-6-[2-fluoro-1-(fluoromethyl)ethoxy]-1-(1-formylpiperidin-4-yl)-2,4-dioxo-1,4-dihydroquinazolin-3(2H)-yl}methyl)-2-methoxyphenyl 1-methylethyl carbonate | 608 |

-continued

| | | | |
|---|---|---|---|
| 400 | 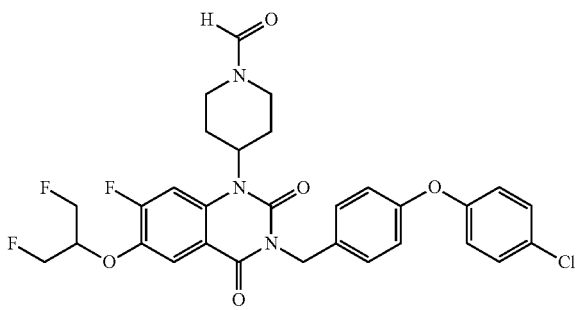 [SMILES: O=CN1CCC(n2c(=O)n(Cc3ccc(Oc4ccc(Cl)cc4)cc3)c(=O)c3cc(OC(CF)CF)c(F)cc32)CC1] | 4-{3-[4-(4-chlorophenoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 602 |
| 401 | 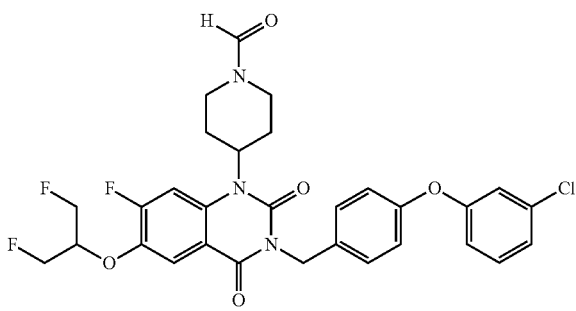 [SMILES: O=CN1CCC(n2c(=O)n(Cc3ccc(Oc4cccc(Cl)c4)cc3)c(=O)c3cc(OC(CF)CF)c(F)cc32)CC1] | 4-{3-[4-(3-chlorophenoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 602 |
| 402 | 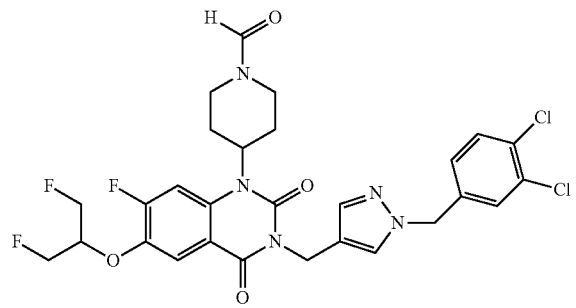 [SMILES: O=CN1CCC(n2c(=O)n(Cc3cnn(Cc4ccc(Cl)c(Cl)c4)c3)c(=O)c3cc(OC(CF)CF)c(F)cc32)CC1] | 4-[3-{[1-(3,4-dichlorobenzyl)-1H-pyrazol-4-yl]methyl}-7-fluoro-6-[2-fluoro-1-(fluoromethyl)ethoxy]-2,4-dioxo-3,4-dihydroquinazolin-1(2H)-yl]piperidine-1-carbaldehyde | 624 |
| 403 | 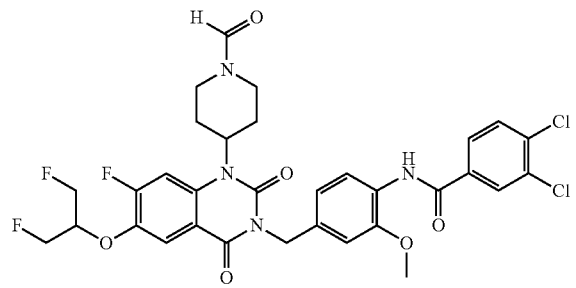 [SMILES: COc1cc(Cn2c(=O)c3cc(OC(CF)CF)c(F)cc3n(C3CCN(C=O)CC3)c2=O)ccc1NC(=O)c1ccc(Cl)c(Cl)c1] | 3,4-dichloro-N-[4-({7-fluoro-6-[2-fluoro-(fluoromethyl)ethoxy]-1-(1-formylpiperidin-4-yl)-2,4-dioxo-1,4-dihydroquinazolin-3(2H)-yl}methyl)-2-methoxyphenyl]benzamide | 693 |
| 404 | 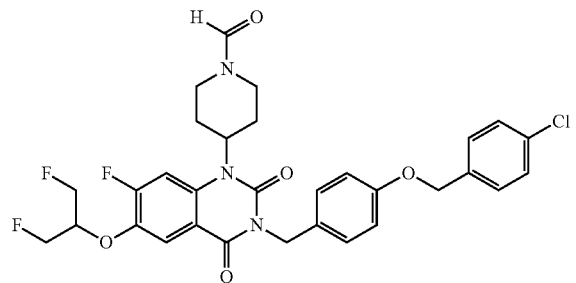 [SMILES: O=CN1CCC(n2c(=O)n(Cc3ccc(OCc4ccc(Cl)cc4)cc3)c(=O)c3cc(OC(CF)CF)c(F)cc32)CC1] | 4-[3-{4-[(4-chlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 616 |

-continued

| | | | |
|---|---|---|---|
| 405 | [structure] | 4-{7-fluoro-6-[2-fluoro-1-(fluoromethyl)ethoxy]-3-[4-(4-fluorophenoxy)benzyl]-2,4-dioxo-3,4-dihydroquinazolin-1(2H)-yl}piperidine-1-carbaldehyde | 586 |
| 406 | [structure] | 4-{3-[4-(3,4-dichlorophenoxy)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 636 |
| 407 | [structure] | 4-[3-({6-[(3,4-dichlorobenzyl)oxy]pyridin-3-yl}methyl)-7-fluoro-6-[2-fluoro-1-(fluoromethyl)ethoxy]-2,4-dioxo-3,4-dihydroquinazolin-1(2H)-yl]piperidine-1-carbaldehyde | 651 |
| 408 | [structure] | 4-[3-{4-[(2-chlorobenzyl)oxy]benzyl}-7-fluoro-6-[2-fluoro-1-(fluoromethyl)ethoxy]-2,4-dioxo-3,4-dihydroquinazolin-1(2H)-yl]piperidine-1-carbaldehyde | 616 |
| 409 | [structure] | 4-[3-{[1-(3,4-dichlorobenzyl)-1H-pyrazol-3-yl]methyl}-7-fluoro-6-[2-fluoro-1-(fluoromethyl)ethoxy]-2,4-dioxo-3,4-dihydroquinazolin-1(2H)-yl]piperidine-1-carbaldehyde | 624 |

| | | | |
|---|---|---|---|
| 410 | 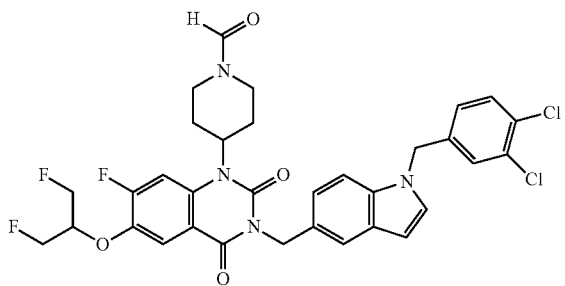 [SMILES: O=CN1CCC(n2c(=O)n(Cc3ccc4c(ccn4Cc4ccc(Cl)c(Cl)c4)c3)c(=O)c3cc(OC(CF)CF)c(F)cc32)CC1] | 4-[3-{[1-(3,4-dichlorobenzyl)-1H-indol-5-yl]methyl}-7-fluoro-6-[2-fluoro-1-(fluoromethyl)ethoxy]-2,4-dioxo-3,4-dihydroquinazolin-1(2H)-yl]piperidine-1-carbaldehyde | 673 |
| 411 | 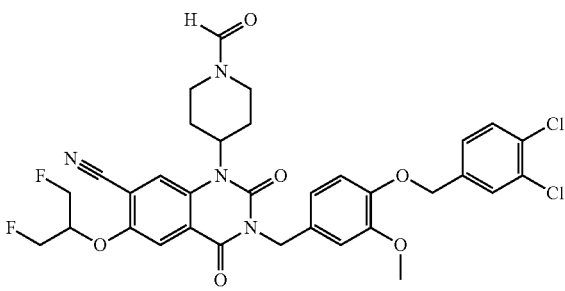 [SMILES: COc1cc(Cn2c(=O)c3cc(OC(CF)CF)c(C#N)cc3n(C3CCN(C=O)CC3)c2=O)ccc1OCc1ccc(Cl)c(Cl)c1] | 3-{4-[(3,4-dichlorobenzyl)oxy]-3-methoxybenzyl}-6-[2-fluoro-1-(fluoromethyl)ethoxy]-1-(1-formylpiperidin-4-yl)-2,4-dioxo-1,2,3,4-tetrahydroquinazoline-7-carbonitrile | 687 |
| 412 | 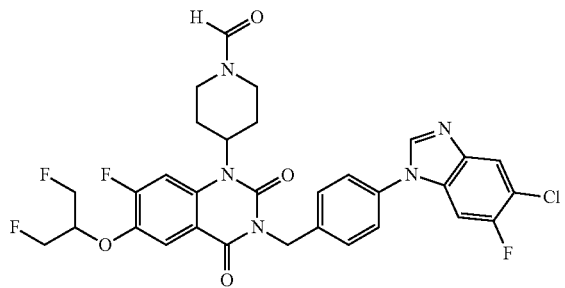 [SMILES: O=CN1CCC(n2c(=O)n(Cc3ccc(-n4cnc5cc(Cl)c(F)cc54)cc3)c(=O)c3cc(OC(CF)CF)c(F)cc32)CC1] | 4-{3-[4-(5-chloro-6-fluoro-1H-benzimidazol-1-yl)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 644 |
| 413 | 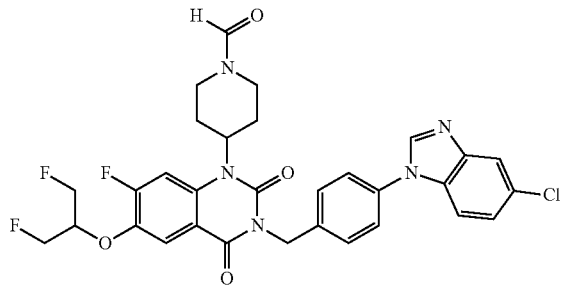 | 4-{3-[4-(5-chloro-1H-benzimidazol-1-yl)benzyl]-7-fluoro-6-[2-fluoro-1-(fluoromethyl)ethoxy]-2,4-dioxo-3,4-dihydroquinazolin-1(2H)-yl}piperidine-1-carbaldehyde | 626 |
| 414 | 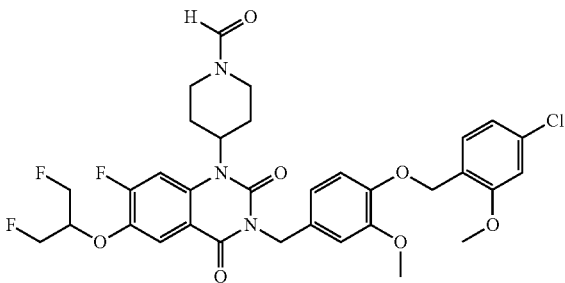 [SMILES: COc1cc(Cl)ccc1COc1ccc(Cn2c(=O)c3cc(OC(CF)CF)c(F)cc3n(C3CCN(C=O)CC3)c2=O)cc1OC] | 4-[3-{4-[(4-chloro-2-methoxybenzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde | 676 |

| 415 | 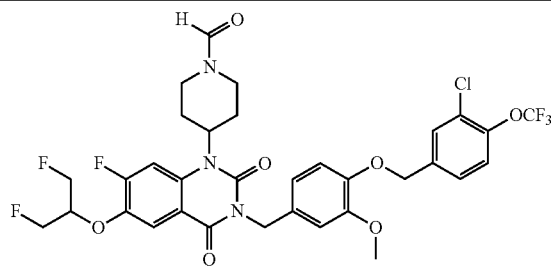 | 4-[3-{4-[3-chloro-4-hydroxy-benzyl)oxy]-3-methoxybenzyl}-7-fluoro-6-[2-fluoro-1-(fluoromethyl)ethoxy]-2,4-dioxo-3,4-dihydroquinazolin-1(2H)-yl]piperidine-1-carbaldehyde 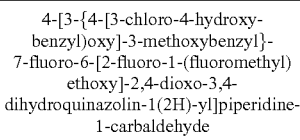 | 730 |

The compounds in accordance with the invention form the subject of pharmacological trials which have shown their advantage as therapeutically active substances.

1) Measurement of the Inhibitory Activity of the Compounds in Accordance with the Invention with Regard to PDE7

The ability of the compounds of formula (I) to inhibit PDE7 is measured using an enzymatic assay based on the separation of radioactive cAMP (substrate of PDE7) from the radioactive 5'-AMP (product of the enzymatic reaction) by thin layer chromatography on polyethyleneimine (PEI) cellulose, after halting the enzymatic reaction. The 5'-AMP is extracted quantitatively from the PEI cellulose and its radioactivity is measured using a liquid scintillation counter.

The inhibitory activity of the compounds of formula (I) with regard to PDE7 is represented by the inhibition constant $IC_{50}$, defined as the concentration of the compound (inhibitor) tested in the assay which makes it possible to reduce the enzymatic activity of PDE7 by 50%. The lower the $IC_{50}$ values, the greater the inhibitory power of the compounds.

Materials

The [$^3$H]-cAMP (NET 275; 25 to 40 Ci/mmol) was purchased from Perkin-Elmer (NEN Life Sciences, Boston, United States), the rolipram was purchased from Sigma (St Louis, Mo., United States) and the sheets of polyethyleneimine cellulose F made of plastic for thin layer chromatography were purchased from Merck (Darmstadt, Germany). All the other products used are of commercial origin.

Enzyme

Human PDE7 was partially purified from the HUT-78 cell line by following a method analogous to that described by Bloom and Beavo (Proc. Natl. Acad. Sci. USA, (1996) 93, 14188-14192). The enzyme preparation obtained is stored at −80° C. in a buffer comprising 20 mM of Tris-HCl (pH 7.0), 5 mM of $MgCl_2$, 4 mM of EDTA, 1 mM of dithiothreitol and 20% of glycerol. As the partially purified PDE7 is contaminated by PDE4, it is necessary to add 10 μM of rolipram (selective inhibitor of PDE4) in the enzymatic assay in order to completely inhibit the PDE4 activity. The Michaelis constant (Km) of PDE7 for cAMP, measured using the radiochemical assay described below, is 21 nM.

Solutions of Compounds in Accordance with the Invention

The compounds of formula (I) to be tested as PDE7 inhibitors are dissolved in DMSO at a concentration of 10 mM. These solutions are subsequently diluted in cascade in DMSO in order to obtain solutions with the desired concentrations. The latter are subsequently diluted to one-twentieth in the assay buffer to give 5% DMSO solutions. The latter are finally diluted to one-fifth in the enzymatic assay.

The solution of rolipram (added in the assay in order to completely inhibit the contaminating PDE4 activity) is prepared in an identical way and contributes 1% of DMSO to the enzymatic assay.

PDE7 Enzymatic Assay

The assay is carried out in 1.5 ml Eppendorf tubes comprising 40 mM of Tris-HCl (pH 7.5), 15 mM of $MgCl_2$, 1 mM of EGTA, 0.5 mg/ml of bovine serum albumin, 0.063 μCi of [$^3$H]-cAMP (corresponding to a cAMP concentration of between 15 and 25 nM), 10 μM of rolipram and PDE7 in a final volume of 100 μl. The assay is carried out in the absence (control sample) or in the presence (treated sample) of the compounds tested as PDE7 inhibitors. The final concentration of DMSO in the assay is 2%. The reaction is initiated by addition of enzyme and the samples are maintained at ambient temperature for 30 minutes. The enzymatic dilution is adjusted so as to obtain a degree of conversion of 10 to 15%. The enzymatic reaction is halted by immersion of the stoppered Eppendorf tubes in a water bath at 100° C. for 3 minutes. Blanks (reaction halted immediately after addition of the enzyme) are included in each experiment. The samples are subsequently centrifuged at 10 000×g for 1 minute and an aliquot portion of 10 μl of supernatant is deposited 2 cm from the bottom edge of a sheet of PEI cellulose on which 10 μg of cAMP and 10 μg of 5'-AMP have been deposited beforehand. In order to facilitate the migration and to make it easier to cut out the strips of PEI cellulose comprising the 5'-AMP, which take place subsequently, 18 migration lanes with a width of 1 cm are delimited per plate by scraping the cellulose with a spatula over a width of 1 mm. The plates are developed over their entire length with a 0.30 M solution of LiCl in water by ascending chromatography. The 5'-AMP (Rf=0.20) and the cAMP (Rf=0.47) are visualized under UV light at 254 nm. The strips of PEI cellulose comprising the 5'-AMP are cut out and the nucleotide is quantitatively extracted in counting flasks with 2 ml of a solution which is 16M in formic acid and 2M in ammonium formate in water (rotary stirrer for 15 min). After addition of 10 ml of scintillation liquid (OptiPhase HiSafe 3 from Perkin-Elmer/Wallac), the radioactivity is counted using a liquid scintillation counter (model 1414, Perkin-Elmer/Wallac). Each assay is carried out in duplicate. The radioactivity specifically associated with the 5'-AMP formed in the enzymatic reaction is obtained by subtracting the mean value of blanks from the mean value of the controls (or treated samples).

The percentage of inhibition of PDE7 at a given concentration of the compound tested (inhibitor) is calculated using the equation: I %=[mean value of the controls−mean value of the treated samples]×100/[mean value of the controls−mean value of the blanks].

The $IC_{50}$ is the concentration of the compound (inhibitor) tested in the assay which makes it possible to reduce the enzymatic activity of PDE7 by 50%.

Results

As illustrative and nonlimiting examples, the following quinazolinediones inhibit PDE7 with the $IC_{50}$ values indicated below:

| Compound | IC$_{50}$ (µM) |
|---|---|
| No. 16: 4-[6-(2,2-difluoroethoxy)-3-(3,4-dimethoxybenzyl)-2,4-dioxo-3,4-dihydroquinazolin-1(2H)-yl]piperidine-1-carbaldehyde | 0.015 |
| No. 11: 4-[3-(3,4-dimethoxybenzyl)-6-[2-fluoro-1-(fluoromethyl)ethoxy]-2,4-dioxo-3,4-dihydroquinazolin-1(2H)-yl]piperidine-1-carbaldehyde | 0.039 |
| No. 72: 4-[3-(3,4-dimethoxybenzyl)-6-(2-hydroxyethoxy)-2,4-dioxo-3,4-dihydroquinazolin-1(2H)-yl]piperidine-1-carbaldehyde | 0.089 |
| No. 77: N-{[3-(3,4-dimethoxybenzyl)-1-(1-formylpyrrolidin-3-yl)-2,4-dioxo-1,2,3,4-tetrahydroquinazolin-6-yl]methyl}acetamide | 0.82 |
| No. 97: 4-[5,7-dichloro-3-(3,4-dimethoxybenzyl)-2,4-dioxo-3,4-dihydroquinazolin-1(2H)-yl]piperidine-1-carbaldehyde | 0.061 |
| No. 111: 4-[6-(difluoromethoxy)-3-(3,4-dimethoxybenzyl)-2,4-dioxo-3,4-dihydroquinazolin-1(2H)-yl]piperidine-1-carbaldehyde | 0.0067 |

2) Measurement of the Inhibitory Activity of the Compounds in Accordance with the Invention with Regard to PDE8

By using for PDE8 an enzymatic assay equivalent to that described for PDE7, the following IC$_{50}$ values are obtained:

| Compound | IC$_{50}$ PDE7 (µM) | IC$_{50}$ PDE8 (µM) |
|---|---|---|
| No. 11 | 0.039 | 0.14 |
| No. 251 | 0.046 | 0.39 |
| No. 294 | 0.037 | 0.015 |

3) Evaluation of the Compounds in Accordance with the Invention in an In Vitro Model of Microglial Activation The glial cells actively participate in the neurodegenerative mechanism by the production of neurotoxic factors. The production of these mediators forms part of the neuroinflammatory process observed in neurodegenerative diseases and in particular in Parkinson's disease and Alzheimer's disease.

Numerous studies have demonstrated that the inhibition of glial activation and consequently the reduction in the production of proinflammatory factors, such as interleukin-1, released by activated glial cells significantly reduces neuronal degeneration.

The compounds according to the invention have been evaluated in an in vitro model of microglial activation. After activation by lipopolysaccharide (LPS), the microglial cells secrete large amounts of interleukin-1, which amounts can be quantified by specific assaying in the cell supernatants.

Cultures of microglial cells of the MG7 line derived from the mouse cortex are incubated in the presence of variable concentrations of compounds according to the invention. After incubating at 37° C. for 1 hour, the cells are brought together with LPS, which induces the production of interleukin-1. After treating for 24 h, the amounts of interleukin-1β are measured in the culture supernatants by ELISA assay.

Compound No. 297 significantly decreases, in a concentration-dependent fashion, the secretion of interleukin-1β by MG7 microglial cells activated by LPS. The maximum inhibitory effect observed is 47% at 3 µM.

According to the invention, the compound of formula (I) defined above in accordance with the invention can be used as medicament or in the preparation of a medicament intended for the treatment and/or prevention of disorder(s) related to the central nervous system and/or related to the peripheral nervous system.

According to the invention, the compound of formula (I) in accordance with the invention can be used as medicament or in the preparation of a medicament intended for the treatment and/or prevention of psychiatric disorder(s) and/or neurological disorder(s).

According to the invention, the compounds of formula (I) in accordance with the invention can be used as medicaments or in the preparation of a medicament intended for the treatment or prevention of psychiatric disorders chosen from anxiety, depression, mood disorders, insomnia, delusion disorders, obsessive disorders, psychoses, disorders related to schizophrenia, attention deficit hyperactivity disorders (ADHD) in hyperkinetic children, disorders related to the use of psychotropic substances, in particular in the case of abuse of a substance and/or of dependency on a substance, including alcohol dependence and/or nicotine dependence, migraine, stress, disorders related to illnesses of psychosomatic origin, panic attacks, epilepsy, memory disorders, cognitive disorders, in particular senile dementia or disorders related to Alzheimer's disease, and disorders of attention or of vigilance, ischaemia, disorders related to brain trauma or disorders related to acute or chronic neurodegenerative diseases, including chorea and Huntington's chorea.

According to the invention, the compounds of formula (I) in accordance with the invention can be used as medicaments or in the preparation of a medicament intended for the treatment and/or prevention of neurological disorders which may be reflected by movement anomalies or motor disorders associated with a pathology chosen from dyskinesia, Parkinson's disease, postencephalitic parkinsonism, dopa-sensitive dystonia, Shy-Drager syndrome, periodic limb movement disorder (PLMD) syndrome, periodic limb movements in sleep (PLMS) syndrome, Tourette's syndrome or restless legs syndrome (RLS).

According to one embodiment, the compounds of formula (I) in accordance with the invention can be used as medicaments or to manufacture a medicament intended for the treatment of at least one movement anomaly or motor disorder related to Parkinson's disease; in particular, the said movement anomaly or the said motor disorder is chosen from resting tremor, rigidity, bradykinesia and deficiency in postural reflexes.

According to one embodiment, the compounds of formula (I) in accordance with the invention can be used as medicaments or for manufacturing a medicament intended for the prevention and/or treatment of neurological disorders reflected by movement anomalies or motor disorders associated with trauma of the spinal cord, in particular in the treatment of spinal trauma. Within the meaning of the present invention, the term "trauma of the spinal cord" is understood to mean acute or chronic pathologies which have an external origin and which destroy the spinal tract and/or spinal neurones, and which occur, for example, during a fall, impact, crushing episode or road crash.

Advantageously, the compounds of formula (I) in accordance with the invention can be used as medicaments or to manufacture a medicament intended for the prevention and/or treatment of disorders:

related to schizophrenia, in particular (i) in the prevention and/or treatment of positive or negative symptoms and/or (ii) in the prevention and/or treatment of memory deficiency;

associated with Parkinson's disease, in particular (i) in the symptomatic prevention and/or treatment of motor disorders, depression and/or cognitive disorders and/or (ii) in its basic (neuroprotective) treatment and/or related to Alzheimer's disease, in particular (i) in the symptomatic prevention and/or treatment of cognitive disorders and/or behavioural disorders (aggression, depression) and/or (ii) in its basic (neuroprotective) treatment.

The use of the compounds of general formula (I) in accordance with the invention as medicaments or to manufacture a medicament intended to treat and/or prevent the abovementioned disorders or pathologies forms an integral part of the invention, and in particular compounds of formula (I) chosen from compounds Nos. 1 to 6, 11 to 14, 16, 20, 22 to 25, 32 to 43, 47 to 52, 55 to 59, 72, 74, 76, 78, 79, 89 to 91, 97, 102, 108, 111, 112, 114, 116 to 118, 124, 130, 131, 133 to 135, 143, 145, 155, 158, 160, 165 to 167, 170, 175, 178, 183 to 186, 188, 189, 190, 193, 194, 200, 201, 203, 206, 207, 212, 213, 215, 216, 218, 223, 224, 226, 228, 230, 232 to 234, 239, 240, 242, 243, 245, 246, 250, 251, 254, 258, 263, 264, 270, 275, 276, 278 to 280, 282, 283, 285 to 287, 289, 292, 294, 295, 287 to 302, 305 to 312, 315 to 345, 349 to 355, 357, 358, 360, 362, 369, 371, 373, 375 to 377, 379 to 394 and 403.

Another subject-matter of the invention is a compound corresponding to the general formula (I) as defined above in the treatment and/or prevention of disorders related to the central nervous system and/or related to the peripheral nervous system, the said disorder(s) advantageously being chosen from psychiatric disorders and neurological disorders.

Pharmaceutical compositions comprising, as active principle, at least one compound in accordance with the invention are of use in the present invention. These pharmaceutical compositions comprise an effective dose of at least one compound of formula (I) in accordance with the invention and also at least one pharmaceutically acceptable excipient.

The said excipients are chosen, according to the pharmaceutical form and the method of administration desired, from the usual excipients which are known to a person skilled in the art.

In the pharmaceutical compositions of use in the present invention for oral, sublingual, subcutaneous, intramuscular, intravenous, topical, local, intratracheal, intranasal, transdermal or rectal administration, the active principle of formula (I) above or its optional salt, solvate or hydrate can be administered in unit administration form, as a mixture with conventional pharmaceutical excipients, to animals and human beings for the prophylaxis or treatment of the above disorders or diseases.

The appropriate unit administration forms comprise forms by the oral route, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. Use may be made, for topical application, of the compounds according to the invention in creams, gels, ointments or lotions.

By way of example, a unit administration form of a compound in accordance with the invention in the form of a tablet can comprise the following components:

| | |
|---|---|
| Compound No. 1 (2-{[3-(3,4-dimethoxybenzyl)-1-(1-formylpiperidin-4-yl)-2,4-dioxo-1,2,3,4-tetrahydroquinazolin-6-yl]oxy}propanenitrile) | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The said unit forms comprise doses in order to make possible daily administration of 0.5 mg to 800 mg of active principle per individual, more particularly of 0.5 mg to 200 mg, according to the pharmaceutical dosage form.

There may be cases where higher or lower dosages are appropriate; such dosages do not depart from the scope of the invention. According to the usual practice, the dosage appropriate to each patient is determined by the physician according to the method of administration and the weight and response of the said patient.

A method for the treatment and/or prevention of the pathologies indicated above comprises the administration, to a patient, of an effective dose of a compound in accordance with the invention or of one of its hydrates or solvates.

The invention claimed is:

1. A method of treating a disorder selected from the group consisting of Parkinson's disease and Alzheimer's disease in a patient in need thereof comprising administering to said patient a therapeutically effective amount of a compound of Formula (I):

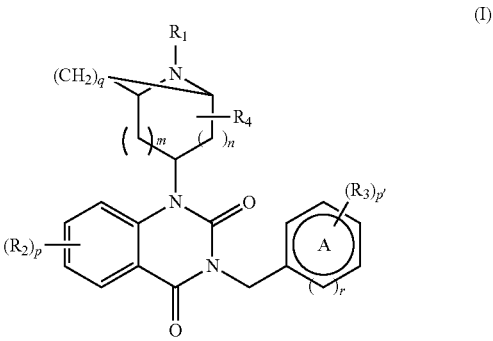

in which
A represents an aryl group;
$R_1$ represents:
a hydrogen atom,
—C(O)R in which R is a hydrogen atom, a ($C_1$-$C_6$) alkoxy group, an aryl group, a ($C_3$-$C_6$) cycloalkyl group or a ($C_1$-$C_6$) alkyl group, the said alkyl optionally being substituted by:
one or more hydroxyl group(s),
a benzyloxy group,
a ($C_1$-$C_6$) alkoxy group, optionally substituted by an aryl, or
a ($C_3$-$C_6$) cycloalkyl group,
an optionally substituted ($C_1$-$C_6$) alkyl group;
$R_2$ represents:
a hydrogen atom,
a halogen atom,
a cyano group,
a nitro group,
a ($C_1$-$C_6$) alkyl group optionally substituted by an —$NH_2$ or else by an —NHC(O)Rb group, with Rb as defined below,
an —ORa group in which Ra represents:
a hydrogen atom,
a ($C_1$-$C_6$) alkyl group optionally substituted by one or more halogen atom(s), by one or more hydroxyl group(s), by an aryl group and/or by one or more cyano group(s),
a ($C_2$-$C_6$) alkynyl group,
an aryl group;

R₃ represents:
a hydrogen atom,
a halogen atom,
a hydroxyl group,
a cyano group,
an —SCF₃ group,
a nitro group,
an oxo group,
  an —S(O)₀₋₂-alkyl group, an —S(O)₀₋₂-heterocycloalkyl group, an —O—SO₂-aryl group optionally substituted by one or more halogen atom(s);
  an -alkylaminoalkyl or -cycloalkylaminoalkyl group, each optionally substituted on the end alkyl,
  an optionally substituted sulphonamide group,
  an aryl group or a heteroaryl group, the said group being monocyclic or polycyclic and in addition optionally being substituted by a (C₁-C₆) alkyl group, by one or more halogen atom(s) or by a (C₁-C₆) alkoxy group,
  a heterocycloalkyl group optionally substituted by a (C₁-C₆) alkyl group,
a (C₁-C₆) alkyl group optionally substituted by:
  one or more halogen atom(s),
  an aryl group which can be substituted by one or more halogen atom(s) or by one or more hydroxyl group(s),
  a heteroaryl group,
  one or more hydroxyl group(s) which can be substituted by an aryl group itself optionally substituted by one or more halogen atom(s), or
  a heterocycloalkyl group optionally substituted by a CO(O)Ra group or by a (C₁-C₆) alkyl group, with Ra as defined above,
a —C(O)NRbRc group, with Rb and Rc as defined below,
a —C(O)ORc group or an —O—C(O)ORc group, with Rc as defined below,
a (C₁-C₆) alkoxy group, optionally substituted by
  an aminoalkyl group,
  an aminocycloalkyl group,
  a cycloalkyl group,
  a heterocycloalkyl group,
  a monocyclic or polycyclic heteroaryl group,
  one or more hydroxyl group(s),
  one or more halogen atom(s),
  a (C₁-C₆) alkoxy group,
  a —C(O)ORc group, with Rc as defined below,
  a —C(O)NRbRc group, with Rb and Rc as defined below,
  an oxo group, and/or
  an aryl group, itself optionally substituted by one or more halogen atom(s), a cyano group, a (C₁-C₆) alkoxy group, an —O-haloalkyl group and/or a haloalkyl group,
an —O-cycloalkyl group, an —O-aryl group or an —O-heterocycloalkyl group, each optionally substituted by
  an aryl group, itself optionally substituted by one or more halogen atom(s) or by a (C₁-C₆) alkyl group,
  an oxo group,
  one or more halogen atom(s), and/or
  a (C₁-C₆) alkyl group, which can itself be substituted by an aryl group and/or an oxo group,
and —NH—CO—NH-aryl group, an —NH—CO—NH-heteroaryl group or an —NH—CO—NH—(C₁-C₆) alkyl group, each optionally being substituted by one or more halogen atom(s), by a cyano group, by a nitro group, by one or more hydroxyl group(s) or by a (C₁-C₆) alkoxy group,
an —N—(C₁-C₆) alkyl group, it being possible for the (C₁-C₆) alkyl group to be substituted by
  one or more oxo group(s), and/or
  one or more aryl group(s) optionally substituted by one or more halogen atom(s) and/or by an SO₂ group,
  an —NH—CO-aryl group or an —NH—CO-heteroaryl group, each optionally being substituted by one or more halogen atom(s);
  R₄ represents a hydrogen atom, an oxo group or a (C₁-C₆) alkyl group;
Rb represents:
a hydrogen atom,
a (C₁-C₆) alkyl group optionally substituted by one or more halogen atom(s), by one or more hydroxyl, cyano, amino, heterocycloalkyl or (C₁-C₆) alkoxy group(s) or by an aryl group optionally substituted by one or more halogen atom(s),
a (C₃-C₆) cycloalkyl group,
a (C₂-C₆) alkynyl group,
a (C₁-C₆) alkoxy group,
an aryl group optionally substituted by one or more halogen atom(s);
Rc represents a hydrogen atom or a (C₁-C₆) alkyl group optionally substituted by one or more halogen atom(s);
or then Rb and Rc form, together with the nitrogen atom to which they are attached, a polycyclic heteroaryl group or a heterocycloalkyl group;
  m and n represent, independently of one another, the value 0, 1 or 2, it being understood that m+n≤3;
  p and p' represent, independently of one another, the value 1, 2 or 3, it being understood that, when p is greater than or equal to 2, then the R₂ groups are on separate carbon atoms and can be different from one another and, when p' is greater than or equal to 2, then the R₃ groups are on separate carbon atoms and can be different from one another;
  q represents the value 0 or 2, it being understood that, when q=0, then the nitrogenous heterocyclic group attached to the nitrogen situated in the 1 position of the 2,4-dioxo-1,2,3,4-tetrahydroquinazoline ring system is no longer bridged and is of the type:

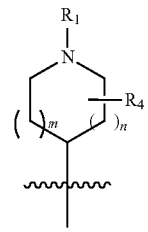

with R₁, R₄, m and n as defined above,
r represents the value 0 or 1;
in the form of the base or of an addition salt with an acid.

2. The method of claim 1 wherein the treating of Parkinson's disease comprises the treating and/or preventing of motor disorders, depression and/or cognitive disorders.

3. The method of claim 2 wherein the anomalies or motor disorders are chosen from resting tremor, rigidity, bradykinesia and deficiency in postural reflexes.

4. The method of claim 1 wherein the treating of Alzheimer's disease comprises preventing and/or treating of cognitive disorders and/or behavioural disorders.

\* \* \* \* \*